United States Patent
Jeanguenat et al.

(10) Patent No.: US 8,580,785 B2
(45) Date of Patent: *Nov. 12, 2013

(54) INSECTICIDES

(75) Inventors: André Jeanguenat, Stein (CH); Roger Graham Hall, Stein (CH); Olivier Loiseleur, Stein (CH); Stephan Trah, Stein (CH); Patricia Durieux, Allschwill (CH); Andrew Edmunds, Stein (CH); André Stoller, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 821 days.

This patent is subject to a terminal disclaimer.

(21) Appl. No.: 12/063,864

(22) PCT Filed: Aug. 14, 2006

(86) PCT No.: PCT/EP2006/008040
§ 371 (c)(1),
(2), (4) Date: Jun. 26, 2008

(87) PCT Pub. No.: WO2007/020050
PCT Pub. Date: Feb. 22, 2007

(65) Prior Publication Data
US 2009/0221587 A1    Sep. 3, 2009

(30) Foreign Application Priority Data
Aug. 15, 2005 (GB) .................. 0516703.6

(51) Int. Cl.
| A01N 43/653 | (2006.01) |
| A01N 43/40 | (2006.01) |
| A01N 43/54 | (2006.01) |
| A01N 43/60 | (2006.01) |
| A01P 7/04 | (2006.01) |
| C07D 401/14 | (2006.01) |
| C07D 403/14 | (2006.01) |
| C07D 413/14 | (2006.01) |
| C07D 417/14 | (2006.01) |

(52) U.S. Cl.
USPC ...... 514/243; 514/249; 514/266.21; 514/338; 514/339; 544/183; 544/284; 544/353; 546/171; 546/268.4; 546/268.7; 546/269.1; 546/270.1; 546/271.7; 546/273.4; 546/275.4; 546/275.7

(58) Field of Classification Search
None
See application file for complete search history.

(56) References Cited

FOREIGN PATENT DOCUMENTS

| WO | 03015519 | 3/2003 |
| WO | 03024222 | 3/2003 |
| WO | 2005053406 | 6/2005 |
| WO | 2005085234 | 9/2005 |

OTHER PUBLICATIONS

Robert V. Hoffman, Organic Chemistry: An Intermediate Text; Chapter 6. Stereochemical and Conformational Isomerism, 2nd Ed., John Wiley & Sons, Inc., 124-182 (2004).*
Database Beilstein; XP002410240; retrieved from XFIRE; Database Accession No. BRN 524946.
Database Beilstein; XP002410241; retrieved from XFIRE; Database Accession No. BRN 1075308.
Database Beilstein; XP002410242; retrieved from XFIRE; Database Accession No. BRN 1075668.
Database Beilstein; XP002410243; retrieved from XFIRE; Database Accession No. BRN 8391893.
Database Beilstein; XP002410244; retrieved from XFIRE; Database Accession No. BRN 164439.
Database Beilstein; XP002410245; retrieved from XFIRE; Database Accession No. BRN 140431.
Database Beilstein; XP002410246; retrieved from XFIRE; Database Accession No. BRN 6202394.
Database CA; Chemical Abstracts Service, Columbus, Ohio; US; XP002410247; retrieved fro STN; Database Accession No. RN 267665-25-8; abstract.
Database CA; Chemical Abstracts Service, Columbus, Ohio, US; XP002410248; retrieved from STN; Database accession No. RN 32863-22-2; abstract.

* cited by examiner

*Primary Examiner* — Janet Andres
*Assistant Examiner* — Timothy R Rozof
(74) *Attorney, Agent, or Firm* — R. Kody Jones

(57) ABSTRACT

Compounds of formula (I), wherein the substituents are as defined in claim (1), and the agrochemically acceptable salts and all stereoisomers and tautomeric forms of the compounds of formula (I) can be used as agrochemical active ingredients and can be prepared in a manner known per se.

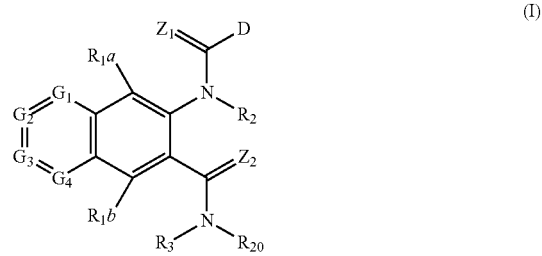

(I)

8 Claims, No Drawings

INSECTICIDES

This application is a 371 of International Application No. PCT/EP2006/008040 filed Aug. 14, 2006, which claims priority to GB 0516703.6 filed Aug. 15, 2005, the contents of which are incorporated herein by reference.

The present invention relates to bicyclic bisamide derivatives, to processes for their preparation, to compositions comprising those compounds, and to their use for controlling insects or representatives of the order Acarina.

Bisamide derivatives with insecticidal action are known and described, for example, in US 2003/0229050 and WO/2005/085234.

There have now been found novel bicyclic bisamide derivatives with pesticidal properties. The present invention accordingly relates to compounds of formula I

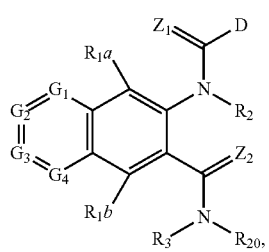

(I)

wherein
$G_1, G_2, G_3$ and $G_4$ form together with the two carbon atoms to which $G_1$ and $G_4$ are attached, an aromatic ring system; wherein
$G_1$ is nitrogen, sulfur, oxygen, a direct bond or C—$R_{5a}$;
$G_2$ is nitrogen, sulfur, oxygen, a direct bond or C—$R_{5b}$;
$G_3$ is nitrogen, sulfur, oxygen, a direct bond or C—$R_{5c}$;
$G_4$ is nitrogen, sulfur, oxygen, a direct bond or C—$R_{5d}$, with the provisos that
a) at least one substituent G represents nitrogen, sulfur or oxygen,
b) not more than 1 substituent G can at the same time form a direct bond,
c) not more than 2 substituents G can be oxygen or sulfur, and
d) 2 substituents G as oxygen and/or sulfur are separated by at least one carbon atom; each of $R_{1a}$, $R_{1b}$, $R_{5a}$, $R_{5b}$, $R_{5c}$, and $R_{5d}$ which may be the same or different, represents hydrogen, halogen, nitro, cyano, hydroxy, CHO, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$alkoxy-$C_1$-$C_4$alkoxy-$C_1$-$C_4$alkyl, $C_1$-$C_4$haloalkoxy, $C_1$-$C_4$alkylthio, $C_1$-$C_4$haloalkylthio, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_1$-$C_4$alkylsulfonyl-$C_1$-$C_4$alkyl, $C_1$-$C_4$alkylsulfoximino-$C_1$-$C_4$alkyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_1$-$C_4$alkoxyimino-$C_1$-$C_4$alkyl, $C_3$-$C_6$trialkylsilyl, phenyl, benzyl or phenoxy; or phenyl, benzyl or phenoxy mono-, di- or trisubstituted by halogen, cyano, nitro, halogen, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_3$-$C_6$trialkylsilyl or $C_1$-$C_4$haloalkylsulfonyloxy;

each of $R_2$ and $R_3$, which may be the same or different, represents hydrogen, $C_1$-$C_6$alkyl, $C_2$-$C_6$alkenyl, $C_2$-$C_6$alkynyl or $C_3$-$C_8$cycloalkyl; or $C_1$-$C_6$alkyl, $C_2$-$C_6$alkenyl, $C_2$-$C_6$alkynyl or $C_3$-$C_8$cycloalkyl substituted by one or more substituents selected from halogen nitro, cyano, hydroxy, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino and $C_1$-$C_6$alkyl-$C_3$-$C_6$cycloalkylamino;

D is 2-pyridyl, 3-pyridyl or 4-pyridyl; or phenyl, 2-pyridyl, 3-pyridyl or 4-pyridyl mono-, di- or trisubstituted by $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl or $C_1$-$C_4$haloalkylsulfonyl;

or D is a group

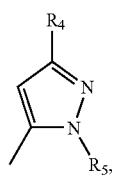

(D1)

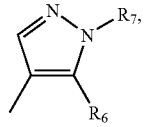

(D2)

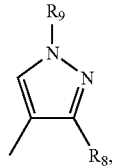

(D3)

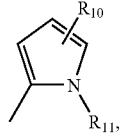

(D4)

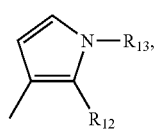

(D5)

-continued

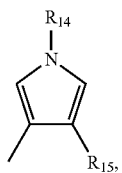
(D6)

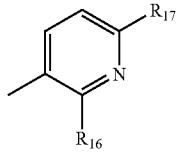
(D7)

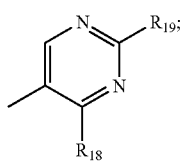
(D8)

or D is additionally phenyl if $Z_1$ is sulfur;

$R_4$, $R_{10}$, $R_{17}$, and $R_{19}$ independently from each other, are hydrogen, $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_2$-$C_4$alkoxycarbonyl, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl or $C_1$-$C_4$haloalkylsulfonyl;

$R_5$, $R_6$, $R_8$, $R_{11}$, $R_{12}$, $R_{15}$, $R_{16}$ and $R_{18}$ independently from each other, are $C_1$-$C_6$alkyl, or $C_1$-$C_6$alkyl mono-, di- or trisubstituted by halogen, cyano, nitro, hydroxy, $C_1$-$C_4$alkoxy, $C_2$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylamino, $C_2$-$C_4$dialkylamino or $C_3$-$C_6$cycloalkylamino; or are phenyl, 2-pyridyl, 3-pyridyl, 4-pyridyl; or are or phenyl, 2-pyridyl, 3-pyridyl or 4-pyridyl mono-, di- or trisubstituted by $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl or $C_1$-$C_4$haloalkylsulfonyl;

$R_7$, $R_9$, $R_{13}$ and $R_{14}$ independently from each other, are hydrogen, $C_1$-$C_6$alkyl, $C_1$-$C_6$haloalkyl, $C_2$-$C_6$alkenyl, $C_2$-$C_6$haloalkenyl, $C_3$-$C_6$alkenyl or $C_3$-$C_6$haloalkenyl;

$R_{20}$ is hydrogen, $C_1$-$C_6$alkyl, $C_2$-$C_6$alkenyl, $C_2$-$C_6$alkynyl, or $C_2$-$C_6$cycloalkyl; or is $C_1$-$C_6$alkyl, $C_2$-$C_6$ alkenyl, $C_2$-$C_6$ alkynyl or $C_2$-$C_6$ cycloalkyl substituted with one, two or three substituents selected from the group consisting of halogen, cyano, nitro, hydroxy, $C_1$-$C_4$alkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_2$-$C_6$ alkoxycarbonyl, $C_2$-$C_6$ alkylcarbonyl, $C_2$-$C_6$trialkylsilyl, benzyl, phenoxy and a three- to ten-membered, monocyclic or fused bicyclic ring system which may be aromatic, partially saturated or fully saturated, it being possible for said benzyl, phenoxy and three- to ten-membered, monocyclic or fused bicyclic ring system in turn to be substituted by one to three substituents independently selected from the group consisting of $C_1$-$C_4$alkyl, $C_2$-$C_4$alkenyl, $C_2$-$C_4$alkynyl, $C_2$-$C_6$cycloalkyl, $C_1$-$C_4$haloalkyl, $C_2$-$C_4$haloalkenyl, $C_2$-$C_4$haloalkynyl, $C_2$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_2$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_2$-$C_8$ dialkylaminocarbonyl and $C_2$-$C_6$ trialkylsilyl;

or $R_{20}$ is $C_1$-$C_4$alkoxy, $C_1$-$C_4$alkylamino, $C_2$-$C_8$dialkylamino, $C_2$-$C_6$ cycloalkylamino, $C_2$-$C_6$alkoxycarbonyl or $C_2$-$C_6$alkylcarbonyl;

each of $Z_1$ and $Z_2$, which may be the same or different, represents oxygen or sulfur; and agronomically acceptable salts/isomers/enantiomers/tautomers/N-oxides of those compounds.

Compounds I which have at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine. Where appropriate, the corresponding internal salts can furthermore be formed. Preferred within the scope of the invention are agrochemically advantageous salts; however, the invention also encompasses salts which have disadvantage for agrochemical use, for example salts which are toxic to bees or fish, and which are employed, for example, for the isolation or purification of free compounds I or agrochemically utilizable salts thereof. Owing to the close relationship between the compounds I in free form and in the form of their salts, for the purposes of the invention the free compounds I or their salts hereinabove and hereinbelow are respectively to be understood as including, where appropriate, the corresponding salts or the free compounds I. The same applies analogously to tautomers of compounds I and salts thereof. In general, the free form is preferred in each case.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl and hexyl and their branched isomers. Alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Suitable haloalkenyl groups are alkenyl groups which are mono- or polysubstituted by halogen, halogen being fluorine, chlorine, bromine and iodine and in particular fluorine and chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Among the $C_3$-$C_{20}$alkenyl groups which are mono-, di- or trisubstituted by halogen, preference is given to those having a chain length of from 3 to 5 carbon atoms.

Suitable haloalkynyl groups are, for example, alkynyl groups which are mono- or polysubstituted by halogen, halogen being bromine, iodine and in particular fluorine and chlorine, for example 3-fluoropropynyl, 3-chloropropynyl, 3-bromopropynyl, 3,3,3-trifluoropropynyl and 4,4,4-trifluorobut-2-yn-1-yl. Among the alkynyl groups which are mono- or polysubstituted by halogen, preference is given to those having a chain length of from 3 to 5 carbon atoms.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy.

Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tertbutoxycarbonyl; preferably methoxycarbonyl or ethoxycarbonyl. Haloalkoxy groups preferably have a chain length of from 1 to 6 carbon atoms. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy. Alkylthio groups preferably have a chain length of from 1 to 6 carbon atoms. Alkylthio is, for example, methylthio, ethylthio, propylthio, isopropylthio, n-butylthio, isobutylthio, sec-butylthio or tert-butylthio, preferably methylthio and ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl, tert-butylsulfinyl; preferably methylsulfinyl and ethylsulfinyl.

Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl; preferably methylsulfonyl or ethylsulfonyl.

Alkylamino is, for example, methylamino, ethylamino, n-propylamino, isopropylamino or the isomeric butylamines. Dialkylamino is, for example, dimethylamino, methylethylamino, diethylamino, n-propylmethylamino, dibutylamino and diisopropylamino. Preference is given to alkylamino groups having a chain length of from 1 to 4 carbon atoms.

Alkoxyalkyl groups preferably have a chain length of 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkylthioalkyl groups preferably have from 1 to 8 carbon atoms. Alkylthioalkyl is, for example, methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl.

The cycloalkyl groups preferably have from 3 to 6 ring carbon atoms, for example cyclopropyl, cyclobutyl, cyclopentyl and cyclohexyl. Phenyl, also as part of a substituent such as phenoxy, benzyl, benzyloxy, benzoyl, phenylthio, phenylalkyl, phenoxyalkyl, may be substituted. In this case, the substituents can be in ortho, meta and/or para position.

The preferred substituent positions are the ortho and para positions to the ring attachment point.

According to the present invention, a three- to ten-membered monocyclic or fused bicyclic ring system which may be aromatic, partially saturated or fully saturated is, depending of the number of ring members, for example, selected from the group consisting of

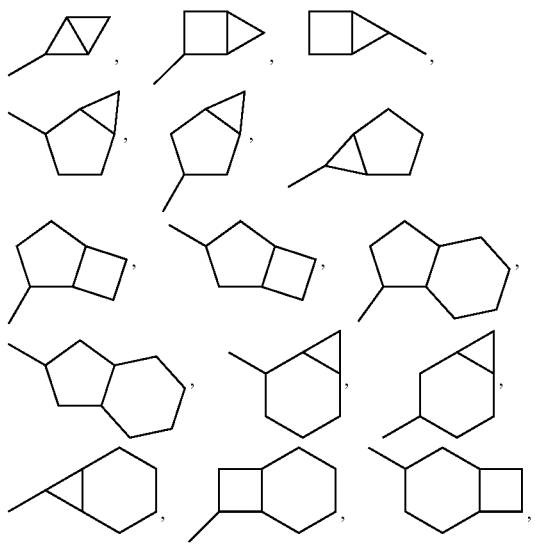

cyclopropyl, cyclobutyl, cyclopentyl, cyclohexyl, where said cycloalkyl groups for their part may be preferably unsubstituted or substituted by $C_1$-$C_6$alkyl or halogen, or is naphthyl or the following heterocyclic groups: pyrrolyl; pyridyl; pyrazolyl; pyrimidyl; pyrazinyl; imidazolyl; thiadiazolyl; quinazolinyl; furyl; oxadiazolyl; indolizinyl; pyranyl; isobenzofuranyl; thienyl; naphthyridinyl; (1-methyl-1H-pyrazol-3-yl)-; (1-ethyl-1H-pyrazol-3-yl)-; (1-propyl-1H-pyrazol-3-yl)-; (1H-pyrazol-3-yl)-; (1,5-dimethyl-1H-pyrazol-3-yl)-; (4-chloro-1-methyl-1H-pyrazol-3-yl)-; (1H-pyrazol-1-yl)-; (3-methyl-1H-pyrazol-1-yl)-; (3,5-dimethyl-1H-pyrazol-1-yl)-; (3-isoxazolyl)-; (5-methyl-3-isoxazolyl)-; (3-methyl-5-isoxazolyl)-; (5-isoxazolyl)-; (1H-pyrrol-2-yl)-; (1-methyl-1H-pyrrol-2-yl)-; (1H-pyrrol-1-yl)-; (1-methyl-1H-pyrrol-3-yl)-; (2-furanyl)-; (5-methyl-2-furanyl)-; (3-furanyl)-; (5-methyl-2-thienyl)-; (2-thienyl)-; (3-thienyl)-; (1-methyl-1H-imidazol-2-yl)-; (1H-imidazol-2-yl)-; (1-methyl-1H-imidazol-4-yl)-; (1-methyl-1H-imidazol-5-yl)-; (4-methyl-2-oxazolyl)-; (5-methyl-2-oxazolyl)-; (2-oxazolyl)-; (2-methyl-5-oxazolyl)-; (2-methyl-4-oxazolyl)-; (4-methyl-2-thiazolyl)-; (5-methyl-2-thiazolyl)-; (2-thiazolyl)-; (2-methyl-5-thiazolyl)-; (2-methyl-4-thiazolyl)-; (3-methyl-4-isothiazolyl)-; (3-methyl-5-isothiazolyl)-; (5-methyl-3-isothiazolyl)-; (1-methyl-1H-1,2,3-triazol-4-yl)-; (2-methyl-2H-1,2,3-triazol-4-yl)-; (4-methyl-2H-1,2,3-triazol-2-yl)-; (1-methyl-1H-1,2,4-triazol-3-yl)-; (1,5-dimethyl-1H-1,2,4-triazol-3-yl)-; (3-methyl-1H-1,2,4-triazol-1-yl)-; (5-methyl-1H-1,2,4-triazol-1-yl)-; (4,5-dimethyl-4H-1,2,4-triazol-3-yl)-; (4-methyl-4H-1,2,4-triazol-3-yl)-; (4H-1,2,4-triazol-4-yl)-; (5-methyl-1,2,3-oxadiazol-4-yl)-; (1,2,3-oxadiazol-4-yl)-; (3-methyl-1,2,4-oxadiazol-5-yl)-; (5-methyl-1,2,4-oxadiazol-3-yl)-; (4-methyl-3-furazanyl)-; (3-furazanyl)-; (5-methyl-1,2,4-oxadiazol-2-yl)-; (5-methyl-1,2,3-thiadiazol-4-yl)-; (1,2,3-thiadiazol-4-yl)-; (3-methyl-1,2,4-thiadiazol-5-yl)-; (5-methyl-1,2,4-thiadiazol-3-yl)-; (4-methyl-1,2,5-thiadiazol-3-yl)-; (5-methyl-1,3,4-thiadiazol-2-yl)-; (1-methyl-1H-tetrazol-5-yl)-; (1H-tetrazol-5-yl)-; (5-methyl-1H-tetrazol-1-yl)-; (2-methyl-2H-tetrazol-5-yl)-; (2-ethyl-2H-tetrazol-5-yl)-; (5-methyl-2H-tetrazol-2-yl)-; (2H-tetrazol-2-yl)-;

(2-pyridyl)-; (6-methyl-2-pyridyl)-; (4-pyridyl)-; (3-pyridyl)-; (6-methyl-3-pyridazinyl)-; (5-methyl-3-pyridazinyl)-; (3-pyridazinyl)-; (4,6-dimethyl-2-pyrimidinyl)-; (4-methyl-2-pyrimidinyl)-; (2-pyrimidinyl)-; (2-methyl-4-pyrimidinyl)-; (2-chloro-4-pyrimidinyl)-; (2,6-dimethyl-4-pyrimidinyl)-; (4-pyrimidinyl)-; (2-methyl-5-pyrimidinyl)-; (6-methyl-2-pyrazinyl)-; (2-pyrazinyl)-; (4,6-dimethyl-1,3,5-triazin-2-yl)-; (4,6-dichloro-1,3,5-triazin-2-yl)-; (1,3,5-triazin-2-yl)-; (4-methyl-1,3,5-triazin-2-yl)-; (3-methyl-1,2,4-triazin-5-yl)-; (3-methyl-1,2,4-triazin-6-yl)-;

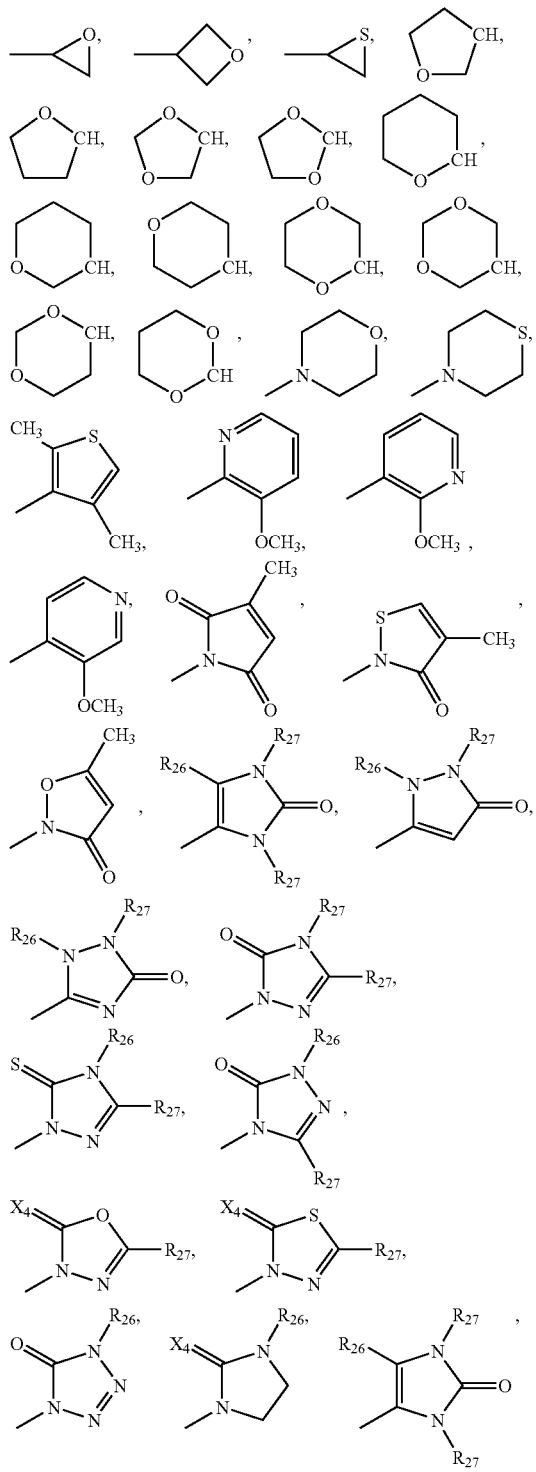

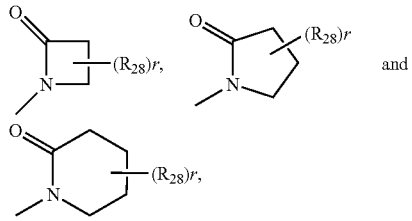

wherein each $R_{26}$ is methyl, each $R_{27}$ and each $R_{28}$ are independently hydrogen, $C_1$-$C_3$alkyl, $C_1$-$C_3$alkoxy, $C_1$-$C_3$alkylthio or trifluoromethyl, $X_4$ is oxygen or sulfur and r is 1, 2, 3 or 4.

Where no free valency is indicated in those definitions, for example as in

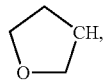

the linkage site is located at the carbon atom labelled "CH" or in a case such as, for example

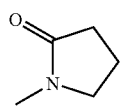

at the bonding site indicated at the bottom left.

Preference is given to subgroups of compounds of formula I wherein $G_1$, $G_2$, $G_3$ and $G_4$ form together with the two carbon atoms to which $G_1$ and $G_4$ are attached, an aromatic ring system as described in the compounds of formulae T1 to T103 mentioned below.

From the formulae T1 to T120, the compounds of formulae T1 to T103 are preferred. From the compounds of formulae T1 to T120, the compounds of formulae T1, T3, T5, T7, T8, T14, T19, T20, T21, T22, T23, T35, T36, T37, T39, T40, T41, T51, T52, T53, T54, T81, T82, T94, T105, T111, T112, T113, T114, T115, T117, T118, T119 and T120 are especially preferred.

From the compounds of formulae T1 to T103, the compounds of formulae T1, T7, T8, T19, T20, T21, T22, T35 and T37 are especially preferred.

Preferably $Z_1$ and/or $Z_2$ is oxygen.

Further compounds of formula I are preferred, wherein $R_2$ and/or $R_3$ is hydrogen. $R_{20}$ is preferably methyl, ethyl, i-propyl, tert.-butyl, $CH_2$—$C_3H_5$, $C(CH_2CH_2)$—$C_3H_5$, $C(CH_3)_2CH_2SCH_3$, $C(CH_3)_2CH_2S(O)CH_3$, $C(CH_3)_2CH_2S(O)_2CH_3$.

Special emphasis should also be given to compounds of formula I wherein D is a group $D_1$, wherein $R_5$ is in particular 2-pyridyl which can be substituted by halogen, preferably chloro, at the 3-position of the pyridine ring and $R_4$ is halogen preferably chloro or bromo, $C_1$-$C_6$haloalkyl, $C_1$-$C_4$haloalkoxy most preferably 2,2,2-trifluoroethoxy, preferably $C_1$-$C_6$haloalkyl, most preferably trifluoromethyl.

Special mention should be made of compounds of formula I wherein each of $R_{1a}$, $R_{1b}$, $R_{5a}$, $R_{5b}$, $R_{5c}$, and $R_{5d}$ which may be the same or different, represents hydrogen, halogen, cyano, hydroxy, CHO, $C_1$-$C_6$alkyl, $C_3$-$C_6$cycloalkyl, $C_1$-$C_6$haloalkyl, $C_1$-$C_4$alkoxy, $C_1$-$C_4$alkoxy-$C_1$-$C_4$alkoxy-$C_1$-$C_4$alkyl, $C_1$-$C_4$alkylthio, $C_1$-$C_4$alkylsulfinyl, $C_1$-$C_4$alkylsulfonyl, $C_1$-$C_4$alkylsulfonyl-$C_1$-$C_4$alkyl, $C_1$-$C_4$alkylsulfoximino-$C_1$-$C_4$alkyl, $C_2$-$C_4$dialkylamino or $C_1$-$C_4$alkoxyimino-$C_1$-$C_4$alkyl.

A outstanding group of compounds of formula I is represented by the formula Ib

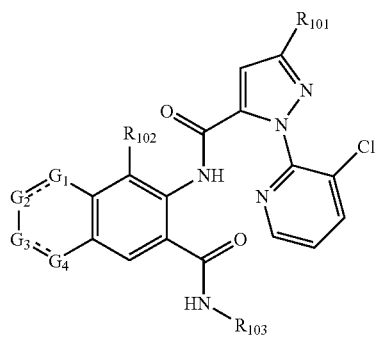

wherein
$G_1$, $G_2$, $G_3$ and $G_4$ have the meaning as given for formula I above;
$R_{101}$ is halogen, haloalkyl, haloalkoxy, especially trifluoromethyl, chlorine, bromine or O—CH$_2$—CF$_3$;
$R_{102}$ is halogen, $C_1$-$C_6$-alkyl, especially methyl, chlorine or bromine; and
$R_{103}$ is methyl, ethyl, i-propyl tert.-butyl, CH$_2$—C$_3$H$_5$, C(CH$_2$CH$_2$)—C$_3$H$_5$, C(CH$_3$)$_2$CH$_2$SCH$_3$, C(CH$_3$)$_2$CH$_2$S(O)CH$_3$, C(CH$_3$)$_2$CH$_2$S(O)$_2$CH$_3$.

The process according to the invention for preparing compounds of formula I is carried out analogously to known processes, for example as described in described, for example, in US 2003/0229050 and WO/2005/085234.

A general preparation of the compounds of formula I is shown in the following reaction scheme 1.

Reaction scheme 1

Preparation of Compounds of Formula I:

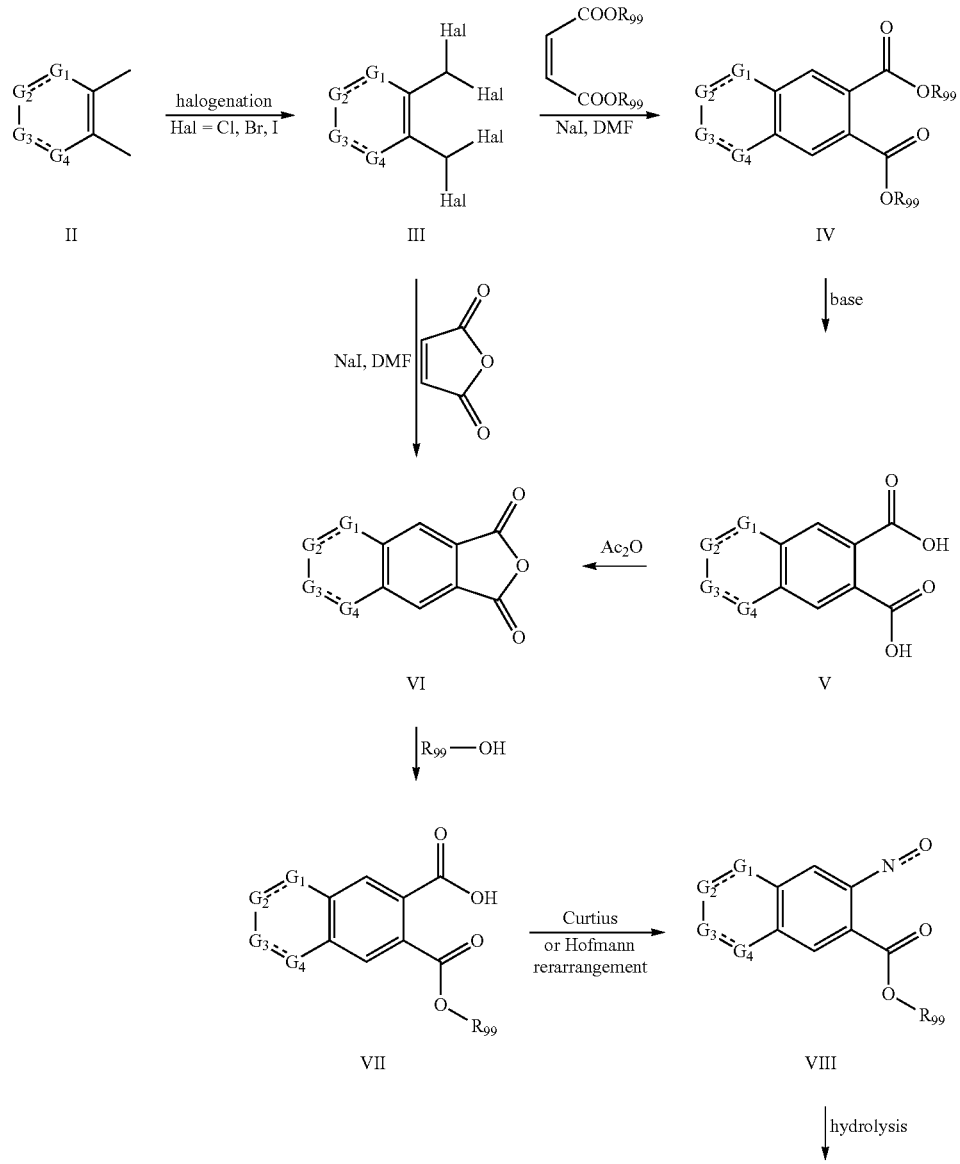

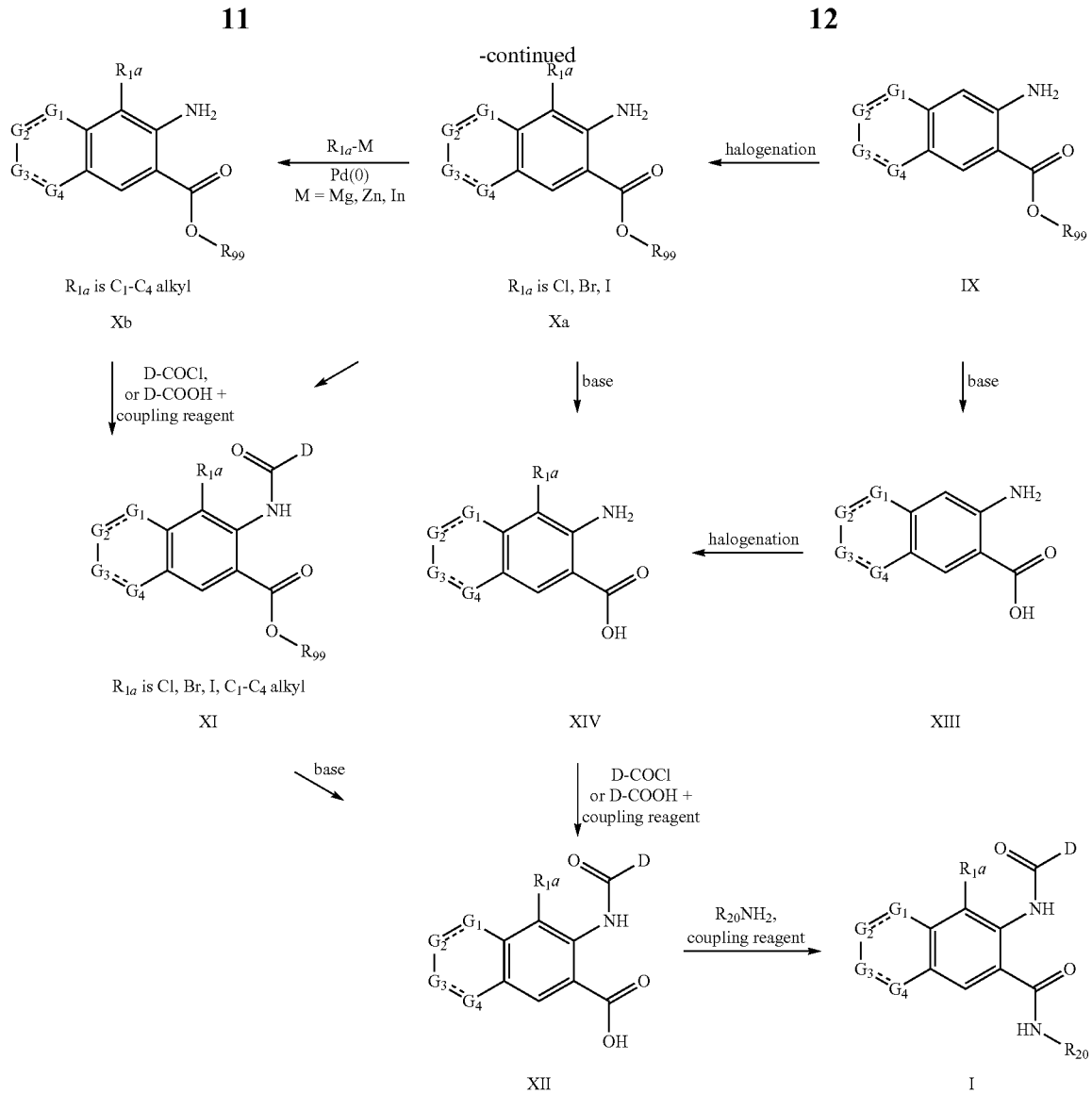

The starting compounds of formula II and intermediates of formulas III, IV, V, VI, VII, VIII, IX, Xa, Xb, XI, XII, XIII and XIV of reaction scheme 1 are in many cases known in the literature or can be prepared according to methods known to a person skilled in the art. In reaction scheme 1, $R_{99}$ is $C_1$-$C_4$alkyl.

Halogenation reagents are typically $(Hal)_2$ (Hal is Cl, Br, I), N-chlorosuccinimide, N-bromosuccinimide, N-iodosuccinimide, 2-chlorobenzotriazole. The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl) amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diaza-bicyclo[5.4.0]undec-7-ene (DBU). The choice of the appropriate base depends upon the reaction to be carried out. It is apparent to one skilled in the art that hydrolysis of an ester, for example conversion of a compound of formula IX, wherein $G_1$ to $G_4$ are as defined as in Formula I and $R_{99}$ is $C_1$-$C_4$-alkyl, to a compound of formula XIII is preferably carried out using alkali metal or alkaline earth metal hydroxides, such as lithium, sodium or potassium hydroxide with water as a solvent optionally in the presence and inert water miscible solvent such as an alcohol (for example methanol or ethanol), tetrahydrofurane, or dioxane. The transformation of an intermediate III to an aromatic system IV with a dienophile (e.g. maleic anhydride, dialkylmaleate) is a known procedure (o-quinodimethane chemistry: e.g. J. L. Segura et al. Chem. Rev. 1999, 99, 3199). The transformation of a carboxylic acid to an amine is made via classical Curtius or Hoffmann rearrangement (J. March, Advanced Organic Chemistry, 4$^{th}$ edition, Wiley, 1992, p. 1090 and 1091).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound I can be converted in a manner known per se into another compound I by replacing one or more substituents of the starting compound I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Alternatively, compounds of formula I can be prepared by the novel routes shown in schemes 2 and 3:

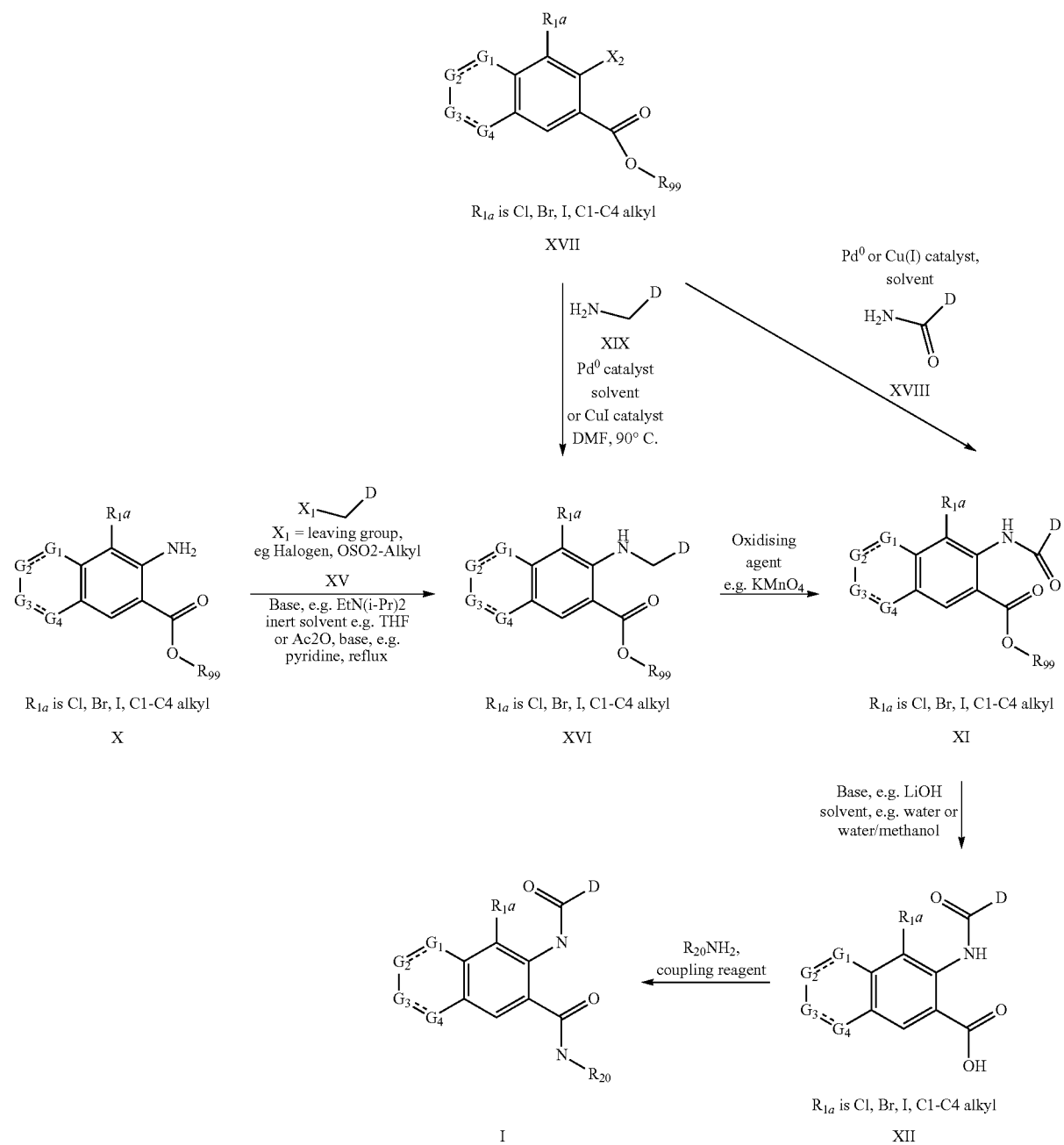

In scheme 2, a compound of formula X wherein $R_{1a}$ is Halogen or $C_1$-$C_4$-alkyl, $R_{99}$ is $C_1$-$C_4$-alkyl and $G_1$-$G_4$ are as defined for formula I, is first N-alkylated with a compound of formula XV (wherein D is as defined for formula I and $X_1$ is a leaving group such as halogen, mesylate or tosylate). Such reactions are well known in the literature (see for example *Bioorganic & Medicinal Chemistry Letters* (2006), 16(7), 1864-1868 or *Indian Journal of Heterocyclic Chemistry* (2005), 15(1), 79-80). The compound of formula XVI thus obtained can then be converted to a compound of formula XI by treatment with an oxidising agent (for example potassium permanganate) in an inert solvent such as dichloromethane in the presence of a phase transfer catalyst (such as benzyltriethylammonium chloride) at temperatures between 0-100° C., preferably 0-20° C. Similar reactions have been reported in the literature (Finkelstein et al., *Synthetic Communications* (1997), 27(7), 1285-1290). Compounds of formula XI are then converted to compounds of formula I by standard methodology (ester hydrolysis and subsequent amide bond formation) well known to those skilled in the art. $R_{20}$ in scheme 2 is as defined under formula I above. The intermediate of formula XVI, wherein $R_{1a}$, $R_{99}$ and $G_1$-$G_4$ are as previously defined can also be prepared from an intermediate of formula XVII, wherein $R_{1a}$, $R_{99}$ and $G_1$-$G_4$ are as previously defined and $X_2$ is a leaving group such as halogen, or $OSO_2$—$C_1$-$C_4$-haloalkyl, by treating with and amine of formula XIX, wherein D is as defined for formula I, in the presence of a copper catalyst, such as copper(I) iodide, an amide ligand, such as picolinamide or N,N-diethylsalicylamide, and a base such as $K_3PO_4$ and $K_2CO_3$ optionally in an inert solvent such as dimethylformamide, at a temperature of 0-90° C. Such Ullmann type couplings are well known in the literature (Buchwald et. al, *Organic Letters* (2003), 5(6), 793-796). Alternatively, the coupling of XVII to XIX can be achieved using Palladium catalysis (Buchwald-Hartwig amination) as described for example in *Journal of Organic Chemistry*, (2003), 68(16), 6215-6221. The intermediate XVI obtained is then converted to compounds of formula I as described in scheme 2. Similarly, Buchwald-Hartwig or Ullmann coupling of the intermediate of formula XVII with the primary amide of formula XVIII, wherein D is as defined in formula I, gives compounds of formula XI which are subsequently converted to compounds of formula I as shown in schemes 2 and 3. Such Ullmann reactions of primary amides of formula a XVIII with aryl halides are known in the literature (*Chinese Journal of Chemistry*, 23(9), 1241-1246; 2005) as well as Buchwald-Hartwig palladium catalysed amidations (Buchwald and Yin, *Org. Lett.*, 2 (8), 1101-1104, 2000).

Reaction Scheme 3

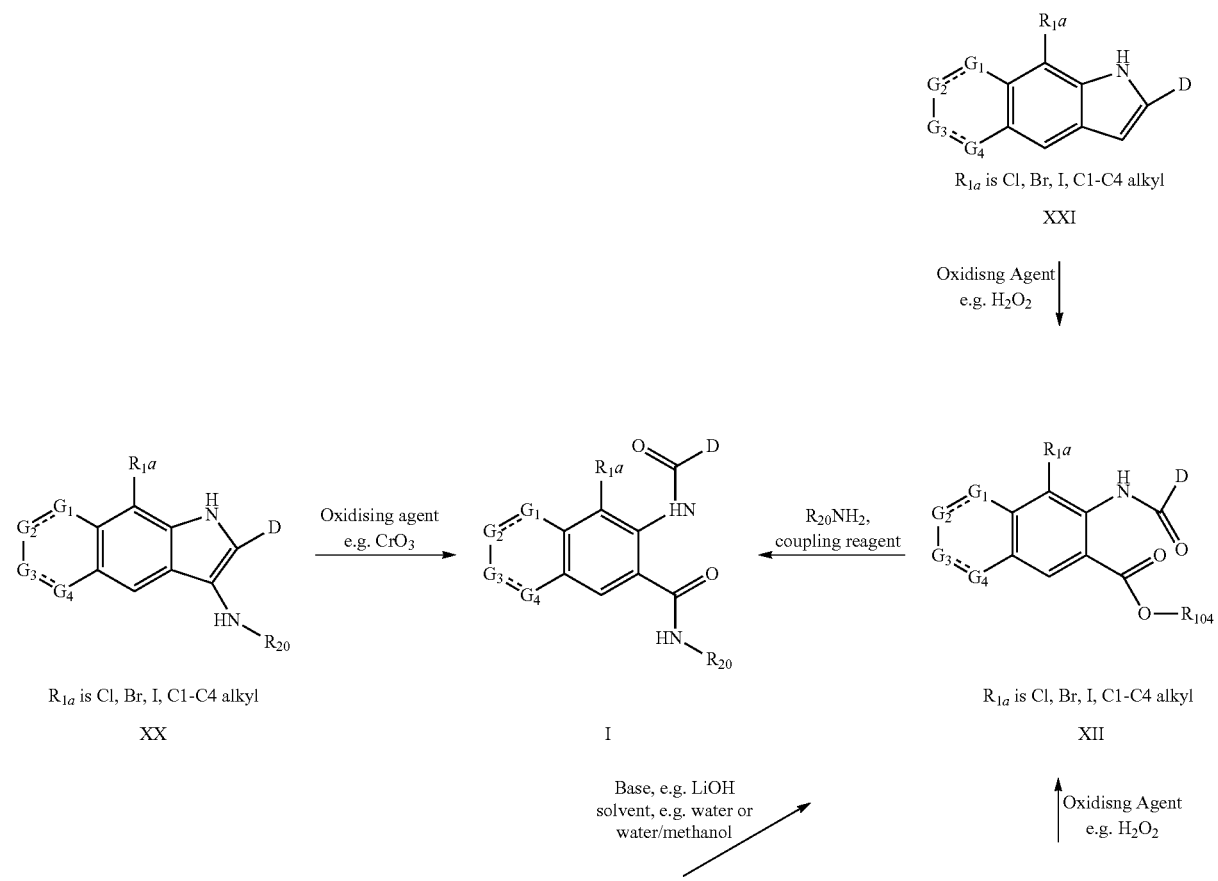

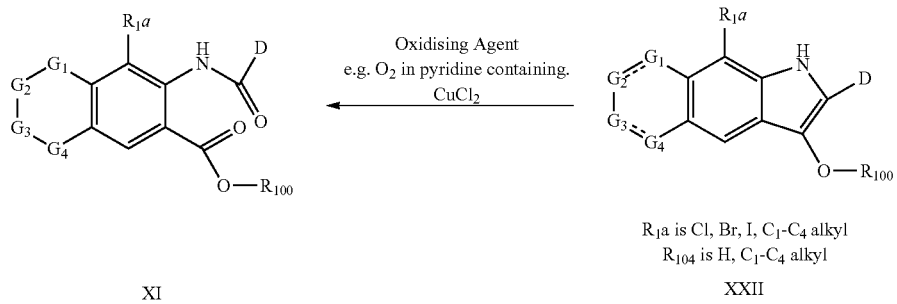

XI $R_{1a}$ is Cl, Br, I, $C_1$-$C_4$ alkyl
$R_{104}$ is H, $C_1$-$C_4$ alkyl

XXII

In reaction scheme 3, an indole of formula XX, wherein $G_1$, $G_2$, $G_3$, $G_4$, $R_{1a}$, $R_{20}$, and D are as defined in formula I, is oxidatively cleaved directly to a compound of formula I, in the presence of an oxidising agent, for example chromium (VI)oxide, as described by Saniccollo, *Journal of Organic Chemistry*, (1983), 48, 2924-2925. Alternatively, indoles of formulae XXI and XXII can be oxidatively cleaved to compounds of formulae XII or XI. Such reactions are well precendented in the chemical and patent literature using various oxidising reagents (see *Chemical & Pharmaceutical Bulletin* (1979), 27(2), 551-3, *Tetrahedron Letters* (2004), 45(43), 8061-8064, *Indian Journal of Chemistry, Section B*: (1978), 16B(3), 240-1, *Tetrahedron Letters* (1976), (45), 4079-82, *Bulletin de la Societe Chimique de France* (1952), 218-19 and JP2005 336123. Compounds of formulae XII and XI are converted to the compounds of formula I as previously described in Scheme 1.

Indoles of formulae XX, XXI, and XXII are known in the literature or can be prepared by analogous methods to those reported in the literature. For example, scheme 4 shows the synthesis of indoles of formula XXI via palladium catalysed Suzuki, Negishi, or Stille couplings of compounds of formula XXV with compounds of formula XXVI, wherein $X_5$ is a leaving group such as halogen, preferably bromine, and D is as defined in formula I. Such reactions are well documented in the literature (see Passarella et al., *Tetrahedron* (1998), 54(46), 14081-14088).

Reaction Scheme 4

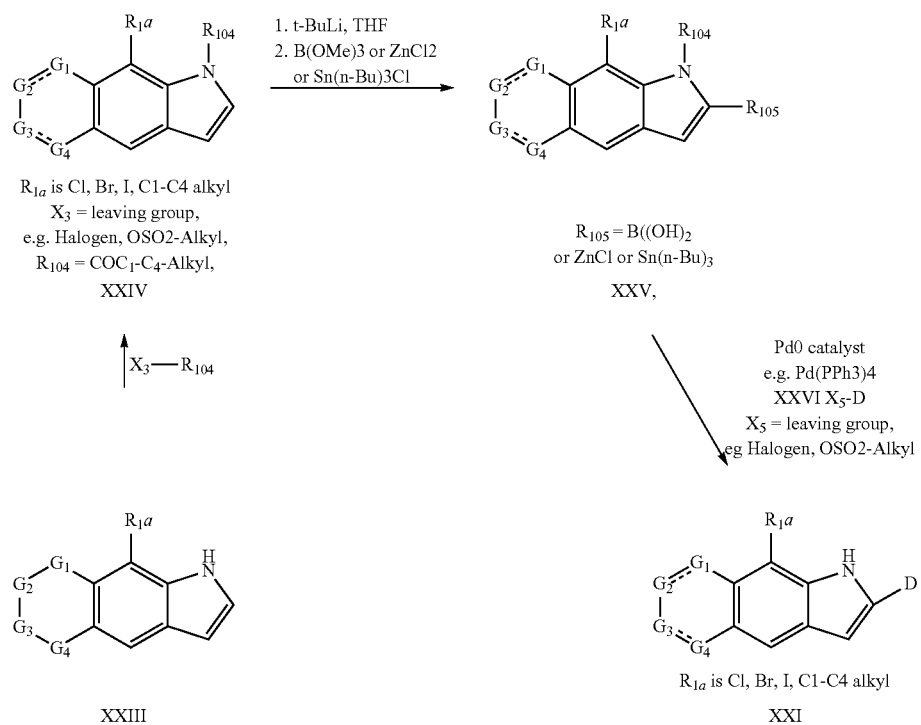

The processes according to reaction schemes 2 and 3 are novel and especially developed for the synthesis of the compounds of formula I and constitute a further object of the present invention. Accordingly, a compound of formula I can be prepared by a) reacting a compound of formula XVII

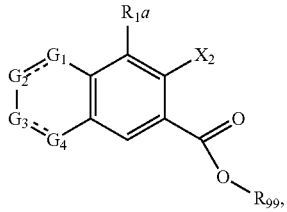
(XVII)

wherein $G_1$, $G_2$, $G_3$, $G_4$, $R_1a$, $R_{99}$ and $X_2$ have the meanings as given under scheme 2 above, in the presence of a Pd° or Cu(1) catalyst and an inert solvent, such as dimethylformamide with a compound of formula XVIII

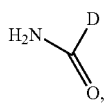
(XVIII)

wherein D has the meaning as given under scheme 2 above, to a compound of formula XI

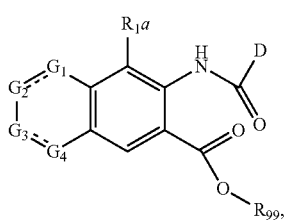
(XI)

wherein $G_1$, $G_2$, $G_3$, $G_4$, $R_1a$, $R_{99}$ and D have the meanings as given under scheme 2 above, and then reacting the compound of formula XI in the presence of a base and an inert solvent to a compound of formula XII

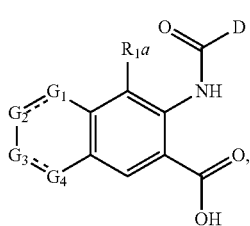
(XII)

wherein $G_1$, $G_2$, $G_3$, $G_4$, $R_1a$, and D have the meanings as given under scheme 2 above, and then converting the compound of formula XII in the presence of $R_{20}$—$NH_2$ wherein $R_{20}$ has the meaning as given under formula I in claim 1, and a coupling agent, for example dicyclohexylcarbodiimide, to the compound of formula I; or b) reacting a compound of formula XVII

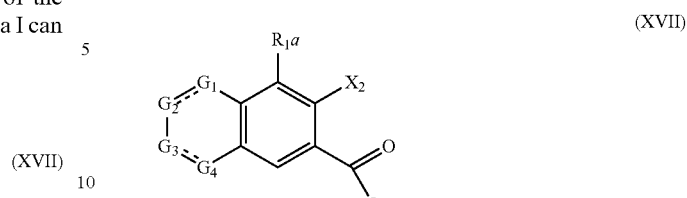
(XVII)

wherein $G_1$, $G_2$, $G_3$, $G_4$, $R_1a$, $R_{99}$ and $X_2$ have the meanings as given under scheme 2 above, in the presence of a Pd° or Cu(I) catalyst and in an inert solvent with a compound of formula XIX

$H_2N$—$CH_2$-D  (XIX), wherein D has the meaning as given under scheme 2 above, to the compound of formula XVI

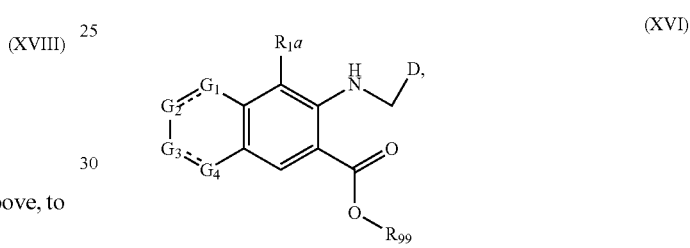
(XVI)

wherein $G_1$, $G_2$, $G_3$, $G_4$, $R_1a$, $R_{99}$ and D have the meanings as given under scheme 2 above, and then reacting the compound of formula XVI with an oxidising agent to the compound of formula XI

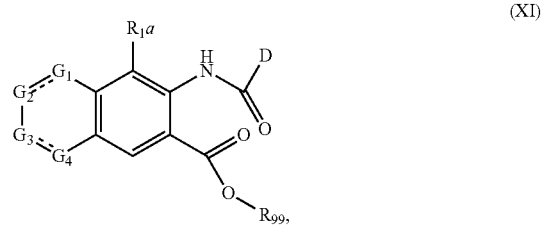
(XI)

wherein $G_1$, $G_2$, $G_3$, $G_4$, $R_1a$, $R_{99}$ and D have the meanings as given under scheme 2 above and then reacting the compound of formula XI in the presence of a base and an inert solvent to a compound of formula XII

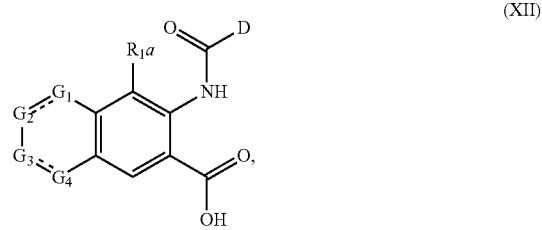
(XII)

wherein G₁, G₂, G₃, G₄, R₁a, and D have the meanings as given under scheme 2 above and then converting the compound of formula XII in the presence of $R_{20}$—$NH_2$ and a coupling agent, for example dicyclohexylcarbodimide, to the compound of formula I; or c) reacting a compound of formula X

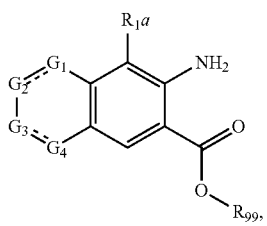
(X)

wherein G₁, G₂, G₃, G₄, R₁a and R₉₉ have the meanings as given under scheme 2 above, with a compound of formula XV $X_1$—$CH_2$-D  (XV), wherein X₁ is a leaving group, in the presence of a base and an inert solvent to a compound of formula XVI

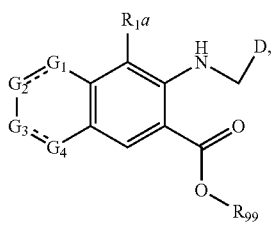
(XVI)

wherein G₁, G₂, G₃, G₄, R₁a, R₉₉ and D have the meanings as given under scheme 2 above, and then reacting the compound of formula XVI with an oxidising agent to the compound of formula XI

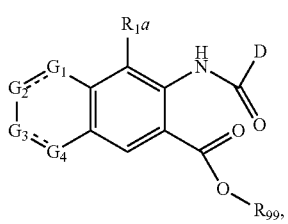
(XI)

wherein G₁, G₂, G₃, G₄, R₁a, R₉₉ and D have the meanings as given under scheme 2 above, and then saponifying the compound of formula XI in the presence of a base and an inert solvent to a compound of formula XII

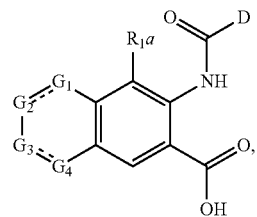
(XII)

wherein G₁, G₂, G₃, G₄, R₁a, and D have the meanings as given under scheme 2 above; and converting the compound of formula XII in the presence of $R_{20}$—$NH_2$ and a coupling agent, for example dicyclohexylcarbodimide to the compound of formula I; or d) reacting a compound of formula XXV

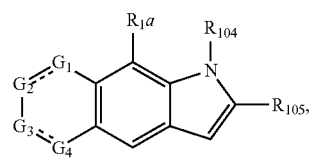
(XXV)

wherein G₁, G₂, G₃, G₄, R₁₀₄, R₁₀₅ and R₁a have the meanings as given under scheme 4 above, in the presence of a Pd⁰ catalyst with a compound of formula XXVI $X_5$-D  (XXV), wherein X₅ is a leaving group, and D is as defined under formula I above, to a compound of formula XXI

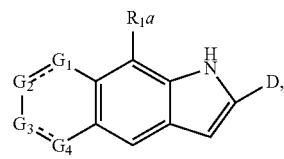
(XXI)

wherein G₁, G₂, G₃, G₄ and R₁a have the meanings as given under scheme 2 above, and then reacting the compound of formula XXI in the presence of an oxidising agent to a compound of formula XII

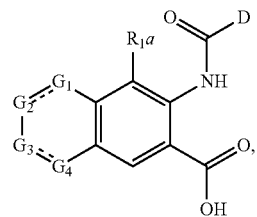
(XII)

wherein G₁, G₂, G₃, G₄, R₁a, and D have the meanings as given under scheme 2 above; and converting the compound of formula XII in the presence of a compound of formula $R_{20}$—$NH_2$, wherein R₂₀ is as defined under formula I above, and a coupling agent, for example dicyclohexylcarbodimide to the compound of formula I.

The compounds of formulae XXXIII, XXXIV, XXXV, XIVb, XIVc, XIVd, XXXVIII, XXXIX, XXXX and XXXXII, shown in the are novel and are represented by formula XIVe

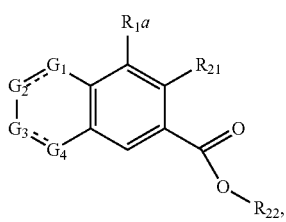

(XIVe)

wherein $G_1$, $G_2$, $G_3$, $G_4$ and $R_1a$, are as defined under formula I, $R_{21}$ is Nitro, $NH_2$, hydrogen, or halogen and $R_{22}$ is hydrogen or $C_1$-$C_4$alkyl. Preferred compounds of formula XIVe are the compounds of formula XIVa

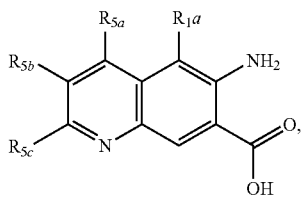

(XIVa)

wherein $R_1a$, $R_5a$, $R_5b$ and $R_5c$ are as defined under formula I.

Compounds of formula XVIII

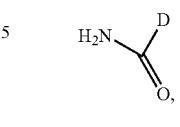

(XVIII)

wherein D has the meaning as given under scheme 2 above, are novel, especially developed for the preparation of the compounds of formula I and therefore represent a further object of the present invention.

Compounds of formula XIX $$H_2N-CH_2-D \qquad (XIX),$$

wherein D has the meaning as given under scheme 2 above, are novel, especially developed for the preparation of the compounds of formula I and therefore represent a further object of the present invention.

Intermediates of formula XIVa

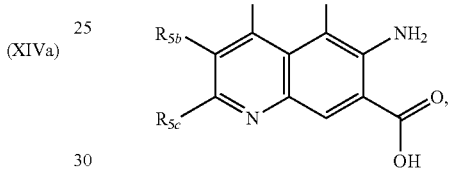

(XIVa)

wherein $R_1a$, $R_5a$, $R_5b$ and $R_5c$ are as defined under formula I, are novel and syntheses were developed specifically for these compounds. The syntheses of compounds of formula XIVa are shown in the reaction schemes 5 and 6.

Reaction Schema 5

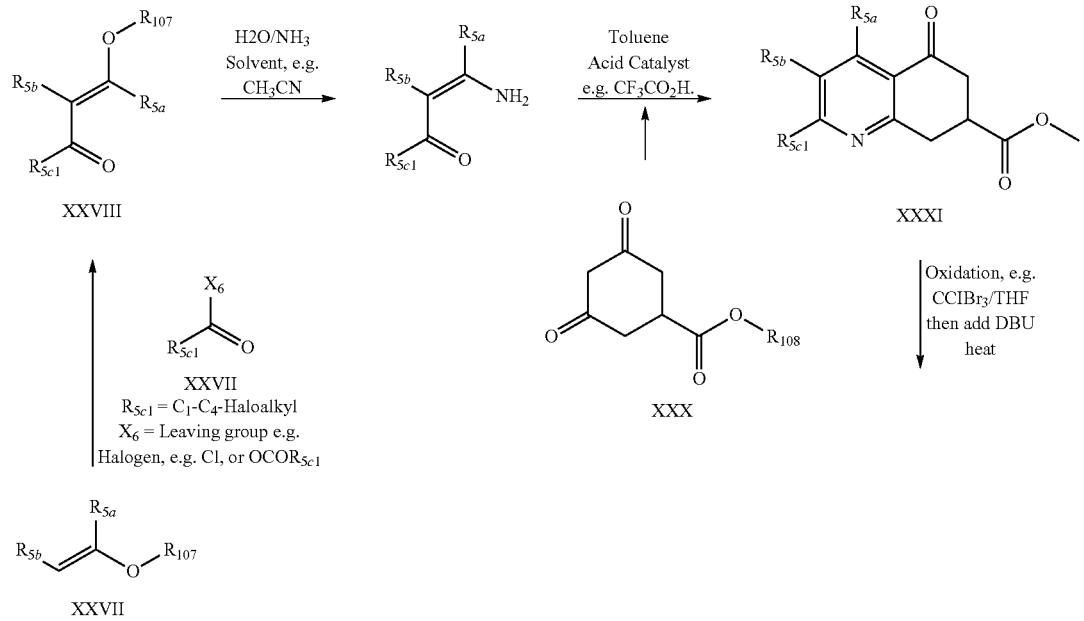

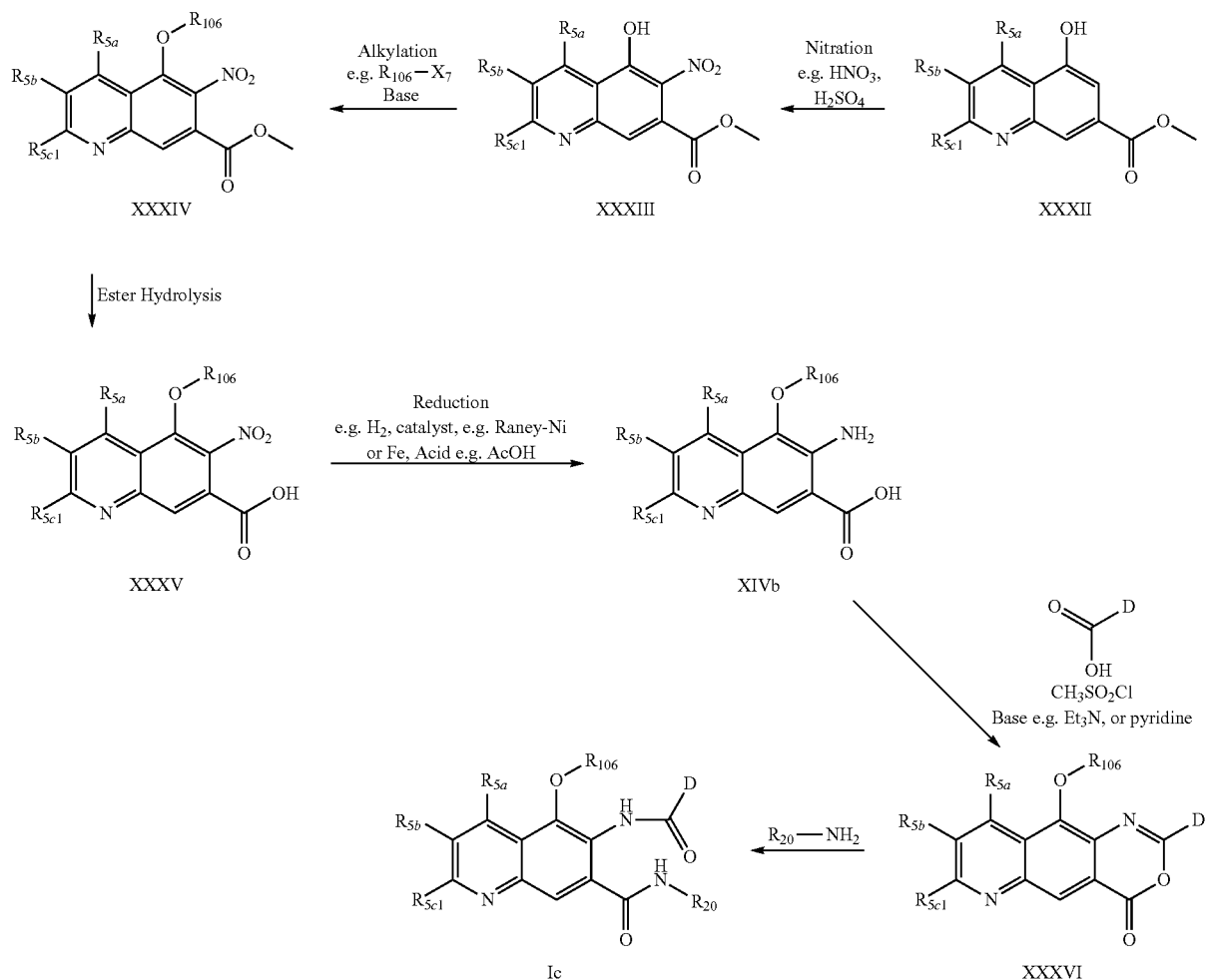

In reaction scheme 5, a compound of formula XXIX, where $R_{5a}$, $R_{5b}$ are as defined in formula I, and $R_{5c1}$ is $C_1$-$C_4$-haloalkyl, is condensed with a compound of formula XXX to produce compounds of formula XXXI by heating in an inert solvent such as toluene, in the presence of an acid catalyst such as trifluoroacetic acid in a Dean-Stark apparatus (analogue *Heterocycles*, Vol. 46, 1997, pages 129-132). Compounds of formula XXXI can then be oxidised to compounds of formula XXXII by treatment with a halogenating reagent, for example bromotrichloromethane, in the presence of a non-nucleophilic base, for example 1,8-Diazabicyclo[5.4.0]-7-undecene. The compound of formula XXXII, wherein $R_{5a}$, $R_{5b}$ are as defined in formula I and $R_{5c1}$ is $C_1$-$C_4$-Haloalkyl, is then nitrated with fuming nitric acid in concentrated sulphuric acid, at a temperature of 0-60° C., preferably 0-60° C. to yield selectively compounds of formula XXXIII. Compounds of formula XXXIII can then be alkylated with an reagent $R_{106}$—$X_7$, where $R_{106}$ is $C_1$-$C_4$-Alkyl and $X_7$ is a leaving group, such a halogen in the presence of a base, such as potassium carbonate, in a solvent such as acetonitrile, to give compounds of formula XXXIV, wherein $R_{5a}$, $R_{5b}$ are as defined in formula I, $R_{5c1}$ is $C_1$-$C_4$-haloalkyl, and $R_{106}$ is $C_1$-$C_4$-alkyl. Alternatively, the compound of formula XXXIII can be alkylated with a reagent of formula $[(R_{107})_3O]^+[BF_4]^-$, wherein $R_{107}$ is $C_1$-$C_4$-alkyl, for example $[(CH_3)_3O]^+[BF_4]^-$, in the presence of a base such as N,N,N',N'-Tetramethyl-naphthalene-1,8-diamine ("proton sponge") in an inert solvent, such as methylene dichloride to yield compounds of formula XXXIV (analogue *Tetrahedron Letters* (1994), 35(39), 7171-2). Esters of formula XXXIV can then be hydrolysed to the corresponding acids of formula XXXV by methods obvious to those skilled in the art. Reduction of the nitro group can be achieved by known standard processes, for example Bechamp reduction or catalytic hydrogenation as described in *Organikum*, 21$^{st}$ Ed. Wiley-VCH, page 626-629. Anthranilic acids of formula XIVb obtained by this process can then be converted to intermediates of formula XXXVI upon treatment a carboxylic acid of formula D-CO2H, wherein D is as defined in the formula I, with mesyl chloride in the presence of pyridine in a inert solvent such as acetonitrile. Compounds of formula XXXVI after treatment with amines of formula $R_{20}$—$NH_2$ yield the compounds of formula Ic, wherein D, $R_{5a}$, $R_{5b}$ are as defined in formula I, $R_{5c1}$ is $C_1$-$C_4$-haloalkyl, $R_{106}$ is $C_1$-$C_4$-alkyl, and $R_{20}$ has the specific meaning given in the corresponding line, appropriately selected from the 168 lines A.1.1 to A.1.168 of the Table A. Similar procedures for producing compounds of formula I from anthranilic acids have been reported in WO 2003/015518.

Reaction Scheme 6

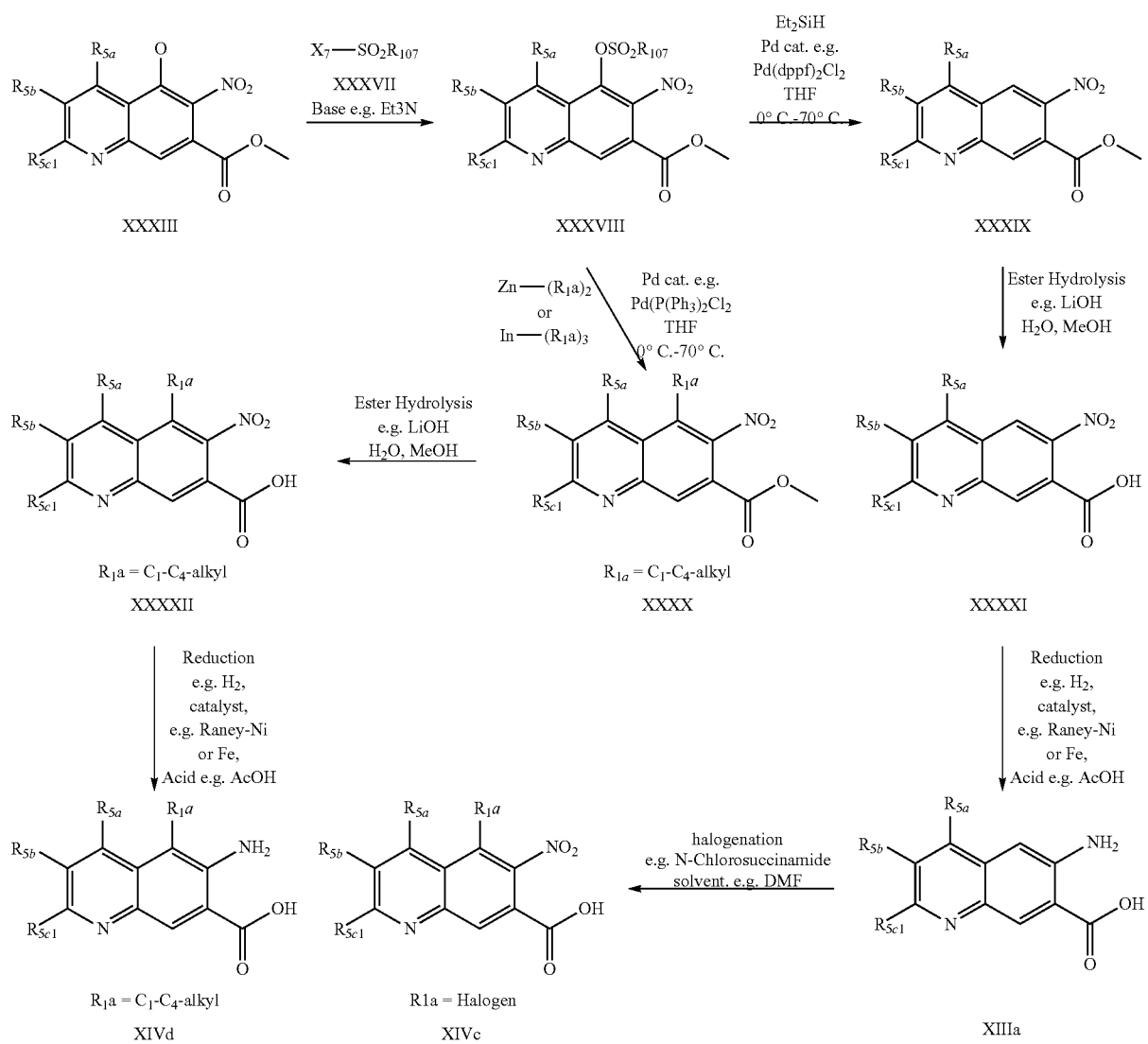

In reaction scheme 6, the hydroxy group of intermediate of formula XXXIII is converted to a leaving group, by treatment of the compound of formula XXXIII with, for example a compound of formula XXXVII, wherein $X_7$ is a leaving group, for example $OSO_2$—$R_{107}$, wherein $R_{107}$ is $C_1$-$C_4$-haloalkyl, in the presence of a base, for example triethylamine and a catalytic amount of dimethylaminopyridine, in an inert solvent such as methylene dichloride, to give a compound of formula XXXVIII. The compound of formula XXXVIII can be reduced to give a compound of formula XXXIX with an alkyl silane, for example triethyl silane in the presence of a palladium catalyst by analogy to reported procedures (for example, *Synthesis* (1995), (11), 1348-1350). Alternatively, compounds of formula XXXVIII can be converted to compounds of formula XXXX, wherein $R_1a$ is $C_1$-$C_4$-alkyl, by treatment of XXXVIII with an organozinc compound of formula $Zn(R_1a)_2$ or an organoindium compound of formula $IN(R_1a)_3$, in the presence of a palladium catalyst, for example $Pd(PPh_3)_4$, in an inert solvent at temperatures from 0-60° C. Such reactions are also well precedented in the chemical literature (see for example, *Tetrahedron Letters* (2004), 45(4), 817-819 and *Organic Letters* (1999), 1(8), 1267-126. The compounds of formulae XXXX and XXXIX can be readily hydrolysed to the carboxylic acids of formulas XXXXI and XXXXII by methodology well known to those skilled in the art. The reduction of the nitro groups of compounds of formulae XXXXI and XXXXII can be achieved by known standard processes, for example Bechamp reduction or catalytic hydrogenation as described in *Organikum*, 21$^{st}$ Ed. Wiley-VCH, page 626-629. Compounds of formulas XIVd and XIIIa are then converted to compounds of formula I by the routes shown in schemes I and 5.

Compounds of formula XIIIa are converted to compounds of formula XIVc by treating with a halogenating reagent, for example N-halosuccinimide, in an inert solvent, such as dimethylformamide, at temperatures between 0-90° C. The compound of formula XIVc is further converted to compounds of formula I by the routes shown in schemes I and 5.

Alternatively, an intermediate Xa in scheme 1 can be prepared e.g. according to methods described in scheme 7. Halogenation reagents are typically $Hal_2$ (Hal is Cl, Br, I), N-chlorosuccinimide, N-bromosuccinimide, N-iodosuccinimide, 2-chlorobenzotriazole. Cyanation is made through Cu or Pd(0) catalysis with a source of CN such as CuCN, NaCN, KCN, $Zn(CN)_2$ according to known procedures (P. Kasap et al. Collect. Czech. Chem. C, 2000, 65, 729; M. Beller et al.

Eur. J. Inorg. Chem. 2003, 3513). Synthesis of intermediate Xa in scheme 7 from a corresponding isatin can be made according to known literature procedures (S. E. Webber et al. J. Med. Chem. 1993, 36, 733).

Reaction Scheme 7: Preparation of Intermediate Xa or Xb:

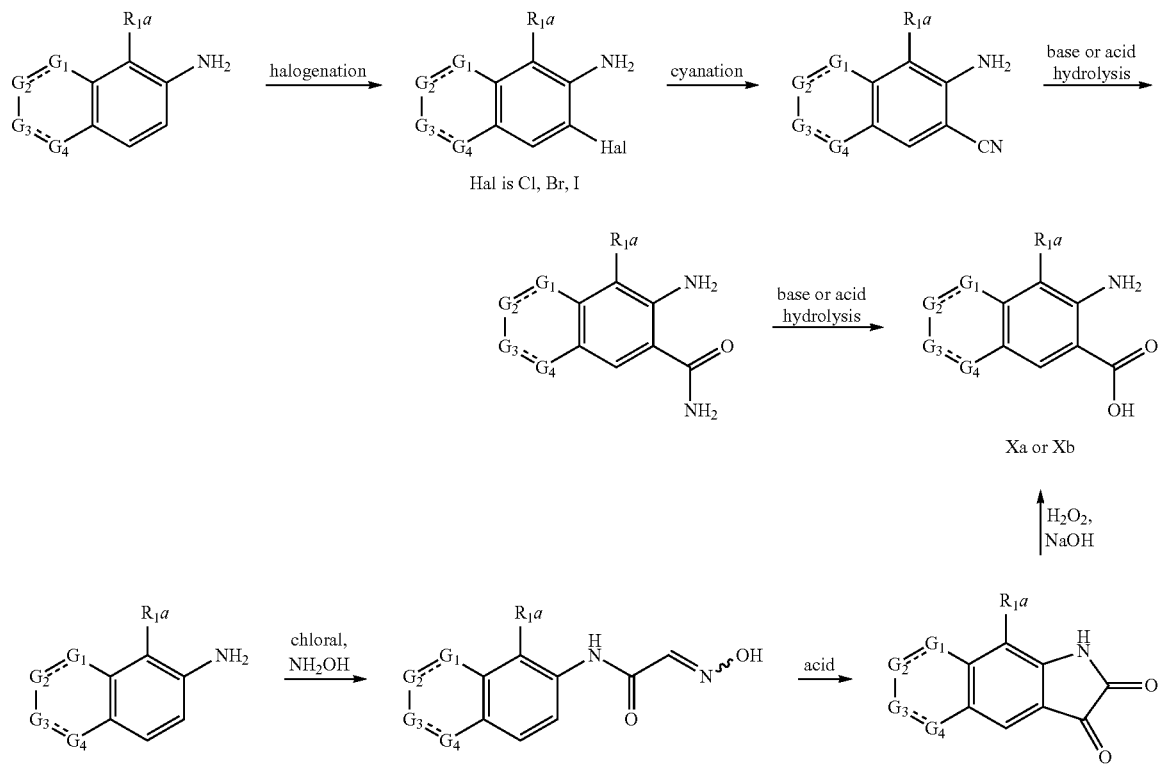

Alternatively intermediates of formulae Xa, Xb, Xc (benzimidazoles: $G_1=NR_{200}$, $G_2=$bond, $G_3=R_{201}C$, $CH_3O—C$ and $CH_3S—C$, $G_4=N$; benzothiadiazoles: $G_1=N$, $G_2=$bond, $G_3=S$, $G_4=N$; quinoxalines: $G_1=N$, $G_2=G_3=H_3C—C$, $G_4=N$; benzothiazoles: $G_1=S$, $G_2=$bond, $G_3=R_{202}C$, $CH_3O—C$ and $CH_3S—C$, $G_4=N$; benzoxazoles: $G_1=O$, $G_2=$bond, $G_3=R_{203}C$, $G_4=N$) can be made via cyclisation of intermediates of formulae XXXXIII, XXXXIV or XXXXV as depicted in scheme 8.

Reaction Scheme 8: Alternative Preparation of Intermediate Xa, Xb or Xc:

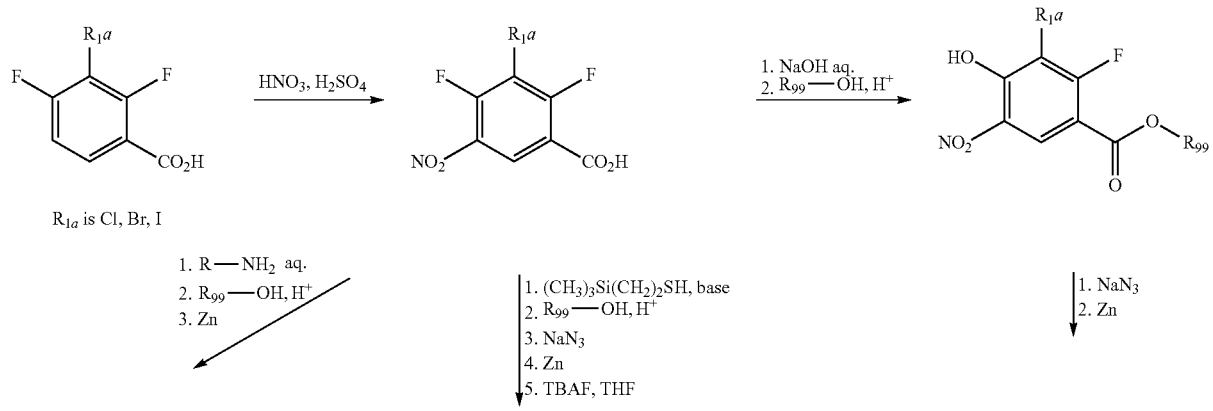

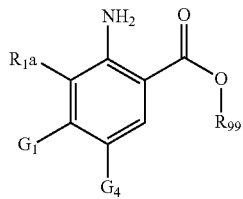

XXXXIII
$G_4 = NH_2$
$G_1 = R_{200}$—NH
($R_{200} = CH_3$, H)
cyclization:
$SOCl_2$
$G_3 = S$, $G_2 =$ bond
$R_{201}$—$CO_2H$, heating
$R_{201} = $ H, Me, Et, $CH_2(C_3H_4)$, $CH_2OCH_3$, $CH_2SCH_3$, $CF_3$, $CH_2F$, $CHF_2$
$G_3 = C(R_{201})$, $G_2 =$ bond
$[CH_3C(O)]_2$, EtOH
$G_2 = G_3 = C(CH_3)$
$C(OMe)_4$, AcOH
$G_3 = C(OCH_3)$, $G_2 =$ bond
1. $CS_2$, NaOH, EtOH
2. MeI, $Et_3N$
$G_3 = C(SCH_3)$, $G_2 =$ bond

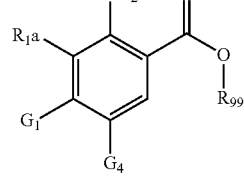

XXXXIV
$G_4 = NH_2$
$G_1 = SH$
$C(OMe)_4$, AcOH
$G_3 = C(OCH_3)$,
$G_2 =$ bond
1. $CS_2$, NaOH
2. MeI, $Et_3N$
$G_3 = C(SCH_3)$,
$G_2 =$ bond cyclization:
$R_{202}$—$CO_2H$, heating
$R_{202} = $ H, Me, Et, $CH_2(C_3H_4)$, $CH_2OCH_3$
$G_3 = C(R_{202})$
$G_2 =$ bond

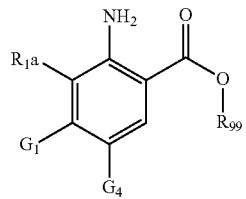

$G_4 = NH_2$
$G_1 = OH$

XXXXV
cyclization:
$R_{203}$—$CO_2H$, heating
$R_{203} = $ H, Me, Et, $CH_2(C_3H_4)$, $CH_2OCH_3$
$G_3 = C(R_{203})$, $G_2 =$ bond

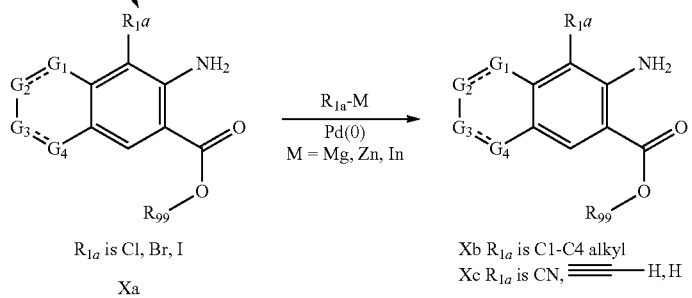

$R_{1a}$ is Cl, Br, I
Xa

Xb $R_{1a}$ is C1-C4 alkyl
Xc $R_{1a}$ is CN, ≡—H, H

Preferred intermediates for the preparation of the compounds of formula I according to the present invention have the general formula XIVe

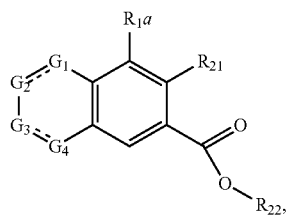

(XIVe)

wherein $G_1$, $G_2$, $G_3$, $G_4$ and $R_1a$ are as defined under formula I in claim 1, $R_{21}$ is Nitro, $NH_2$, Hydrogen or halogen and $R_{22}$ is hydrogen or $C_1$-$C_4$alkyl are novel, especially developed for the preparation of the compounds of formula I and therefore represent a further object of the present invention. Especially preferred compounds of the formula XIVe are described in the following Table B:

TABLE B

| Intermediates: | |
|---|---|
| Intermediate Structure | F/MS/NMR |
| ![structure] | 266/268 (M + 1)+ |

(Structure: quinoxaline with $H_3C$ groups at 2,3 positions, Cl, $NH_2$, $CO_2H$ substituents)

TABLE B-continued
Intermediates:
| Intermediate Structure | F/MS/NMR |
|---|---|
| 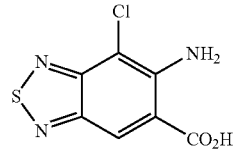 [SMILES: Nc1c(C(=O)O)cc2nsnc2c1Cl] | 230/232 (M + 1)+ |
| 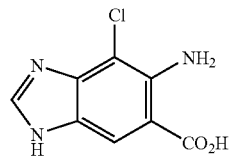 [SMILES: Nc1c(C(=O)O)cc2[nH]cnc2c1Cl] | 212/214 (M + 1)+ |
| 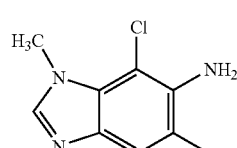 | 226/228 (M + 1)+ |
| 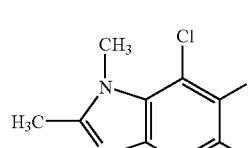 | 240/242 (M + 1)+ |
| 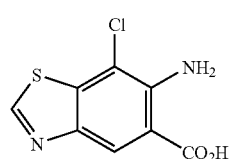 | 229/231 (M + 1)+ |
| 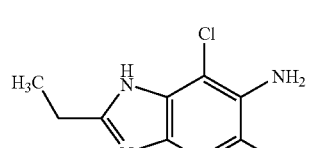 | 238/240 (M − 1)− |
| 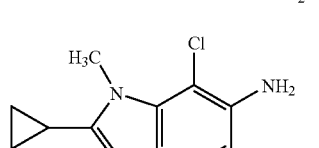 | 266/268 (M + 1)+ |
| 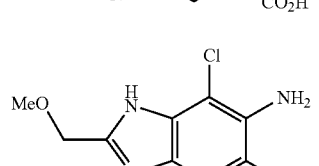 | 256/258 (M + 1)+ |
| 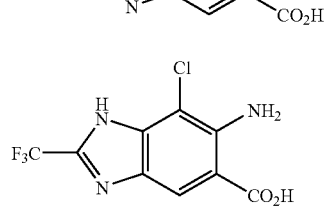 | 278/280 (M − 1)− |

TABLE B-continued

Intermediates:

| Intermediate Structure | F/MS/NMR |
|---|---|
| benzimidazole: 4-Cl, 5-NH2, 6-CO2H, 2-CHF2 | 262/264 (M + 1)+ |
| benzimidazole: 4-Cl, 5-NH2, 6-CO2H, 2-CH2F | 244/246 (M + 1)+ |
| benzimidazole: 1-CH3, 4-Cl, 5-NH2, 6-CO2H, 2-CF3 | 294/296 (M + 1)+ |
| benzimidazole: 4-Cl, 5-NH2, 6-CO2CH3, 2-SH | 258/260 (M + 1)+ |
| benzimidazole: 4-Cl, 5-NH2, 6-CO2H, 2-SCH3 | 258/260 (M + 1)+ |
| benzimidazole: 1-CH3, 4-Cl, 5-NH2, 6-CO2CH3, 2-SH | 272/274 (M + 1)+ |
| benzimidazole: 1-CH3, 4-Cl, 5-NH2, 6-CO2H, 2-SCH3 | 272/274 (M + 1)+ |
| benzimidazole: 4-Cl, 5-NH2, 6-CO2H, 2-CH2SCH3 | 272/274 (M + 1)+ |
| benzimidazole: 4-Cl, 5-NH2, 6-CO2CH3, 2-CH2S(O)CH3 | 302/304 (M + 1)+ |

TABLE B-continued

Intermediates:

| Intermediate Structure | F/MS/NMR |
|---|---|
| [Structure: 2-(methylsulfonylmethyl)-benzimidazole with Cl, NH2, CO2CH3] | 318/320 (M + 1)+ |
| [Structure: 2-methyl-benzothiazole with Cl, NH2, CO2H] | 243/245 (M + 1)+ |
| [Structure: 2-ethyl-benzothiazole with Cl, NH2, CO2CH3] | ¹H-NMR (CDCl₃, 300 MHz): δ ppm = 1.46 (t, 3H), 3.00-3.11 (m, 2H), 3.91 (s, 3H), 6.24 (s, 2H), 8.42 (s, 1H) ppm |
| [Structure: 2-mercapto-benzothiazole with Cl, NH2, CO2CH3] | 275/277 (M + 1)+ |
| [Structure: 2-methylthio-benzothiazole with Cl, NH2, CO2H] | 275/277 (M + 1)+ |
| [Structure: 2-(cyclopropylmethyl)-benzimidazole with Cl, NH2, CO2H] | 266/268 (M + 1)+ |
| [Structure: 2-methoxy-benzothiazole with Cl, NH2, CO2H] | 259/261 (M + 1)+ |
| [Structure: 2-methoxy-benzimidazole with Cl, NH2, CO2H] | 242/244 (M + 1)+ |
| [Structure: 2-methyl-benzimidazole with Cl, NH2, CO2H] | 226/228 (M + 1)+ |

TABLE B-continued
Intermediates:
| Intermediate Structure | F/MS/NMR |
|---|---|
| 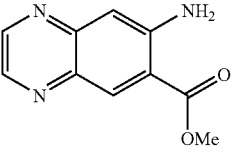 [SMILES: COC(=O)c1cc2nccnc2cc1N] | 180-182° C. |
| 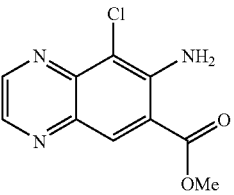 [SMILES: COC(=O)c1cc2nccnc2c(Cl)c1N] | 182-184° C. |
| 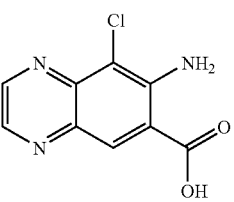 [SMILES: Nc1c(C(=O)O)cc2nccnc2c1Cl] | 224/226 (M + 1)⁺ |
| 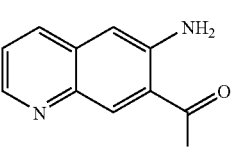 | ¹H-NMR (CDCl₃, 300 MHz): δ ppm = 3.98 (s, 3H), 5.72 (s, b, 2H), 6.90 (s, 1H), 7.30 (m, 1H), 7.85 (d, 1H), 8.68 (m, 1H), 8.76 (s, 1H) ppm |
| 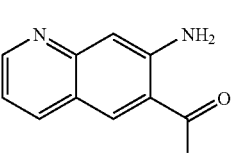 | ¹H-NMR (CDCl₃, 300 MHz): δ ppm = 3.98 (s, 3H), 5.75 (s, b, 2H), 7.12 (dd, 1H), 7.21 (s, 1H), 8.01 (d, 1H), 8.49 (s, 1H), 8.72 (m, 1H) ppm |
| 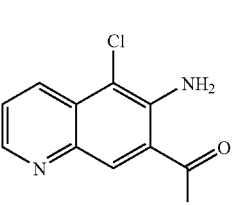 | ¹H-NMR (CDCl₃, 300 MHz): δ ppm = 4.00 (s, 3H), 6.30 (s, b, 2H), 7.42 (dd, 1H), 8.30 (d, 1H), 8.70 (m, 2H) ppm |
| 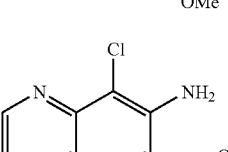 | ¹H-NMR (CDCl₃, 300 MHz): δ ppm = 4.00 (s, 3H), 6.50 (s, b, 2H), 7.20 (dd, 1H), 8.05 (d, 1H), 8.42 (s, 1H), 8.97 (m, 1H) ppm |
| 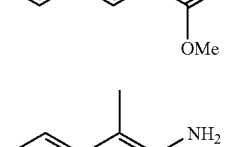 | 219 (M + 1)⁺ |

TABLE B-continued

Intermediates:

| Intermediate Structure | F/MS/NMR |
|---|---|
| 4-methyl-6-amino-7-cyano-1-hydroxyisoquinoline | 200 (M + 1)+ |
| 4-methyl-6-amino-7-bromo-1-hydroxyisoquinoline | 253/255 (M + 1)+ |
| 5-chloro-6-amino-2-(trifluoromethyl)quinoline-7-carboxylic acid triethylammonium salt | $^1$H-NMR (CDCl$_3$, 400 MHz): δ ppm = 1.38 (t, 9H), 3.14 (q, 6H), 7.67 (d, 1H), 8.40 (d, 1H), 8.83 ppm (s, 1H)<br>291/293 (M + 1)+ (Free acid) |
| 6-amino-2-(trifluoromethyl)quinoline-7-carboxylic acid | 257 (M + 1)+ |
| 5-bromo-6-amino-2-(trifluoromethyl)quinoline-7-carboxylic acid triethylammonium salt | $^1$H-NMR (CDCl$_3$, 400 MHz): δ ppm = 1.38 (t, 9H), 3.15 (q, 6H), 7.65 (d, 1H), 8.37 (d, 1H), 8.86 ppm (s, 1H) |
| 5-methoxy-6-amino-2-(trifluoromethyl)quinoline-7-carboxylic acid | $^1$H-NMR (d6-DMSO, 400 MHz): δ ppm = 3.20-3.49 (br, 2H), 3.81 (s, 3H), 7.81 (d, 1H), 8.40 (d, 1H), 8.42 ppm (s, 1H)<br>287 (M + 1)+ |
| 5-methyl-6-amino-2-(trifluoromethyl)quinoline-7-carboxylic acid | $^1$H-NMR (d6-DMSO, 400 MHz): δ ppm = 2.38 (s, 3H), 7.77 (d, 1H), 8.50 (s, 1H), 8.51 ppm (s, 1H)<br>271 (M + 1)+ |

The reactions to give compounds of formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide or N-methylpyrrolidinone. The reaction temperatures are advantageously between −20° C. and +120° C. In general, the reactions are slightly exothermic and, as a rule, they can be carried out at ambient temperature. To shorten the reaction time, or else to start the reaction, the mixture may be heated briefly to the boiling point of the reaction mixture. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5-diazabicyclo-[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example a crown ether, in particular 18-crown-6, or a tetraalkylammonium salt.

The compounds of formula I can be isolated in the customary manner by concentrating and/or by evaporating the solvent and purified by recrystallization or trituration of the solid residue in solvents in which they are not readily soluble, such as ethers, aromatic hydrocarbons or chlorinated hydrocarbons.

Salts of compounds I can be prepared in a manner known per se. Thus, for example, acid addition salts of compounds I are obtained by treatment with a suitable acid or a suitable ion exchanger reagent and salts with bases are obtained by treatment with a suitable base or with a suitable ion exchanger reagent.

Salts of compounds I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds I can be converted in a manner known per se into other salts of compounds I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds I, which have salt-forming properties can be obtained in free form or in the form of salts.

The compounds I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:
from the order Acarina, for example,
*Acarus siro, Aceria sheldoni, Aculus schlechtendali, Amblyomma* spp., *Argas* spp., *Boophilus* spp., *Brevipalpus* spp., *Bryobia praetiosa, Calipitrimerus* spp., *Chorioptes* spp., *Dermanyssus gallinae, Eotetranychus carpini, Eriophyes* spp., *Hyalomma* spp., *Ixodes* spp., *Olygonychus pratensis, Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Tarsonemus* spp. and *Tetranychus* spp.;

from the order Anoplura, for example,
Haematopinus spp., Linognathus spp., Pediculus spp., Pemphigus spp. and Phylloxera spp.;
from the order Coleoptera, for example,
Agriotes spp., Anthonomus spp., Atomaria linearis, Chaetocnema tibialis, Cosmopolites spp., Curculio spp., Dermestes spp., Diabrotica spp., Epilachna spp., Eremnus spp., Leptinotarsa decemlineata, Lissorhoptrus spp., Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;
from the order Diptera, for example,
Aedes spp., Antherigona soccata, Bibio hortulanus, Calliphora erythrocephala, Ceratitis spp., Chrysomyia spp., Culex spp., Cuterebra spp., Dacus spp., Drosophila melanogaster, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., Oscinella frit, Pegomyia hyoscyami, Phorbia spp., Rhagoletis pomonella, Sciara spp., Stomoxys spp., Tabanus spp., Tannia spp. and Tipula spp.;
from the order Heteroptera, for example,
Cimex spp., Distantiella theobroma, Dysdercus spp., Euchistus spp., Eurygaster spp., Leptocorisa spp., Nezara spp., Piesma spp., Rhodnius spp., Sahlbergella singularis, Scotinophara spp. and Triatoma spp.;
from the order Homoptera, for example,
Aleurothrixus floccosus, Aleyrodes brassicae, Aonidiella spp., Aphididae, Aphis spp., Aspidiotus spp., Bemisia tabaci, Ceroplaster spp., Chrysomphalus aonidium, Chrysomphalus dictyospermi, Coccus hesperidum, Empoasca spp., Eriosoma larigerum, Erythroneura spp., Gascardia spp., Laodelphax spp., Lecanium corni, Lepidosaphes spp., Macrosiphus spp., Myzus spp., Nephotettix spp., Nilaparvata spp., Parlatoria spp., Pemphigus spp., Planococcus spp., Pseudaulacaspis spp., Pseudococcus spp., Psylla spp., Pulvinaria aethiopica, Quadraspidiotus spp., Rhopalosiphum spp., Saissetia spp., Scaphoideus spp., Schizaphis spp., Sitobion spp., Trialeurodes vaporariorum, Trioza erytreae and Unaspis citri;
from the order Hymenoptera, for example,
Acromyrmex, Atta spp., Cephus spp., Diprion spp., Diprionidae, Gilpinia polytoma, Hoplocampa spp., Lasius spp., Monomorium pharaonis, Neodiprion spp., Solenopsis spp. and Vespa spp.;
from the order Isoptera, for example,
Reticulitermes spp.;
from the order Lepidoptera, for example,
Acleris spp., Adoxophyes spp., Aegeria spp., Agrotis spp., Alabama argillaceae, Amylois spp., Anticarsia gemmatalis, Archips spp., Argyrotaenia spp., Autographa spp., Busseola fusca, Cadra cautella, Carposina nipponensis, Chilo spp., Choristoneura spp., Clysia ambiguella, Cnaphalocrocis spp., Cnephasia spp., Cochylis spp., Coleophora spp., Crocidolomia binotalis, Cryptophlebia leucotreta, Cydia spp., Diatraea spp., Diparopsis castanea, Earias spp., Ephestia spp., Eucosma spp., Eupoecilia ambiguella, Euproctis spp., Euxoa spp., Grapholita spp., Hedya nubiferana, Heliothis spp., Hellula undalis, Hyphantria cunea, Keiferia lycopersicella, Leucoptera scitella, Lithocollethis spp., Lobesia botrana, Lymantria spp., Lyonetia spp., Malacosoma spp., Mamestra brassicae, Manduca sexta, Operophtera spp., Ostrinia nubilalis, Pammene spp., Pandemis spp., Panolis flammea, Pectinophora gossypiela, Phthorimaea operculella, Pieris rapae, Pieris spp., Plutella xylostella, Prays spp., Scirpophaga spp., Sesamia spp., Sparganothis spp., Spodoptera spp., Synanthedon spp., Thaumetopoea spp., Tortrix spp., Trichoplusia ni and Yponomeuta spp.;
from the order Mallophaga, for example,
Damalinea spp. and Trichodectes spp.;
from the order Orthoptera, for example,
Blatta spp., Blattella spp., Gryllotalpa spp., Leucophaea maderae, Locusta spp., Periplaneta spp. and Schistocerca spp.;
from the order Psocoptera, for example,
Liposcelis spp.;
from the order Siphonaptera, for example,
Ceratophyllus spp., Ctenocephalides spp. and Xenopsylla cheopis;
from the order Thysanoptera, for example,
Frankliniella spp., Hercinothrips spp., Scirtothrips aurantii, Taeniothrips spp., Thrips palmi and Thrips tabaci; and
from the order Thysanura, for example,
Lepisma saccharina.

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling Aphis craccivora, Diabrotica balteata, Heliothis virescens, Myzus persicae, Plutella xylostella and Spodoptera littoralis in cotton, vegetable, maize, rice and soya crops. The active ingredients according to the invention are further especially suitable for controlling Mamestra (preferably in vegetables), Cydia pomonella (preferably in apples), Empoasca (preferably in vegetables, vineyards), Leptinotarsa (preferably in potatoes) and Chilo supressalis (preferably in rice).

The term "crops" is to be understood as including also crops that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosateand glufosinate-resistant maize varieties commercially available under the trade names RoundupReady®, Herculex I® and LibertyLink®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF(a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). Truncated toxins, for example a truncated CryIA(b), are known. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); Nature-Gard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and storerooms and the protection of raw materials, such as wood, textiles, floor coverings or buildings, and also in the hygiene sector, especially the protection of humans, domestic animals and productive livestock against pests of the mentioned type.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis*, *Periplaneta americana*, *Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus*, *Chlorophorus pilosis*, *Anobium punctatum*, *Xestobium rufovillosum*, *Ptilinuspecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthesrugicollis*, *Xyleborus* spec., *Tryptodendron* spec., *Apate monachus*, *Bostrychus capucins*, *Heterobostrychus brunneus*, *Sinoxylon* spec. and *Dinoderus minutus*, and also hymenopterans such as *Sirex juvencus*, *Urocerus gigas*, *Urocerus gigas taignus* and *Urocerus augur*, and termites such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis* and *Coptotermes formosanus*, and bristletails such as *Lepisma saccharina*.

The invention therefore also relates to pesticidal compositions such as emulsifiable concentrates, suspension concentrates, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethyl-ammonium bromide.

Examples of suitable anionic surfactants are water-soluble soaps or water-soluble synthetic surface-active compounds. Examples of suitable soaps are the alkali, alkaline earth or (un-substituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutyl-naphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient. Preferred compositions are composed in particular as follows (%=percent by weight):

| Emulsifiable concentrates: | |
|---|---|
| active ingredient: | 1 to 95%, preferably 5 to 20% |
| surfactant: | 1 to 30%, preferably 10 to 20% |
| solvent: | 5 to 98%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surfactant: | 1 to 40%, preferably 2 to 30% |
| Wettable powders: | |
| active ingredient: | 0.5 to 90%, preferably 1 to 80% |
| surfactant: | 0.5 to 20%, preferably 1 to 15% |
| solid carrier: | 5 to 99%, preferably 15 to 98% |
| Granulates: | |
| active ingredient: | 0.5 to 30%, preferably 3 to 15% |
| solid carrier: | 99.5 to 70%, preferably 97 to 85% |

PREPARATORY EXAMPLES

The preparatory examples below illustrate the invention in more detail, without limiting it.

Example H1

Preparation of 8-chloro-7-{[2-(3-chloro-pyridin-2-yl)-5-trifluoromethyl-2H-pyrazole-3-carbonyl]-amino}-quinoxaline-6-carboxylic acid cyclopropyl-methyl-amide (T1.1.14)

a) Preparation of 2,3-bis-dibromomethyl-pyrazine

A solution of 10.0 g (93.0 mmol) 2,3-dimethylpyrazine and 70.0 g (390 mmol) N-bromo-succinimide in 800 ml $CCl_4$ is irradiated with a 250 Watt lamp at reflux temperature during 20 hours. After cooling the solution is filtered and the organic phase is washed with a 5% sodium thiosulfate solution and water. After evaporation of the organic phase, the residue is crystallised in ethanol to give 29.1 g (74%) of the title compound. m.p.: 167-170° C.

b) Preparation of quinoxaline-6,7-dicarboxylic acid diethyl ester

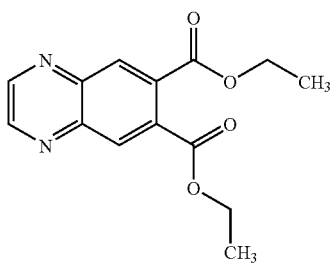 [SMILES: CCOC(=O)c1cc2nccnc2cc1C(=O)OCC]

To a solution of 38.0 g (90.0 mmol) 2,3-bis-dibromomethyl-pyrazine and 70.0 g (400 mmol) diethyl maleate in 450 ml DMF is added 40.0 g (270.0 mmol) NaI and the mixture is heated at a temperature of 80° C. during 20 hours. After evaporation of the solvent, the residue is dissolved in 1000 ml t-butyl-methyl ether and washed with a 5% sodium thiosulfate solution and water (5 times). Evaporation of the solvent and purification of the residue with flash-chromatography yielded 9.1 g dark oil (37%). ¹H-NMR (CDCl₃, 400 MHz): 1.45 ppm (t, 6H), 4.45 (q, 4H), 8.5 (s, 2H), 9.0 (s, 2H).

c) Preparation of quinoxaline-6,7-dicarboxylic acid monomethyl ester

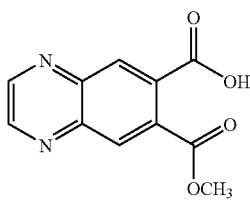 [SMILES: COC(=O)c1cc2nccnc2cc1C(=O)O]

11.8 g (43.0 mmol) quinoxaline-6,7-dicarboxylic acid diethyl ester and 5.0 g (86 mmol) KOH dissolved in 100 ml dioxane and 50 ml water is stirred at ambient temperature during 20 hours. After evaporation of the dioxane, the solution is made slightly acidic (pH ~5) with HCl 2N and is extracted with methylene chloride. After evaporation of the organic phase, 6.6 g diacide is isolated. This product is directly dissolved in 25 ml acetanhydride and heated at reflux during 8 hours. Acetanhydride is evaporated and 6.2 g furo[3,4-g]quinoxaline-6,8-dione is isolated. Without purification, this material is dissolved in 50 ml methanol and heated at reflux during 1 hour. After evaporation of the solvent, the residue is crystallised in diisopropyl ether to give 6.25 g of the title compound (63%): ¹H-NMR (DMSO-d6, 400 MHz): 3.73 ppm (s, 3H), 8.20 (s, 1H), 8.35 (s, 1H), 9.0 (2 s, 2H), 13.6 (s, b, 1H).

d) Preparation of 7-tert-butoxycarbonylamino-quinoxaline-6-carboxylic acid methyl ester

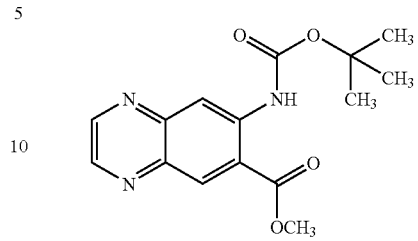

7.1 g (30.6 mmol) quinoxaline-6,7-dicarboxylic acid monomethyl ester, 8 ml NEt₃, 1 g molecular sieve 4 Å and 10 ml (46.40 mmol) diphenylphosphonic azide is successively added to 100 ml t-butanol. The mixture is heated at a temperature of 85° C. during 20 hours. After cooling, the mixture is filtered and the solid is washed with 1000 ml THF. The filtrate is evaporated and submitted to flash-chromatography to give 7.45 g (80%) of the title compound. m.p.: 196-198° C.

e) Preparation of 7-amino-quinoxaline-6-carboxylic acid methyl ester

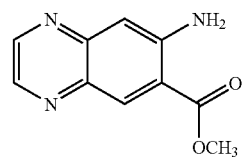 [SMILES: COC(=O)c1cc2nccnc2cc1N]

7.1 g (24.0 mmol) 7-tert-butoxycarbonylamino-quinoxaline-6-carboxylic acid methyl ester is added to 50 ml dioxane and 110 ml HCl 6N and heated at a temperature of 50° C. The dioxane phase is evaporated and the residue is diluted with 150 ml water. The water phase is neutralized with NaOH 2N (~pH 8), saturated with NaCl and extracted with ethyl acetate and THF. After evaporation of the solvent, the residue is submitted to flash-chromatography to give 2.2 g (41%) of the title compound. m.p.: 180-182° C.

f) Preparation of 7-amino-8-chloro-quinoxaline-6-carboxylic acid methyl ester

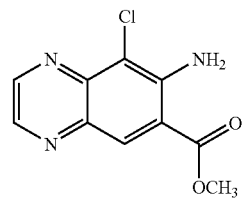 [SMILES: COC(=O)c1cc2nccnc2c(Cl)c1N]

2.07 g (10.2 mmol) 7-amino-quinoxaline-6-carboxylic acid methyl ester and 1.36 g (10.2 mmol) N-chloro-succinimide is suspended in 5 ml DMF and heated at a temperature of 95° C. during 30 min. After cooling, the mixture is poured into 150 ml ice water. The mixture is stirred 15 min and filtered. The compound is dried and crystallised in hexane to give 2.15 g (88%) of the title compound. m.p.: 182-184° C.

g) Preparation of 9-chloro-2-[2-(3-chloro-pyridin-2-yl)-5-trifluoromethyl-2H-pyrazol-3-yl]-3-oxa-1,5,8-triaza-anthracen-4-one

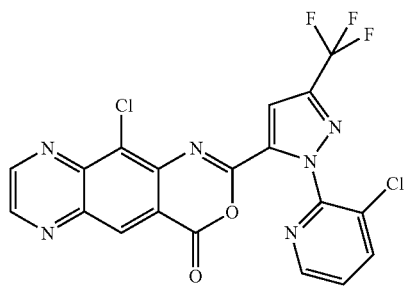 [SMILES: O=c1oc(-c2cc(C(F)(F)F)nn2-c2ncccc2Cl)nc2c(Cl)c3nccnc3cc12]

2.15 g (9.05 mmol) 7-amino-8-chloro-quinoxaline-6-carboxylic acid methyl ester dissolved in 20 ml MeOH, 20 ml dioxane and 12 ml NaOH 1 N is stirred 20 hours at ambient temperature. The mixture is evaporated and the residue is taken twice in toluene and evaporated. The sodium salt obtained is suspended in 70 ml acetonitrile and 2.65 g (9.1 mmol) 2-(3-chloro-pyridin-2-yl)-5-trifluoromethyl-2H-pyrazole-3-carboxylic acid and 3.5 ml (40.7 mmol) pyridine were added. 2.5 ml (31.7 mmol) mesyl chloride in 10 ml acetonitrile were slowly added at a temperature of 0° C. and the mixture is warmed up to ambient temperature and stirred for 1 hour. Then the mixture is poured on ice water (400 ml) and filtered after 15 min. After drying, the compound is crystallised in isopropanol to give 3.77 g (87%) of the title compound. $^1$H-NMR (DMSO-d6, 400 MHz): 7.55 ppm (m, 1H), 7.60 (s, 1H), 8.05 (d, 1H), 8.60 (d, 1H), 9.00 (s, 1H), 9.02 (s, 1H), 9.10 (s, 1H).

h) Preparation of 8-chloro-7-{[2-(3-chloro-pyridin-2-yl)-5-trifluoromethyl-2H-pyrazole-3-carbonyl]-amino}-quinoxaline-6-carboxylic acid cyclopropyl-methyl-amide

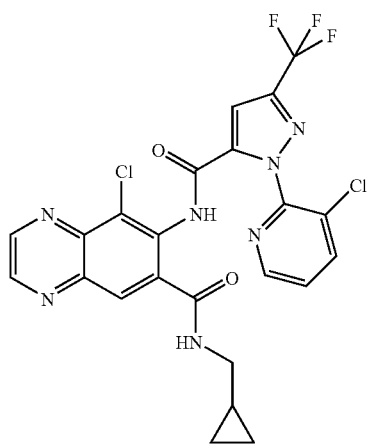 [SMILES: O=C(NCC1CC1)c1cc2nccnc2c(Cl)c1NC(=O)c1cc(C(F)(F)F)nn1-c1ncccc1Cl]

0.55 g (1.15 mol) 9-chloro-2-[2-(3-chloro-pyridin-2-yl)-5-trifluoromethyl-2H-pyrazol-3-yl]-3-oxa-1,5,8-triaza-anthracen-4-one and 0.5 ml C-cyclopropylmethylamine is dissolved in 15 ml THF and stirred for 8 hours. After evaporation, the residue is crystallised in diethyl ether to give 0.47 g (74%) of the title compound. m.p.: 180-183° C.

Example H2

Preparation of 7-chloro-6-{[2-(3-chloro-pyridin-2-yl)-5-trifluoromethyl-2H-pyrazole-3-carbonyl]-amino}-benzo[1,2,5]thiadiazole-5-carboxylic acid isopropylamide: (T20.1.8)

a) Preparation of 4-amino-2-azido-3-chloro-5-nitro-benzoic acid methyl ester

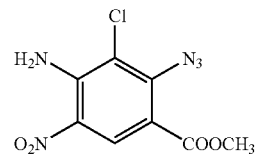

To a solution of 7 g (28.16 mmol) of 4-amino-3-chloro-2-fluoro-5-nitro-benzoic acid methyl ester (known from WO 03/077914) in 140 mL of DMF, 5.49 g (84.44 mmol) of sodium azide and 908 mg (2.82 mmol) of tetrabutyl ammonium bromide is added. Then the mixture is stirred and heated at 50° C. for 4 h. After cooling to ambient temperature, the mixture is diluted in EtOAc and washed with H$_2$O (5 times). The organic phase is dried on Na$_2$SO$_4$, filtrated and evaporated. The crude compound (7.3 g, 26.88 mmol, 95%) obtained as a yellow solid is used without more purification in the next step. $^1$H-NMR (CDCl$_3$, 300 MHz): ? ppm=3.95 (s, 3H), 8.82 (s, 1H).

b) Preparation of 2,4,5-triamino-3-chloro-benzoic acid methyl ester

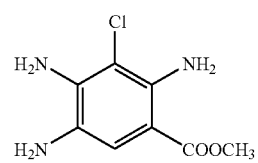 [SMILES: COC(=O)c1cc(N)c(N)c(Cl)c1N]

To a suspension of 4.4 g (16.19 mmol) of 4-amino-2-azido-3-chloro-5-nitro-benzoic acid methyl ester in 161 mL of a mixture EtOH:MeOH 2:1 (v/v), 161 mL of a saturated NH$_4$Cl aqueous solution is added followed by the addition of 88 mL of THF. Then 5.2 g (81 mmol) of powdered zinc is added and the reaction is stirred at ambient temperature during 5 h. The suspension is diluted with CH$_2$Cl$_2$ and the organic phase is washed with brine (2 times) and then dried on Na$_2$SO$_4$. After filtration and evaporation 3.2 g (14.84 mmol, 92%) of a dark violet-red solid were obtained and used directly in the next step without more purification. LC/MS: 216/218 (M+1)$^+$ c) Preparation of 6-amino-7-chloro-benzo[1,2,5]thiadiazole-5-carboxylic acid methyl ester

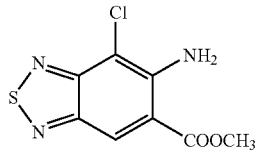 [SMILES: COC(=O)c1cc2nsnc2c(Cl)c1N]

To a suspension of 20 mg (93 mmol) of 2,4,5-triamino-3-chloro-benzoic acid methyl ester in 1 ml of acetonitrile, is added 32 ml (0.19 mmol) of N,N-diisopropylethylamine followed by 9 ml (0.13 mmol) of thionyl chloride. The mixture is stirred at 80° C. over the night. Then, 32 ml of N,N-diisopropylethylamine is added again as well as 9 ml of thionyl chloride and the mixture is again stirred for 5 hours at a temperature of 80° C. The solvent is evaporated and the residue is suspended in EtOAc. After filtration, EtOAc is evaporated and 18 mg (73.9 mmol, 80%) of a yellowish-brown solid is obtained. LC/MS: 244/246 (M+1)$^+$.

d) Preparation of 6-amino-7-chloro-benzo[1,2,5]thiadiazole-5-carboxylic acid

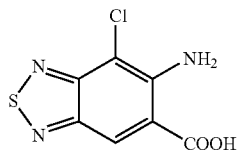 [SMILES: Nc1c(C(=O)O)cc2nsnc2c1Cl]

To a solution of 0.37 g (1.50 mmol) of 6-amino-7-chloro-benzo[1,2,5]thiadiazole-5-carboxylic acid methyl ester in 7.32 mL of dioxane and 0.92 mL of MeOH, is added 2.25 mL (2.25 mmol) of an aqueous solution of NaOH 1 N. The mixture is stirred at ambient temperature during 2 hours and then the solvents were evaporated. The residue is suspended in H$_2$O and the mixture is acidified to pH 2-3 with an aqueous 1 N HCl solution. The reddish-violet precipitate obtained is filtrated and washed with a minimum of H$_2$O. 291 mg (1.27 mmol) of the expected product can be isolated. The aqueous phase is extracted with EtOAc (2 times) and then the organic layer is washed once with brine, dried on Na$_2$SO$_4$, filtrated and concentrated under reduced pressure. 10 mg (43.54 ?mol) of the acid is obtained more giving a total amount of 301 mg (1.31 mmol, 87%) of a dark violet solid. LC/MS: 230/232 (M+1)$^+$.

e) Preparation of 4-chloro-6-[2-(3-chloro-pyridin-2-yl)-5-trifluoromethyl-2H-pyrazol-3-yl]-7-oxa-2-thia-1,3,5-triaza-cyclopenta[b]naphthalen-8-one To a suspension of 300 mg (1.31 mmol) of 6-amino-7-chloro-benzo[1,2,5]thiadiazole-5-carboxylic acid in 12 ml of acetonitrile, is added 381 mg (1.31 mmol) of 2-(3-chloro-pyridin-2-yl)-5-trifluoromethyl-2H-pyrazole-3-carboxylic acid followed by 0.47 ml (5.88 mmol) of pyridine. The mixture is stirred at ambient temperature during 30 min. Then the suspension is cooled at a temperature of 0° C. and 0.36 ml (4.57 mmol) of methanesulfonyl chloride is added dropwise. The mixture is stirred at a temperature of 0° C. during 30 min and 2 hours at ambient temperature. Then the solvent is evaporated and the residue is precipitated in a minimum of cold H$_2$O. After filtration and washing of the solid with a minimum of cold H$_2$O, 585 mg (1.21 mmol, 92%) of a dark violet solid is obtained. LC/MS: 485/487 (M+1)$^+$.

f) Preparation of 7-chloro-6-{[2-(3-chloro-pyridin-2-yl)-5-trifluoromethyl-2H-pyrazole-3-carbonyl]-amino}-benzo[1,2,5]thiadiazole-5-carboxylic acid isopropylamide (T20.1.8)

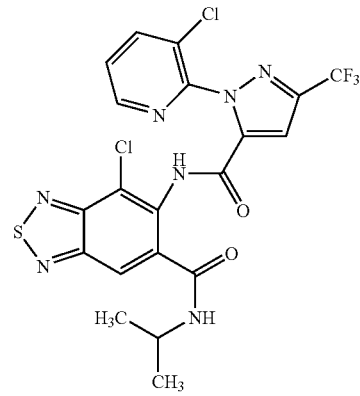 [SMILES: CC(C)NC(=O)c1cc2nsnc2c(Cl)c1NC(=O)c1cc(C(F)(F)F)nn1-c1ncccc1Cl]

To a mixture of 25 mg (52 mmol) of 4-chloro-6-[2-(3-chloro-pyridin-2-yl)-5-trifluoromethyl-2H-pyrazol-3-yl]-7-oxa-2-thia-1,3,5-triaza-cyclopenta[b]naphthalen-8-one in 0.5 ml of THF, is added dropwise 7 ml (77 mmol) of isopropylamine. The reaction is stirred for 18 hours at ambient temperature. Then, the solvent is evaporated and the residue is suspended in a mixture of hexanes and a minimum of EtOAc. After decantation the solid is washed with a minimum of hexanes and after drying 24.5 mg (45 mmol, 87%) of a slightly brown solid were obtained. LC/MS: 544/546 (M+1)$^+$.

Example H3

Preparation of 7-chloro-6-{[2-(3-chloro-pyridin-2-yl)-5-trifluoromethyl-2H-pyrazole-3-carbonyl]-amino}-benzo[1,2,5]thiadiazole-5-carboxylic acid methylamide (T20.1.2)

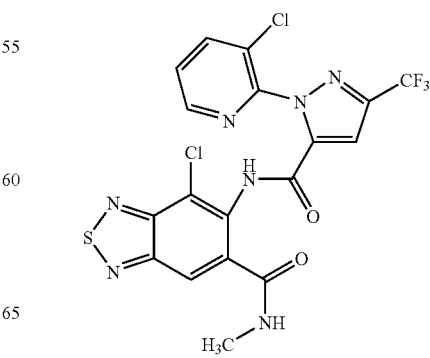

See step f) of Example H2 using 4-chloro-6-[2-(3-chloro-pyridin-2-yl)-5-trifluoromethyl-2H-pyrazol-3-yl]-7-oxa-2-thia-1,3,5-triaza-cyclopenta[b]naphthalen-8-one as starting material and methylamine (40% in H$_2$O). After overnight reaction and chromatography column purification, a slightly brown solid is obtained (75%). LC/MS: 538/539 (M+Na)$^+$.

Example H4

Preparation of 7-chloro-6-{[2-(3-chloro-pyridin-2-yl)-5-trifluoromethyl-2H-pyrazole-3-carbonyl]-amino}-benzo[1,2,5]thiadiazole-5-carboxylic acid cyclopropylmethyl-amide (T20.1.14)

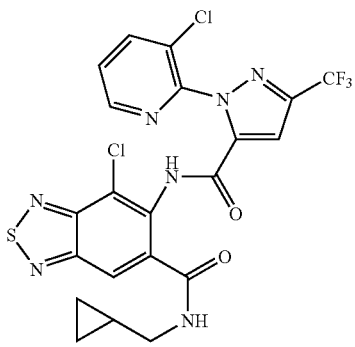 [SMILES: O=C(NCC1CC1)c1cc2nsnc2c(Cl)c1NC(=O)c1cc(C(F)(F)F)nn1-c1ncccc1Cl]

See step f) of example H2 using 4-chloro-6-[2-(3-chloro-pyridin-2-yl)-5-trifluoromethyl-2H-pyrazol-3-yl]-7-oxa-2-thia-1,3,5-triaza-cyclopenta[b]naphthalen-8-one as starting material and cyclopropanemethylamine. After 18 hours reaction and chromatography column purification, a slightly brown solid is obtained (85%). LC/MS: 556/558 (M+1)$^+$.

Example H5

Preparation of 8-chloro-7-{[2-(3-chloro-pyridin-2-yl)-5-trifluoromethyl-2H-pyrazole-3-carbonyl]-amino}-2,3-dimethyl-quinoxaline-6-carboxylic acid methylamide (2.1)

a) Preparation of 7-amino-8-chloro-2,3-dimethyl-quinoxaline-6-carboxylic acid methyl ester

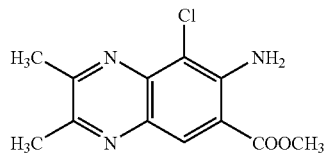 [SMILES: COC(=O)c1cc2nc(C)c(C)nc2c(Cl)c1N]

To a solution of 1.5 g (6.96 mmol) of 2,4,5-triamino-3-chloro-benzoic acid methyl ester in 27 ml of EtOH, is added 0.81 ml (9.18 mmol) of 2,3-butanedione. The mixture is stirred under reflux during 1 hour. After cooling the mixture to ambient temperature EtOAc is added and the organic phase is washed with H$_2$O (2 times). The organic phase is dried on Na$_2$SO$_4$, filtrated and evaporated. After purification by flash chromatography on silica gel, 1.18 g (4.22 mmol, 62%) of an orange-coloured solid were obtained. $^1$H-NMR (CDCl$_3$, 300 MHz): ? ppm=2.67 (s, 3H), 2.75 (s, 3H), 3.97 (s, 3H), 6.47 (s br, 2H), 8.58 (s, 1H).

b) Preparation of 7-amino-8-chloro-2,3-dimethyl-quinoxaline-6-carboxylic acid

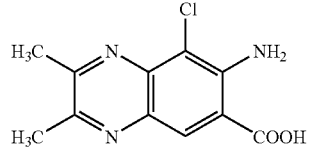 [SMILES: Cc1nc2cc(C(=O)O)c(N)c(Cl)c2nc1C]

See step d) of example H2 for the reaction conditions starting from 7-amino-8-chloro-2,3-dimethyl-quinoxaline-6-carboxylic acid methyl ester and heating under reflux (70° C.) for 4 hours. After evaporation of all the solvents, the residue is directly used in the next step without work-up nor purification. LC/MS: 266/268 (M+1)$^+$.

c) Preparation of 9-chloro-2-[2-(3-chloro-pyridin-2-yl)-5-trifluoromethyl-2H-pyrazol-3-yl]-6,7-dimethyl-3-oxa-1,5,8-triaza-anthracen-4-one

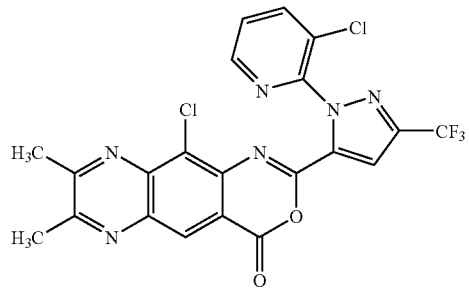 [SMILES: Cc1nc2cc3c(=O)oc(-c4cc(C(F)(F)F)nn4-c4ncccc4Cl)nc3c(Cl)c2nc1C]

See step e) of example H2 using 7-amino-8-chloro-2,3-dimethyl-quinoxaline-6-carboxylic acid as starting material. After 3 hours of reaction, H$_2$O is added to the suspension and the precipitate formed is filtrated and the isolated solid is dissolved in THF. After evaporation of the solvent, an orange solid (66%) is obtained and used directly in the next step. $^1$H-NMR (CDCl$_3$, 300 MHz): ? ppm=2.79 (s, 3H), 2.84 (s, 3H), 7.51-7.53 (dd, 1H), 7.57 (s, 1H), 7.96-8.04 (dd, 1H), 8.58-8.60 (dd, 1H), 8.82 (s, 1H).

d) Preparation of 8-chloro-7-{[2-(3-chloro-pyridin-2-yl)-5-trifluoromethyl-2H-pyrazole-3-carbonyl]-amino}-2,3-dimethyl-quinoxaline-6-carboxylic acid methylamide (2.1)

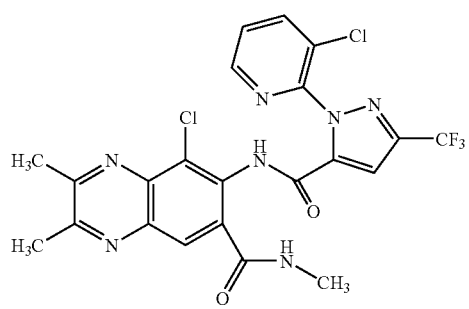 [SMILES: CNC(=O)c1cc2nc(C)c(C)nc2c(Cl)c1NC(=O)c1cc(C(F)(F)F)nn1-c1ncccc1Cl]

See example H3 for the reaction conditions using 9-chloro-2-[2-(3-chloro-pyridin-2-yl)-5-trifluoromethyl-2H-pyrazol-3-yl]-6,7-dimethyl-3-oxa-1,5,8-triaza-anthracen-4-one as starting material and 2 equivalents of methylamine (40% in H₂O). After 10 hours reaction time and purification by flash chromatography on silica gel, a white solid is obtained in 68% yield. m.p.: 221-224° C.

Example H5

Preparation of 8-chloro-7-{[2-(3-chloro-pyridin-2-yl)-5-trifluoromethyl-2H-pyrazole-3-carbonyl]-amino}-2,3-dimethyl-quinoxaline-6-carboxylic acid isopropylamide (T19.1.8)

See step f) of example H2 for the reaction conditions starting from 9-chloro-2-[2-(3-chloro-pyridin-2-yl)-5-trifluoromethyl-2H-pyrazol-3-yl]-6,7-dimethyl-3-oxa-1,5,8-triaza-anthracen-4-one and 2 equivalents of isopropylamine. After 18 hours reaction time and purification by flash chromatography on silica gel, a white solid is obtained within 42% yield. m.p.: 243-244° C.

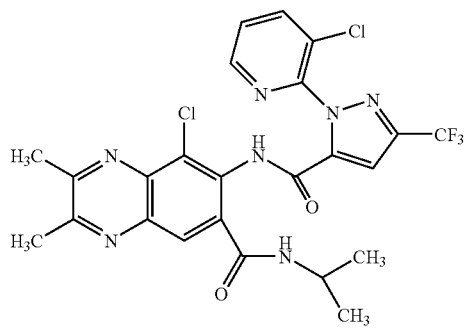 [SMILES: Cc1nc2cc(C(=O)NC(C)C)c(NC(=O)c3cc(C(F)(F)F)nn3-c3ncccc3Cl)c(Cl)c2nc1C]

Example H6

Preparation of 8-chloro-7-{[2-(3-chloro-pyridin-2-yl)-5-trifluoromethyl-2H-pyrazole-3-carbonyl]-amino}-2,3-dimethyl-quinoxaline-6-carboxylic acid cyclopropylamide (T19.1.14)

See example H4 for the reaction conditions using 9-chloro-2-[2-(3-chloro-pyridin-2-yl)-5-trifluoromethyl-2H-pyrazol-3-yl]-6,7-dimethyl-3-oxa-1,5,8-triaza-anthracen-4-one as starting material and 2 equivalents of cyclopropanemethylamine. After 18 hours reaction and purification by flash chromatography on silica gel, a white solid is obtained within 69% yield. m.p.: 255-258° C.

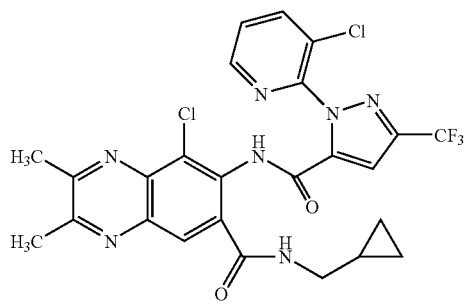 [SMILES: Cc1nc2cc(C(=O)NCC3CC3)c(NC(=O)c3cc(C(F)(F)F)nn3-c3ncccc3Cl)c(Cl)c2nc1C]

Example H7

Preparation of 7-chloro-6-{[2-(3-chloro-pyridin-2-yl)-5-trifluoromethyl-2H-pyrazole-3-carbonyl]-amino}-1-methyl-1H-benzoimidazole-5-carboxylic acid isopropylamide (T22.1.8)

a) Preparation of 3-chloro-2-fluoro-4-methylamino-5-nitro-benzoic acid

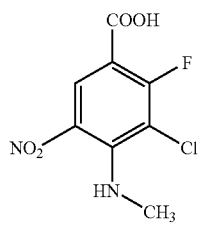 [SMILES: CNc1c([N+](=O)[O-])cc(C(=O)O)c(F)c1Cl]

A suspension of 5 g (21.05 mmol) of 3-chloro-2,4-difluoro-5-nitro-benzoic acid (known from WO 03/077914) in 50 mL of H₂O is cooled to a temperature of 0° C. Then 5.86 ml (42.10 mmol) of triethylamine were added dropwise followed by the dropwise addition of 1.82 ml (21.05 mmol) of methylamine (40% in H₂O). After 30 min of stirring at 0° C., 0.18 ml (2.11 mmol) of methylamine (40% in H₂O) is added and the mixture is stirred again during 30 min at a temperature of 0° C. The pH of the mixture is adjusted to 1-0.5 by the addition of concentrated HCl at a temperature of 0° C. The product is extracted with tert-butyl methyl ether (2 times) and the organic phase is washed once with brine, dried on Na₂SO₄, filtrated and the solvent is evaporated. 5.35 g (21.52 mmol, 102%) of a crude yellow solid were obtained and used directly in the next step without purification. LC/MS: 247/249 (M−1)⁻.

b) Preparation of 3-chloro-2-fluoro-4-methylamino-5-nitro-benzoic acid methyl ester

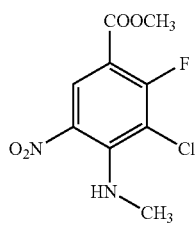

A solution of 5.30 g (21.32 mmol) of 3-chloro-2-fluoro-4-methylamino-5-nitro-benzoic acid in 53 mL of THF and 13.75 ml of MeOH is cooled to a temperature of 0° C. Then, 13.86 ml (27.72 mmol) of trimethylsilyl-diazomethane (2 M in diethylether) were added portion wise at a temperature of 0° C. The mixture is stirred 30 min at a temperature of 0° C. and 30 min at ambient temperature. The reaction mixture is evaporated with acetic acid in the trap. The yellow residue is titurated in diethyl ether and after decantation, 4.3 g (16.37 mmol, 77%) of a yellow solid is isolated. The Et₂O phase is evaporated and 1.5 g of impure product is recovered. The crude product is used directly in the next step without purification. ¹H-NMR (CDCl₃, 300 MHz): ? ppm=3.30 (d, 3H), 3.95 (s, 3H), 7.80 (s br, 1H), 8.70 (d, 1H).

c) Preparation of 2-azido-3-chloro-4-methylamino-5-nitro-benzoic acid methyl ester

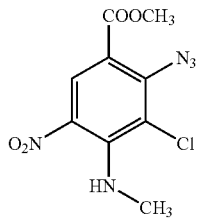 [SMILES: CNc1c([N+](=O)[O-])cc(C(=O)OC)c(N=[N+]=[N-])c1Cl]

See step a) of example H2 using 3-chloro-2-fluoro-4-methylamino-5-nitro-benzoic acid methyl ester as starting material. After 4 hours of reaction at a temperature of 50° C. the same work-up is made and gave 4.7 g (16.45 mmol, 101%) of a yellow sticky solid which is used directly in the next step without purification. $^1$H-NMR (CDCl$_3$, 300 MHz): ? ppm=3.20 (d, 3H), 3.95 (s, 3H), 7.42 (s br, 1H), 8.60 (s, 1H).

d) Preparation of 2,5-diamino-3-chloro-4-methylamino-benzoic acid methyl ester

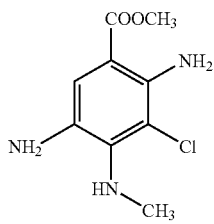

See step c) of example H2 using 2-azido-3-chloro-4-methylamino-5-nitro-benzoic acid methyl ester as starting material. The reaction is complete after 1 hour and the same work-up is made giving 4.4 g (19.16 mmol, 109%) of a crude sticky black residue which is kept at a temperature of 4° C. and used directly in the next step without purification. LC/MS: 230/232 (M+1)$^+$.

e) Preparation of 6-amino-7-chloro-1-methyl-1H-benzoimidazole-5-carboxylic acid methyl ester

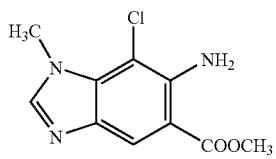 [SMILES: COC(=O)c1cc2ncn(C)c2c(Cl)c1N]

To a solution of 1 g (4.35 mmol) of 2,5-diamino-3-chloro-4-methylamino-benzoic acid methyl ester in 153 ml of EtOH, is added 700 mg (6.53 mmol) of formamidine acetate. The mixture is stirred at a temperature of 80° C. for 24 hours. EtOAc is added and the organic phase is washed once with H$_2$O and once with brine. Then the organic layer is dried on Na$_2$SO$_4$, filtrated and concentrated. After purification by flash chromatography on silica gel 0.68 g (2.84 mmol, 65%) of a dark violet solid were obtained. LC/MS: 240/242 (M+1)$^+$.

f) Preparation of 6-amino-7-chloro-1-methyl-1H-benzoimidazole-5-carboxylic acid

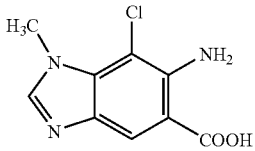

See step d) of example H2 using 6-amino-7-chloro-1-methyl-1H-benzoimidazole-5-carboxylic acid methyl ester as starting material and 1.5 equivalents of NaOH (1 N aqueous solution). After 5 h of stirring at ambient temperature and for 18 hours reaction at a temperature of 50° C., the solvents is evaporated and the work-up is made as already described. A total amount of 614 mg (2.72 mmol, 87%) of a pink-red solid were obtained. LC/MS: 226/228 (M+1)$^+$.

g) Preparation of 4-chloro-6-[2-(3-chloro-pyridin-2-yl)-5-trifluoromethyl-2H-pyrazol-3-yl]-3-methyl-3H-7-oxa-1,3,5-triaza-cyclopenta[b]naphthalen-8-one

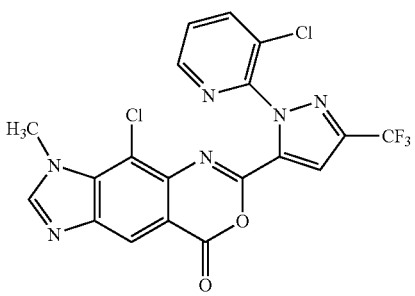 [SMILES: Cn1cnc2cc3c(=O)oc(-c4cc(C(F)(F)F)nn4-c4ncccc4Cl)nc3c(Cl)c21]

See step e) of example H2 starting from 6-amino-7-chloro-1-methyl-1H-benzoimidazole-5-carboxylic acid. After 18 hours reaction at ambient temperature, the same work-up as already described gives the expected product in 95% yield. LC/MS: 481/483 (M+1)+ h) Preparation of 7-chloro-6-{[2-(3-chloro-pyridin-2-yl)-5-trifluoromethyl-2H-pyrazole-3-carbonyl]-amino}-1-methyl-1H-benzoimidazole-5-carboxylic acid isopropylamide (T22.1.8)

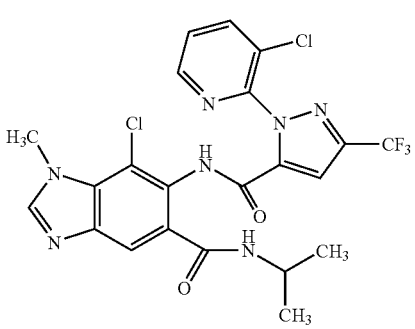 [SMILES: CC(C)NC(=O)c1cc2ncn(C)c2c(Cl)c1NC(=O)c1cc(C(F)(F)F)nn1-c1ncccc1Cl]

See step f) of example H2 with 4-chloro-6-[2-(3-chloro-pyridin-2-yl)-5-trifluoromethyl-2H-pyrazol-3-yl]-3-methyl-3H-7-oxa-1,3,5-triaza-cyclopenta[b]naphthalen-8-one as starting material. After 18 hours reaction at ambient temperature all the solvent is evaporated and after the same work-up already described a slightly brown solid is obtained in 90% yield. m.p.: 150-155° C.; LC/MS: 540/542 (M+1)$^+$.

Example H8

Preparation of 7-chloro-6-{[2-(3-chloro-pyridin-2-yl)-5-trifluoromethyl-2H-pyrazole-3-carbonyl]-amino}-1-methyl-1H-benzoimidazole-5-carboxylic acid cyclopropylamide (T22.1.14)

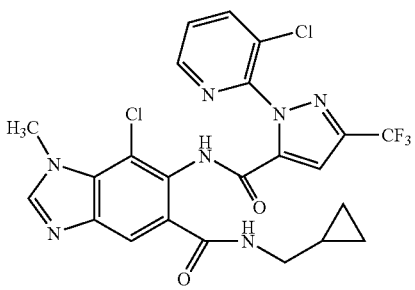 [SMILES: Cn1cnc2cc(C(=O)NCC3CC3)c(NC(=O)c3cc(C(F)(F)F)nn3-c3ncccc3Cl)c(Cl)c21]

See example H4 starting from 4-chloro-6-[2-(3-chloro-pyridin-2-yl)-5-trifluoromethyl-2H-pyrazol-3-yl]-3-methyl-3H-7-oxa-1,3,5-triaza-cyclopenta[b]naphthalen-8-one. After 18 hours reaction the solvent is evaporated and the residue is suspended in hexanes and a minimum of EtOAc. After decantation and washing with hexanes a slightly brown solid is obtained in 91% yield. m.p.: 148-151° C.; LC/MS: 552/554 (M+1)$^+$.

Example H9

Preparation of 7-chloro-6-{[2-(3-chloro-pyridin-2-yl)-5-trifluoromethyl-2H-pyrazole-3-carbonyl]-amino}-1,2-dimethyl-1H-benzoimidazole-5-carboxylic acid isopropylamide (T35.1.8)

a) Preparation of 6-amino-7-chloro-1,2-dimethyl-1H-benzoimidazole-5-carboxylic acid methyl ester

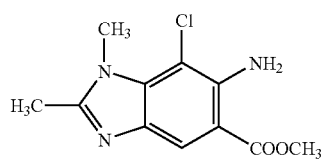 [SMILES: COC(=O)c1cc2nc(C)n(C)c2c(Cl)c1N]

To a suspension of 1 g (3.48 mmol) of 2,5-diamino-3-chloro-4-methylamino-benzoic acid methyl ester (synthesis described in example H7) in 153 mL of EtOH is added 680 mg (6.97 mmol) of acetamidine hydrochloride. The mixture is stirred 2 days at a temperature of 80° C. Then, all the solvent is evaporated and the residue is suspended in EtOAc, the formed precipitate is filtrated and after evaporation the filtrate is purified by flash chromatography on silica gel and gave 510 mg (2.01 mmol, 58%) of a brown-reddish solid. LC/MS: 254/256 (M+1)$^+$.

b) Preparation of 6-amino-7-chloro-1,2-dimethyl-1H-benzoimidazole-5-carboxylic acid

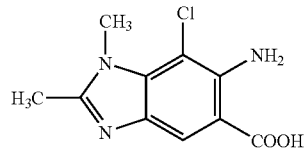 [SMILES: Cc1nc2cc(C(=O)O)c(N)c(Cl)c2n1C]

See step d) of example 2 using 6-amino-7-chloro-1,2-dimethyl-1H-benzoimidazole-5-carboxylic acid methyl ester as starting material. The reaction is stirred 5 hours at ambient temperature and 18 hours at a temperature of 50° C. Then the same work-up as already described is performed and gave a dark red solid with 89% yield. LC/MS: 240/242 (M+1)$^+$ c) Preparation of 4-chloro-6-[2-(3-chloro-pyridin-2-yl)-5-trifluoromethyl-2H-pyrazol-3-yl]-2,3-dimethyl-3H-7-oxa-1,3,5-triaza-cyclopenta[b]naphthalen-8-one

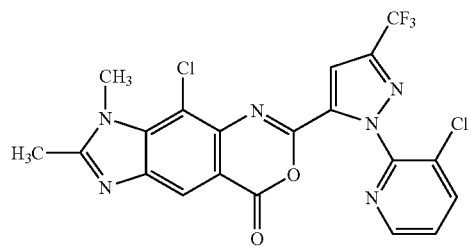 [SMILES: Cc1nc2cc3c(=O)oc(-c4cc(C(F)(F)F)nn4-c4ncccc4Cl)nc3c(Cl)c2n1C]

See step e) of example 2 starting from 6-amino-7-chloro-1,2-dimethyl-1H-benzoimidazole-5-carboxylic acid. Similar reaction time and work-up gave a red-brownish solid (101%) which is used without purification in the next step. LC/MS: 495/497 (M+1)$^+$ d) Preparation of 7-chloro-6-{[2-(3-chloro-pyridin-2-yl)-5-trifluoromethyl-2H-pyrazole-3-carbonyl]-amino}-1,2-dimethyl-1H-benzoimidazole-5-carboxylic acid isopropylamide (T35.1.8)

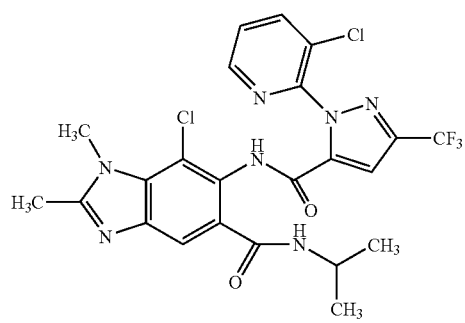 [SMILES: Cc1nc2cc(C(=O)NC(C)C)c(NC(=O)c3cc(C(F)(F)F)nn3-c3ncccc3Cl)c(Cl)c2n1C]

See step f) of example 2 with 4-chloro-6-[2-(3-chloro-pyridin-2-yl)-5-trifluoromethyl-2H-pyrazol-3-yl]-2,3-dimethyl-3H-7-oxa-1,3,5-triaza-cyclopenta[b]naphthalen-8-one as starting material. After purification by flash chromatography on silica gel, a slightly brown solid is obtained with 55% yield. m.p.: 248-250° C.; LC/MS: 554/556 (M+1)⁺

Example H10

Preparation of 7-chloro-6-{[2-(3-chloro-pyridin-2-yl)-5-trifluoromethyl-2H-pyrazole-3-carbonyl]-amino}-1,2-dimethyl-1H-benzoimidazole-5-carboxylic acid cyclopropylamide (T35.1.14)

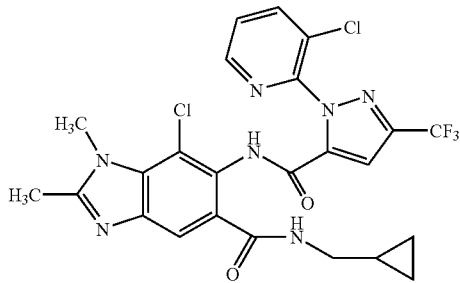 [SMILES: Cc1nc2cc(C(=O)NCC3CC3)c(NC(=O)c3cc(C(F)(F)F)nn3-c3ncccc3Cl)c(Cl)c2n1C]

See example H4 using 4-chloro-6-[2-(3-chloro-pyridin-2-yl)-5-trifluoromethyl-2H-pyrazol-3-yl]-2,3-dimethyl-3H-7-oxa-1,3,5-triaza-cyclopenta[b]naphthalen-8-one as starting material. After purification by flash chromatography on silica gel, a slightly brown solid is obtained with 54% yield. m.p.: 233-235° C.; LC/MS: 566/568 (M+1)⁺

Example H11

Preparation of 7-chloro-6-{[2-(3-chloro-pyridin-2-yl)-5-trifluoromethyl-2H-pyrazole-3-carbonyl]-amino}-2-cyclopropyl-1-methyl-1H-benzoimidazole-5-carboxylic acid cyclopropylamide (T37.1.14)

a) Preparation of 6-amino-7-chloro-2-cyclopropyl-1-methyl-1H-benzoimidazole-5-carboxylic acid methyl ester

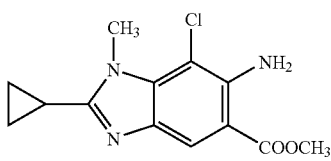 [SMILES: COC(=O)c1cc2nc(C3CC3)n(C)c2c(Cl)c1N]

To a suspension of 1 g (3.48 mmol) of 2,5-diamino-3-chloro-4-methylamino-benzoic acid methyl ester (synthesis described in example H7) in 153 ml of EtOH, is added 866 mg (6.97 mmol) of cyclopropane carboxamidine hydrochloride. After 24 hours of reaction under reflux, 866 mg (6.97 mmol) of cyclopropane carboxamidine hydrochloride were added more and the reaction is stirred under reflux 2 days more. Again 433 mg (3.48 mmol) of cyclopropane carboxamidine hydrochloride is added and after again 2 days of reaction under reflux, the reaction is stopped and the solvent is evaporated. The residue is suspended in EtOAc and the precipitate is filtrated. The filtrate obtained is evaporated and purified by flash chromatography on silica gel and gives 100 mg (0.36 mmol, 10%) of a brown solid. LC/MS: 280/282 (M+1)⁺ b) Preparation of 6-amino-7-chloro-2-cyclopropyl-1-methyl-1H-benzoimidazole-5-carboxylic acid

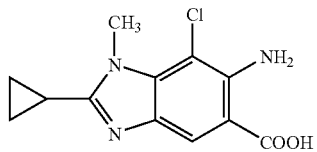 [SMILES: Cn1c(C2CC2)nc2cc(C(=O)O)c(N)c(Cl)c21]

See step d) of example H2 with 6-amino-7-chloro-2-cyclopropyl-1-methyl-1H-benzoimidazole-5-carboxylic acid methyl ester as starting material. After 5 hours of reaction at ambient temperature and stirring for 18 hours at a temperature of 50° C., the solvent is evaporated and the residue suspended in H₂O and acidified to pH 2-3 with concentrated HCl. The precipitate is filtered and washed with a minimum of H₂O. The dark violet solid is obtained in 68% yield. LC/MS: 266/268 (M+1)⁺ c) Preparation of 4-chloro-6-[2-(3-chloro-pyridin-2-yl)-5-trifluoromethyl-2H-pyrazol-3-yl]-2-cyclopropyl-3-methyl-3H-7-oxa-1,3,5-triaza-cyclopenta[b]naphthalen-8-one

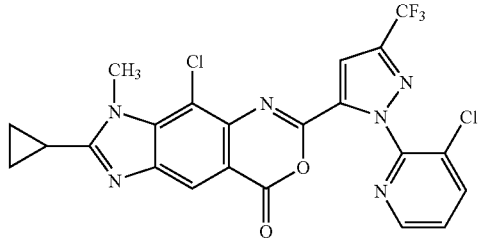 [SMILES: Cn1c(C2CC2)nc2cc3c(=O)oc(-c4cc(C(F)(F)F)nn4-c4ncccc4Cl)nc3c(Cl)c21]

See step e) of example H2 using 6-amino-7-chloro-2-cyclopropyl-1-methyl-1H-benzoimidazole-5-carboxylic acid as starting material. After the same reaction time and the same work-up a red-brown solid is obtained in 85% yield. LC/MS: 521/523 (M+1)⁺ d) Preparation of 7-chloro-6-{[2-(3-chloro-pyridin-2-yl)-5-trifluoromethyl-2H-pyrazole-3-carbonyl]-amino}-2-cyclopropyl-1-methyl-1H-benzoimidazole-5-carboxylic acid cyclopropylamide (T37.1.14)

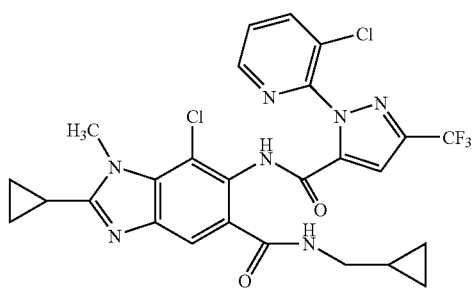 [SMILES: Cn1c(C2CC2)nc2cc(C(=O)NCC3CC3)c(NC(=O)c3cc(C(F)(F)F)nn3-c3ncccc3Cl)c(Cl)c21]

See example H4 with 4-chloro-6-[2-(3-chloro-pyridin-2-yl)-5-trifluoromethyl-2H-pyrazol-3-yl]-2-cyclopropyl-3-methyl-3H-7-oxa-1,3,5-triaza-cyclopenta[b]naphthalen-8-one as starting material. A slightly brown solid is obtained in 66% yield. m.p.: 233-235° C.; LC/MS: 592/594 (M+1)$^+$ Example H12

7-chloro-6-{[2-(3-chloro-pyridin-2-yl)-5-trifluoromethyl-2H-pyrazole-3carbonyl]-amino}-2-cyclopropyl-1-methyl-1H-benzoimidazole-5-carboxylic acid isopropylamide (T37.1.8)

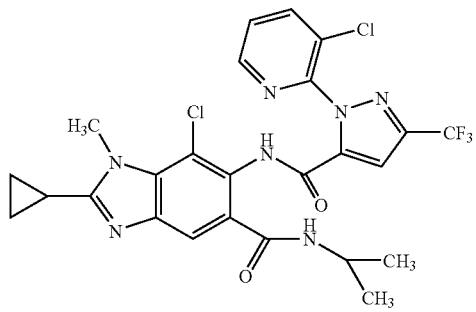 [SMILES: CC(C)NC(=O)c1cc2nc(C3CC3)n(C)c2c(Cl)c1NC(=O)c1cc(C(F)(F)F)nn1-c1ncccc1Cl]

See step f) of example H2 with 4-chloro-6-[2-(3-chloro-pyridin-2-yl)-5-trifluoromethyl-2H-pyrazol-3-yl]-2-cyclopropyl-3-methyl-3H-7-oxa-1,3,5-triaza-cyclopenta[b]naphthalen-8-one as starting material. After purification by flash chromatography on silica gel a slightly brown solid is obtained in 74% yield. m.p.: 242-244° C.; LC/MS: 580/582 (M+1)$^+$.

Example H13

Preparation of 7-chloro-6-{[2-(3-chloro-pyridin-2-yl)-5-trifluoromethyl-2H-pyrazole-3-carbonyl]-amino}-3H-benzoimidazole-5-carboxylic acid methylamide (T21.1.2)

a) Preparation of 6-amino-7-chloro-1H-benzoimidazole-5-carboxylic acid methyl ester

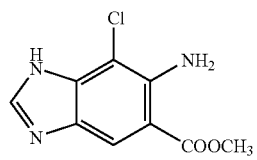 [SMILES: COC(=O)c1cc2nc[nH]c2c(Cl)c1N]

See step e) of example H7 using 2,4,5-triamino-3-chloro-benzoic acid methyl ester as starting material and 2 equivalents of formamidine acetate. The reaction is stirred 2 days at a temperature of 80° C. Then the mixture is extracted with a solution of NaHCO$_3$ saturated (2 times) and EtOAc. The organic phase is washed once with brine, dried on Na$_2$SO$_4$, filtrated and evaporated. A red-violet solid is obtained within 64% yield. LC/MS: 226/228 (M+1)$^+$ b) Preparation of 6-amino-7-chloro-1H-benzoimidazole-5-carboxylic acid

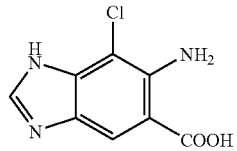

See step d) of example H2 starting from 6-amino-7-chloro-1H-benzoimidazole-5-carboxylic acid methyl ester and 2 equivalents of a solution of NaOH 1 N. The reaction is stirred for 18 hours at 70° C. After evaporation, the residue is suspended in EtOAc and H$_2$O, then the aqueous phase is acidified to pH 2-3 with concentrated HCl. The aqueous phase is coevaporated with toluene and the crude reddish solid is used directly in the next step without further purification. LC/MS: 212/214 (M+1)$^+$ c) Preparation of 4-chloro-6-[2-(3-chloro-pyridin-2-yl)-5-trifluoromethyl-2H-pyrazol-3-yl]-1H-7-oxa-1,3,5-triaza-cyclopenta[b]naphthalen-8-one

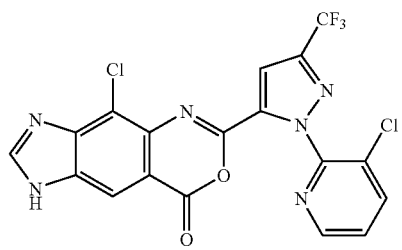 [SMILES: O=c1oc(-c2cc(C(F)(F)F)nn2-c2ncccc2Cl)nc2c(Cl)c3nc[nH]c3cc12]

See step e) of example H2 using 6-amino-7-chloro-1H-benzoimidazole-5-carboxylic acid as starting material. The reaction is stirred 90 min at a temperature of 0° C. and 3 hours at ambient temperature. The same work-up as described before is made and a reddish solid is obtained in 67% yield. MS: 467/469 (M+1)$^+$ d) Preparation of 7-chloro-6-{[2-(3-chloro-pyridin-2-yl)-5-trifluoromethyl-2H-pyrazole-3-carbonyl]-amino}-3H-benzoimidazole-5-carboxylic acid methylamide (T21.1.2)

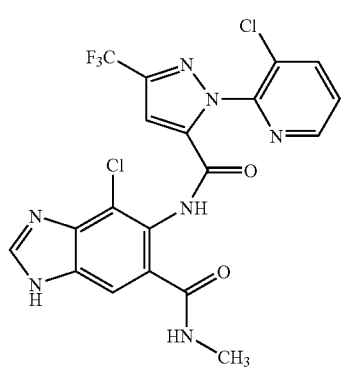 [SMILES: CNC(=O)c1cc2[nH]cnc2c(Cl)c1NC(=O)c1cc(C(F)(F)F)nn1-c1ncccc1Cl]

See example H3 using 4-chloro-6-[2-(3-chloro-pyridin-2-yl)-5-trifluoromethyl-2H-pyrazol-3-yl]-1H-7-oxa-1,3,5-triaza-cyclopenta[b]naphthalen-8-one as starting material and 3 equivalents of methylamine (40% in H₂O). A white solid is obtained within 26% yield. m.p.: 190-192° C.; LC/MS: 498/500 (M+1)⁺.

Example H14

Preparation of 7-chloro-6-{[2-(3-chloro-pyridin-2-yl)-5-trifluoromethyl-2H-pyrazole-3-carbonyl]-amino}-3H-benzoimidazole-5-carboxylic acid isopropylamide (T21.1.8)

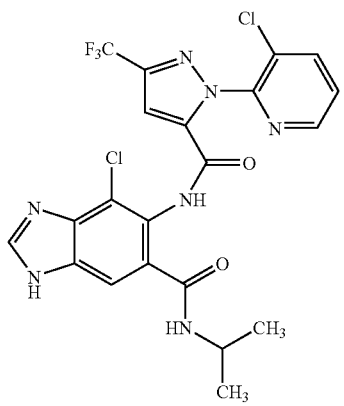 [SMILES: CC(C)NC(=O)c1cc2[nH]cnc2c(Cl)c1NC(=O)c1cc(C(F)(F)F)nn1-c1ncccc1Cl]

See step f) of example H2 with 4-chloro-6-[2-(3-chloro-pyridin-2-yl)-5-trifluoromethyl-2H-pyrazol-3-yl]-1H-7-oxa-1,3,5-triaza-cyclopenta[b]naphthalen-8-one as starting material and 2 equivalents of isopropylamine. After overnight stirring at ambient temperature, 2 equivalents of amine were added and the reaction is stopped after 5 hours. After purification by flash chromatography on silica gel, a white solid is obtained in 50% yield. m.p.: 200-203° C.; LC/MS: 526/528 (M+1)⁺.

Example H15

Preparation of 7-chloro-6-{[2-(3-chloro-pyridin-2-yl)-5-trifluoromethyl-2H-pyrazole-3-carbonyl]-amino}-3H-benzoimidazole-5-carboxylic acid cyclopropylamide (T21.1.14)

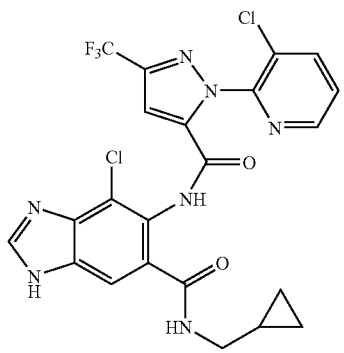 [SMILES: O=C(NCC1CC1)c1cc2[nH]cnc2c(Cl)c1NC(=O)c1cc(C(F)(F)F)nn1-c1ncccc1Cl]

See example H4 with -chloro-6-[2-(3-chloro-pyridin-2-yl)-5-trifluoromethyl-2H-pyrazol-3-yl]-1H-7-oxa-1,3,5-triaza-cyclopenta[b]naphthalen-8-one as starting material and 3 equivalents of cyclopropanemethylamine. After purification by flash chromatography on silica gel, a white solid is obtained in 43% yield. m.p.: 198-201° C.; LC/MS: 538/540 (M+1)⁺.

Example H16

Preparation of Compound No. T7.1.7

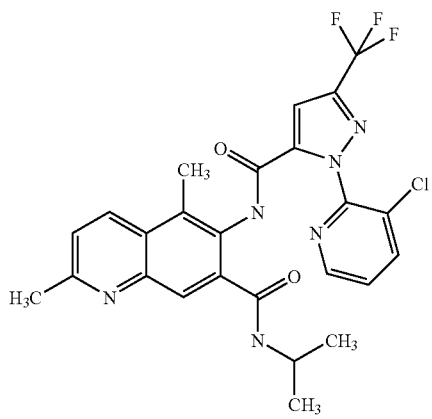 [SMILES: Cc1ccc2c(C)c(NC(=O)c3cc(C(F)(F)F)nn3-c3ncccc3Cl)c(C(=O)NC(C)C)cc2n1]

1.70 g (3.53 mMol) N-(4-amino-2-methyl-6-(((1-methylethyl)amino)carbonyl)phenyl)-1-(3-chloro-2-pyridinyl)-3-(trifluoromethyl)-1H-pyrazole-5-carboxamide (known from WO 03/016284) and 41 mg (0.18 mMol) benzyltriethylammonium chloride in 35 ml conc. HCl and 35 ml toluene are stirred intensively and heated to a temperature of 60° C. Then 0.58 ml (7.0 mMol) crotonaldehyde is added and the reaction mixture refluxed for 1 hour. After cooling the mixture is diluted with 10 ml ethylacetate/THF (1:1) and neutralized with conc. NH₄OH. The organic phase is separated, washed with NaCl-solution, dried and the solvent evaporated. Chromatography of the residue on silica gel (eluent: dichloromethane/THF=3:1) gave compound T 7.1.7, which was recrystallised from THF/hexane: m.p. 236-239° C.

Example H17

Preparation of 7-chloro-6-{[2-(3-chloro-pyridin-2-yl)-5-trifluoromethyl-2H-pyrazole-3-carbonyl]-amino}-2-methoxy-3a,7a-dihydro-benzothiazole-5-carboxylic acid cyclopropylmethyl-amide (T115.1.14)

a) Preparation of 3-chloro-2-fluoro-5-nitro-4-(2-trimethylsilanyl-ethylsulfanyl)-benzoic acid

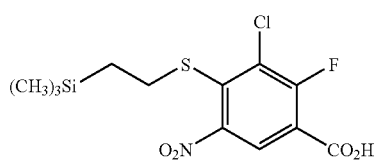

To a mixture of 3.52 g (16.96 mmol) of 3-chloro-2,4-difluoro-5-nitro-benzoic acid (prepared as described in WO 03/077914) in 70 mL of EtOH, is added 6.56 g (47.48 mmol, 2.8 eq.) of K₂CO₃ dissolved in 30 mL of H₂O. Then, 2.67 mL (16.96 mmol) of 2-(trimethylsilyl)ethanethiol are added in 10 minutes. The mixture is stirred at 50° C. during 1 h and then cooled to ambient temperature. After addition of a saturated NH₄Cl aqueous solution, the product is extracted with EtOAc (3 times). The regrouped organic phases are dried with Na₂SO₄, filtered and evaporated. The crude 3-chloro-2-fluoro-5-nitro-4-(2-trimethylsilanyl-ethylsulfanyl)-benzoic acid is contaminated by 3-chloro-5-nitro-2,4-bis-(2-trimethylsilanyl-ethylsulfanyl)-benzoic acid. NMR integrals indicated a ratio 74:26 in favour of the desired compound. ¹H-NMR of 3-chloro-2-fluoro-5-nitro-4-(2-trimethylsilanyl-ethylsulfanyl)-benzoic acid (CDCl₃, 300 MHz): 0.04 (s, 9H), 0.76-0.81 (m, 2H), 2.90-2.94 (m, 2H), 7.93 (d, 1H) ppm. The mixture is used directly in the next step without further purification.

b) Preparation of 3-chloro-2-fluoro-5-nitro-4-(2-trimethylsilanyl-ethylsulfanyl)-benzoic acid methyl ester

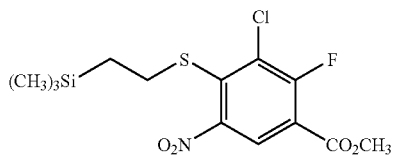

The crude 3-chloro-2-fluoro-5-nitro-4-(2-trimethylsilanyl-ethylsulfanyl)-benzoic acid is dissolved in 30 mL of MeOH and cooled to 0° C. After slow addition of 15 mL of concentrated H₂SO₄, the reaction is stirred over the night at 65° C. The mixture is cooled to ambient temperature and then poured onto cold H₂O. The pH is adjusted to 8-9 with a saturated Na₂CO₃ aqueous solution and the product is extracted with EtOAc (3 times). The combined organic phases are dried with Na₂SO₄, filtered and evaporated. After column purification on silica gel, 5.45 g (83% over two steps) of a mixture 3-chloro-2-fluoro-5-nitro-4-(2-trimethylsilanyl-ethylsulfanyl)-benzoic acid methyl ester: 3-chloro-5-nitro-2,4-bis-(2-trimethylsilanyl-ethylsulfanyl)-benzoic acid methyl ester) in a ratio 74:36 (NMR integrals) is obtained. ¹H-NMR of 3-chloro-2-fluoro-5-nitro-4-(2-trimethylsilanyl-ethylsulfanyl)-benzoic acid methyl ester (CDCl₃, 300 MHz): 0.03 (s, 9H), 0.77-0.86 (m, 2H), 2.94-3.05 (m, 2H), 3.96 (s, 3H), 8.14 (d, 1H) ppm. This mixture is used without further purification in the next step.

c) Preparation of 2-azido-3-chloro-5-nitro-4-(2-trimethylsilanyl-ethylsulfanyl)-benzoic acid methyl ester

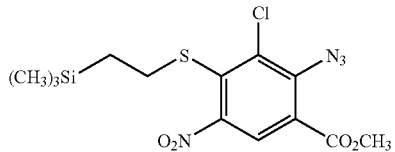

5.45 g of a mixture 3-chloro-2-fluoro-5-nitro-4-(2-trimethylsilanyl-ethylsulfanyl)-benzoic acid methyl ester: 3-chloro-5-nitro-2,4-bis-(2-trimethylsilanyl-ethylsulfanyl)-benzoic acid methyl ester) in a ratio 74:36 (NMR integrals) are dissolved in 60 mL of MeCN. Then, 2.91 g (44.76 mmol) of sodium azide are added followed by 481 mg (1.49 mmol) of tetrabutyl ammonium bromide. The reaction is stirred at 50° C. over the night. The mixture is diluted with EtOAc and then washed with brine (3 times). The organic layer is dried with Na₂SO₄, filtered and evaporated. Column purification over silica gel with hexanes and EtOAc afforded 5.34 g (82%) of a mixture 2-azido-3-chloro-5-nitro-4-(2-trimethylsilanyl-ethylsulfanyl)-benzoic acid methyl ester: 3-chloro-5-nitro-2,4-bis-(2-trimethylsilanyl-ethylsulfanyl)-benzoic acid methyl ester) in a ratio 74:36 (NMR integrals). ¹H-NMR of 2-azido-3-chloro-5-nitro-4-(2-trimethylsilanyl-ethylsulfanyl)-benzoic acid methyl ester (CDCl₃, 300 MHz): 0.01 (s, 9H), 0.75-0.85 (m, 2H), 2.93-3.00 (m, 2H), 3.96 (s, 3H), 8.04 (d, 1H) ppm. This mixture is used without further purification in the next step.

d) Preparation of 2,5-diamino-3-chloro-4-(2-trimethylsilanyl-ethylsulfanyl)-benzoic acid methyl ester

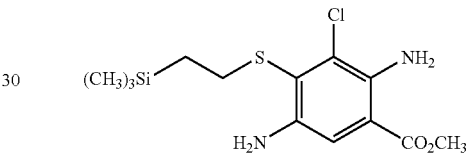

1.06 g of a mixture 2-azido-3-chloro-5-nitro-4-(2-trimethylsilanyl-ethylsulfanyl)-benzoic acid methyl ester: 3-chloro-5-nitro-2,4-bis-(2-trimethylsilanyl-ethylsulfanyl)-benzoic acid methyl ester) in a ratio 74:36 (NMR integrals), are suspended in 16 ml of EtOH and 20 ml of MeOH. Then, 16 ml of a saturated NH₄Cl aqueous solution are added followed by 20 ml of THF. 788 mg (0.012 mol, 4.4 eq.) of dust powdered zinc are added and the reaction is stirred during 1 h 30. 50 ml of a saturated NH₄Cl aqueous solution are added to the mixture and the product is extracted with CH₂Cl₂ (3 times). The regrouped organic phases are dried with Na₂SO₄, filtered and evaporated. A column chromatography purification on silica gel with hexanes and EtOAc gave 680 mg (78%) of pure 2,5-diamino-3-chloro-4-(2-trimethylsilanyl-ethylsulfanyl)-benzoic acid methyl ester; ¹H-NMR (CDCl₃, 300 MHz): 0.02 (s, 9H), 0.78-0.89 (m, 2H), 2.83-2.91 (m, 2H), 3.88 (s, 3H), 7.33 (d, 1H) ppm.

e) Preparation of 2,5-diamino-3-chloro-4-mercapto-benzoic acid methyl ester

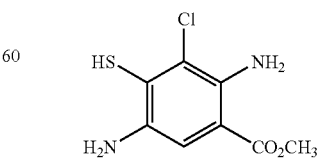

To a solution under Ar, of 60.9 mg (0.19 mmol) of 2,5-diamino-3-chloro-4-(2-trimethylsilanyl-ethylsulfanyl)-benzoic acid methyl ester in 3 ml of anhydrous THF, is added 0.38 ml (0.38 mmol) of TBAF (solution 1 M in THF). The reaction is stirred under Argon during 1 h 30 then a saturated NH$_4$Cl aqueous solution is added to quench the reaction and the product is extracted with CH$_2$Cl$_2$ (2 times). The combined organic phases are dried with Na$_2$SO$_4$, filtered and evaporated. After column chromatography purification, 30.8 mg (0.13 mmol, 69%) of 2,5-diamino-3-chloro-4-mercapto-benzoic acid methyl ester are obtained; LC/MS: 233/235 (M+1)$^+$.

f) Preparation of 6-amino-7-chloro-2-methoxy-3a,7a-dihydro-benzothiazole-5-carboxylic acid methyl ester

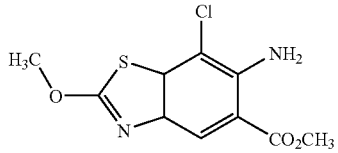

6-amino-7-chloro-2-methoxy-3a,7a-dihydro-benzothiazole-5-carboxylic acid methyl ester is prepared as described in *J. Med. Chem.* 2004, 47, 2853 starting from the crude 2,5-diamino-3-chloro-4-mercapto-benzoic acid methyl ester. After column chromatography purification the expected product is obtained within 18% yield over two steps (steps e and f); LC/MS: 273/275 (M+1)$^+$.

g) Preparation of 6-amino-7-chloro-2-methoxy-3a,7a-dihydro-benzothiazole-5-carboxylic acid

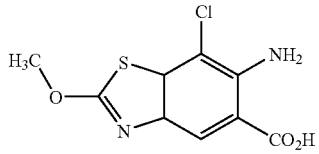

See step d) of example H2 for the reaction conditions starting from 6-amino-7-chloro-2-methoxy-3a,7a-dihydro-benzothiazole-5-carboxylic acid methyl ester and heating the reaction at 55° C. during 2 h. After evaporation of all the solvents, the crude -amino-7-chloro-2-methoxy-3a,7a-dihydro-benzothiazole-5-carboxylic acid is used directly in the next step; LC/MS: 259/261 (M+1)$^+$.

h) Preparation of 4-chloro-6-[2-(3-chloro-pyridin-2-yl)-5-trifluoromethyl-2H-pyrazol-3-yl]-2-methoxy-3a,9a-dihydro-7-oxa-3-thia-1,5-diaza-cyclopenta[b]naphthalen-8-one

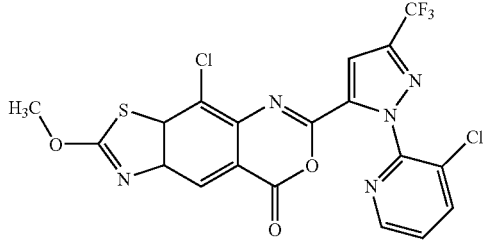

See step e) of example H2 starting from 6-amino-7-chloro-2-methoxy-3a,7a-dihydro-benzothiazole-5-carboxylic acid. The expected product is obtained in 60% yield over two steps; LC/MS: 514/516 (M+1)$^+$.

i) Preparation of 7-chloro-6-{[2-(3-chloro-pyridin-2-yl)-5-trifluoromethyl-2H-pyrazole-3-carbonyl]-amino}-2-methoxy-3a,7a-dihydro-benzothiazole-5-carboxylic acid cyclopropylmethyl-amide (T115.1.14)

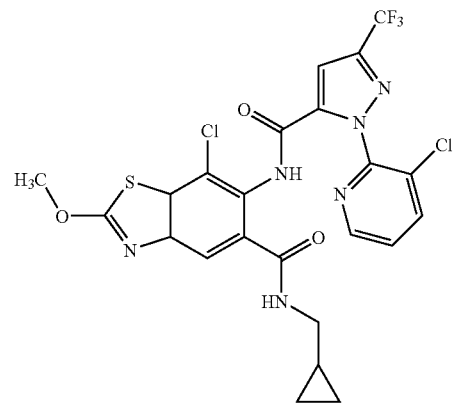

See step f) of example H2 using 4-chloro-6-[2-(3-chloro-pyridin-2-yl)-5-trifluoromethyl-2H-pyrazol-3-yl]-2-methoxy-3a,9a-dihydro-7-oxa-3-thia-1,5-diaza-cyclopenta[b]naphthalen-8-one as starting material and cyclopropanemethylamine. After overnight reaction and chromatography column purification, the expected product is obtained within 34%; LC/MS: 585/587 (M+1)$^+$; m.p.: 199-201° C.

Example H18

Preparation of 7-chloro-6-{[2-(3-chloro-pyridin-2-yl)-5-trifluoromethyl-2H-pyrazole-3-carbonyl]-amino}-2-methylsulfanyl-3a,7a-dihydro-benzothiazole-5-carboxylic acid cyclopropylmethyl-amide (T94.1.14)

a) Preparation of 6-amino-7-chloro-2-mercapto-3a,7a-dihydro-benzothiazole-5-carboxylic acid methyl ester

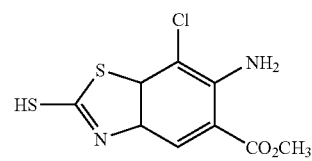

This compound is synthesized as reported in U.S. Pat. No. 4,454,148. 2,5-Diamino-3-chloro-4-(2-trimethylsilanyl-ethylsulfanyl)-benzoic acid methyl ester (step d in example H17) is used as starting material and after thiol deprotection (step f in example H17), the crude 2,5-diamino-3-chloro-4-mercapto-benzoic acid methyl ester is cyclized with CS$_2$, NaOH in EtOH at 70° C. The crude is directly used in the next step without further purification; LC/MS: 275/277 (M+1)$^+$.

b) Preparation of 6-amino-7-chloro-2-methylsulfanyl-3a,7a-dihydro-benzothiazole-5-carboxylic acid methyl ester

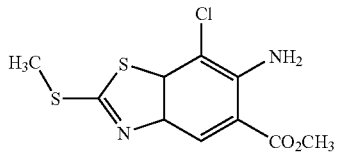 [SMILES: COC(=O)C1=CC2N=C(OC)SC2C(Cl)=C1N]

This compound is prepared as described in *Acta. Chim. Slov.* 2002, 49, 871 using the crude 6-amino-7-chloro-2-mercapto-3a,7a-dihydro-benzothiazole-5-carboxylic acid methyl ester as starting material. Methylation is performed with MeI and Et₃N in DMF. The 6-amino-7-chloro-2-methylsulfanyl-3a,7a-dihydro-benzothiazole-5-carboxylic acid methyl ester is obtained, after column chromatography purification over silica gel, in 59% over 3 steps from 2,5-diamino-3-chloro-4-(2-trimethylsilanyl-ethylsulfanyl)-benzoic acid methyl ester (step d in example H17); LC/MS: 289/291 (M+1)⁺.

c) Preparation of 6-amino-7-chloro-2-methylsulfanyl-3a,7a-dihydro-benzothiazole-5-carboxylic acid

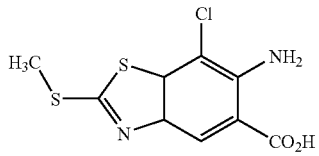 [SMILES: COC1=NC2C=C(C(=O)O)C(N)=C(Cl)C2S1]

See step d) of example H2 for the reaction conditions starting with 6-amino-7-chloro-2-methylsulfanyl-3a,7a-dihydro-benzothiazole-5-carboxylic acid methyl ester and heating the reaction at 55° C. during 2 h. After evaporation of all the solvents, the crude 6-amino-7-chloro-2-methylsulfanyl-3a,7a-dihydro-benzothiazole-5-carboxylic acid is used directly in the next step; LC/MS: 275/277 (M+1)⁺.

d) Preparation of 4-chloro-6-[2-(3-chloro-pyridin-2-yl)-5-trifluoromethyl-2H-pyrazol-3-yl]-2-methylsulfanyl-3a,9a-dihydro-7-oxa-3-thia-1,5-diaza-cyclopenta[b]naphthalen-8-one

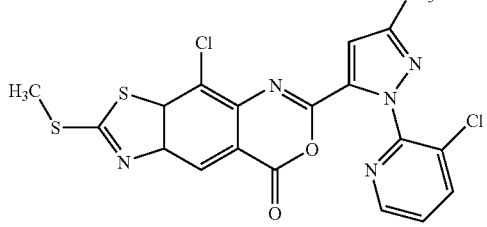

See step e) of example H2 starting with the crude 6-amino-7-chloro-2-methylsulfanyl-3a,7a-dihydro-benzothiazole-5-carboxylic acid. The expected product is obtained in 52% yield over two steps; LC/MS: 530/532 (M+1)⁺.

e) Preparation of 7-chloro-6-{[2-(3-chloro-pyridin-2-yl)-5-trifluoromethyl-2H-pyrazole-3-carbonyl]-amino}-2-methylsulfanyl-3a,7a-dihydro-benzothiazole-5-carboxylic acid cyclopropylmethyl-amide (T94.1.14)

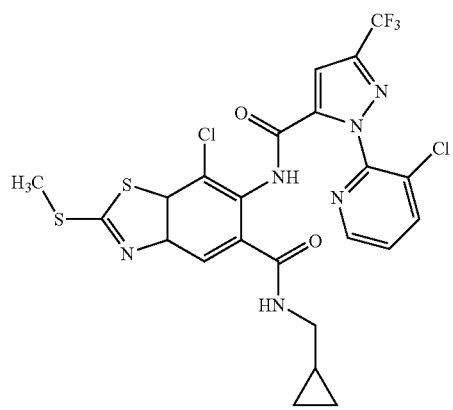 [SMILES: CSC1=NC2C=C(C(=O)NCC3CC3)C(NC(=O)c3cc(C(F)(F)F)nn3-c3ncccc3Cl)=C(Cl)C2S1]

See step f) of example H2 using 4-chloro-6-[2-(3-chloro-pyridin-2-yl)-5-trifluoromethyl-2H-pyrazol-3-yl]-2-methylsulfanyl-3a,9a-dihydro-7-oxa-3-thia-1,5-diaza-cyclopenta[b]naphthalen-8-one as starting material and cyclopropanemethylamine. After overnight reaction and chromatography column purification, the expected product is obtained within 57%; LC/MS: 601/603 (M+1)⁺; m.p.: 221-223° C.

Example H-19

Preparation of 6-{[2-(3-Chloro-pyridin-2-yl)-5-trifluoromethyl-2H-pyrazole-3-carbonyl]-amino}-5-methyl-2-trifluoromethyl-quinoline-7-carboxylic acid methyl amide (T8.1.1)

a) Preparation of 5-Oxo-2-trifluoromethyl-5,6,7,8-tetrahydro-quinoline-7-carboxylic acid methyl ester

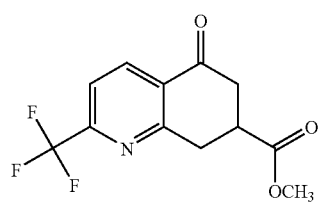 [SMILES: COC(=O)C1CC(=O)c2ccc(C(F)(F)F)nc2C1]

A solution of 3,5-Dioxo-cyclohexanecarboxylic acid methyl ester (3.6 g, 21.16 mmol, preparation as in *Journal of the Chemical Society, Perkin Transactions* 1 (1976), (13), 1382-4), (Z)-4-Amino-1,1,1-trifluoro-but-3-en-2-one (2.94 g, 21.16 mmol, prepared as in EP 744400 (1996)), trifluoroacetic acid (1.21 g, 10.58 mmol), and ammonium trifluoroacetate (1.39 g, 10.58 mmol) in toluene (50 ml) are heated at reflux temperature in a Dean-Stark apparatus. After reaction completion, the reaction mixture is cooled, diluted with ethyl acetate and then washed successively with saturated aqueous sodium bicarbonate and water. The organic phase is dried over anhydrous sodium sulphate, filtered, and concentrated in vacuo. The residue is purified by flash chromatography, eluting with 4:1 hexane to give the title compound (1.5 g, 68%) as white crystals.

¹H NMR (CDCl₃, 400 MHz): δ ppm: 2.93-3.05 (m, 2H); 3.30-3.37 (m, 1H); 3.47 (dd, 1H); 3.56 (dd, 1H); 3.74 (s, 3H); 7.69 (d, 1H); 8.46 ppm (d, 1H).

b) Preparation of 5-Hydroxy-2-trifluoromethyl-quinoline-7-carboxylic acid methyl ester

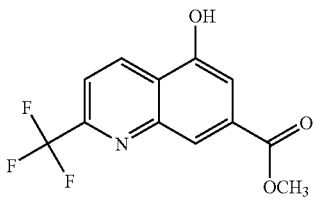 [SMILES: COC(=O)c1cc(O)c2ccc(C(F)(F)F)nc2c1]

A solution of 5-Oxo-2-trifluoromethyl-5,6,7,8-tetrahydroquinoline-7-carboxylic acid methyl ester (50.0 g, 183.01 mmol) is dissolved in methylene chloride (500 ml) and treated drop wise with a solution of bromotrichloromethane (54.43 g, 274.51 mmol) and 1,8-diazabicyclo[5.4.0]undec-7-ene (DBU, 55.72 g, 366.02 mmol) in methylene chloride (100 ml) at 0-5° C. After the addition is complete, the reaction mixture is allowed to warm to room temperature and stirred for 1 hr where TLC analysis (4:1 hexane:ethyl acetate) shows reaction completion. The reaction mixture is diluted with ethyl acetate and then washed successively with dilute aqueous hydrochloric acid and brine. The ethyl acetate phase is dried over anhydrous sodium sulphate, filtered, and concentrated in vacuo. The residue is purified by recrystallisation from hexane:ethyl acetate to give the title compound (47.13 g, 95%) as pale yellow crystals.

¹H NMR (CDCl₃, 400 MHz): δ ppm: 3.97 (s, 3H); 7.77 (d, 1H); 7.81 (s, 1H); 8.48 (s, 1H); 8.84 (d, 1H); 10.87 ppm (br s, 1H).

c) Preparation of 5-Hydroxy-6-nitro-2-trifluoromethyl-quinoline-7-carboxylic acid methyl ester

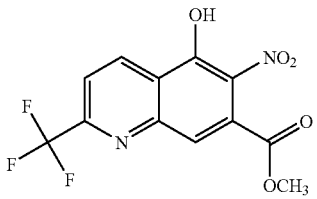 [SMILES: COC(=O)c1cc2nc(C(F)(F)F)ccc2c(O)c1[N+](=O)[O-]]

5-Hydroxy-2-trifluoromethyl-quinoline-7-carboxylic acid methyl ester (46.0 g, 169.63 mmol) is dissolved in 200 ml of concentrated (97%) sulphuric acid at 0-5° C. To this cooled solution is added drop wise fuming (100%) nitric acid (7 ml, 10.69 g, 169.63 mmol). After the addition is complete, the reaction mixture is allowed to warm to room temperature. TLC analysis (4:1 hexane:ethyl acetate) after 30 min shows reaction completion. The reaction mixture is slowly poured onto an ice/water mixture (ca. 2 l), and the crystals then filtered at the pump, thoroughly washed with water, and dried in vacuo. This affords the title compound (47.0 g, 87.6%) as pale yellow crystals.

¹H NMR (CDCl₃, 400 MHz): δ ppm: 4.01 (s, 3H); 7.89 (s, 1H); 7.94 (s, 1H); 9.02 (s, 1H); 11.71 ppm (br s, 1H). Electron Spray MS (positive mode) 317 (M+H); (negative mode) 315 (M−H).

d) Preparation of 6-Nitro-5-trifluoromethanesulfonyloxy-2-trifluoromethyl-quinoline-7-carboxylic acid methyl ester

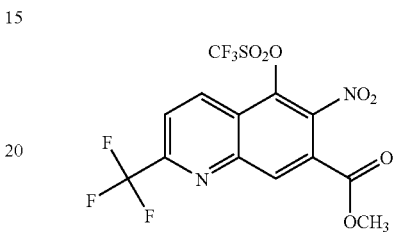

A solution of 5-Hydroxy-6-nitro-2-trifluoromethyl-quinoline-7-carboxylic acid methyl ester (6.82 g, 21.569 mmol) methylene chloride (50 ml) is treated with triethylamine (6.69 g, 23.726 mmol) and a catalytic amount of 4-dimethylaminopyridine (0.26 g, 2.157 mmol). To this solution is added trifluormethansulphonic anhydride, maintaining the temperature at 25° C. TLC analysis after 1 hr shows reaction completion. The reaction mixture is diluted with methylene chloride and then washed successively with dilute aqueous hydrochloric acid, water, saturated aqueous sodium bicarbonate, and water. The methylene chloride phase is dried over anhydrous sodium sulphate, filtered, and concentrated in vacuo. The residue is purified by flash chromatography, eluting with 9:1 hexane:ethyl acetate to give the title compound (6.6 g, 68%) as pale yellow crystals.

¹H NMR (CDCl₃, 400 MHz): δ ppm: 4.04 (s, 3H); 8.12 (d, 1H); 8.65 (d, 1H); 9.0 ppm (s, 1H).

e) Preparation of 5-Methyl-6-nitro-2-trifluoromethyl-quinoline-7-carboxylic acid methyl ester

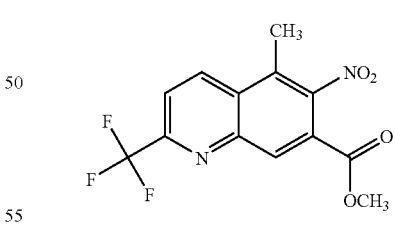

A suspension of indium trichloride (2.0 g, 9.04 mmol) in 5 ml of dry THF under argon is cooled to −78° C. and then treated drop wise with methyl magnesium chloride (3M in THF, 9.1 ml, 27.12 mmol). The milky suspension is allowed to warm to room temperature and then added drop wise to a refluxing solution of bis(triphenylphosphine)palladium(II) dichloride (0.19 g, 0.27 mmol) and 6-Nitro-5-trifluoromethanesulfonyloxy-2-trifluoromethyl-quinoline-7-carboxylic acid methyl ester (4.05 g, 9.042 mmol) in 35 ml of dry THF. The mixture is refluxed under argon, monitoring by TLC. After reaction completion, the reaction mixture is concentrated in vacuo, and the residue taken up in diethyl ether and washed successively with dilute aqueous hydrochloric acid and brine. The diethyl ether phase is dried over anhydrous sodium sulphate, filtered, and concentrated in vacuo. The residue (2.9 g) is purified by flash column chromatography, eluting with 4:1 hexane:ethyl acetate. This gives 2.0 g (70%) of the title product as yellow crystals. ¹H NMR (CDCl₃, 400 MHz): δ ppm: 2.7 (s, 3H); 4.0 (s, 3H); 7.98 (d, 1H); 8.68 (d, 1H); 8.83 ppm (s, 1H). LC/MS: 315 (M+1)⁺ f) Preparation of 5-Methyl-6-nitro-2-trifluoromethyl-quinoline-7-carboxylic acid

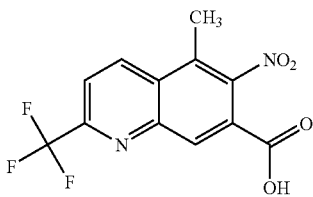

5-Methyl-6-nitro-2-trifluoromethyl-quinoline-7-carboxylic acid methyl ester (3.78 g, 12.03 mmol) are dissolved in 200 ml of methanol/water (3:1 mixture), and treated with lithium hydroxide hydrate (1.06 g, 0.046 mol) at room temperature. After reaction completion the mixture is poured into ethyl acetate and 2 N hydrochloric acid, the organic phase is washed three times with water, dried with sodium sulphate, filtered and concentrated in vacuo. The residue is triturated with a little hexane. Filtration gives 3.50 g (97% of theory) of the title compound as white crystals. ¹H NMR (d6-DMSO₃, 400 MHz): δ ppm: 2.65 (s, 3H); 8.25 (d, 1H); 8.56 (s, 1H); 9.05 ppm (d, 1H).

g) Preparation of 6-Amino-5-methyl-2-trifluoromethyl-quinoline-7-carboxylic acid

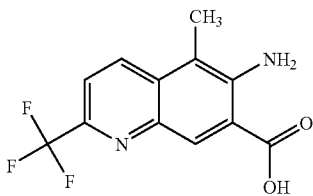 [SMILES: Cc1c(N)c(C(=O)O)cc2nc(C(F)(F)F)ccc12]

A solution of 5-Methyl-6-nitro-2-trifluoromethyl-quinoline-7-carboxylic acid (1.40 g, 4.66 mmol) in ethanol (100 ml) is hydrogenated at atmospheric pressure and ambient temperature in the presence of Raney-nickel catalyst. TLC analysis after 12 hr shows reaction completion. The mixture is filtered over hyflo and the filtrate concentrated in vacuo. The residue is recrystallised from hexane/ethyl acetate to give 0.9 g (71%) of the title compound as yellow crystals.

¹H NMR (d6-DMSO₃, 400 MHz): δ ppm: 2.38 (s, 3H); 7.78 (d, 1H); 8.50 (s, 1H); 8.52 ppm (d, 1H). LC/MS: 271 (M+1)⁺ h) Preparation of 2-[2-(3-Chloro-pyridin-2-yl)-5-trifluoromethyl-2H-pyrazol-3-yl]-9-methyl-6-trifluoromethyl-3-oxa-1,5-diaza-anthracen-4-one

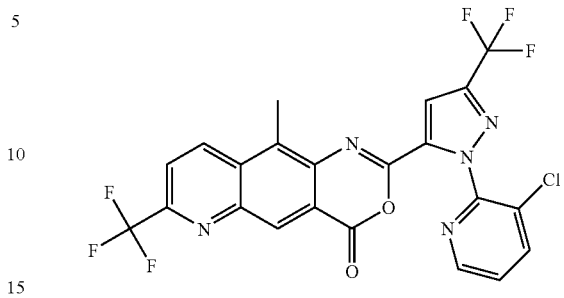

A solution of 6-Amino-5-methyl-2-trifluoromethyl-quinoline-7-carboxylic acid (0.60 g, 2.22 mmol), 2-(3-Chloro-pyridin-2-yl)-5-trifluoromethyl-2H-pyrazole-3-carboxylic acid (0.65 g 2.22 mmol) and pyridine (0.79 g, 9.992 mmol) in acetonitrile (30 ml) is cooled to 0-5° C. and treated drop wise with methane sulphonyl chloride (0.89 g, 7.77 mmol) dissolved in ca. 2 ml of acetonitrile. TLC analysis (4:1 hexane: ethyl acetate) after 2 hr shows reaction completion. The reaction mixture is concentrated to ca. 2/3 the original volume in vacuo and then poured onto 75 ml of ice/water. The resultant crystals are filtered at the pump, washed with water and dried in vacuo. This gives the title compound (1.0 g, 85.7%) as orange crystals.

¹H NMR (d6-DMSO₃, 400 MHz): δ ppm: 2.15 (s, 3H); 7.86 (dd, 1H); 7.96 (s, 1H); 8.12 (d, 1H); 8.45 (d, 1H); 8.71 (m, 2H); 8.89 ppm (d, 1H).

i) Preparation of 6-{[2-(3-Chloro-pyridin-2-yl)-5-trifluoromethyl-2H-pyrazole-3-carbonyl]-amino}-5-methyl-2-trifluoromethyl-quinoline-7-carboxylic acid methyl amide (T8.1.1)

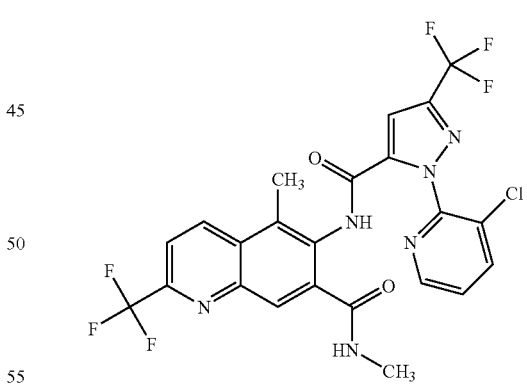

2-[2-(3-Chloro-pyridin-2-yl)-5-trifluoromethyl-2H-pyrazol-3-yl]-9-methyl-6-trifluoromethyl-3-oxa-1,5-diaza-anthracen-4-one (0.249, 0.456 mmol) in 20 ml of tetrahydrofurane is treated with methylamine (0.11 ml of 8M solution in ethanol, 0.9 mmol) and stirred at room temperature. TLC analysis (hexane:ethyl acetate 4:1) after 12 h shows reaction completion. The mixture is concentrated in vacuo, and then purified by flash column chromatography to give the title compound as white crystals.

LC/MS: 557/559 (M+1)⁺; m.p.: 227-230° C.

Example H-19

6-{[5-Bromo-2-(3-chloro-pyridin-2-yl)-2H-pyrazole-3-carbonyl]-amino}-2 trifluoromethyl-quinoline-7-carboxylic acid methylamide (T8.1.153)

a) Preparation of 6-Nitro-2-trifluoromethyl-quinoline-7-carboxylic acid methyl ester

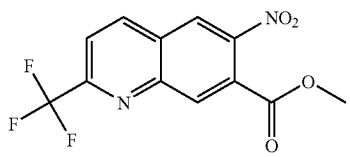 [SMILES: COC(=O)c1cc2nc(C(F)(F)F)ccc2cc1[N+](=O)[O-]]

A solution of 6-Nitro-5-trifluoromethanesulfonyloxy-2-trifluoromethyl-quinoline-7-carboxylic acid methyl ester (12.0 g, 24.094 mmol, step d, example H-18) is dissolved in dimethylformamide (50 ml) under argon and then treated with palladium(II)acetate (0.16 g, 0.723 mmol) and 1,1'bis(diphenylphosphino)ferrocene (0.4 g, 0.723 mmol). To this mixture at room temperature is added triethyl silane (7.0 g, 7.234 mmol) and the reaction then stirred overnight at room temperature. The reaction mixture is diluted with ethyl acetate and washed with brine. The ethyl acetate phase is dried over sodium sulphate, filtered and concentrated in vacuo. Purification of the residue by flash column chromatography (hexane:ethyl acetate, 6:1 as eluent) gives the title compound (4.5 g, 62%) as white crystals.
LC/MS: 301 (M+1)+ b) Preparation of 6-Nitro-2-trifluoromethyl-quinoline-7-carboxylic acid

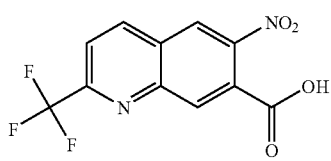 [SMILES: Nc1cc2ccc(C(F)(F)F)nc2cc1C(=O)O]

A sample of 6-Nitro-2-trifluoromethyl-quinoline-7-carboxylic acid methyl ester is hydrolysed to the title product analogously to the method described for step f) of example H-18. The product is recrystallised from hexane/ethyl acetate to give the title compound as white crystals.
LC/MS: 287 (M+1)+ c) Preparation of 6-Amino-2-trifluoromethyl-quinoline-7-carboxylic acid

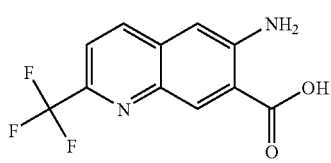

6-Nitro-2-trifluoromethyl-quinoline-7-carboxylic acid is hydrogenated in ethanol in the presence of Raney-Ni analogously to the procedure described for example H-18, step g). This gives the title product as yellow crystals. LC/MS: 257 (M+1)+.

d) Preparation of 2-[5-Bromo-2-(3-chloro-pyridin-2-yl)-2H-pyrazol-3-yl]-6-trifluoromethyl-3-oxa-1,5-diaza-anthracen-4-one

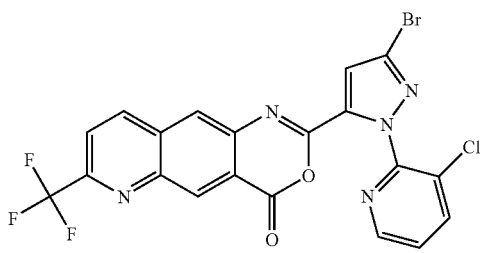 [SMILES: O=c1oc(-c2cc(Br)nn2-c2ncccc2Cl)nc2cc3ccc(C(F)(F)F)nc3cc12]

Prepared from 6-Amino-2-trifluoromethyl-quinoline-7-carboxylic acid and 5-Bromo-2-(3-chloro-pyridin-2-yl)-2H-pyrazole-3-carboxylic acid analogously to the procedure described in step h) of example H-18. This gives the title compound as orange crystals.

e) Preparation of 6-{[5-Bromo-2-(3-chloro-pyridin-2-yl)-2H-pyrazole-3-carbonyl]-amino}-2-trifluoromethyl-quinoline-7-carboxylic acid methyl amide (T8.1.153)

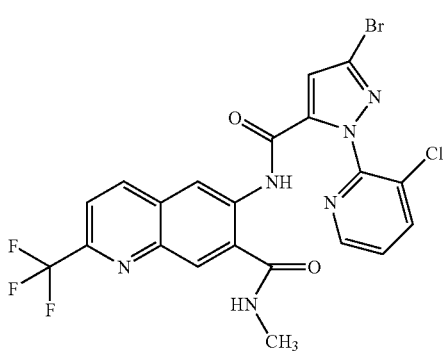 [SMILES: CNC(=O)c1cc2nc(C(F)(F)F)ccc2cc1NC(=O)c1cc(Br)nn1-c1ncccc1Cl]

2-[5-Bromo-2-(3-chloro-pyridin-2-yl)-2H-pyrazol-3-yl]-6-trifluoromethyl-3-oxa-1,5-diaza-anthracen-4-one is reacted with methylamine in THF analogously to the procedure given in step i) of example H-18. The title product is obtained as pale yellow crystals after flash column chromatography. LC/MS: 553/555/557 (M+1)+; m.p.: 127-129° C.

Example H-20

5-Chloro-6-{[2-(3-chloro-pyridin-2-yl)-5-trifluoromethyl-2H-pyrazole-3carbonyl]-amino}-2-trifluoromethyl-quinoline-7-carboxylic acid methyl amide (T8.1.2)

a) Preparation of 6-Amino-5-chloro-2-trifluoromethyl-quinoline-7-carboxylic acid triethyl ammonium salt

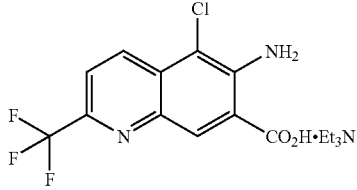

6-Amino-2-trifluoromethyl-quinoline-7-carboxylic acid (0.50 g, 1.952 mmol is dissolved in dimethyl formamide (10 ml) and treated with N-chlorosuccinamide (0.26 g, 1.952 mmol) and the mixture warmed to 80° C. After 1 hr the reaction is complete as shown by LC/MS analysis. The reaction mixture is cooled, diluted with ethyl acetate, and then washed successively with water and brine. The organic phase is dried over sodium sulphate, filtered and the filtrate concentrated in vacuo. The residue was purified by flash chromatography eluting with eluting with a mixture of toluene, ethyl alcohol, dioxane, triethylamine and water (100:40:20:20:5 parts by volume) to give the title compound as a viscous oil.

$^1$H-NMR (CDCl$_3$, 400 MHz): δ ppm=1.38 (t, 9H), 3.14 (q, 6H), 7.67 (d, 1H), 8.40 (d, 1H), 8.83 ppm (s, 1H). LC/MS: 291/293 (M+1)$^+$ (Free acid)

b) Preparation of 9-Chloro-2-[2-(3-chloro-pyridin-2-yl)-5-trifluoromethyl-2H-pyrazol-3-yl]-6-trifluoromethyl-3-oxa-1,5-diaza-anthracen-4-one

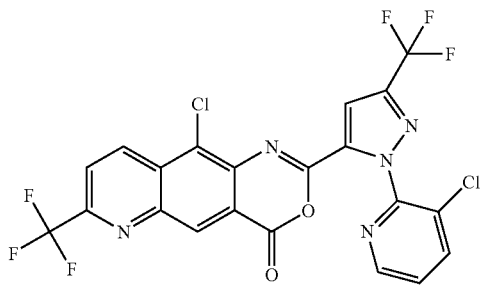

Prepared from 6-Amino-5-chloro-2-trifluoromethyl-quinoline-7-carboxylic acid triethyl ammonium salt and 2-(3-Chloro-pyridin-2-yl)-5-trifluoromethyl-2H-pyrazole-3-carboxylic analogously to the procedure described in step h) of example H-18. This gives the title compound as yellow crystals.

$^1$H NMR (d6-DMSO$_3$, 400 MHz): δ ppm: 7.84 (dd, 1H); 8.03 (s, 1H); 8.26 (d, 1H); 8.43 (dd, 1H); 8.68 (dd, 1H); 8.82 (s, 1H); 8.92 ppm (d, 1H).

c) Preparation of 5-Chloro-6-{[2-(3-chloro-pyridin-2-yl)-5-trifluoromethyl-2H-pyrazole-3-carbonyl]-amino}-2-trifluoromethyl-quinoline-7-carboxylic acid methyl amide

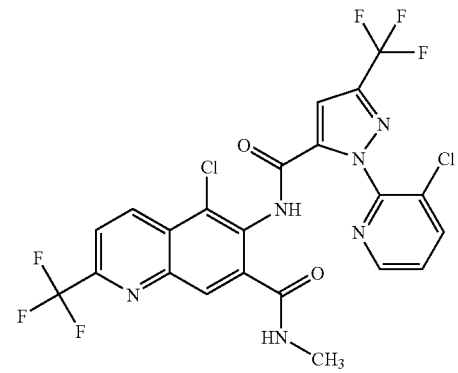 [SMILES: CNC(=O)c1cc2nc(C(F)(F)F)ccc2c(Cl)c1NC(=O)c1cc(C(F)(F)F)nn1-c1ncccc1Cl]

9-Chloro-2-[2-(3-chloro-pyridin-2-yl)-5-trifluoromethyl-2H-pyrazol-3-yl]-6-trifluoromethyl-3-oxa-1,5-diaza-anthracen-4-one is reacted with methylamine in THF analogously to the procedure given in step i) of example H-18. The title product is obtained as yellow crystals after flash column chromatography eluting with 1:1 hexane:ethyl acetate. m.p.: 235-237° C.

Example H-21

Preparation of 6-{[2-(3-Chloro-pyridin-2-yl)-5-trifluoromethyl-2H-pyrazole-3-carbonyl]-amino}-5-methoxy-2-trifluoromethyl-quinoline-7-carboxylic acid methyl amide (T8.1.121)

a) Preparation of 5-Methoxy-6-nitro-2-trifluoromethyl-quinoline-7-carboxylic acid methyl ester

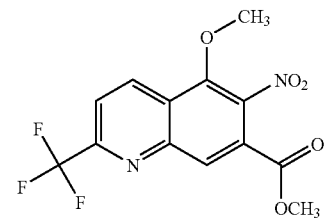 [SMILES: COC(=O)c1cc2nc(C(F)(F)F)ccc2c(OC)c1[N+](=O)[O-]]

A solution of 5-Hydroxy-6-nitro-2-trifluoromethyl-quinoline-7-carboxylic acid methyl ester (1.5 g, 4.744 mmol) in methylene chloride is treated with N,N,N',N'-Tetramethyl-1,8-naphthalendiamine (3.05 g, 14.232 mmol) and Trimethyloxonium-tetrafluorborate (2.11 g, 14.232 mmol) at 0-5° C. under argon. The reaction mixture is allowed to warm to room temperature with stirring. The reaction is complete after 2.5 hr as shown by TLC analysis. The reaction mixture is diluted with methylene chloride, and then washed successively with 2N aqueous hydrochloric acids, water, and brine. The organic phase is dried over anhydrous sodium sulphate, filtered, and concentrated in vacuo. The residue (2.9 g) is purified by flash column chromatography, eluting with 3:1 hexane:ethyl acetate. This gives the title compound (1.2 g, 76%) as yellow crystals.

$^1$H-NMR (CDCl$_3$, 400 MHz): δ ppm=4.00 (s, 3H); 4.15 (s, 3H); 7.96 (d, 1H); 8.40 (d, 1H); 8.72 (s, 1H); 8.72 ppm (d, 1H).

b) Preparation of 5-Methoxy-6-nitro-2-trifluoromethyl-quinoline-7-carboxylic acid

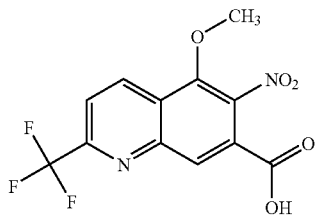 [SMILES: COc1c(N)c(C(=O)O)cc2nc(C(F)(F)F)ccc12]

A sample of 5-Methoxy-6-nitro-2-trifluoromethyl-quinoline-7-carboxylic acid methyl ester is hydrolysed to the title product analogously to the method described for step f) of example H-18. The product is triturated with hexane to give the title compound as yellow crystals. $^1$H-NMR (CDCl$_3$, 400 MHz): δ ppm=4.17 (s, 3H); 8.00 (d, 1H); 8.77 (d, 1H); 8.8 ppm (s, 1H).

c) Preparation of 6-Amino-5-methoxy-2-trifluoromethyl-quinoline-7-carboxylic acid

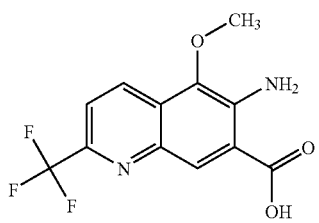

A sample of 5-Methoxy-6-nitro-2-trifluoromethyl-quinoline-7-carboxylic acid is hydrogenated in ethanol in the presence of Raney-Ni analogously to the procedure described for example H-18, step g). This gives the title product as yellow crystals.

$^1$H-NMR (d6-DMSO, 400 MHz): δ ppm=3.20-3.49 (br, 2H), 3.81 (s, 3H), 7.81 (d, 1H), 8.40 (d, 1H), 8.42 ppm (s, 1H). LC/MS: 287 (M+1)$^+$.

d) Preparation of 2-[2-(3-Chloro-pyridin-2-yl)-5-trifluoromethyl-2H-pyrazol-3-yl]-9-methoxy-6-trifluoromethyl-3-oxa-1,5-diaza-anthracen-4-one

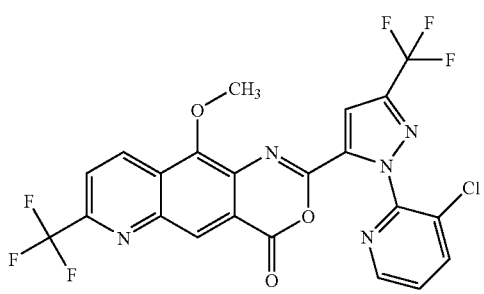 [SMILES: COc1c2ccc(C(F)(F)F)nc2cc2c(=O)oc(-c3cc(C(F)(F)F)nn3-c3ncccc3Cl)nc12]

Prepared from 6-Amino-5-methoxy-2-trifluoromethyl-quinoline-7-carboxylic acid and 2-(3-Chloro-pyridin-2-yl)-5-trifluoromethyl-2H-pyrazole-3-carboxylic analogously to the procedure described in step h) of example H-18. This gives the title compound as orange crystals.

$^1$H NMR (d6-DMSO$_3$, 400 MHz): δ ppm: 7.87 (dd, 1H); 7.96 (s, 1H); 8.12 (d, 1H); 8.43 (dd, 1H); 8.861 (s, 1H); 8.68 (dd, 1H); 8.85 ppm (d, 1H).

e) Preparation of 6-{[2-(3-Chloro-pyridin-2-yl)-5-trifluoromethyl-2H-pyrazole-3-carbonyl]-amino}-5-methoxy-2-trifluoromethyl-quinoline-7-carboxylic acid methyl amide (T8.1.121)

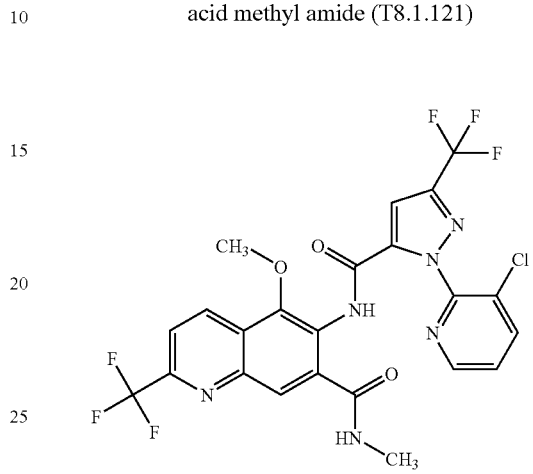

2-[2-(3-Chloro-pyridin-2-yl)-5-trifluoromethyl-2H-pyrazol-3-yl]-9-methoxy-6-trifluoromethyl-3-oxa-1,5-diaza-anthracen-4-one is reacted with methylamine in THF analogously to the procedure given in step i) of example H-18. The title product is obtained as yellow crystals after flash column chromatography eluting with 1:1 hexane:ethyl acetate. m.p.: 209-211° C.

TABLE P

Physical data of the compounds of formula I:

| Compound No. | Melting Point | MS/NMR |
|---|---|---|
| T1.1.2 | 205-208° C. | |
| T1.1.8 | >250° C. | |
| T1.1.14 | 180-183° C. | |
| T1.1.73 | 202-205° C. | |
| T1.1.17 | 241-245° C. | |
| T1.1.56 | 229-232° C. | |
| T1.1.62 | 203-206° C. | |
| T1.1.68 | 200-203° C. | |
| T1.1.74 | 158-162° C. | |
| T1.1.71 | 207-210° C. | |
| T20.1.8 | | LC/MS: 544/546 (M + 1)$^+$. |
| T20.1.2 | | LC/MS: 538/539 (M + Na)$^+$ |
| T20.1.14 | | LC/MS: 556/558 (M + 1)$^+$ |
| T19.1.2 | 221-224 | |
| T19.1.8 | 243-244° C. | |
| T19.1.14 | 255-258° C. | |
| T22.1.8 | 150-155° C. | LC/MS: 540/542 (M + 1)$^+$ |
| T22.1.14 | 148-151° C. | LC/MS: 552/554 (M + 1)$^+$ |
| T35.1.8 | 248-250° C. | LC/MS: 554/556 (M + 1)$^+$ |
| T35.1.14 | 233-235° C. | LC/MS: 566/568 (M + 1)$^+$ |
| T37.1.14 | 233-235° C. | LC/MS: 592/594 (M + 1)$^+$ |
| T37.1.8 | 242-244° C. | LC/MS: 580/582 (M + 1)$^+$ |
| T21.1.2 | 190-192° C. | LC/MS: 498/500 (M + 1)$^+$ |
| T21.1.8 | 200-203° C. | LC/MS: 526/528 (M + 1)$^+$ |
| T21.1.14 | 198-201° C. | LC/MS: 538/540 (M + 1)$^+$ |
| T7.1.1 | 224-227° C. | |
| T7.1.4 | | LC/MS: 517/519 (M + 1)$^+$ |
| T7.1.7 | 236-239° C. | |
| T3.1.38 | 209-212° C. | |
| T3.1.56 | 220-223° C. | |
| T5.1.38 | 221-224° C. | |

TABLE P-continued

Physical data of the compounds of formula I:

| Compound No. | Melting Point | MS/NMR |
|---|---|---|
| T5.1.56 | 218-220° C. | |
| T3.1.53 | 215-218° C. | |
| T3.1.71 | 185-188° C. | |
| T5.1.53 | 238-242° C. | |
| T5.1.71 | 233-236° C. | |
| T14.1.7 | 215-224 | |
| T111.1.7 | | LC/MS: 580/582 (M + 1)$^+$ |
| T112.1.7 | 231-234 | |
| T113.1.7 | | LC/MS: 547/549 (M + 1)$^+$ |
| T23.1.2 | 226-228° C. | LC/MS: 515/517 (M + 1)$^+$ |
| T23.1.8 | 247-249° C. | LC/MS: 543/545 (M + 1)$^+$ |
| T23.1.14 | 239-241° C. | LC/MS: 55/557 (M + 1)$^+$ |
| T23.1.17 | 255-257° C. | LC/MS: 581/583 (M + 1)$^+$ |
| T23.1.73 | — | LC/MS: 603/605 (M + 1)$^+$ |
| T36.1.8 | — | LC/MS: 554/556 (M + 1)$^+$ |
| T36.1.14 | — | LC/MS: 564/566 (M + 1)$^+$ |
| T39.1.8 | 151-154° C. | LC/MS: 570/572 (M + 1)$^+$ |
| T39.1.14 | 218-220° C. | LC/MS: 585/584 (M + 1)$^+$ |
| T40.1.8 | 255-260° C. | LC/MS: 594/596 (M + 1)$^+$ |
| T40.1.14 | 224-227° C. | LC/MS: 606/608 (M + 1)$^+$ |
| T41.1.8 | 184-186° C. | LC/MS: 576/578 (M + 1)$^+$ |
| T41.1.14 | 245-246° C. | LC/MS: 588/590 (M + 1)$^+$ |
| T41.1.17 | 205-207° C. | LC/MS: 614/616 (M + 1)$^+$ |
| T51.1.8 | 190-192° C. | LC/MS: 572/574 (M + 1)$^+$ |
| T51.1.14 | 262-263° C. | LC/MS: 584/586 (M + 1)$^+$ |
| T52.1.8 | — | LC/MS: 585/588 (M + 1)$^+$ |
| T52.1.14 | — | LC/MS: 598/600 (M + 1)$^+$ |
| T53.1.8 | >310° C. | LC/MS: 602/604 (M + 1)$^+$ |
| T53.1.14 | 230-235° C. | LC/MS: 614/616 (M + 1)$^+$ |
| T54.1.8 | — | LC/MS: 618/620 (M + 1)$^+$ |
| T54.1.14 | — | LC/MS: 630/632 (M + 1)$^+$ |
| T81.1.8 | 230-233° C. | LC/MS: 557/559 (M + 1)$^+$ |
| T81.1.14 | 236-238° C. | LC/MS: 569/571 (M + 1)$^+$ |
| T81.1.17 | 240-242° C. | LC/MS: 595/597 (M + 1)$^+$ |
| T82.1.8 | 243-245° C. | LC/MS: 571/573 (M + 1)$^+$ |
| T82.1.14 | 235-237° C. | LC/MS: 583/585 (M + 1)$^+$ |
| T94.1.2 | 269-271° C. | LC/MS: 561/563 (M + 1)$^+$ |
| T94.1.8 | 237-239° C. | LC/MS: 589/591 (M + 1)$^+$ |
| T94.1.14 | 221-223° C. | LC/MS: 601/603 (M + 1)$^+$ |
| T94.1.17 | 238-240° C. | LC/MS: 627/629 (M + 1)$^+$ |
| T114.1.8 | 228-230° C. | LC/MS: 580/582 (M + 1)$^+$ |
| T114.1.14 | 240-241° C. | LC/MS: 595/594 (M + 1)$^+$ |
| T115.1.8 | 224-225° C. | LC/MS: 573/575 (M + 1)$^+$ |
| T115.1.14 | 199-201° C. | LC/MS: 585/587 (M + 1)$^+$ |
| T115.1.17 | 211-212° C. | LC/MS: 611/613 (M + 1)$^+$ |
| T116.1.8 | 227-228° C. | LC/MS: 586/588 (M + 1)$^+$ |
| T116.1.14 | 207-208° C. | LC/MS: 598/600 (M + 1)$^+$ |
| T116.1.17 | 245-246° C. | LC/MS: 624/626 (M + 1)$^+$ |
| T117.1.8 | 245-247° C. | LC/MS: 608/610 (M + 1)$^+$ |
| T117.1.14 | 200-204° C. | LC/MS: 620/622 (M + 1)$^+$ |
| T117.1.17 | 240-242° C. | LC/MS: 646/648 (M + 1)$^+$ |
| T118.1.8 | 181-184° C. | LC/MS: 556/558 (M + 1)$^+$ |
| T118.1.14 | 260-261° C. | LC/MS: 568/570 (M + 1)$^+$ |
| T118.1.17 | 164-170° C. | LC/MS: 594/596 (M + 1)$^+$ |
| T119.1.8 | 184-196° C. | LC/MS: 540/542 (M + 1)$^+$ |
| T119.1.14 | 166-179° C. | LC/MS: 552/554 (M + 1)$^+$ |
| T8.1.43 | 191-194° C. | |
| T8.1.1 | 227-230° C. | |
| T8.1.37 | 210-215° C. | |
| T8.1.19 | 171-174° C. | |
| T8.1.84 | 160-165° C. | |
| T8.1.82 | 190-193° C. | |
| T8.1.8 | 240-242° C. | |
| T8.1.5 | 165-168° C. | |
| T8.1.2 | 233-237° C. | |
| T8.1.3 | 260-262° C. | |
| T8.1.6 | 160-162° C. | |
| T8.1.9 | 230-232° C. | |
| T8.1.153 | 120-127° C. | 553/555/557(M + 1)$^+$ |
| T8.1.122 | 170-173° C. | |
| T8.1.121 | 209-211° C. | |
| T8.1.123 | 145-148° C. | |
| T8.1.139 | 150-152° C. | |
| T8.1.131 | 180-182° C. | |
| T8.1.138 | 155-157° C. | |
| T8.1.125 | 180-182° C. | |
| T8.1.129 | 152-154° C. | |
| T8.1.137 | 145-147° C. | |
| T8.1.22 | 188-190° C. | |
| T8.1.130 | 158-160° C. | |
| T8.1.34 | 204-207° C. | |
| T8.1.52 | 202-205° C. | |
| T8.1.16 | 255-257° C. | |
| T8.1.4 | 209-212° C. | |
| T8.1.7 | 180-183° C. | |
| T120.1.19 | | LC/MS: 493/495/497 (M + Na)$^+$ |
| T120.1.25 | | LC/MS: 521/523/525 (M + Na)$^+$ |
| T120.1.31 | | LC/MS: 533/535/537 (M + Na)$^+$ |
| T120.1.55 | | LC/MS: 535/537 (M + 1)$^+$ |
| T8.1.169 | 178-180° C. | |
| T8.1.170 | 169-172° C. | |
| T120.1.171 | | LC/MS: 487/489 (M + 1)$^+$ |
| T120.1.172 | | LC/MS: 515/517 (M + 1)$^+$ |

The compounds according to the following tables can be prepared analogously. The examples which follow are intended to illustrate the invention and show preferred compounds of formula I.

TABLE A

Compounds of formula Ia:

(Ia)

| Line | $R_{1a}$ | $R_{100}$ | $R_{20}$ |
|---|---|---|---|
| A.1.1 | $CH_3$ | $CF_3$ | $CH_3$ |
| A.1.2 | Cl | $CF_3$ | $CH_3$ |
| A.1.3 | Br | $CF_3$ | $CH_3$ |
| A.1.4 | $CH_3$ | $CF_3$ | $CH_2CH_3$ |
| A.1.5 | Cl | $CF_3$ | $CH_2CH_3$ |
| A.1.6 | Br | $CF_3$ | $CH_2CH_3$ |
| A.1.7 | $CH_3$ | $CF_3$ | $CH(CH_3)CH_3$ |
| A.1.8 | Cl | $CF_3$ | $CH(CH_3)CH_3$ |
| A.1.9 | Br | $CF_3$ | $CH(CH_3)CH_3$ |
| A.1.10 | $CH_3$ | $CF_3$ | $C(CH_3)(CH_3)CH_3$ |
| A.1.11 | Cl | $CF_3$ | $C(CH_3)(CH_3)CH_3$ |
| A.1.12 | Br | $CF_3$ | $C(CH_3)(CH_3)CH_3$ |
| A.1.13 | $CH_3$ | $CF_3$ | cyclopropylmethyl |
| A.1.14 | Cl | $CF_3$ | cyclopropylmethyl |
| A.1.15 | Br | $CF_3$ | cyclopropylmethyl |

TABLE A-continued

Compounds of formula Ia:

(Ia)

[Structure: pyrazole carboxamide linked via NH to a phenyl ring bearing R1a, G1-G4 substituents and a C(O)NH-R20 group; pyrazole N substituted with 3-chloropyridin-2-yl; R100 on pyrazole]

| Line | R₁a | R₁₀₀ | R₂₀ |
|---|---|---|---|
| A.1.16 | CH₃ | CF₃ | 1-methylcyclopropyl-cyclopropyl |
| A.1.17 | Cl | CF₃ | 1-methylcyclopropyl-cyclopropyl |
| A.1.18 | Br | CF₃ | 1-methylcyclopropyl-cyclopropyl |
| A.1.19 | CH₃ | Cl | CH₃ |
| A.1.20 | Cl | Cl | CH₃ |
| A.1.21 | Br | Cl | CH₃ |
| A.1.22 | CH₃ | Cl | CH₂CH₃ |
| A.1.23 | Cl | Cl | CH₂CH₃ |
| A.1.24 | Br | Cl | CH₂CH₃ |
| A.1.25 | CH₃ | Cl | CH(CH₃)CH₃ |
| A.1.26 | Cl | Cl | CH(CH₃)CH₃ |
| A.1.27 | Br | Cl | CH(CH₃)CH₃ |
| A.1.28 | CH₃ | Cl | C(CH₃)(CH₃)CH₃ |
| A.1.29 | Cl | Cl | C(CH₃)(CH₃)CH₃ |
| A.1.30 | Br | Cl | C(CH₃)(CH₃)CH₃ |
| A.1.31 | CH₃ | Cl | CH₂-cyclopropyl |
| A.1.32 | Cl | Cl | CH₂-cyclopropyl |
| A.1.33 | Br | Cl | CH₂-cyclopropyl |
| A.1.34 | CH₃ | Cl | 1-methylcyclopropyl-cyclopropyl |
| A.1.35 | Cl | Cl | 1-methylcyclopropyl-cyclopropyl |
| A.1.36 | Br | Cl | 1-methylcyclopropyl-cyclopropyl |
| A.1.37 | CH₃ | Br | CH₃ |
| A.1.38 | Cl | Br | CH₃ |
| A.1.39 | Br | Br | CH₃ |
| A.1.40 | CH₃ | Br | CH₂CH₃ |
| A.1.41 | Cl | Br | CH₂CH₃ |
| A.1.42 | Br | Br | CH₂CH₃ |
| A.1.43 | CH₃ | Br | CH(CH₃)CH₃ |
| A.1.44 | Cl | Br | CH(CH₃)CH₃ |
| A.1.45 | Br | Br | CH(CH₃)CH₃ |
| A.1.46 | CH₃ | Br | C(CH₃)(CH₃)CH₃ |
| A.1.47 | Cl | Br | C(CH₃)(CH₃)CH₃ |
| A.1.48 | Br | Br | C(CH₃)(CH₃)CH₃ |
| A.1.49 | CH₃ | Br | CH₂-cyclopropyl |
| A.1.50 | Cl | Br | CH₂-cyclopropyl |
| A.1.51 | Br | Br | CH₂-cyclopropyl |
| A.1.52 | CH₃ | Br | 1-methylcyclopropyl-cyclopropyl |
| A.1.53 | Cl | Br | 1-methylcyclopropyl-cyclopropyl |
| A.1.54 | Br | Br | 1-methylcyclopropyl-cyclopropyl |
| A.1.55 | CH₃ | OCH₂CF₃ | CH₃ |
| A.1.56 | Cl | OCH₂CF₃ | CH₃ |
| A.1.57 | Br | OCH₂CF₃ | CH₃ |
| A.1.58 | CH₃ | OCH₂CF₃ | CH₂CH₃ |
| A.1.59 | Cl | OCH₂CF₃ | CH₂CH₃ |
| A.1.60 | Br | OCH₂CF₃ | CH₂CH₃ |
| A.1.61 | CH₃ | OCH₂CF₃ | CH(CH₃)CH₃ |
| A.1.62 | Cl | OCH₂CF₃ | CH(CH₃)CH₃ |

TABLE A-continued

Compounds of formula Ia:

Structure (Ia): A benzene ring bearing substituents G1, G2, G3, G4, R1a, with an NH-C(=O) group linked to a pyrazole (bearing R100) whose N1 is attached to a 3-chloropyridin-2-yl group; the benzene also bears a C(=O)-NH-R20 group.

| Line | R₁a | R₁₀₀ | R₂₀ |
|---|---|---|---|
| A.1.63 | Br | OCH₂CF₃ | CH(CH₃)CH₃ |
| A.1.64 | CH₃ | OCH₂CF₃ | C(CH₃)(CH₃)CH₃ |
| A.1.65 | Cl | OCH₂CF₃ | C(CH₃)(CH₃)CH₃ |
| A.1.66 | Br | OCH₂CF₃ | C(CH₃)(CH₃)CH₃ |
| A.1.67 | CH₃ | OCH₂CF₃ | CH₂-cyclopropyl |
| A.1.68 | Cl | OCH₂CF₃ | CH₂-cyclopropyl |
| A.1.69 | Br | OCH₂CF₃ | CH₂-cyclopropyl |
| A.1.70 | CH₃ | OCH₂CF₃ | 1-methyl-1-cyclopropyl (spirocyclopropyl) |
| A.1.71 | Cl | OCH₂CF₃ | 1-methyl-1-cyclopropyl |
| A.1.72 | Br | OCH₂CF₃ | 1-methyl-1-cyclopropyl |
| A.1.73 | Cl | CF₃ | C(CH₃)₂CH₂SCH₃ |
| A.1.74 | Cl | OCH₂CF₃ | C(CH₃)₂CH₂SCH₃ |
| A.1.75 | Br | CF₃ | C(CH₃)₂CH₂SCH₃ |
| A.1.76 | Br | OCH₂CF₃ | C(CH₃)₂CH₂SCH₃ |
| A.1.77 | CH₃ | CF₃ | C(CH₃)₂CH₂SCH₃ |
| A.1.78 | CH₃ | OCH₂CF₃ | C(CH₃)₂CH₂SCH₃ |
| A.1.79 | CH₃ | CF₃ | C(CH₃)₂CH₂SCH₃ |
| A.1.80 | CH₃ | CF₃ | C(CH₃)₂CH₂SOCH₃ |
| A.1.81 | CH₃ | CF₃ | C(CH₃)₂CH₂SO₂CH₃ |
| A.1.82 | CH₃ | Br | C(CH₃)₂CH₂SCH₃ |
| A.1.83 | CH₃ | Br | C(CH₃)₂CH₂SOCH₃ |
| A.1.84 | CH₃ | Br | C(CH₃)₂CH₂SO₂CH₃ |
| A.1.85 | CH₃ | Cl | C(CH₃)₂CH₂SCH₃ |
| A.1.86 | CH₃ | Cl | C(CH₃)₂CH₂SOCH₃ |
| A.1.87 | CH₃ | Cl | C(CH₃)₂CH₂SO₂CH₃ |
| A.1.88 | Cl | CF₃ | C(CH₃)₂CH₂SCH₃ |
| A.1.89 | Cl | CF₃ | C(CH₃)₂CH₂SOCH₃ |
| A.1.90 | Cl | CF₃ | C(CH₃)₂CH₂SO₂CH₃ |
| A.1.91 | Cl | Br | C(CH₃)₂CH₂SCH₃ |
| A.1.92 | Cl | Br | C(CH₃)₂CH₂SOCH₃ |
| A.1.93 | Cl | Br | C(CH₃)₂CH₂SO₂CH₃ |
| A.1.94 | Cl | Cl | C(CH₃)₂CH₂SCH₃ |
| A.1.95 | Cl | Cl | C(CH₃)₂CH₂SOCH₃ |
| A.1.96 | Cl | Cl | C(CH₃)₂CH₂SO₂CH₃ |
| A.1.97 | CN | CF₃ | CH₃ |
| A.1.98 | CN | CF₃ | CH₂CH₃ |
| A.1.99 | CN | CF₃ | CH(CH₃)₂ |
| A.1.100 | CN | CF₃ | CH₂-cyclopropyl |
| A.1.101 | CN | CF₃ | 1-methyl-1-cyclopropyl |
| A.1.102 | CN | CF₃ | C(CH₃)₂CH₂SCH₃ |
| A.1.103 | CN | CF₃ | C(CH₃)₂CH₂SOCH₃ |
| A.1.104 | CN | CF₃ | C(CH₃)₂CH₂SO₂CH₃ |
| A.1.105 | CN | Br | CH₃ |
| A.1.106 | CN | Br | CH₂CH₃ |
| A.1.107 | CN | Br | CH(CH₃)₂ |
| A.1.108 | CN | Br | CH₂-cyclopropyl |
| A.1.109 | CN | Br | 1-methyl-1-cyclopropyl |
| A.1.110 | CN | Br | C(CH₃)₂CH₂SCH₃ |
| A.1.111 | CN | Br | C(CH₃)₂CH₂SOCH₃ |
| A.1.112 | CN | Br | C(CH₃)₂CH₂SO₂CH₃ |
| A.1.113 | CN | Cl | CH₃ |
| A.1.114 | CN | Cl | CH₂CH₃ |
| A.1.115 | CN | Cl | CH(CH₃)₂ |
| A.1.116 | CN | Cl | CH₂-cyclopropyl |
| A.1.117 | CN | Cl | 1-methyl-1-cyclopropyl |
| A.1.118 | CN | Cl | C(CH₃)₂CH₂SCH₃ |
| A.1.119 | CN | Cl | C(CH₃)₂CH₂SOCH₃ |
| A.1.120 | CN | Cl | C(CH₃)₂CH₂SO₂CH₃ |
| A.1.121 | OCH₃ | CF₃ | CH₃ |
| A.1.122 | OCH₃ | CF₃ | CH₂CH₃ |
| A.1.123 | OCH₃ | CF₃ | CH(CH₃)₂ |

TABLE A-continued

Compounds of formula Ia:

(Ia)

| Line | R₁a | R₁₀₀ | R₂₀ |
|---|---|---|---|
| A.1.124 | OCH₃ | CF₃ | cyclopropylmethyl |
| A.1.125 | OCH₃ | CF₃ | 1-methyl-1-cyclopropyl-cyclopropyl |
| A.1.126 | OCH₃ | CF₃ | C(CH₃)₂CH₂SCH₃ |
| A.1.127 | OCH₃ | CF₃ | C(CH₃)₂CH₂SOCH₃ |
| A.1.128 | OCH₃ | CF₃ | C(CH₃)₂CH₂SO₂CH₃ |
| A.1.129 | OCH₃ | Br | CH₃ |
| A.1.130 | OCH₃ | Br | CH₂CH₃ |
| A.1.131 | OCH₃ | Br | CH(CH₃)₂ |
| A.1.132 | OCH₃ | Br | cyclopropylmethyl |
| A.1.133 | OCH₃ | Br | 1-methyl-1-cyclopropyl-cyclopropyl |
| A.1.134 | OCH₃ | Br | C(CH₃)₂CH₂SCH₃ |
| A.1.135 | OCH₃ | Br | C(CH₃)₂CH₂SOCH₃ |
| A.1.136 | OCH₃ | Br | C(CH₃)₂CH₂SO₂CH₃ |
| A.1.137 | OCH₃ | Cl | CH₃ |
| A.1.138 | OCH₃ | Cl | CH₂CH₃ |
| A.1.139 | OCH₃ | Cl | CH(CH₃)₂ |
| A.1.140 | OCH₃ | Cl | cyclopropylmethyl |
| A.1.141 | OCH₃ | Cl | 1-methyl-1-cyclopropyl-cyclopropyl |
| A.1.142 | OCH₃ | Cl | C(CH₃)₂CH₂SCH₃ |
| A.1.143 | OCH₃ | Cl | C(CH₃)₂CH₂SOCH₃ |
| A.1.144 | OCH₃ | Cl | C(CH₃)₂CH₂SO₂CH₃ |
| A.1.145 | H | CF₃ | CH₃ |
| A.1.146 | H | CF₃ | CH₂CH₃ |
| A.1.147 | H | CF₃ | CH(CH₃)₂ |
| A.1.148 | H | CF₃ | cyclopropylmethyl |
| A.1.149 | H | CF₃ | 1-methyl-1-cyclopropyl-cyclopropyl |
| A.1.150 | H | CF₃ | C(CH₃)₂CH₂SCH₃ |
| A.1.151 | H | CF₃ | C(CH₃)₂CH₂SOCH₃ |
| A.1.152 | H | CF₃ | C(CH₃)₂CH₂SO₂CH₃ |
| A.1.153 | H | Br | CH₃ |
| A.1.154 | H | Br | CH₂CH₃ |
| A.1.155 | H | Br | CH(CH₃)₂ |
| A.1.156 | H | Br | cyclopropylmethyl |
| A.1.157 | H | Br | 1-methyl-1-cyclopropyl-cyclopropyl |
| A.1.158 | H | Br | C(CH₃)₂CH₂SCH₃ |
| A.1.159 | H | Br | C(CH₃)₂CH₂SOCH₃ |
| A.1.160 | H | Br | C(CH₃)₂CH₂SO₂CH₃ |
| A.1.161 | H | Cl | CH₃ |
| A.1.162 | H | Cl | CH₂CH₃ |
| A.1.163 | H | Cl | CH(CH₃)₂ |
| A.1.164 | H | Cl | cyclopropylmethyl |
| A.1.165 | H | Cl | 1-methyl-1-cyclopropyl-cyclopropyl |
| A.1.166 | H | Cl | C(CH₃)₂CH₂SCH₃ |
| A.1.167 | H | Cl | C(CH₃)₂CH₂SOCH₃ |
| A.1.168 | H | Cl | C(CH₃)₂CH₂SO₂CH₃ |
| A.1.169 | CH₃ | Cl | CH(CH₂)₂ |
| A.1.170 | CH₃ | CF₃ | CH(CH₂)₂ |
| A.1.171 | CH₃ | CHF₂ | CH₃ |
| A1.172 | CH₃ | CHF₂ | iso-propyl |

TABLE 1

This table discloses the 172 compounds T1.1.1 to T1.1.172 of formula

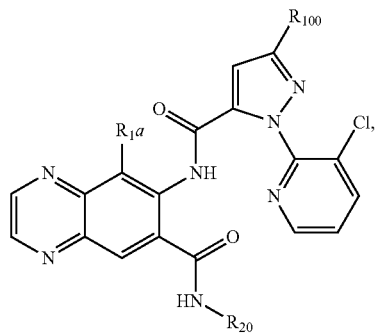

(T1)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A. For example, the specific compound T1.1.23 is the compound of formula T1, in which each of the of the variables $R_{1a}$, $R_{20}$ and $R_{100}$ has the specific meaning given in the line A.1.23 of the Table A. According to the same system, also all of the other 172 specific compounds disclosed in the Table 1 as well as all of the specific compounds disclosed in the Tables 2 to 103 are specified analogously.

TABLE 2

This table discloses the 172 compounds T2.1.1 to T2.1.172 of formula

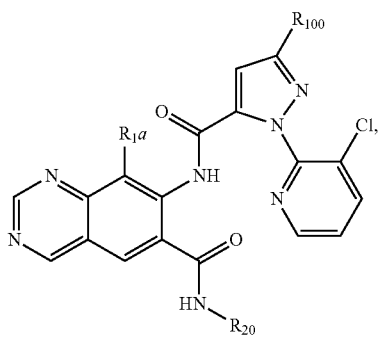

(T2)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 3

This table discloses the 172 compounds T3.1.1 to T3.1.172 of formula

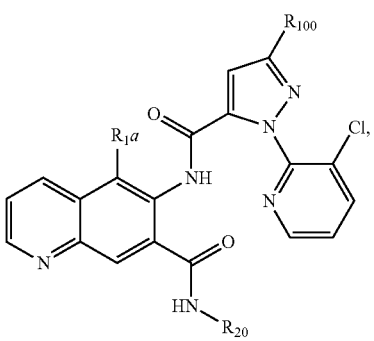

(T3)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 4

This table discloses the 172 compounds T4.1.1 to T4.1.172 of formula

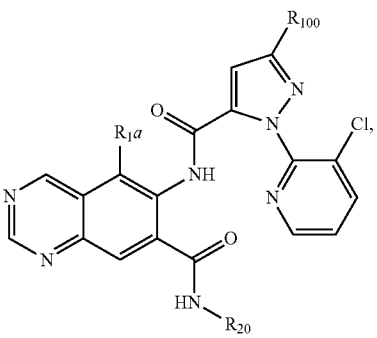

(T4)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 5

This table discloses the 172 compounds T5.1.1 to T5.1.172 of formula (T5)

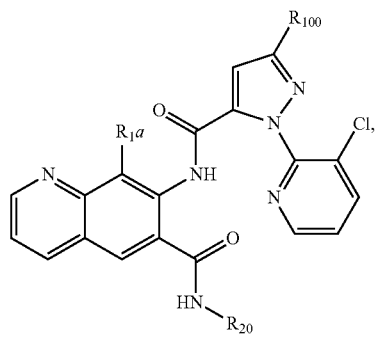

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 6

This table discloses the 172 compounds T6.1.1 to T6.1.172 of formula (T6)

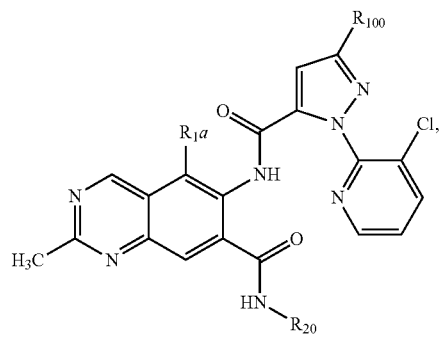

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 7

This table discloses the 172 compounds T7.1.1 to T7.1.172 of formula (T7)

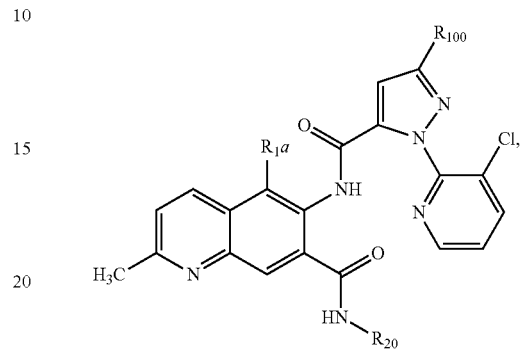

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 8

This table discloses the 172 compounds T8.1.1 to T8.1.172 of formula (T8)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 9

This table discloses the 172 compounds T9.1.1 to T9.1.172 of formula

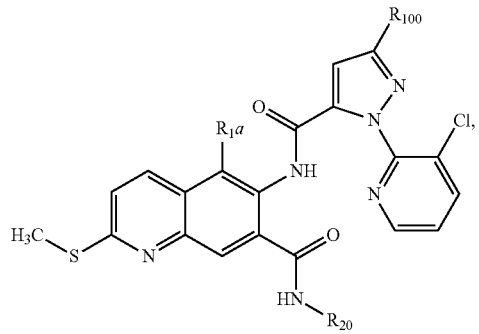

(T9)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 10

This table discloses the 172 compounds T10.1.1 to T10.1.172 of formula

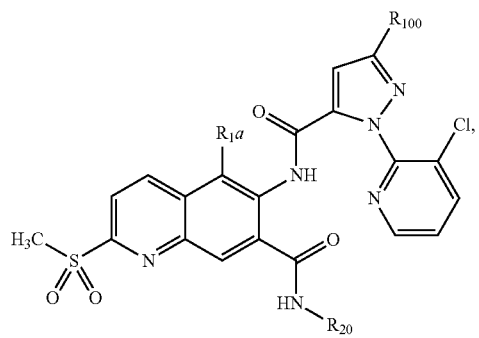

(T10)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 11

This table discloses the 172 compounds T11.1.1 to T11.1.172 of formula

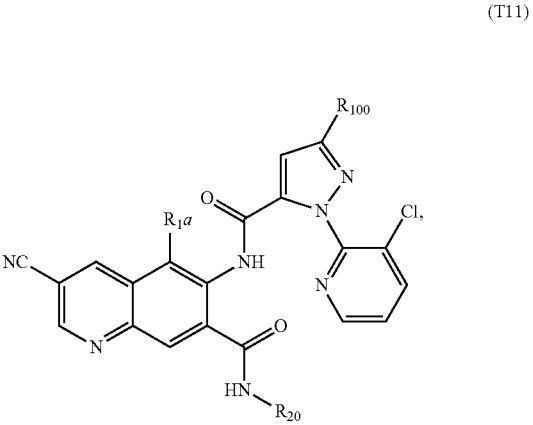

(T11)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 12

This table discloses the 172 compounds T12.1.1 to T12.1.172 of formula

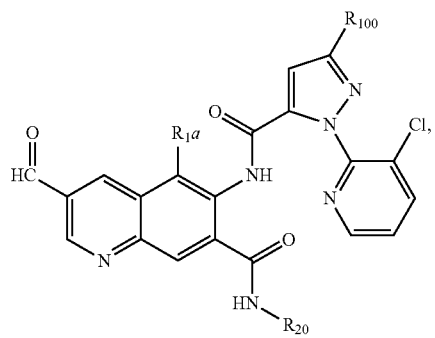

(T12)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 13

This table discloses the
172 compounds T13.1.1 to T13.1.172 of formula (T11)

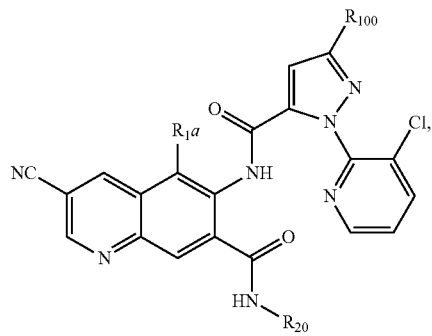

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 14

This table discloses the
172 compounds T14.1.1 to T14.1.172 of formula (T12)

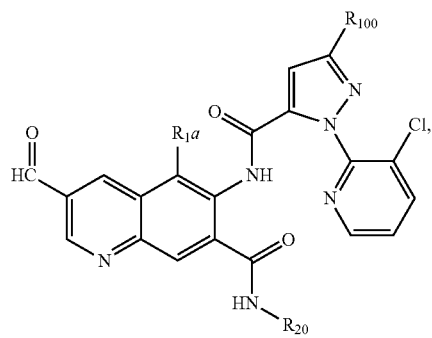

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 15

This table discloses the
172 compounds T15.1.1 to T15.1.172 of formula (T15)

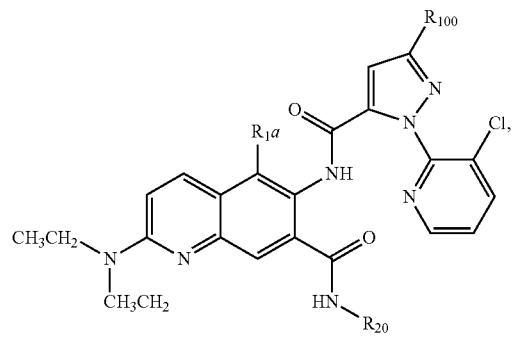

in which, for each of these 172 specific compounds, each of the of the variables $R_{1a}$, A20 and $R_{100}$ has the specific meaning given in the corresponding line, appropriately selected from the 172 lines A.1.1 to A.1.172 of the Table A.

TABLE 16

This table discloses the
172 compounds T16.1.1 to T16.1.172 of formula (T16)

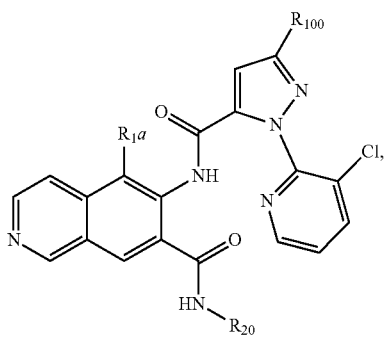

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 17

This table discloses the 172 compounds T17.1.1 to T17.1.172 of formula

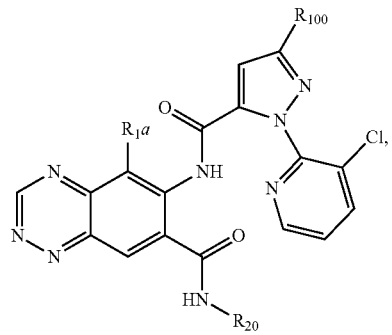

(T17)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 18

This table discloses the 172 compounds T18.1.1 to T18.1.172 of formula

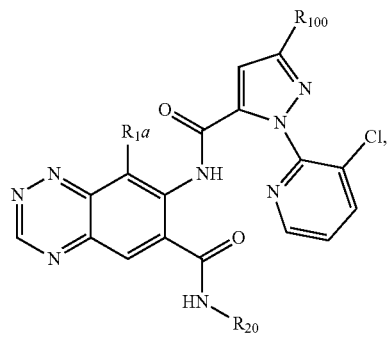

(T18)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 19

This table discloses the 172 compounds T19.1.1 to T19.1.172 of formula

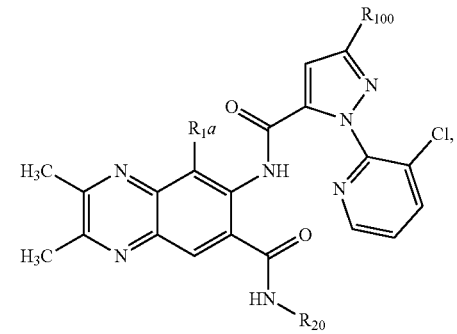

(T19)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 20

This table discloses the 172 compounds T20.1.1 to T20.1.172 of formula

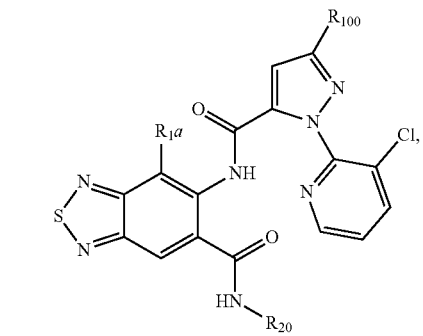

(T20)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 21

This table discloses the
172 compounds T21.1.1 to T21.1.172 of formula (T21)

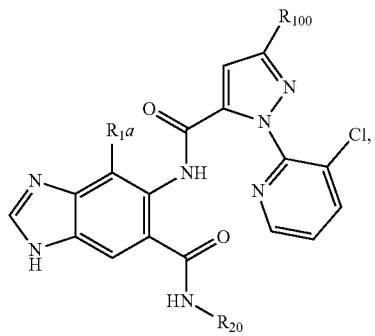

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 22

This table discloses the
172 compounds T22.1.1 to T22.1.172 of formula (T22)

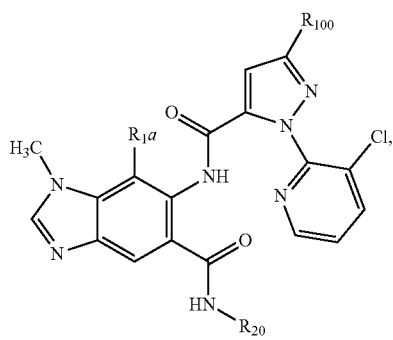

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 23

This table discloses the
172 compounds T23.1.1 to T23.1.172 of formula (T23)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 24

This table discloses the
172 compounds T24.1.1 to T24.1.172 of formula (T24)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 25

This table discloses the 172 compounds T25.1.1 to T25.1.172 of formula (T25)

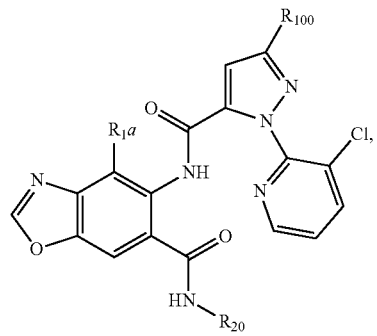

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 26

This table discloses the 172 compounds T26.1.1 to T26.1.172 of formula (T26)

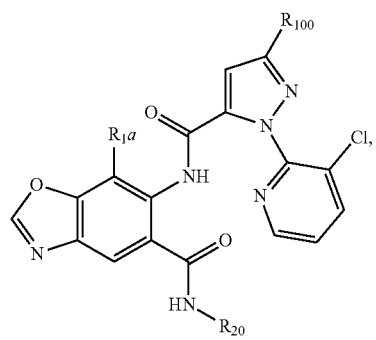

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 27

This table discloses the 172 compounds T27.1.1 to T27.1.172 of formula (T27)

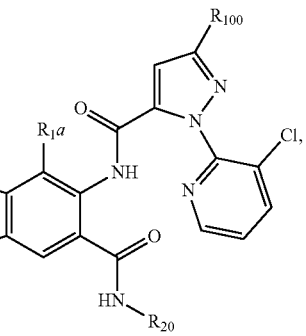

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 28

This table discloses the 172 compounds T28.1.1 to T28.1.172 of formula (T28)

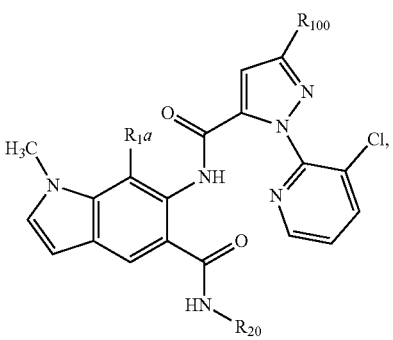

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 29

This table discloses the 172 compounds T29.1.1 to T29.1.172 of formula

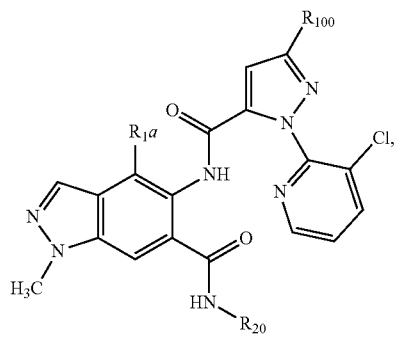

(T29)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 30

This table discloses the 172 compounds T30.1.1 to T30.1.172 of formula

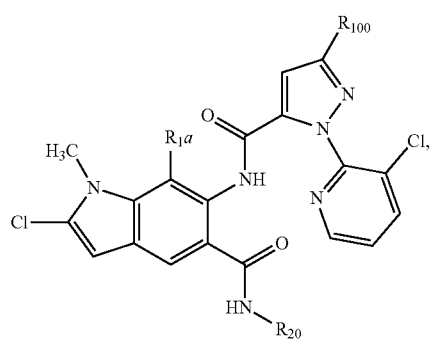

(T30)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 31

This table discloses the 172 compounds T31.1.1 to T31.1.172 of formula

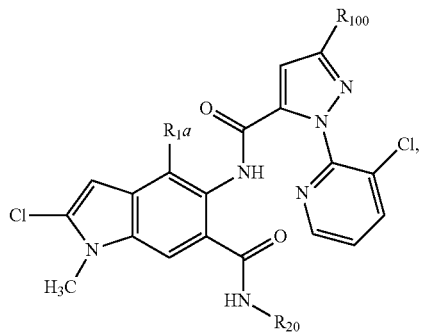

(T31)

in which, for each of these 172 specific compounds, each of the variables $R_{1a}$, $R_{20}$ and $R_{100}$ has the specific meaning given in the corresponding line, appropriately selected from the 172 lines A.1.1 to A.1.172 of the Table A.

TABLE 32

This table discloses the 172 compounds T32.1.1 to T32.1.172 of formula

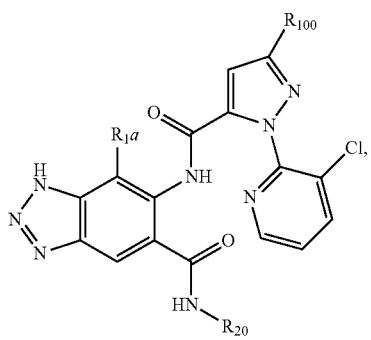

(T32)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 33

This table discloses the 172 compounds T33.1.1 to T33.1.172 of formula

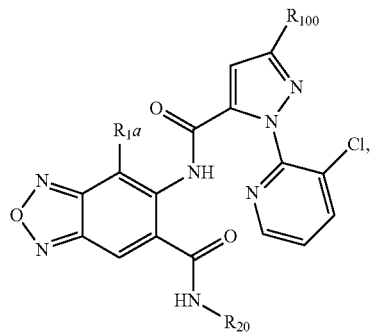

(T33)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 34

This table discloses the 172 compounds T34.1.1 to T34.1.172 of formula

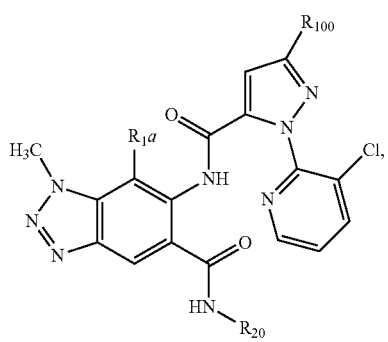

(T34)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 35

This table discloses the 172 compounds T35.1.1 to T35.1.172 of formula

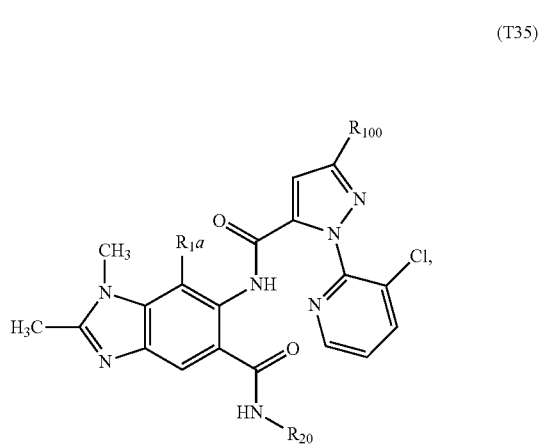

(T35)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 36

This table discloses the 172 compounds T36.1.11 to T36.1.172 of formula

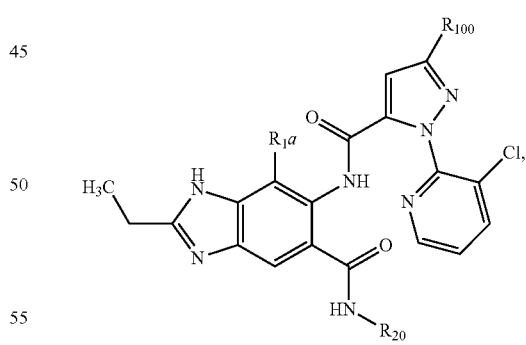

(T36)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 37

This table discloses the 172 compounds T37.1.1 to T37.1.172 of formula (T37)

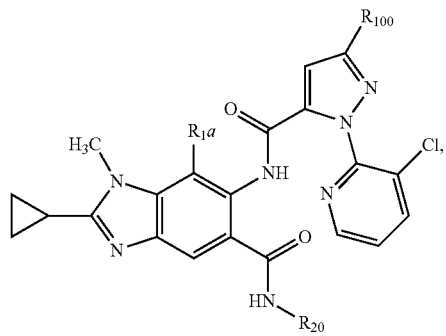

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 38

This table discloses the 172 compounds T38.1.1 to T38.1.172 of formula (T38)

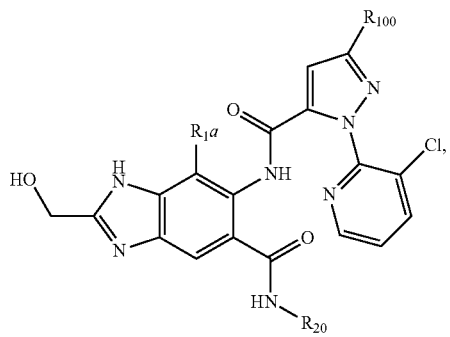

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 39

This table discloses the 172 compounds T39.1.1 to T39.1.172 of formula (T39)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 40

This table discloses the 172 compounds T40.1.1 to T40.1.172 of formula (T40)

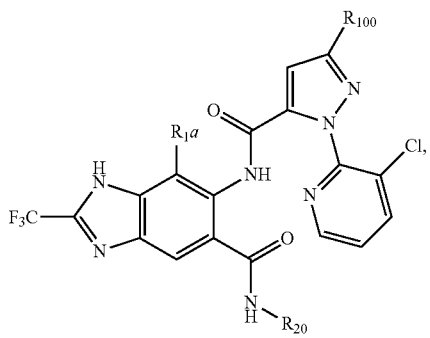

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 41

This table discloses the 172 compounds T41.1.1 to T41.1.172 of formula

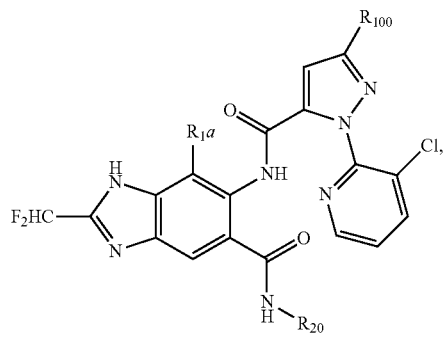

(T41)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 42

This table discloses the 172 compounds T42.1.1 to T42.1.172 of formula

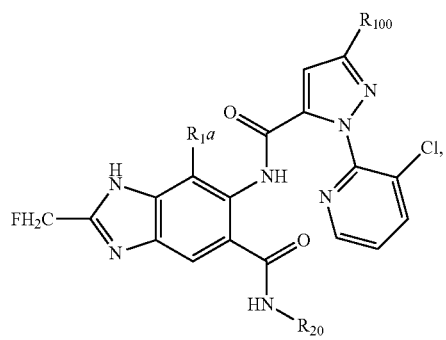

(T42)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 43

This table discloses the 172 compounds T43.1.1 to T43.1.172 of formula

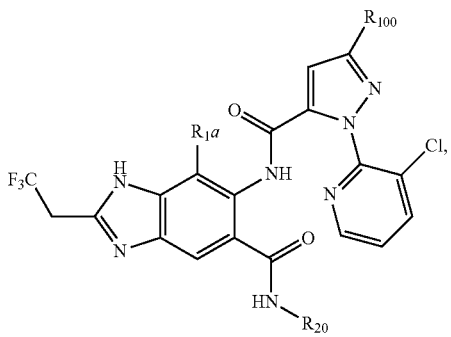

(T43)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 44

This table discloses the 172 compounds T44.1.1 to T44.1.172 of formula

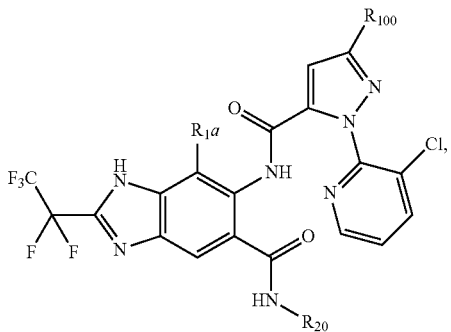

(T44)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 45

This table discloses the 172 compounds T45.1.1 to T45.1.172 of formula (T45)

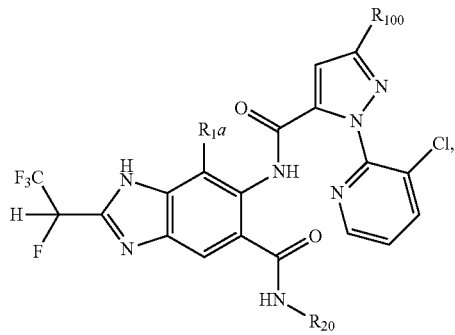

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 46

This table discloses the 172 compounds T46.1.1 to T46.1.172 of formula (T46)

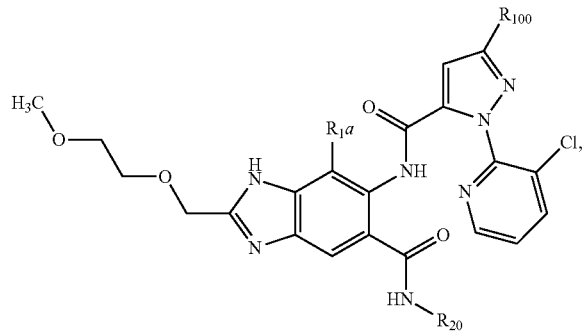

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 47

This table discloses the 172 compounds T47.1.1 to T47.1.172 of formula (T47)

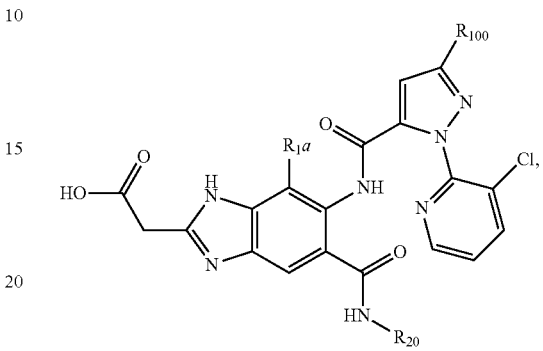

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 48

This table discloses the 172 compounds T48.1.1 to T48.1.172 of formula (T48)

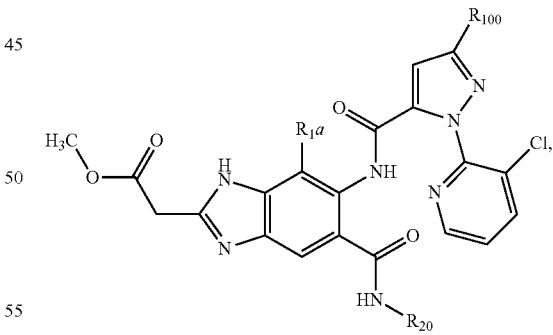

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 49

This table discloses the 172 compounds T49.1.1 to T49.1.172 of formula

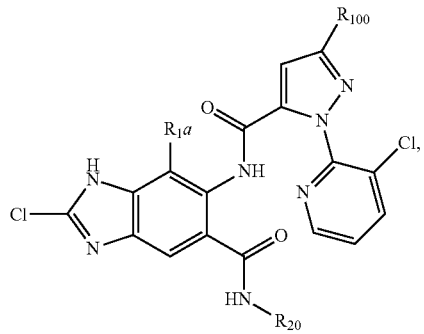

(T49)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 50

This table discloses the 172 compounds T50.1.1 to T50.1.172 of formula

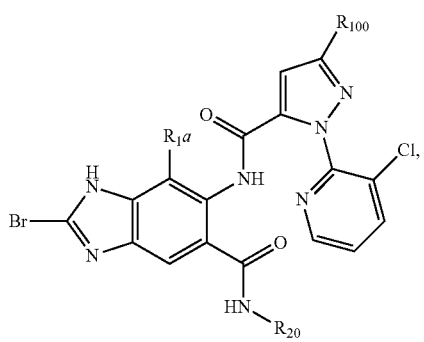

(T50)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 51

This table discloses the 172 compounds T51.1.1 to T51.1.172 of formula

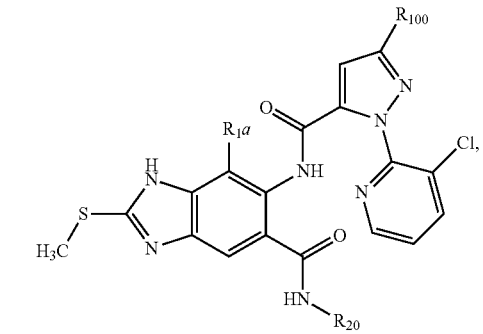

(T51)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 52

This table discloses the 172 compounds T52.1.1 to T52.1.172 of formula

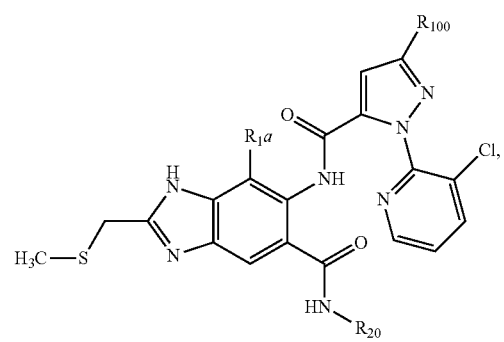

(T52)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 53

This table discloses the 172 compounds T53.1.1 to T53.1.172 of formula (T53)

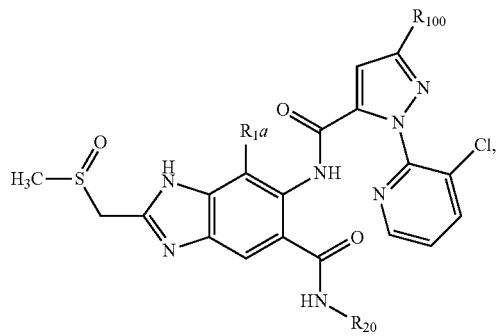

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 54

This table discloses the 172 compounds T54.1.1 to T54.1.172 of formula (T54)

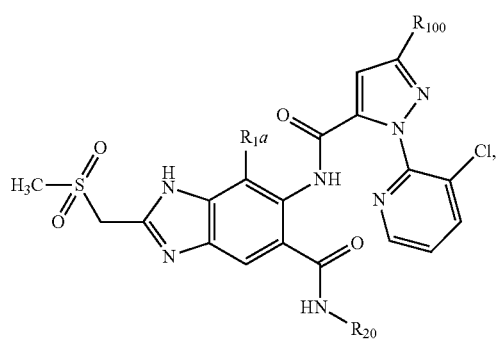

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 55

This table discloses the 172 compounds T55.1.1 to T55.1.172 of formula (T55)

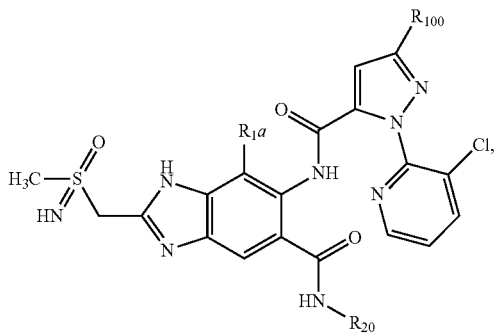

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 56

This table discloses the 172 compounds T56.1.1 to T56.1.172 of formula (T56)

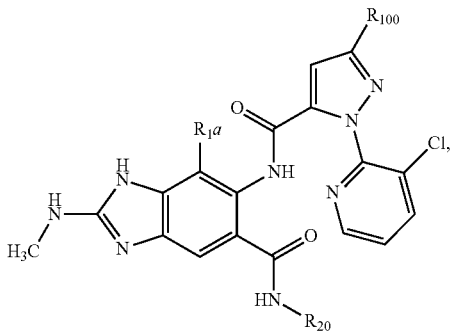

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 57

This table discloses the 172 compounds T57.1.1 to T57.1.172 of formula

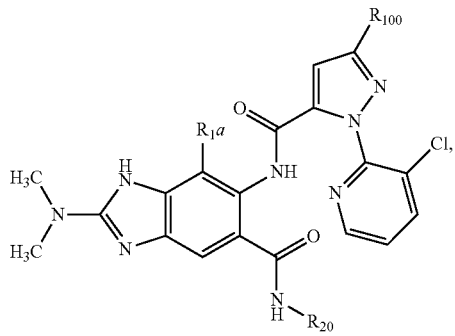

(T57)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 58

This table discloses the 172 compounds T58.1.1 to T58.1.172 of formula

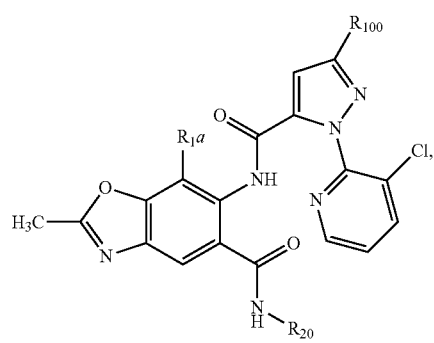

(T58)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 59

This table discloses the 172 compounds T59.1.1 to T59.1.172 of formula

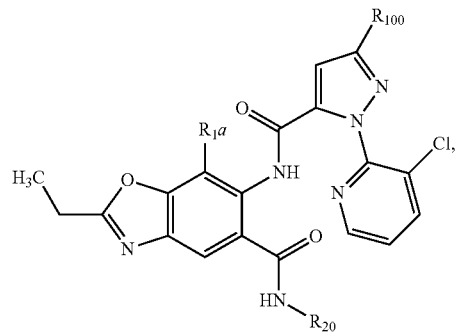

(T59)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 60

This table discloses the 172 compounds T60.1.1 to T60.1.172 of formula

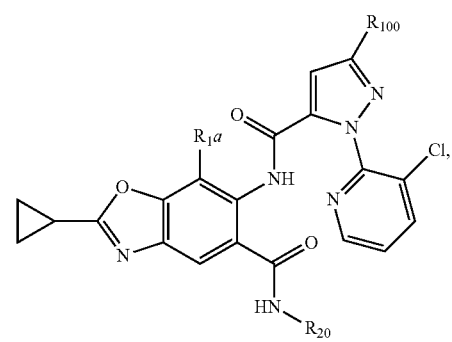

(T60)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 61

This table discloses the
172 compounds T61.1.1 to T61.1.172 of formula

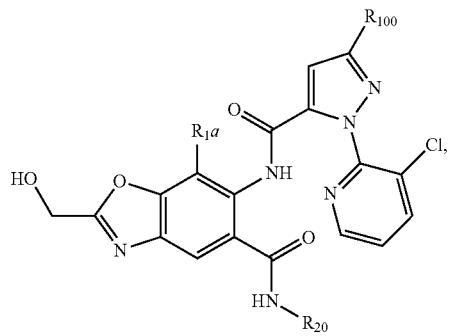

(T61)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 62

This table discloses the
172 compounds T62.1.1 to T62.1.172 of formula

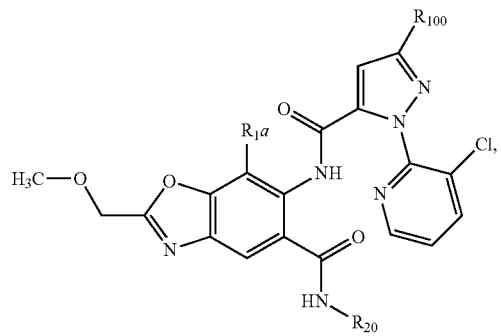

(T62)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 63

This table discloses the
172 compounds T63.1.1 to T63.1.172 of formula

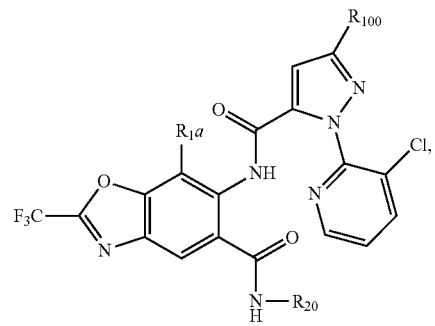

(T63)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 64

This table discloses the
172 compounds T64.1.1 to T64.1.172 of formula (T64)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 65

This table discloses the
172 compounds T65.1.1 to T65.1.172 of formula (T65)

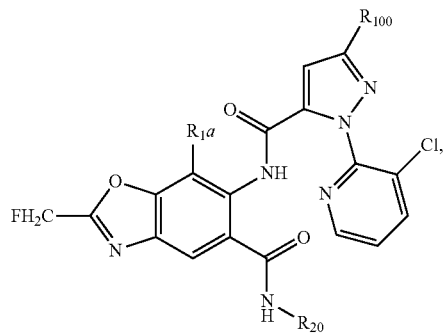

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 66

This table discloses the
172 compounds T66.1.1 to T66.1.172 of formula (T66)

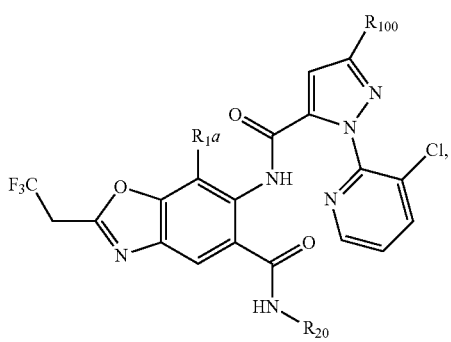

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 67

This table discloses the
172 compounds T67.1.1 to T67.1.172 of formula (T67)

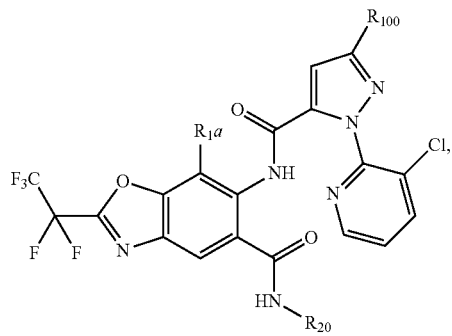

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 68

This table discloses the
172 compounds T68.1.1 to T68.1.172 of formula (T68)

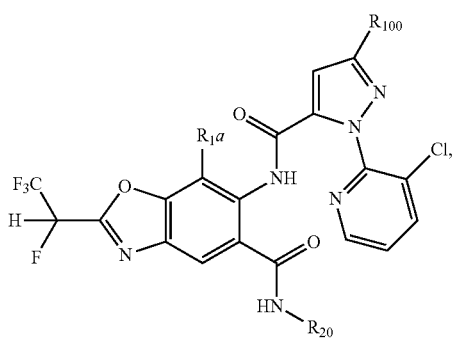

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 69

This table discloses the 172 compounds T69.1.1 to T69.1.172 of formula (T69)

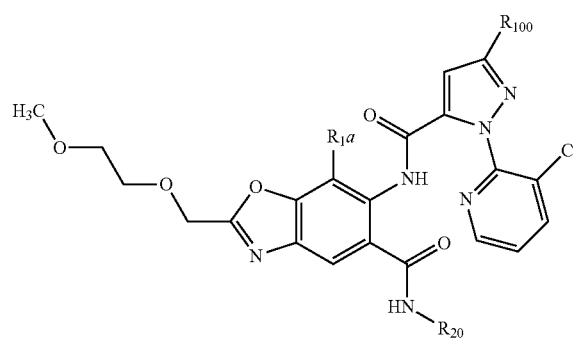

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 70

This table discloses the 172 compounds T70.1.1 to T70.1.172 of formula (T70)

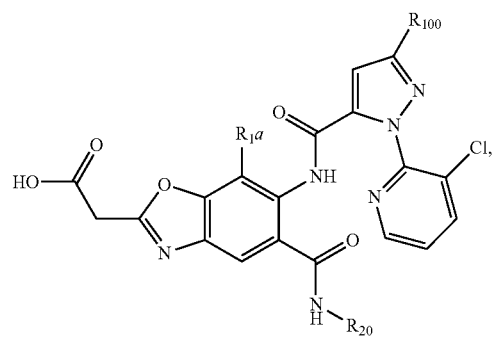

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 71

This table discloses the 172 compounds T71.1.1 to T71.1.172 of formula (T71)

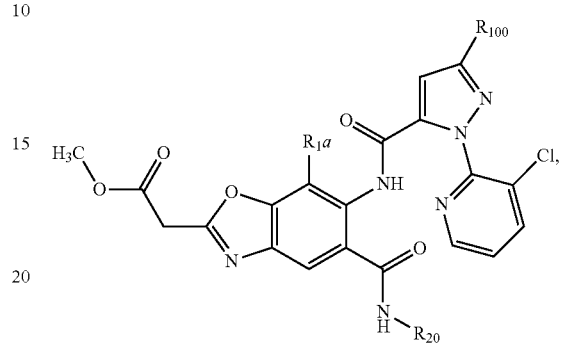

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 72

This table discloses the 172 compounds T72.1.1 to T72.1.172 of formula (T72)

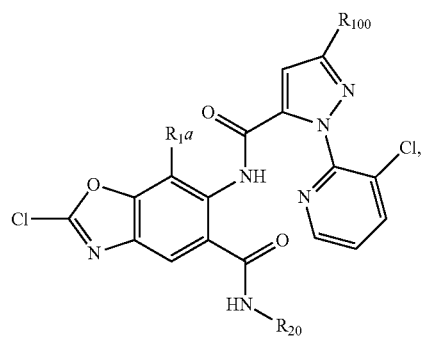

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 73

This table discloses the
172 compounds T73.1.1 to T73.1.172 of formula (T73)

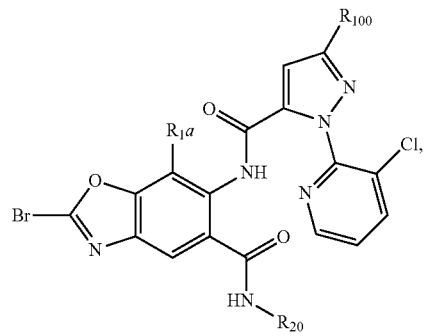

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 74

This table discloses the
172 compounds T74.1.1 to T74.1.172 of formula (T74)

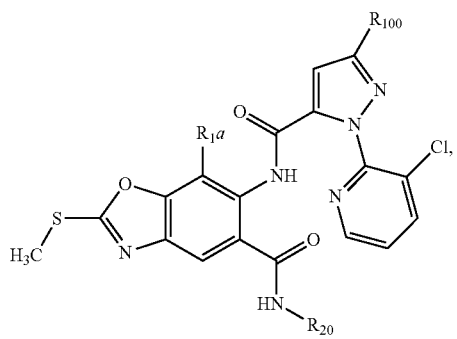

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 75

This table discloses the
172 compounds T75.1.1 to T75.1.172 of formula (T75)

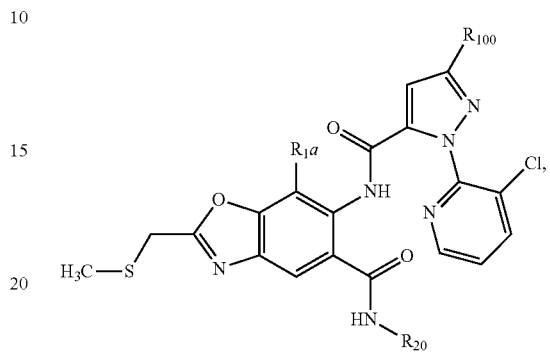

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 76

This table discloses the
172 compounds T76.1.1 to T76.1.172 of formula (T76)

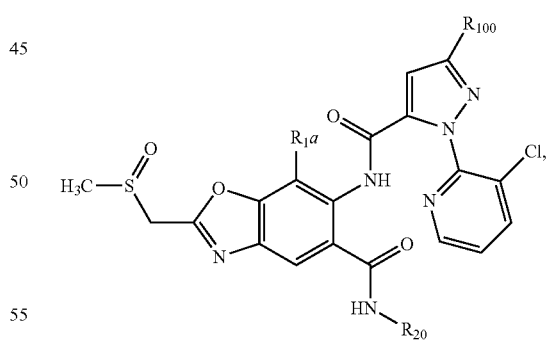

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 77

This table discloses the
172 compounds T77.1.1 to T77.1.172 of formula (T77)

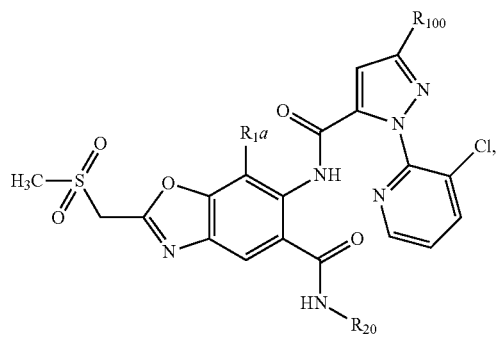

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 78

This table discloses the
172 compounds T78.1.1 to T78.1.172 of formula (T78)

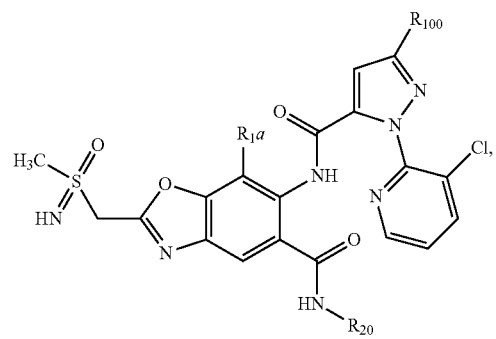

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 79

This table discloses the
172 compounds T79.1.1 to T79.1.172 of formula (T79)

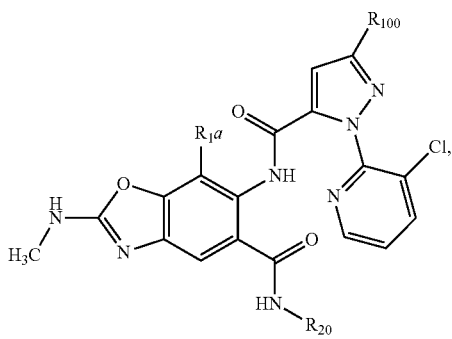

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 80

This table discloses the
172 compounds T80.1.1 to T80.1.172 of formula (T80)

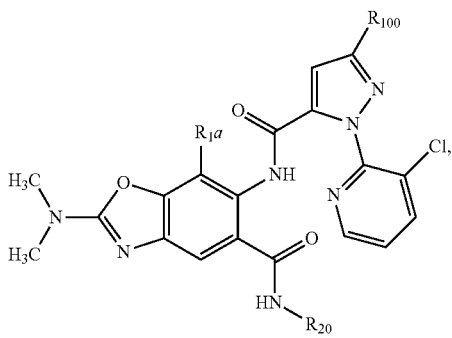

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 81

This table discloses the
172 compounds T81.1.1 to T81.1.172 of formula (T81)

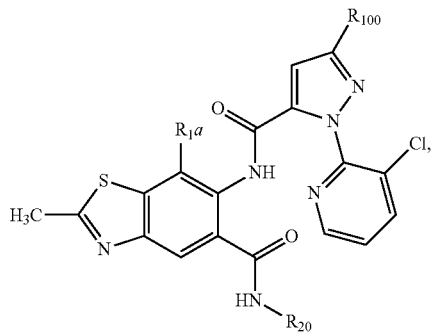

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 82

This table discloses the
172 compounds T82.1.1 to T82.1.172 of formula (T82)

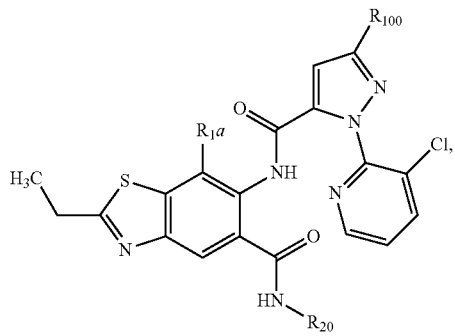

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 83

This table discloses the
172 compounds T83.1.1 to T83.1.172 of formula (T83)

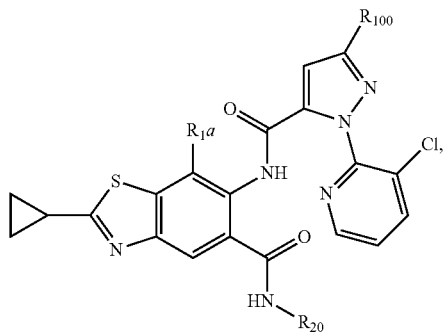

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 84

This table discloses the
172 compounds T84.1.1 to T84.1.172 of formula (T84)

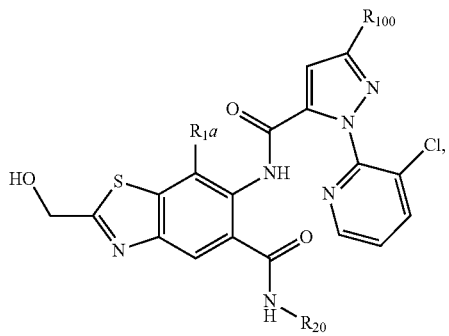

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 85

This table discloses the
172 compounds T85.1.1 to T85.1.172 of formula (T85)

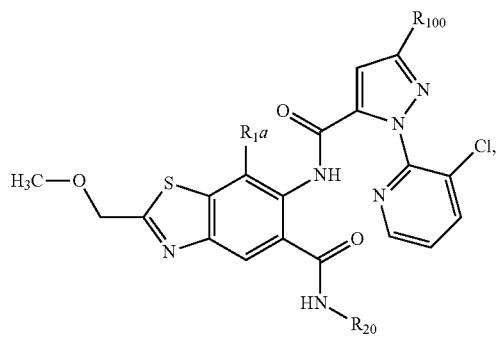

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 86

This table discloses the
172 compounds T86.1.1 to T86.1.172 of formula (T86)

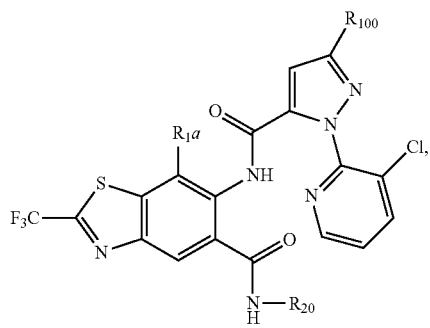

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 87

This table discloses the
172 compounds T87.1.1 to T87.1.172 of formula (T87)

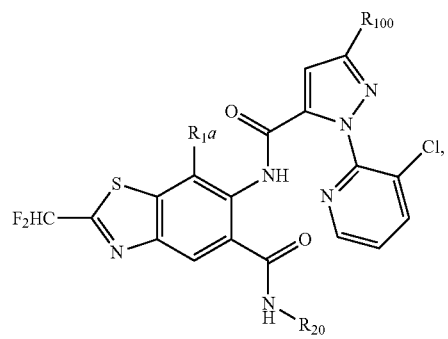

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 88

This table discloses the
172 compounds T88.1.1 to T88.1.172 of formula (T88)

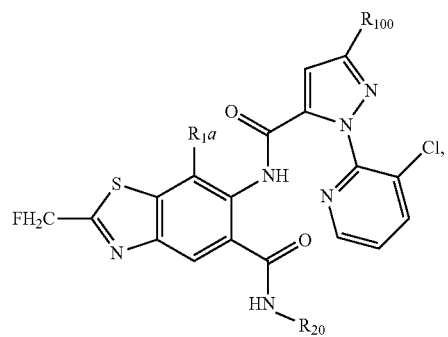

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 89

This table discloses the 172 compounds T89.1.1 to T89.1.172 of formula (T89)

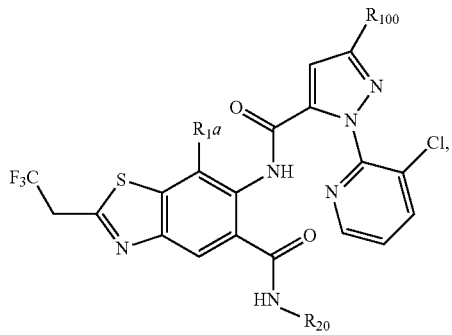

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 90

This table discloses the 172 compounds T90.1.1 to T90.1.172 of formula (T90)

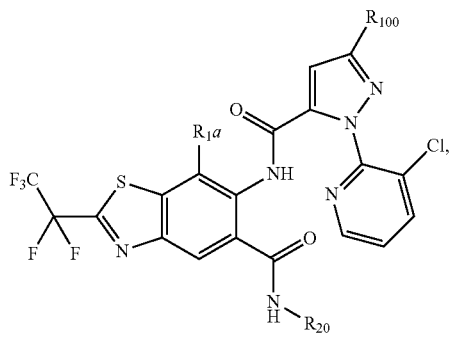

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 91

This table discloses the 172 compounds T91.1.1 to T91.1.172 of formula (T91)

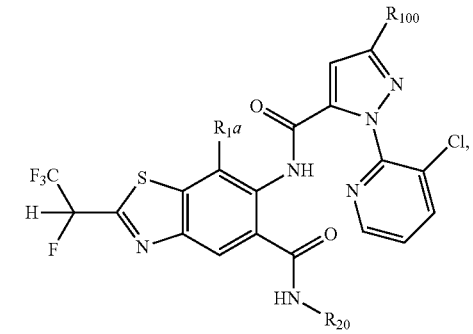

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 92

This table discloses the 172 compounds T92.1.1 to T92.1.172 of formula (T92)

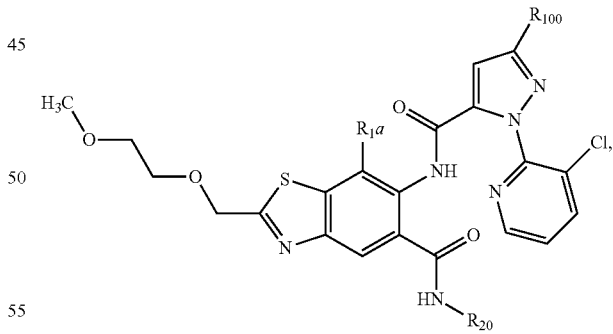

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 93

This table discloses the
172 compounds T93.1.1 to T93.1.172 of formula

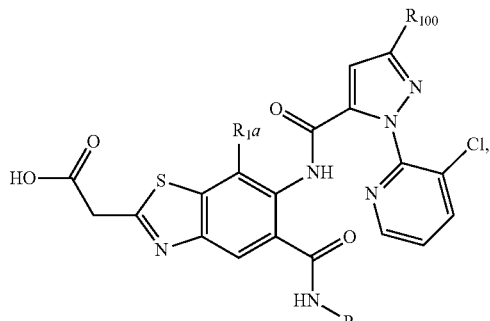

(T93)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 94

This table discloses the
172 compounds T94.1.1 to T94.1.172 of formula

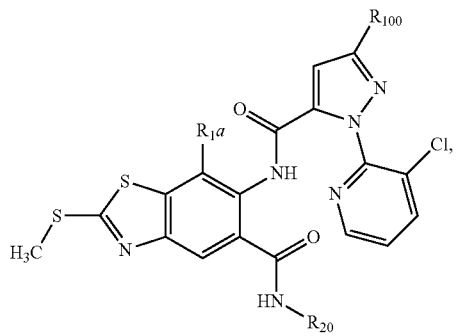

(T94)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 95

This table discloses the
172 compounds T95.1.1 to T95.1.172 of formula

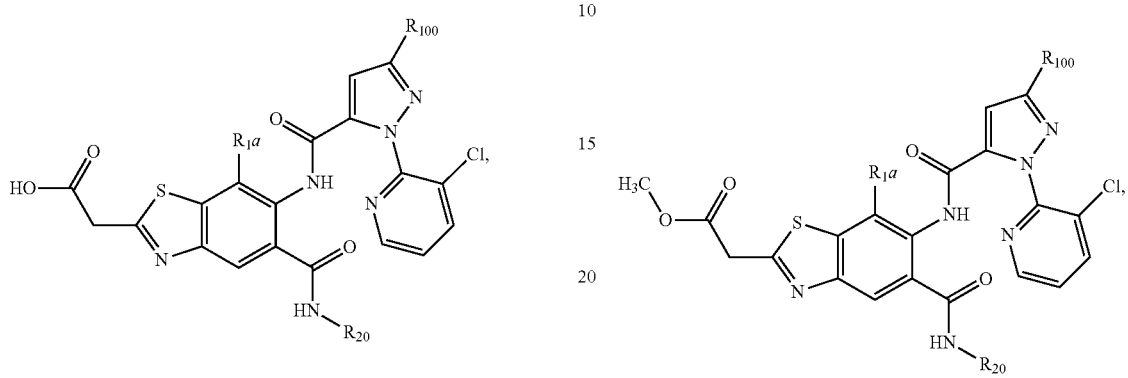

(T95)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 96

This table discloses the
172 compounds T96.1.1 to T96.1.172 of formula

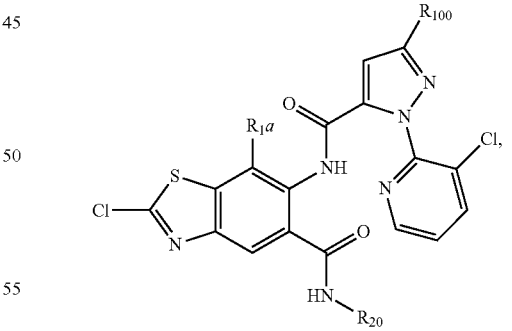

(T96)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 97

This table discloses the 172 compounds T97.1.1 to T97.1.172 of formula

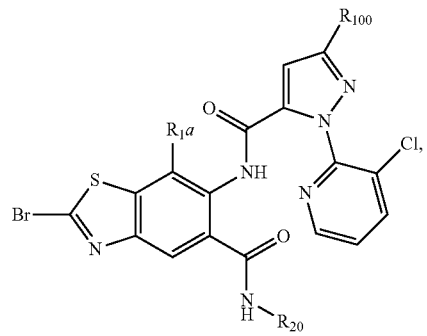

(T97)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 98

This table discloses the 172 compounds T98.1.1 to T98.1.172 of formula

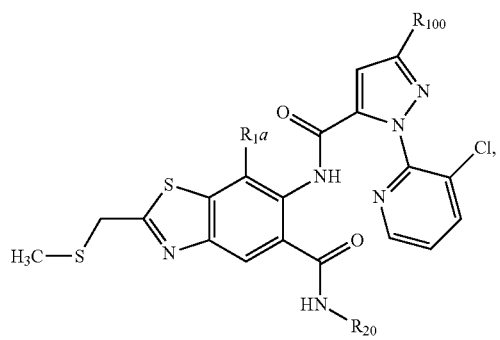

(T98)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 99

This table discloses the 172 compounds T99.1.1 to T99.1.172 of formula

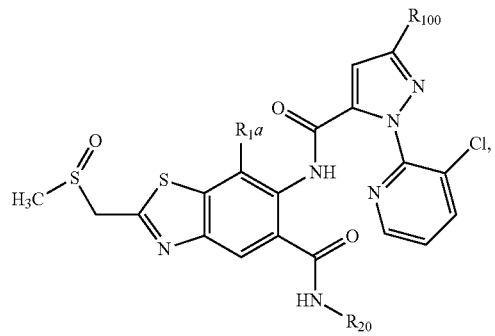

(T99)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 100

This table discloses the 172 compounds T100.1.1 to T100.1.172 of formula (T100)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 101

This table discloses the 172 compounds T101.1.1 to T101.1.172 of formula

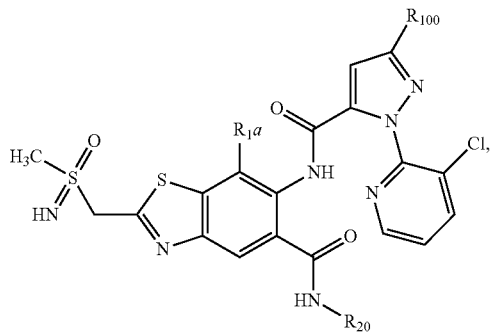

(T101)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 102

This table discloses the 172 compounds T102.1.1 to T102.1.172 of formula

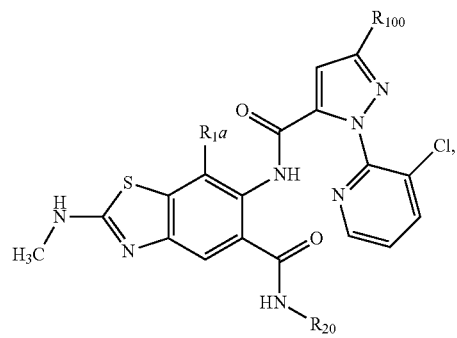

(T102)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 103

This table discloses the 172 compounds T103.1.1 to T103.1.172 of formula

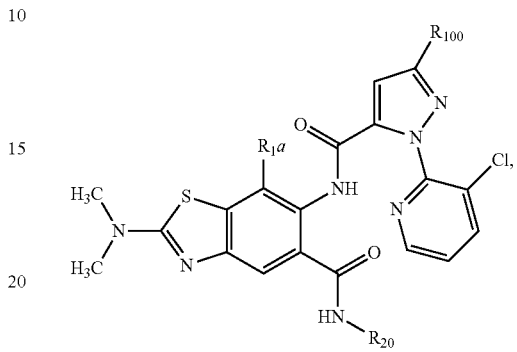

(T103)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 104

This table discloses the 172 compounds T104.1.1 to T104.1.172 of formula

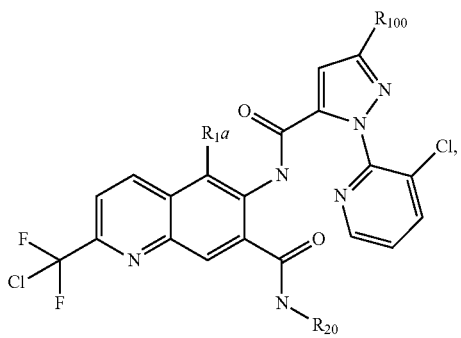

(T104)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 105

This table discloses the 172 compounds T105.1.1 to T105.1.172 of formula

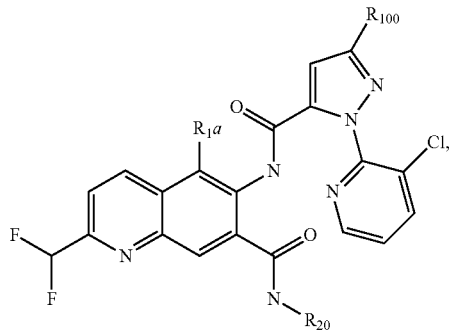

(T105)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 106

This table discloses the 172 compounds T106.1.1 to T106.1.172 of formula

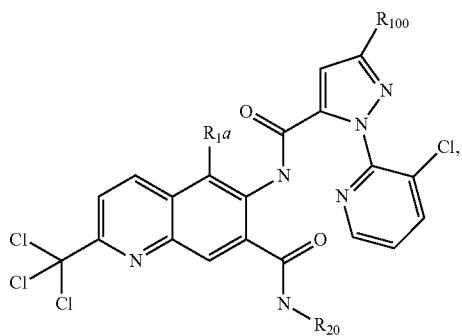

(T106)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 107

This table discloses the 172 compounds T107.1.1 to T107.1.172 of formula

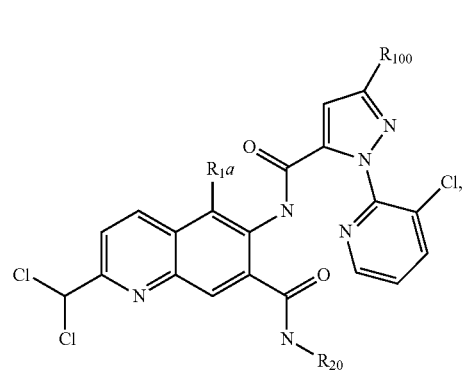

(T107)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 108

This table discloses the 172 compounds T108.1.1 to T108.1.172 of formula

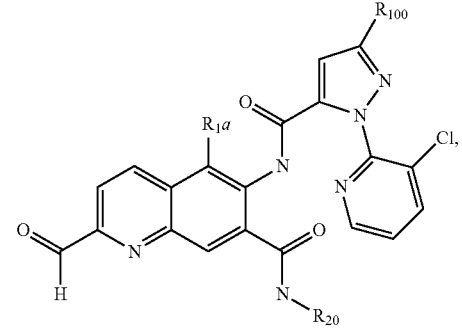

(T108)

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 109

This table discloses the 172 compounds T109.1.1 to T109.1.172 of formula (T109)

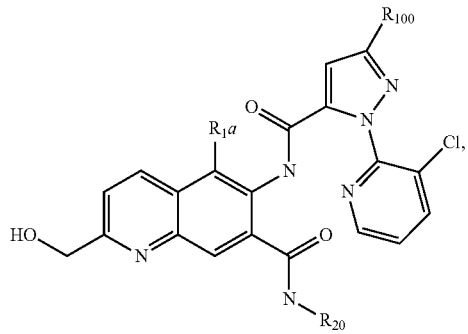

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 110

This table discloses the 172 compounds T110.1.1 to T109.1.172 of formula (T110)

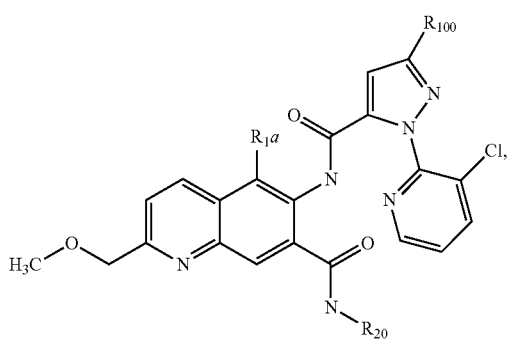

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 111

This table discloses the 172 compounds T111.1.1 to T111.1.172 of formula (T111)

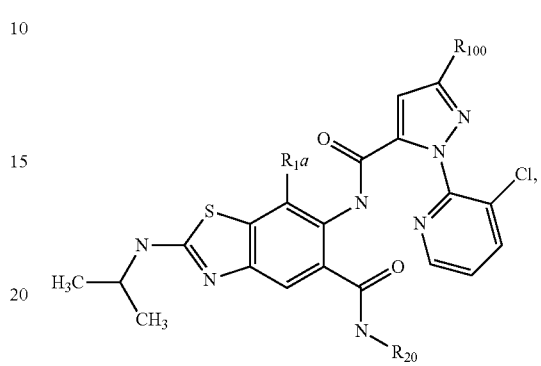

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 112

This table discloses the 172 compounds T112.1.1 to T112.1.172 of formula (T112)

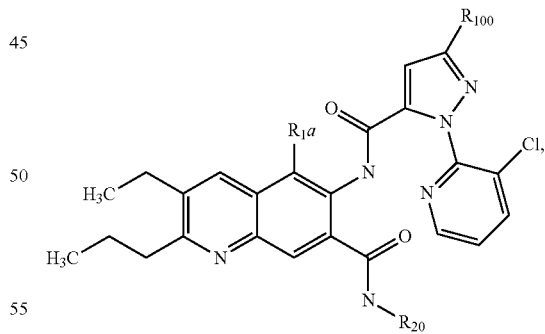

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 113

This table discloses the 172 compounds T113.1.1 to T113.1.172 of formula (T113)

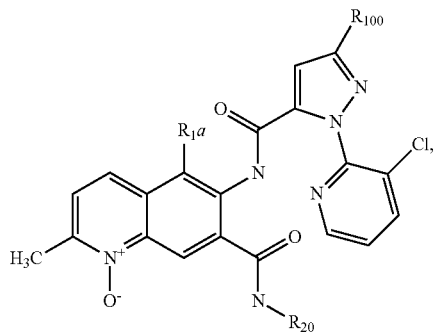

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 114

This table discloses the 172 compounds T114.1.1 to T114.1.172 of formula (T114)

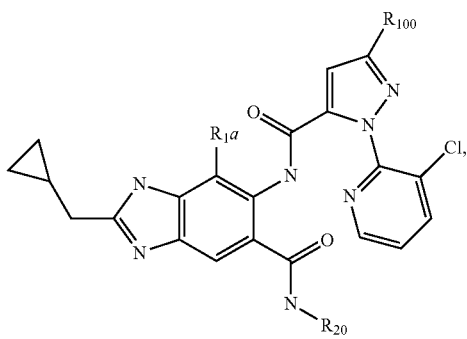

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 115

This table discloses the 172 compounds T115.1.1 to T115.1.172 of formula (T115)

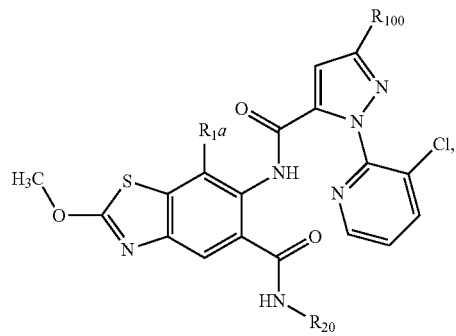

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 116

This table discloses the 172 compounds T116.1.1 to T116.1.172 of formula (T116)

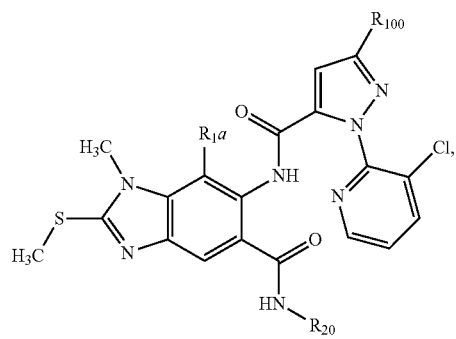

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 117

This table discloses the 172 compounds T117.1.1 to T117.1.172 of formula (T117)

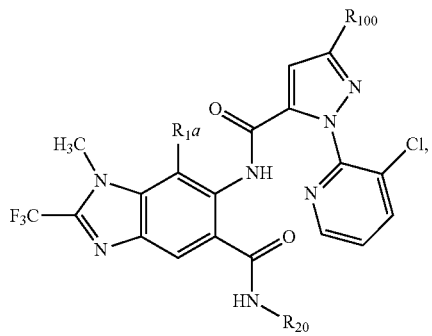

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 118

This table discloses the 172 compounds T118.1.1 to T118.1.172 of formula (T118)

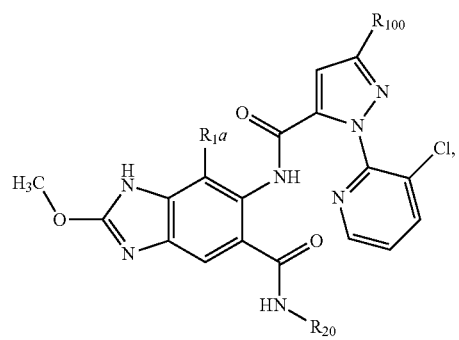

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 119

This table discloses the 172 compounds T119.1.1 to T119.1.172 of formula (T119)

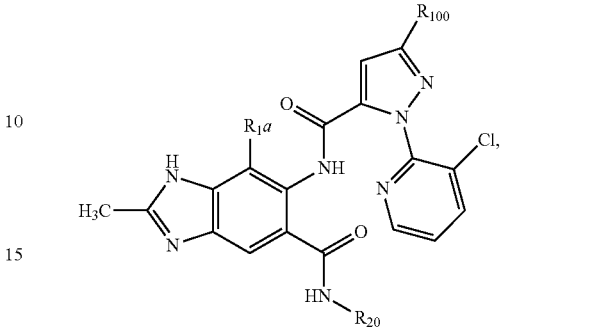

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

TABLE 120

This table discloses the 172 compounds T120.1.1 to T120.1.172 of formula (T120)

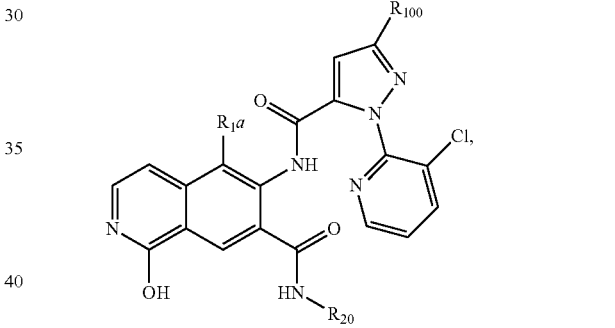

in which, for each of these 172 specific compounds, each of the of the variables $R_{1a}$, $R_{20}$ and $R_{100}$ has the specific meaning given in the corresponding line, appropriately selected from the 172 lines A.1.1 to A.1.172 of the Table A.

FORMULATION EXAMPLES

%=Percent by Weight

Example F1

Emulsion Concentrates

| | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

Example F2

Solutions

|  | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

Example F3

Granules

|  | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

Example F4

Dusts

|  | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

Example F5

Wettable Powders

|  | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

Example F6

Extruder Granules

| Active ingredient | 10% |
|---|---|
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

Example F7

Coated Granules

| Active ingredient | 3% |
|---|---|
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

Example F8

Suspension Concentrate

| Active ingredient | 40% |
|---|---|
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridyl-methyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds of formulae T1 to T120 described in Tables 1 to 120 of the present invention"):

an adjuvant selected from the group of substances consisting of petroleum oils (alternative name) (628) and TX, an acaricide selected from the group of substances consisting of 1,1-bis(4-chlorophenyl)-2-ethoxyethanol (IUPAC name) (910) and TX, 2,4-dichlorophenyl benzenesulfonate (IUPAC/Chemical Abstracts name) (1059) and TX, 2-fluoro-N-methyl-N-1-naphthylacetamide (IUPAC name) (1295) and TX, 4-chlorophenyl phenyl sulfone (IUPAC name) (981) and TX, abamectin (1) and TX, acequinocyl (3) and TX, acetoprole [CCN] and TX, acrinathrin (9) and TX, aldicarb (16) and TX, aldoxycarb (863) and TX, alpha-cypermethrin (202) and TX, amidithion (870) and TX, amidoflumet [CCN] and TX, amidothioate (872) and TX, amiton (875) and TX, amiton hydrogen oxalate (875) and TX, amitraz (24) and TX, aramite (881) and TX, arsenous oxide (882) and TX, AVI 382 (compound code) and TX, AZ 60541 (compound code) and TX, azinphos-ethyl (44) and TX, azinphos-methyl (45) and TX, azobenzene (IUPAC name) (888) and TX, azocyclotin (46) and TX, azothoate (889) and TX, benomyl (62) and TX, benoxafos (alternative name) [CCN] and TX, benzoximate (71) and TX, benzyl benzoate (IUPAC name) [CCN] and TX, bifenazate (74) and TX, bifenthrin (76) and TX, binapacryl (907) and TX, brofenvalerate (alternative name) and TX, bromocyclen (918) and TX, bromophos (920) and TX, bromophos-ethyl (921) and TX, bromopropylate (94) and TX, buprofezin (99) and TX, butocarboxim (103) and TX, butoxycarboxim (104) and TX, butylpyridaben (alternative name) and TX, calcium polysulfide (IUPAC name) (111) and TX, camphechlor (941) and TX, carbanolate (943) and TX, carbaryl (115) and TX, carbofuran (118) and TX, carbophenothion (947) and TX, CGA 50'439 (development code) (125) and TX, chinomethionat (126) and TX, chlorbenside (959) and TX, chlordimeform (964) and TX, chlordimeform hydrochloride (964) and TX, chlorfenapyr (130) and TX, chlorfenethol (968) and TX, chlorfenson (970) and TX, chlorfensulphide (971) and TX, chlorfenvinphos (131) and TX, chlorobenzilate (975) and TX, chloromebuform (977) and TX, chloromethiuron (978) and TX, chloropropylate (983) and TX, chlorpyrifos (145) and TX, chlorpyrifos-methyl (146) and TX, chlorthiophos (994) and TX, cinerin I (696) and TX, cinerin II (696) and TX, cinerins (696) and TX, clofentezine (158) and TX, closantel (alternative name) [CCN] and TX, coumaphos (174) and TX, crotamiton (alternative name) [CCN] and TX, crotoxyphos (1010) and TX, cufraneb (1013) and TX, cyanthoate (1020) and TX, cyflumetofen (CAS Reg. No.: 400882-07-7) and TX, cyhalothrin (196) and TX, cyhexatin (199) and TX, cypermethrin (201) and TX, DCPM (1032) and TX, DDT (219) and TX, demephion (1037) and TX, demephion-O (1037) and TX, demephion-S (1037) and TX, demeton (1038) and TX, demeton-methyl (224) and TX, demeton-O (1038) and TX, demeton-O-methyl (224) and TX, demeton-S (1038) and TX, demeton-S-methyl (224) and TX, demeton-S-methylsulphon (1039) and TX, diafenthiuron (226) and TX, dialifos (1042) and TX, diazinon (227) and TX, dichlofluanid (230) and TX, dichlorvos (236) and TX, dicliphos (alternative name) and TX, dicofol (242) and TX, dicrotophos (243) and TX, dienochlor (1071) and TX, dimefox (1081) and TX, dimethoate (262) and TX, dinactin (alternative name) (653) and TX, dinex (1089) and TX, dinex-diclexine (1089) and TX, dinobuton (269) and TX, dinocap (270) and TX, dinocap-4 [CCN] and TX, dinocap-6 [CCN] and TX, dinocton (1090) and TX, dinopenton (1092) and TX, dinosulfon (1097) and TX, dinoterbon (1098) and TX, dioxathion (1102) and TX, diphenyl sulfone (IUPAC name) (1103) and TX, disulfiram (alternative name) [CCN] and TX, disulfoton (278) and TX, DNOC (282) and TX, dofenapyn (1113) and TX, doramectin (alternative name) [CCN] and TX, endosulfan (294) and TX, endothion (1121) and TX, EPN (297) and TX, eprinomectin (alternative name) [CCN] and TX, ethion (309) and TX, ethoate-methyl (1134) and TX, etoxazole (320) and TX, etrimfos (1142) and TX, fenazaflor (1147) and TX, fenazaquin (328) and TX, fenbutatin oxide (330) and TX, fenothiocarb (337) and TX, fenpropathrin (342) and TX, fenpyrad (alternative name) and TX, fenpyroximate (345) and TX, fenson (1157) and TX, fentrifanil (1161) and TX, fenvalerate (349) and TX, fipronil (354) and TX, fluacrypyrim (360) and TX, fluazuron (1166) and TX, flubenzimine (1167) and TX, flucycloxuron (366) and TX, flucythrinate (367) and TX, fluenetil (1169) and TX, flufenoxuron (370) and TX, flumethrin (372) and TX, fluorbenside (1174) and TX, fluvalinate (1184) and TX, FMC 1137 (development code) (1185) and TX, formetanate (405) and TX, formetanate hydrochloride (405) and TX, formothion (1192) and TX, formparanate (1193) and TX, gamma-HCH (430) and TX, glyodin (1205) and TX, halfenprox (424) and TX, heptenophos (432) and TX, hexadecyl cyclopropanecarboxylate (IUPAC/Chemical Abstracts name) (1216) and TX, hexythiazox (441) and TX, iodomethane (IUPAC name) (542) and TX, isocarbophos (alternative name) (473) and TX, isopropyl O-(methoxyaminothiophosphoryl)salicylate (IUPAC name) (473) and TX, ivermectin (alternative name) [CCN] and TX, jasmolin I (696) and TX, jasmolin II (696) and TX, jodfenphos (1248) and TX, lindane (430) and TX, lufenuron (490) and TX, malathion (492) and TX, malonoben (1254) and TX, mecarbam (502) and TX, mephosfolan (1261) and TX, mesulfen (alternative name) [CCN] and TX, methacrifos (1266) and TX, methamidophos (527) and TX, methidathion (529) and TX, methiocarb (530) and TX, methomyl (531) and TX, methyl bromide (537) and TX, metolcarb (550) and TX, mevinphos (556) and TX, mexacarbate (1290) and TX, milbemectin (557) and TX, milbemycin oxime (alternative name) [CCN] and TX, mipafox (1293) and TX, monocrotophos (561) and TX, morphothion (1300) and TX, moxidectin (alternative name) [CCN] and TX, naled (567) and TX, NC-184 (compound code) and TX, NC-512 (compound code) and TX, nifluridide (1309) and TX, nikkomycins (alternative name) [CCN] and TX, nitrilacarb (1313) and TX, nitrilacarb 1:1 zinc chloride complex (1313) and TX, NNI-0101 (compound code) and TX, NNI-0250 (compound code) and TX, omethoate (594) and TX, oxamyl (602) and TX, oxydeprofos (1324) and TX, oxydisulfoton (1325) and TX, pp'-DDT (219) and TX, parathion (615) and TX, permethrin (626) and TX, petroleum oils (alternative name) (628) and TX, phenkapton (1330) and TX, phenthoate (631) and TX, phorate (636) and TX, phosalone (637) and TX, phosfolan (1338) and TX, phosmet (638) and TX, phosphamidon (639) and TX, phoxim (642) and TX, pirimiphos-methyl (652) and TX, polychloroterpenes (traditional name) (1347) and TX, polynactins (alternative name) (653) and TX, proclonol (1350) and TX, profenofos (662) and TX, promacyl (1354) and TX, propargite (671) and TX, propetamphos (673) and TX, propoxur (678) and TX, prothidathion (1360) and TX, prothoate (1362) and TX, pyrethrin I (696) and TX, pyrethrin II (696) and TX, pyrethrins (696) and TX, pyridaben (699) and TX, pyridaphenthion (701) and TX, pyrimidifen (706) and TX, pyrimitate (1370) and TX, quinalphos (711) and TX, quintiofos (1381) and TX, R-1492 (development code) (1382) and TX, RA-17 (development code) (1383) and TX, rotenone (722) and TX, schradan (1389) and TX, sebufos (alternative name) and TX, selamectin (alternative name) [CCN] and TX, SI-0009 (compound code) and TX, sophamide (1402) and TX, spirodiclofen (738) and TX, spiromesifen (739) and TX, SSI-121 (development code) (1404) and TX, sulfiram (alternative name) [CCN] and TX, sulfluramid (750) and TX, sulfotep (753) and TX, sulfur (754) and TX, SZI-121 (development code) (757) and TX, tau-fluvalinate (398) and TX, tebufenpyrad (763) and TX, TEPP (1417) and TX, terbam (alternative name) and TX, tetrachlorvinphos (777) and TX, tetradifon (786) and TX, tetranactin (alternative name) (653) and TX, tetrasul (1425) and TX, thiafenox (alternative name) and TX, thiocarboxime (1431) and TX, thiofanox (800) and TX, thiometon (801) and TX, thioquinox (1436) and TX, thuringiensin (alternative name) [CCN] and TX, triamiphos (1441) and TX, triarathene (1443) and TX, triazophos (820) and TX, triazuron (alternative name) and TX, trichlorfon (824) and TX, trifenofos (1455) and TX, trinactin (alternative name) (653) and TX, vamidothion (847) and TX, vaniliprole [CCN] and YI-5302 (compound code) and TX, an algicide selected from the group of substances consisting of bethoxazin [CCN] and TX, copper dioctanoate (IUPAC name) (170) and TX, copper sulfate (172) and TX, cybutryne [CCN] and TX, dichlone (1052) and TX, dichlorophen (232) and TX, endothal (295) and TX, fentin (347) and TX, hydrated lime [CCN] and TX, nabam (566) and TX, quinoclamine (714) and TX, quinonamid (1379) and TX, simazine (730) and TX, triphenyltin acetate (IUPAC name) (347) and triphenyltin hydroxide (IUPAC name) (347) and TX, an anthelmintic selected from the group of substances consisting of abamectin (1) and TX, crufomate (1011) and TX, doramectin (alternative name) [CCN] and TX, emamectin (291) and TX, emamectin benzoate (291) and TX, eprinomectin (alternative name) [CCN] and TX, ivermectin (alternative name) [CCN] and TX, milbemycin oxime (alternative name) [CCN] and TX, moxidectin (alternative name) [CCN] and TX, piperazine [CCN] and TX, selamectin (alternative name) [CCN] and TX, spinosad (737) and thiophanate (1435) and TX, an avicide selected from the group of substances consisting of chloralose (127) and TX, endrin (1122) and TX, fenthion (346) and TX, pyridin-4-amine (IUPAC name) (23) and strychnine (745) and TX, a bactericide selected from the group of substances consisting of 1-hydroxy-1H-pyridine-2-thione (IUPAC name) (1222) and TX, 4-(quinoxalin-2-ylamino)benzenesulfonamide (IUPAC name) (748) and TX, 8-hydroxyquinoline sulfate (446) and TX, bronopol (97) and TX, copper dioctanoate (IUPAC name) (170) and TX, copper hydroxide (IUPAC name) (169) and TX, cresol [CCN] and TX, dichlorophen (232) and TX, dipyrithione (1105) and TX, dodicin (1112) and TX, fenaminosulf (1144) and TX, formaldehyde (404) and TX, hydrargaphen (alternative name) [CCN] and TX, kasugamycin (483) and TX, kasugamycin hydrochloride hydrate (483) and TX, nickel bis(dimethyldithiocarbamate) (IUPAC name) (1308) and TX, nitrapyrin (580) and TX, octhilinone (590) and TX, oxolinic acid (606) and TX, oxytetracycline (611) and TX, potassium hydroxyquinoline sulfate (446) and TX, probenazole (658) and TX, streptomycin (744) and TX, streptomycin sesquisulfate (744) and TX, tecloftalam (766) and TX, and thiomersal (alternative name) [CCN] and TX, a biological agent selected from the group of substances consisting of *Adoxophyes orana* GV (alternative name) (12) and TX, *Agrobacterium radiobacter* (alternative name) (13) and TX, *Amblyseius* spp. (alternative name) (19) and TX, *Anagrapha falcifera* NPV (alternative name) (28) and TX, *Anagrus atomus* (alternative name) (29) and TX, *Aphelinus abdominalis* (alternative name) (33) and TX, *Aphidius colemani* (alternative name) (34) and TX, *Aphidoletes aphidimyza* (alternative name) (35) and TX, *Autographa californica* NPV (alternative name) (38) and TX, *Bacillus firmus* (alternative name) (48) and TX, *Bacillus sphaericus* Neide (scientific name) (49) and TX, *Bacillus thuringiensis* Berliner (scientific name) (51) and TX, *Bacillus thuringiensis* subsp. *aizawai* (scientific name) (51) and TX, *Bacillus thuringiensis* subsp. *israelensis* (scientific name) (51) and TX, *Bacillus thuringiensis* subsp. *japonensis* (scientific name) (51) and TX, *Bacillus thuringiensis* subsp. *kurstaki* (scientific name) (51) and TX, *Bacillus thuringiensis* subsp. *tenebrionis* (scientific name) (51) and TX, *Beauveria bassiana* (alternative name) (53) and TX, *Beauveria brongniartii* (alternative name) (54) and TX, *Chrysoperla carnea* (alternative name) (151) and TX, *Cryptolaemus montrouzieri* (alternative name) (178) and TX, *Cydia pomonella* GV (alternative name) (191) and TX, *Dacnusa sibirica* (alternative name) (212) and TX, *Diglyphus isaea* (alternative name) (254) and TX, *Encarsia formosa* (scientific name) (293) and TX, *Eretmocerus eremicus* (alternative name) (300) and TX, *Helicoverpa zea* NPV (alternative name) (431) and TX, *Heterorhabditis bacteriophora* and *H. megidis* (alternative name) (433) and TX, *Hippodamia convergens* (alternative name) (442) and TX, *Leptomastix dactylopii* (alternative name) (488) and TX, *Macrolophus caliginosus* (alternative name) (491) and TX, *Mamestra brassicae* NPV (alternative name) (494) and TX, *Metaphycus helvolus* (alternative name) (522) and TX, *Metarhizium anisopliae* var. *acridum* (scientific name) (523) and TX, *Metarhizium anisopliae* var. *anisopliae* (scientific name) (523) and TX, *Neodiprion sertifer* NPV and *N. lecontei* NPV (alternative name) (575) and TX, *Orius* spp. (alternative name) (596) and TX, *Paecilomyces fumosoroseus* (alternative name) (613) and TX, *Phytoseiulus persimilis* (alternative name) (644) and TX, *Spodoptera exigua* multicapsid nuclear polyhedrosis virus (scientific name) (741) and TX, *Steinernema bibionis* (alternative name) (742) and TX, *Steinernema carpocapsae* (alternative name) (742) and TX, *Steinernema feltiae* (alternative name) (742) and TX, *Steinernema glaseri* (alternative name) (742) and TX, *Steinernema riobrave* (alternative name) (742) and TX, *Steinernema riobravis* (alternative name) (742) and TX, *Steinernema scapterisci* (alternative name) (742) and TX, *Steinernema* spp. (alternative name) (742) and TX, *Trichogramma* spp. (alternative name) (826) and TX, *Typhlodromus occidentalis* (alternative name) (844) and *Verticillium lecanii* (alternative name) (848) and TX, a soil sterilant selected from the group of substances consisting of iodomethane (IUPAC name) (542) and methyl bromide (537) and TX, a chemosterilant selected from the group of substances consisting of apholate [CCN] and TX, bisazir (alternative name) [CCN] and TX, busulfan (alternative name) [CCN] and TX, diflubenzuron (250) and TX, dimatif (alternative name) [CCN] and TX, hemel [CCN] and TX, hempa [CCN] and TX, metepa [CCN] and TX, methiotepa [CCN] and TX, methyl apholate [CCN] and TX, morzid [CCN] and TX, penfluoron (alternative name) [CCN] and TX, tepa [CCN] and TX, thiohempa (alternative name) [CCN] and TX, thiotepa (alternative name) [CCN] and TX, tretamine (alternative name) [CCN] and uredepa (alternative name) [CCN] and TX, an insect pheromone selected from the group of substances consisting of (E)-dec-5-en-1-yl acetate with (E)-dec-5-en-1-ol (IUPAC name) (222) and TX, (E)-tridec-4-en-1-yl acetate (IUPAC name) (829) and TX, (E)-6-methylhept-2-en-4-ol (IUPAC name) (541) and TX, (E and TX, Z)-tetradeca-4 and TX, 10-dien-1-yl acetate (IUPAC name) (779) and TX, (Z)-dodec-7-en-1-yl acetate (IUPAC name) (285) and TX, (Z)-hexadec-11-enal (IUPAC name) (436) and TX, (Z)-hexadec-11-en-1-yl acetate (IUPAC name) (437) and TX, (Z)-hexadec-13-en-11-yn-1-yl acetate (IUPAC name) (438) and TX, (Z)-icos-13-en-10-one (IUPAC name) (448) and TX, (Z)-tetradec-7-en-1-al (IUPAC name) (782) and TX, (Z)-tetradec-9-en-1-ol (IUPAC name) (783) and TX, (Z)-tetradec-9-en-1-yl acetate (IUPAC name) (784) and TX, (7E and TX, 9Z)-dodeca-7 and TX, 9-dien-1-yl acetate (IUPAC name) (283) and TX, (9Z and TX, 11 E)-tetradeca-9 and TX, 11-dien-1-yl acetate (IUPAC name) (780) and TX, (9Z and TX, 12E)-tetradeca-9 and TX, 12-dien-1-yl acetate (IUPAC name) (781) and TX, 14-methyloctadec-1-ene (IUPAC name) (545) and TX, 4-methylnonan-5-ol with 4-methylnonan-5-one (IUPAC name) (544) and TX, alpha-multistriatin (alternative name) [CCN] and TX, brevicomin (alternative name) [CCN] and TX, codlelure (alternative name) [CCN] and TX, codlemone (alternative name) (167) and TX, cuelure (alternative name) (179) and TX, disparlure (277) and TX, dodec-8-en-1-yl acetate (IUPAC name) (286) and TX, dodec-9-en-1-yl acetate (IUPAC name) (287) and TX, dodeca-8 and TX, 10-dien-1-yl acetate (IUPAC name) (284) and TX, dominicalure (alternative name) [CCN] and TX, ethyl 4-methyloctanoate (IUPAC name) (317) and TX, eugenol (alternative name) [CCN] and TX, frontalin (alternative name) [CCN] and TX, gossyplure (alternative name) (420) and TX, grandlure (421) and TX, grandlure I (alternative name) (421) and TX, grandlure II (alternative name) (421) and TX, grandlure III (alternative name) (421) and TX, grandlure IV (alternative name) (421) and TX, hexylure [CCN] and TX, ipsdienol (alternative name) [CCN] and TX, ipsenol (alternative name) [CCN] and TX, japonilure (alternative name) (481) and TX, lineatin (alternative name) [CCN] and TX, litlure (alternative name) [CCN] and TX, looplure (alternative name) [CCN] and TX, medlure [CCN] and TX, megatomoic acid (alternative name) [CCN] and TX, methyl eugenol (alternative name) (540) and TX, muscalure (563) and TX, octadeca-2 and TX, 13-dien-1-yl acetate (IUPAC name) (588) and TX, octadeca-3 and TX, 13-dien-1-yl acetate (IUPAC name) (589) and TX, orfralure (alternative name) [CCN] and TX, oryctalure (alternative name) (317) and TX, ostramone (alternative name) [CCN] and TX, siglure [CCN] and TX, sordidin (alternative name) (736) and TX, sulcatol (alternative name) [CCN] and TX, tetradec-11-en-1-yl acetate (IUPAC name) (785) and TX, trimedlure (839) and TX, trimedlure A (alternative name) (839) and TX, trimedlure $B_1$ (alternative name) (839) and TX, trimedlure $B_2$ (alternative name) (839) and TX, trimedlure C (alternative name) (839) and trunc-call (alternative name) [CCN] and TX, an insect repellent selected from the group of substances consisting of 2-(octylthio)-ethanol (IUPAC name) (591) and TX, butopyronoxyl (933) and TX, butoxy(polypropylene glycol) (936) and TX, dibutyl adipate (IUPAC name) (1046) and TX, dibutyl phthalate (1047) and TX, dibutyl succinate (IUPAC name) (1048) and TX, diethyltoluamide [CCN] and TX, dimethyl carbate [CCN] and TX, dimethyl phthalate [CCN] and TX, ethyl hexanediol (1137) and TX, hexamide [CCN] and TX, methoquin-butyl (1276) and TX, methylneodecanamide [CCN] and TX, oxamate [CCN] and picaridin [CCN] and TX, an insecticide selected from the group of substances consisting of 1 and TX, 1-dichloro-1-nitroethane (IUPAC/Chemical Abstracts name) (1058) and TX, 1 and TX, 1-dichloro-2 and TX, 2-bis(4-ethylphenyl)ethane (IUPAC name) (1056) and TX, 1 and TX, 2-dichloropropane (IUPAC/Chemical Abstracts name) (1062) and TX, 1 and TX, 2-dichloropropane with 1 and TX, 3-dichloropropene (IUPAC name) (1063) and TX, 1-bromo-2-chloroethane (IUPAC/Chemical Abstracts name) (916) and TX, 2 and TX, 2 and TX, 2-trichloro-1-(3 and TX, 4-dichlorophenyl)ethyl acetate (IUPAC name) (1451) and TX, 2 and TX, 2-dichlorovinyl 2-ethylsulfinylethyl methyl phosphate (IUPAC name) (1066) and TX, 2-(1 and TX, 3-dithiolan-2-yl)phenyl dimethylcarbamate (IUPAC/Chemical Abstracts name) (1109) and TX, 2-(2-butoxyethoxy)ethyl thiocyanate (IUPAC/Chemical Abstracts name) (935) and TX, 2-(4 and TX, 5-dimethyl-1 and TX, 3-dioxolan-2-yl)phenyl methylcarbamate (IUPAC/Chemical Abstracts name) (1084) and TX, 2-(4-chloro-3 and TX, 5-xylyloxy)ethanol (IUPAC name) (986) and TX, 2-chlorovinyl diethyl phosphate (IUPAC name) (984) and TX, 2-imidazolidone (IUPAC name) (1225) and TX, 2-isovalerylindan-1 and TX, 3-dione (IUPAC name) (1246) and TX, 2-methyl(prop-2-ynyl)aminophenyl methylcarbamate (IUPAC name) (1284) and TX, 2-thiocyanatoethyl laurate (IUPAC name) (1433) and TX, 3-bromo-1-chloroprop-1-ene (IUPAC name) (917) and TX, 3-methyl-1-phenylpyrazol-5-yl dimethylcarbamate (IUPAC name) (1283) and TX, 4-methyl(prop-2-ynyl)amino-3 and TX, 5-xylyl methylcarbamate (IUPAC name) (1285) and TX, 5 and TX, 5-dimethyl-3-oxocyclohex-1-enyl dimethylcarbamate (IUPAC name) (1085) and TX, abamectin (1) and TX, acephate (2) and TX, acetamiprid (4) and TX, acethion (alternative name) [CCN] and TX, acetoprole [CCN] and TX, acrinathrin (9) and TX, acrylonitrile (IUPAC name) (861) and TX, alanycarb (15) and TX, aldicarb (16) and TX, aldoxycarb (863) and TX, aldrin (864) and TX, allethrin (17) and TX, allosamidin (alternative name) [CCN] and TX, allyxycarb (866) and TX, alpha-cypermethrin (202) and TX, alpha-ecdysone (alternative name) [CCN] and TX, aluminium phosphide (640) and TX, amidithion (870) and TX, amidothioate (872) and TX, aminocarb (873) and TX, amiton (875) and TX, amiton hydrogen oxalate (875) and TX, amitraz (24) and TX, anabasine (877) and TX, athidathion (883) and TX, AVI 382 (compound code) and TX, AZ 60541 (compound code) and TX, azadirachtin (alternative name) (41) and TX, azamethiphos (42) and TX, azinphos-ethyl (44) and TX, azinphos-methyl (45) and TX, azothoate (889) and TX, *Bacillus thuringiensis* delta endotoxins (alternative name) (52) and TX, barium hexafluorosilicate (alternative name) [CCN] and TX, barium polysulfide (IUPAC/Chemical Abstracts name) (892) and TX, barthrin [CCN] and TX, Bayer 22/190 (development code) (893) and TX, Bayer 22408 (development code) (894) and TX, bendiocarb (58) and TX, benfuracarb (60) and TX, bensultap (66) and TX, beta-cyfluthrin (194) and TX, beta-cypermethrin (203) and TX, bifenthrin (76) and TX, bioallethrin (78) and TX, bioallethrin S-cyclopentenyl isomer (alternative name) (79) and TX, bioethanomethrin [CCN] and TX, biopermethrin (908) and TX, bioresmethrin (80) and TX, bis(2-chloroethyl)ether (IUPAC name) (909) and TX, bistrifluoron (83) and TX, borax (86) and TX, brofenvalerate (alternative name) and TX, bromfenvinfos (914) and TX, bromocyclen (918) and TX, bromo-DDT (alternative name) [CCN] and TX, bromophos (920) and TX, bromophos-ethyl (921) and TX, bufencarb (924) and TX, buprofezin (99) and TX, butacarb (926) and TX, butathiofos (927) and TX, butocarboxim (103) and TX, butonate (932) and TX, butoxycarboxim (104) and TX, butylpyridaben (alternative name) and TX, cadusafos (109) and TX, calcium arsenate [CCN] and TX, calcium cyanide (444) and TX, calcium polysulfide (IUPAC name) (111) and TX, camphechlor (941) and TX, carbanolate (943) and TX, carbaryl (115) and TX, carbofuran (118) and TX, carbon disulfide (IUPAC/Chemical Abstracts name) (945) and TX, carbon tetrachloride (IUPAC name) (946) and TX, carbophenothion (947) and TX, carbosulfan (119) and TX, cartap (123) and TX, cartap hydrochloride (123) and TX, cevadine (alternative name) (725) and TX, chlorbicyclen (960) and TX, chlordane (128) and TX, chlordecone (963) and TX, chlordimeform (964) and TX, chlordimeform hydrochloride (964) and TX, chlorethoxyfos (129) and TX, chlorfenapyr (130) and TX, chlorfenvinphos (131) and TX, chlorfluazuron (132) and TX, chlormephos (136) and TX, chloroform [CCN] and TX, chloropicrin (141) and TX, chlorphoxim (989) and TX, chlorprazophos (990) and TX, chlorpyrifos (145) and TX, chlorpyrifos-methyl (146) and TX, chlorthiophos (994) and TX, chromafenozide (150) and TX, cinerin I (696) and TX, cinerin II (696) and TX, cinerins (696) and TX, cis-resmethrin (alternative name) and TX, cismethrin (80) and TX, clocythrin (alternative name) and TX, cloethocarb (999) and TX, closantel (alternative name) [CCN] and TX, clothianidin (165) and TX, copper acetoarsenite [CCN] and TX, copper arsenate [CCN] and TX, copper oleate [CCN] and TX, coumaphos (174) and TX, coumithoate (1006) and TX, crotamiton (alternative name) [CCN] and TX, crotoxyphos (1010) and TX, crufomate (1011) and TX, cryolite (alternative name) (177) and TX, CS 708 (development code) (1012) and TX, cyanofenphos (1019) and TX, cyanophos (184) and TX, cyanthoate (1020) and TX, cyclethrin [CCN] and TX, cycloprothrin (188) and TX, cyfluthrin (193) and TX, cyhalothrin (196) and TX, cypermethrin (201) and TX, cyphenothrin (206) and TX, cyromazine (209) and TX, cythioate (alternative name) [CCN] and TX, d-limonene (alternative name) [CCN] and TX, d-tetramethrin (alternative name) (788) and TX, DAEP (1031) and TX, dazomet (216) and TX, DDT (219) and TX, decarbofuran (1034) and TX, deltamethrin (223) and TX, demephion (1037) and TX, demephion-O (1037) and TX, demephion-S (1037) and TX, demeton (1038) and TX, demeton-methyl (224) and TX, demeton-O (1038) and TX, demeton-O-methyl (224) and TX, demeton-S (1038) and TX, demeton-S-methyl (224) and TX, demeton-S-methylsulphon (1039) and TX, diafenthiuron (226) and TX, dialifos (1042) and TX, diamidafos (1044) and TX, diazinon (227) and TX, dicapthon (1050) and TX, dichlofenthion (1051) and TX, dichlorvos (236) and TX, dicliphos (alternative name) and TX, dicresyl (alternative name) [CCN] and TX, dicrotophos (243) and TX, dicyclanil (244) and TX, dieldrin (1070) and TX, diethyl 5-methylpyrazol-3-yl phosphate (IUPAC name) (1076) and TX, diflubenzuron (250) and TX, dilor (alternative name) [CCN] and TX, dimefluthrin [CCN] and TX, dimefox (1081) and TX, dimetan (1085) and TX, dimethoate (262) and TX, dimethrin (1083) and TX, dimethylvinphos (265) and TX, dimetilan (1086) and TX, dinex (1089) and TX, dinex-diclexine (1089) and TX, dinoprop (1093) and TX, dinosam (1094) and TX, dinoseb (1095) and TX, dinotefuran (271) and TX, diofenolan (1099) and TX, dioxabenzofos (1100) and TX, dioxacarb (1101) and TX, dioxathion (1102) and TX, disulfoton (278) and TX, dithicrofos (1108) and TX, DNOC (282) and TX, dorametin (alternative name) [CCN] and TX, DSP (1115) and TX, ecdysterone (alternative name) [CCN] and TX, El 1642 (development code) (1118) and TX, emamectin (291) and TX, emamectin benzoate (291) and TX, EMPC (1120) and TX, empenthrin (292) and TX, endosulfan (294) and TX, endothion (1121) and TX, endrin (1122) and TX, EPBP (1123) and TX, EPN (297) and TX, epofenonane (1124) and TX, eprinomectin (alternative name) [CCN] and TX, esfenvalerate (302) and TX, etaphos (alternative name) [CCN] and TX, ethiofencarb (308) and TX, ethion (309) and TX, ethiprole (310) and TX, ethoate-methyl (1134) and TX, ethoprophos (312) and TX, ethyl formate (IUPAC name) [CCN] and TX, ethyl-DDD (alternative name) (1056) and TX, ethylene dibromide (316) and TX, ethylene dichloride (chemical name) (1136) and TX, ethylene oxide [CCN] and TX, etofenprox (319) and TX, etrimfos (1142) and TX, EXD (1143) and TX, famphur (323) and TX, fenamiphos (326) and TX, fenazaflor (1147) and TX, fenchlorphos (1148) and TX, fenethacarb (1149) and TX, fenfluthrin (1150) and TX, fenitrothion (335) and TX, fenobucarb (336) and TX, fenoxacrim (1153) and TX, fenoxycarb (340) and TX, fenpirithrin (1155) and TX, fenpropathrin (342) and TX, fenpyrad (alternative name) and TX, fensulfothion (1158) and TX, fenthion (346) and TX, fenthion-ethyl [CCN] and TX, fenvalerate (349) and TX, fipronil (354) and TX, flonicamid (358) and TX, flubendiamide (CAS. Reg. No.: 272451-65-7) and TX, flucofuron (1168) and TX, flucycloxuron (366) and TX, flucythrinate (367) and TX, fluenetil (1169) and TX, flufenerim [CCN] and TX, flufenoxuron (370) and TX, flufenprox (1171) and TX, flumethrin (372) and TX, fluvalinate (1184) and TX, FMC 1137 (development code) (1185) and TX, fonofos (1191) and TX, formetanate (405) and TX, formetanate hydrochloride (405) and TX, formothion (1192) and TX, formparanate (1193) and TX, fosmethilan (1194) and TX, fospirate (1195) and TX, fosthiazate (408) and TX, fosthietan (1196) and TX, furathiocarb (412) and TX, furethrin (1200) and TX, gamma-cyhalothrin (197) and TX, gamma-HCH (430) and TX, guazatine (422) and TX, guazatine acetates (422) and TX, GY-81 (development code) (423) and TX, halfenprox (424) and TX, halofenozide (425) and TX, HCH (430) and TX, HEOD (1070) and TX, heptachlor (1211) and TX, heptenophos (432) and TX, heterophos [CCN] and TX, hexaflumuron (439) and TX, HHDN (864) and TX, hydramethylnon (443) and TX, hydrogen cyanide (444) and TX, hydroprene (445) and TX, hyquincarb (1223) and TX, imidacloprid (458) and TX, imiprothrin (460) and TX, indoxacarb (465) and TX, iodomethane (IUPAC name) (542) and TX, IPSP (1229) and TX, isazofos (1231) and TX, isobenzan (1232) and TX, isocarbophos (alternative name) (473) and TX, isodrin (1235) and TX, isofenphos (1236) and TX, isolane (1237) and TX, isoprocarb (472) and TX, isopropyl O-(methoxyaminothiophosphoryl) salicylate (IUPAC name) (473) and TX, isoprothiolane (474) and TX, isothioate (1244) and TX, isoxathion (480) and TX, ivermectin (alternative name) [CCN] and TX, jasmolin I (696) and TX, jasmolin II (696) and TX, jodfenphos (1248) and TX, juvenile hormone I (alternative name) [CCN] and TX, juvenile hormone II (alternative name) [CCN] and TX, juvenile hormone III (alternative name) [CCN] and TX, kelevan (1249) and TX, kinoprene (484) and TX, lambda-cyhalothrin (198) and TX, lead arsenate [CCN] and TX, lepimectin (CCN) and TX, leptophos (1250) and TX, lindane (430) and TX, lirimfos (1251) and TX, lufenuron (490) and TX, lythidathion (1253) and TX, m-cumenyl methylcarbamate (IUPAC name) (1014) and TX, magnesium phosphide (IUPAC name) (640) and TX, malathion (492) and TX, malonoben (1254) and TX, mazidox (1255) and TX, mecarbam (502) and TX, mecarphon (1258) and TX, menazon (1260) and TX, mephosfolan (1261) and TX, mercurous chloride (513) and TX, mesulfenfos (1263) and TX, metaflumizone (CCN) and TX, metam (519) and TX, metam-potassium (alternative name) (519) and TX, metam-sodium (519) and TX, methacrifos (1266) and TX, methamidophos (527) and TX, methanesulfonyl fluoride (IUPAC/Chemical Abstracts name) (1268) and TX, methidathion (529) and TX, methiocarb (530) and TX, methocrotophos (1273) and TX, methomyl (531) and TX, methoprene (532) and TX, methoquinbutyl (1276) and TX, methothrin (alternative name) (533) and TX, methoxychlor (534) and TX, methoxyfenozide (535) and TX, methyl bromide (537) and TX, methyl isothiocyanate (543) and TX, methylchloroform (alternative name) [CCN] and TX, methylene chloride [CCN] and TX, metofluthrin [CCN] and TX, metolcarb (550) and TX, metoxadiazone (1288) and TX, mevinphos (556) and TX, mexacarbate (1290) and TX, milbemectin (557) and TX, milbemycin oxime (alternative name) [CCN] and TX, mipafox (1293) and TX, mirex (1294) and TX, monocrotophos (561) and TX, morphothion (1300) and TX, moxidectin (alternative name) [CCN] and TX, naftalofos (alternative name) [CCN] and TX, naled (567) and TX, naphthalene (IUPAC/Chemical Abstracts name) (1303) and TX, NC-170 (development code) (1306) and TX, NC-184 (compound code) and TX, nicotine (578) and TX, nicotine sulfate (578) and TX, nifluridide (1309) and TX, nitenpyram (579) and TX, nithiazine (1311) and TX, nitrilacarb (1313) and TX, nitrilacarb 1:1 zinc chloride complex (1313) and TX, NNI-0101 (compound code) and TX, NNI-0250 (compound code) and TX, nornicotine (traditional name) (1319) and TX, novaluron (585) and TX, noviflumuron (586) and TX, O-5-dichloro-4-iodophenyl O-ethyl ethylphosphonothioate (IUPAC name) (1057) and TX, O,O-diethyl O-4-methyl-2-oxo-2H-chromen-7-yl phosphorothioate (IUPAC name) (1074) and TX, O,O-diethyl O-6-methyl-2-propylpyrimidin-4-yl phosphorothioate (IUPAC name) (1075) and TX, O,O,O',O'-tetrapropyl dithiopyrophosphate (IUPAC name) (1424) and TX, oleic acid (IUPAC name) (593) and TX, ometoate (594) and TX, oxamyl (602) and TX, oxydemeton-methyl (609) and TX, oxydeprofos (1324) and TX, oxydisulfoton (1325) and TX, pp'-DDT (219) and TX, para-dichlorobenzene [CCN] and TX, parathion (615) and TX, parathion-methyl (616) and TX, penfluoron (alternative name) [CCN] and TX, pentachlorophenol (623) and TX, pentachlorophenyl laurate (IUPAC name) (623) and TX, permethrin (626) and TX, petroleum oils (alternative name) (628) and TX, PH 60-38 (development code) (1328) and TX, phenkapton (1330) and TX, phenothrin (630) and TX, phenthoate (631) and TX, phorate (636) and TX, phosalone (637) and TX, phosfolan (1338) and TX, phosmet (638) and TX, phosnichlor (1339) and TX, phosphamidon (639) and TX, phosphine (IUPAC name) (640) and TX, phoxim (642) and TX, phoxim-methyl (1340) and TX, pirimetaphos (1344) and TX, pirimicarb (651) and TX, pirimiphos-ethyl (1345) and TX, pirimiphos-methyl (652) and TX, polychlorodicyclopentadiene isomers (IUPAC name) (1346) and TX, polychloroterpenes (traditional name) (1347) and TX, potassium arsenite [CCN] and TX, potassium thiocyanate [CCN] and TX, prallethrin (655) and TX, precocene I (alternative name) [CCN] and TX, precocene II (alternative name) [CCN] and TX, precocene III (alternative name) [CCN] and TX, primidophos (1349) and TX, profenofos (662) and TX, profluthrin [CCN] and TX, promacyl (1354) and TX, promecarb (1355) and TX, propaphos (1356) and TX, propetamphos (673) and TX, propoxur (678) and TX, prothidathion (1360) and TX, prothiofos (686) and TX, prothoate (1362) and TX, protrifenbute [CCN] and TX, pymetrozine (688) and TX, pyraclofos (689) and TX, pyrazophos (693) and TX, pyresmethrin (1367) and TX, pyrethrin I (696) and TX, pyrethrin II (696) and TX, pyrethrins (696) and TX, pyridaben (699) and TX, pyridalyl (700) and TX, pyridaphenthion (701) and TX, pyrimidifen (706) and TX, pyrimitate (1370) and TX, pyriproxyfen (708) and TX, quassia (alternative name) [CCN] and TX, quinalphos (711) and TX, quinalphos-methyl (1376) and TX, quinothion (1380) and TX, quintiofos (1381) and TX, R-1492 (development code) (1382) and TX, rafoxanide (alternative name) [CCN] and TX, resmethrin (719) and TX, rotenone (722) and TX, RU 15525 (development code) (723) and TX, RU 25475 (development code) (1386) and TX, ryania (alternative name) (1387) and TX, ryanodine (traditional name) (1387) and TX, sabadilla (alternative name) (725) and TX, schradan (1389) and TX, sebufos (alternative name) and TX, selamectin (alternative name) [CCN] and TX, SI-0009 (compound code) and TX, SI-0205 (compound code) and TX, SI-0404 (compound code) and TX, SI-0405 (compound code) and TX, silafluofen (728) and TX, SN 72129 (development code) (1397) and TX, sodium arsenite [CCN] and TX, sodium cyanide (444) and TX, sodium fluoride (IUPAC/Chemical Abstracts name) (1399) and TX, sodium hexafluorosilicate (1400) and TX, sodium pentachlorophenoxide (623) and TX, sodium selenate (IUPAC name) (1401) and TX, sodium thiocyanate [CCN] and TX, sophamide (1402) and TX, spinosad (737) and TX, spiromesifen (739) and TX, spirotetrmat (CCN) and TX, sulcofuron (746) and TX, sulcofuron-sodium (746) and TX, sulfluramid (750) and TX, sulfotep (753) and TX, sulfuryl fluoride (756) and TX, sulprofos (1408) and TX, tar oils (alternative name) (758) and TX, tau-fluvalinate (398) and TX, tazimcarb (1412) and TX, TDE (1414) and TX, tebufenozide (762) and TX, tebufenpyrad (763) and TX, tebupirimfos (764) and TX, teflubenzuron (768) and TX, tefluthrin (769) and TX, temephos (770) and TX, TEPP (1417) and TX, terallethrin (1418) and TX, terbam (alternative name) and TX, terbufos (773) and TX, tetrachloroethane [CCN] and TX, tetrachlorvinphos (777) and TX, tetramethrin (787) and TX, theta-cypermethrin (204) and TX, thiacloprid (791) and TX, thiafenox (alternative name) and TX, thiamethoxam (792) and TX, thicrofos (1428) and TX, thiocarboxime (1431) and TX, thiocyclam (798) and TX, thiocyclam hydrogen oxalate (798) and TX, thiodicarb (799) and TX, thiofanox (800) and TX, thiometon (801) and TX, thionazin (1434) and TX, thiosultap (803) and TX, thiosultap-sodium (803) and TX, thuringiensin (alternative name) [CCN] and TX, tolfenpyrad (809) and TX, tralomethrin (812) and TX, transfluthrin (813) and TX, transpermethrin (1440) and TX, triamiphos (1441) and TX, triazamate (818) and TX, triazophos (820) and TX, triazuron (alternative name) and TX, trichlorfon (824) and TX, trichlormetaphos-3 (alternative name) [CCN] and TX, trichloronat (1452) and TX, trifenofos (1455) and TX, triflumuron (835) and TX, trimethacarb (840) and TX, triprene (1459) and TX, vamidothion (847) and TX, vaniliprole [CCN] and TX, veratridine (alternative name) (725) and TX, veratrine (alternative name) (725) and TX, XMC (853) and TX, xylylcarb (854) and TX, yl-5302 (compound code) and TX, zeta-cypermethrin (205) and TX, zetamethrin (alternative name) and TX, zinc phosphide (640) and TX, zolaprofos (1469) and ZXI 8901 (development code) (858) and TX, a molluscicide selected from the group of substances consisting of bis(tributyltin) oxide (IUPAC name) (913) and TX, bromoacetamide [CCN] and TX, calcium arsenate [CCN] and TX, cloethocarb (999) and TX, copper acetoarsenite [CCN] and TX, copper sulfate (172) and TX, fentin (347) and TX, ferric phosphate (IUPAC name) (352) and TX, metaldehyde (518) and TX, methiocarb (530) and TX, niclosamide (576) and TX, niclosamide-olamine (576) and TX, pentachlorophenol (623) and TX, sodium pentachlorophenoxide (623) and TX, tazimcarb (1412) and TX, thiodicarb (799) and TX, tributyltin oxide (913) and TX, trifenmorph (1454) and TX, trimethacarb (840) and TX, triphenyltin acetate (IUPAC name) (347) and triphenyltin hydroxide (IUPAC name) (347) and TX, a nematicide selected from the group of substances consisting of AKD-3088 (compound code) and TX, 1 and TX, 2-dibromo-3-chloropropane (IUPAC/Chemical Abstracts name) (1045) and TX, 1 and TX, 2-dichloropropane (IUPAC/Chemical Abstracts name) (1062) and TX, 1 and TX, 2-dichloropropane with 1 and TX, 3-dichloropropene (IUPAC name) (1063) and TX, 1 and TX, 3-dichloropropene (233) and TX, 3 and TX, 4-dichlorotetrahydrothiophene 1 and TX, 1-dioxide (IUPAC/Chemical Abstracts name) (1065) and TX, 3-(4-chlorophenyl)-5-methylrhodanine (IUPAC name) (980) and TX, 5-methyl-6-thioxo-1 and TX, 3 and TX, 5-thiadiazinan-3-ylacetic acid (IUPAC name) (1286) and TX, 6-isopentenylaminopurine (alternative name) (210) and TX, abamectin (1) and TX, acetoprole [CCN] and TX, alanycarb (15) and TX, aldicarb (16) and TX, aldoxycarb (863) and TX, AZ 60541 (compound code) and TX, benclothiaz [CCN] and TX, benomyl (62) and TX, butylpyridaben (alternative name) and TX, cadusafos (109) and TX, carbofuran (118) and TX, carbon disulfide (945) and TX, carbosulfan (119) and TX, chloropicrin (141) and TX, chlorpyrifos (145) and TX, cloethocarb (999) and TX, cytokinins (alternative name) (210) and TX, dazomet (216) and TX, DBCP (1045) and TX, DCIP (218) and TX, diamidafos (1044) and TX, dichlofenthion (1051) and TX, dicliphos (alternative name) and TX, dimethoate (262) and TX, doramectin (alternative name) [CCN] and TX, emamectin (291) and TX, emamectin benzoate (291) and TX, eprinomectin (alternative name) [CCN] and TX, ethoprophos (312) and TX, ethylene dibromide (316) and TX, fenamiphos (326) and TX, fenpyrad (alternative name) and TX, fensulfothion (1158) and TX, fosthiazate (408) and TX, fosthietan (1196) and TX, furfural (alternative name) [CCN] and TX, GY-81 (development code) (423) and TX, heterophos [CCN] and TX, iodomethane (IUPAC name) (542) and TX, isamidofos (1230) and TX, isazofos (1231) and TX, ivermectin (alternative name) [CCN] and TX, kinetin (alternative name) (210) and TX, mecarphon (1258) and TX, metam (519) and TX, metam-potassium (alternative name) (519) and TX, metam-sodium (519) and TX, methyl bromide (537) and TX, methyl isothiocyanate (543) and TX, milbemycin oxime (alternative name) [CCN] and TX, moxidectin (alternative name) [CCN] and TX, *Myrothecium verrucaria* composition (alternative name) (565) and TX, NC-184 (compound code) and TX, oxamyl (602) and TX, phorate (636) and TX, phosphamidon (639) and TX, phosphocarb [CCN] and TX, sebufos (alternative name) and TX, selamectin (alternative name) [CCN] and TX, spinosad (737) and TX, terbam (alternative name) and TX, terbufos (773) and TX, tetrachlorothiophene (IUPAC/Chemical Abstracts name) (1422) and TX, thiafenox (alternative name) and TX, thionazin (1434) and TX, triazophos (820) and TX, triazuron (alternative name) and TX, xylenols [CCN] and TX, yl-5302 (compound code) and zeatin (alternative name) (210) and TX, a nitrification inhibitor selected from the group of substances consisting of potassium ethylxanthate [CCN] and nitrapyrin (580) and TX, a plant activator selected from the group of substances consisting of acibenzolar (6) and TX, acibenzolar-S-methyl (6) and TX, probenazole (658) and *Reynoutria sachalinensis* extract (alternative name) (720) and TX, a rodenticide selected from the group of substances consisting of 2-isovalerylindan-1 and TX, 3-dione (IUPAC name) (1246) and TX, 4-(quinoxalin-2-ylamino)benzenesulfonamide (IUPAC name) (748) and TX, alpha-chlorohydrin [CCN] and TX, aluminium phosphide (640) and TX, antu (880) and TX, arsenous oxide (882) and TX, barium carbonate (891) and TX, bisthiosemi (912) and TX, brodifacoum (89) and TX, bromadiolone (91) and TX, bromethalin (92) and TX, calcium cyanide (444) and TX, chloralose (127) and TX, chlorophacinone (140) and TX, cholecalciferol (alternative name) (850) and TX, coumachlor (1004) and TX, coumafuryl (1005) and TX, coumatetralyl (175) and TX, crimidine (1009) and TX, difenacoum (246) and TX, difethialone (249) and TX, diphacinone (273) and TX, ergocalciferol (301) and TX, flocoumafen (357) and TX, fluoroacetamide (379) and TX, flupropadine (1183) and TX, flupropadine hydrochloride (1183) and TX, gamma-HCH (430) and TX, HCH (430) and TX, hydrogen cyanide (444) and TX, iodomethane (IUPAC name) (542) and TX, lindane (430) and TX, magnesium phosphide (IUPAC name) (640) and TX, methyl bromide (537) and TX, norbormide (1318) and TX, phosacetim (1336) and TX, phosphine (IUPAC name) (640) and TX, phosphorus [CCN] and TX, pindone (1341) and TX, potassium arsenite [CCN] and TX, pyrinuron (1371) and TX, scilliroside (1390) and TX, sodium arsenite [CCN] and TX, sodium cyanide (444) and TX, sodium fluoroacetate (735) and TX, strychnine (745) and TX, thallium sulfate [CCN] and TX, warfarin (851) and zinc phosphide (640) and TX, a synergist selected from the group of substances consisting of 2-(2-butoxyethoxy)-ethyl piperonylate (IUPAC name) (934) and TX, 5-(1 and TX, 3-benzodioxol-5-yl)-3-hexylcyclohex-2-enone (IUPAC name) (903) and TX, farnesol with nerolidol (alternative name) (324) and TX, MB-599 (development code) (498) and TX, MGK 264

(development code) (296) and TX, piperonyl butoxide (649) and TX, piprotal (1343) and TX, propyl isomer (1358) and TX, S421 (development code) (724) and TX, sesamex (1393) and TX, sesasmolin (1394) and sulfoxide (1406) and TX, an animal repellent selected from the group of substances consisting of anthraquinone (32) and TX, chloralose (127) and TX, copper naphthenate [CCN] and TX, copper oxychloride (171) and TX, diazinon (227) and TX, dicyclopentadiene (chemical name) (1069) and TX, guazatine (422) and TX, guazatine acetates (422) and TX, methiocarb (530) and TX, pyridin-4-amine (IUPAC name) (23) and TX, thiram (804) and TX, trimethacarb (840) and TX, zinc naphthenate [CCN] and ziram (856) and TX, a virucide selected from the group of substances consisting of imanin (alternative name) [CCN] and ribavirin (alternative name) [CCN] and TX, and a wound protectant selected from the group of substances consisting of mercuric oxide (512) and TX, octhilinone (590) and thiophanate-methyl (802) and TX, the compound of formula A-1 the formula A-3

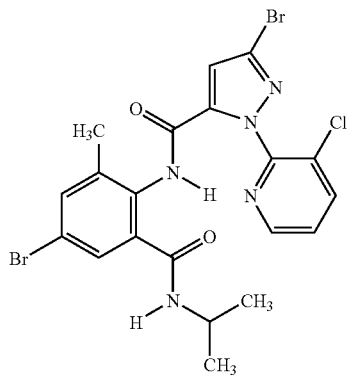

(A-3)

and TX,
the formula A-4

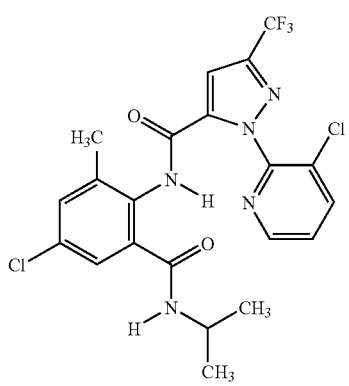

(A-1)

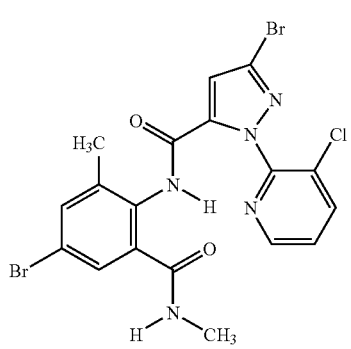

(A-4)

and TX,
the formula A-2 and TX,
the formula A-5

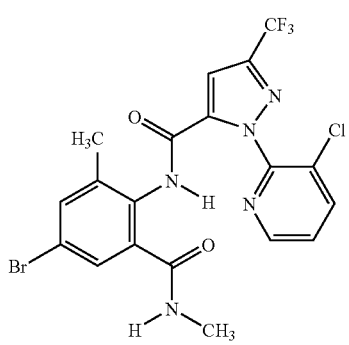

(A-2)

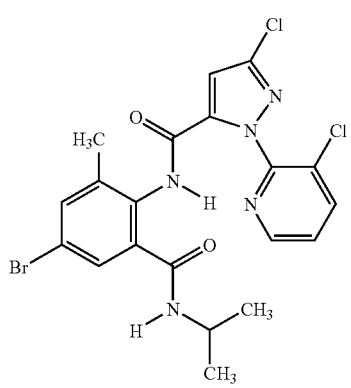

(A-5)

and TX, and TX, the formula A-6
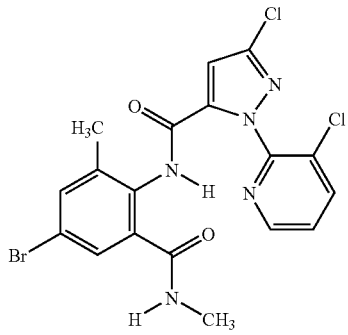
and TX,
the formula A-7
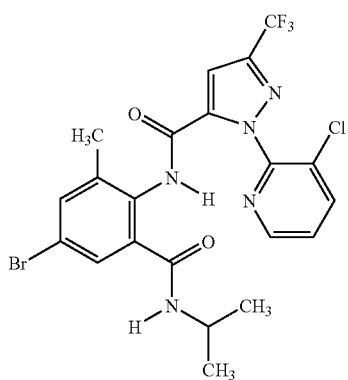
and TX,
the formula A-8
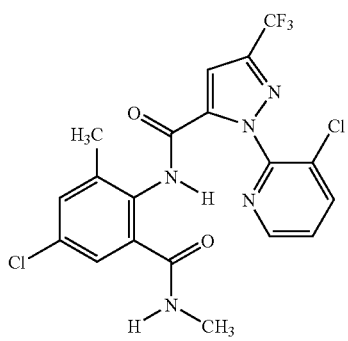
and TX,
the formula A-9
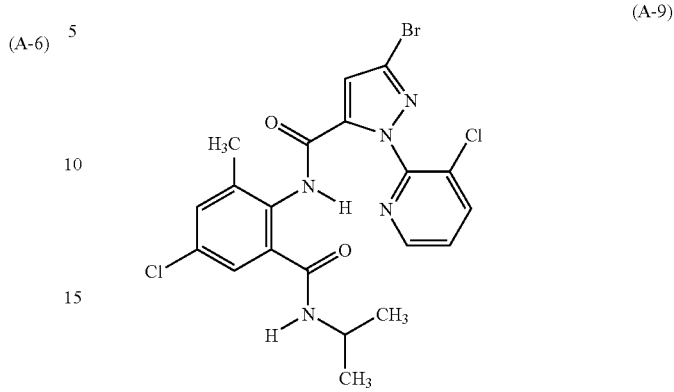
and TX,
the formula A-10
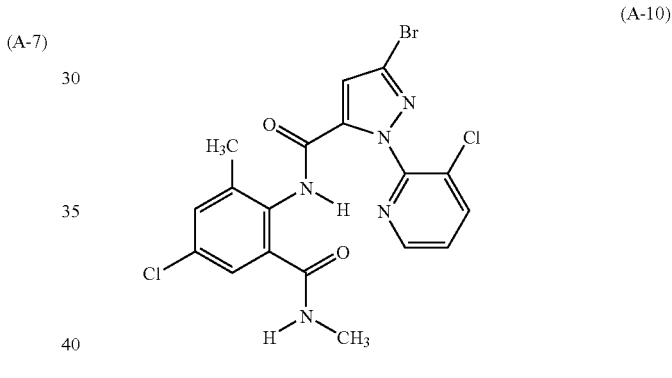
and TX,
the formula A-11
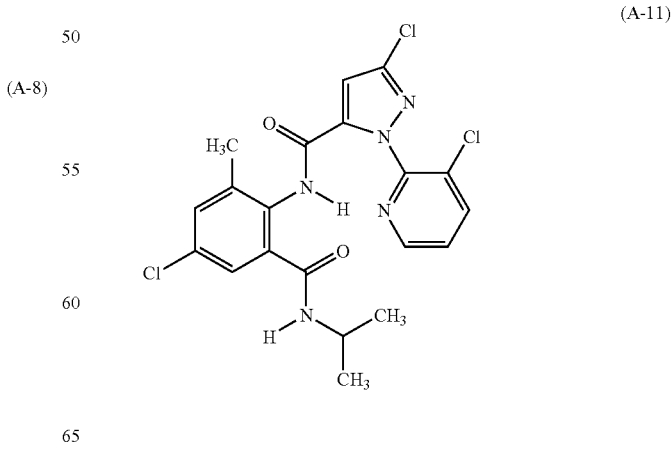
and TX, the formula A-12
(A-12)
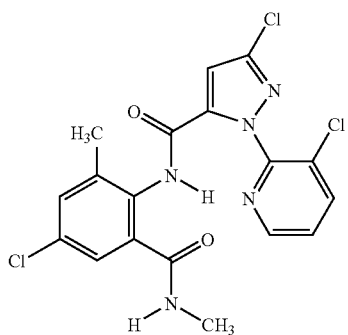
and TX,
the formula A-13
(A-13)
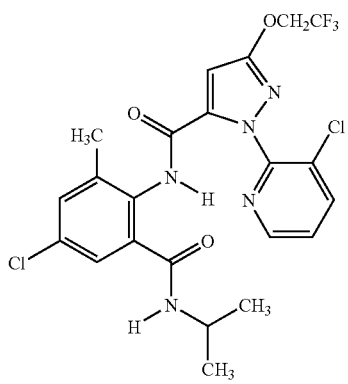
and TX,
the formula A-14
(A-14)
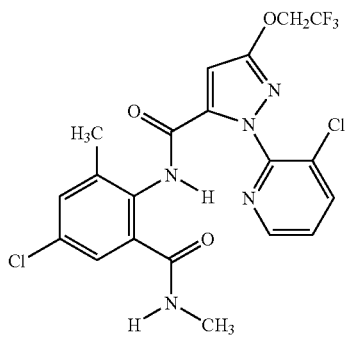
and TX,
the formula A-15
(A-15)
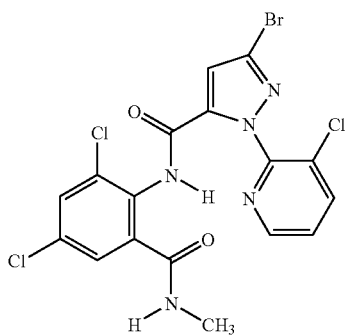
and TX,
the formula A-16
(A-16)
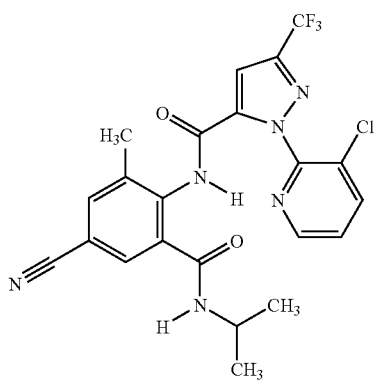
and TX,
the formula A-17
(A-17)
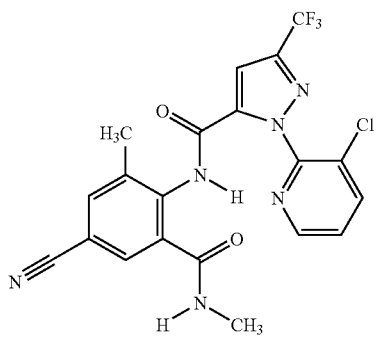
and TX, the formula A-18
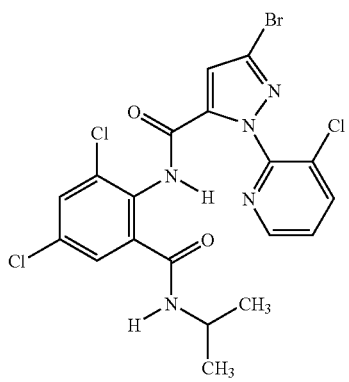
(A-18)
and TX,
the formula A-19
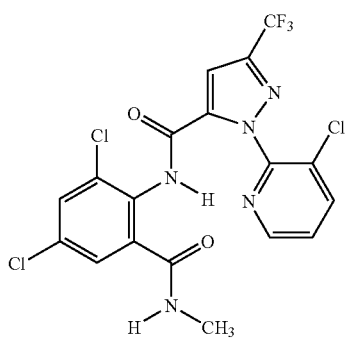
(A-19)
and TX,
the formula A-20
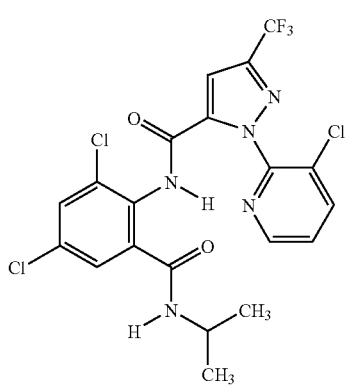
(A-20)
and TX,
the formula A-21
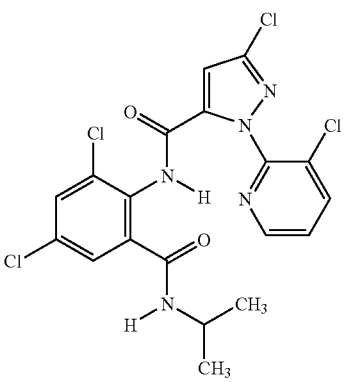
(A-21)
and TX,
the formula A-22
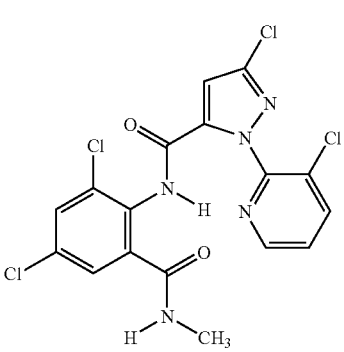
(A-22)
and TX,
the formula A-23
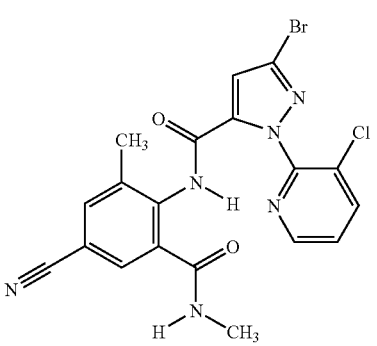
(A-23)
and TX, the formula A-24

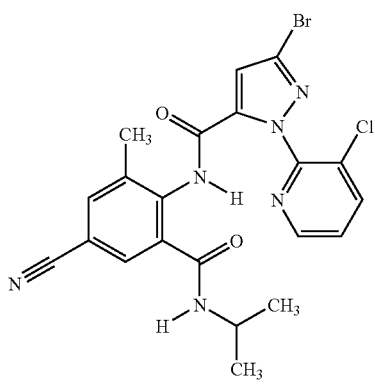

(A-24)

and TX,
the formula A-25

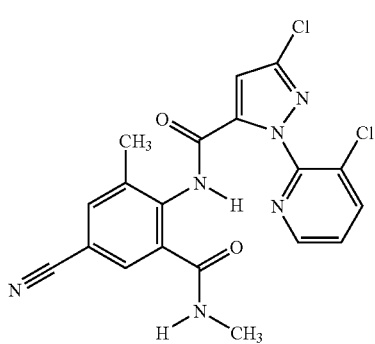

(A-25)

and TX,
the formula A-26

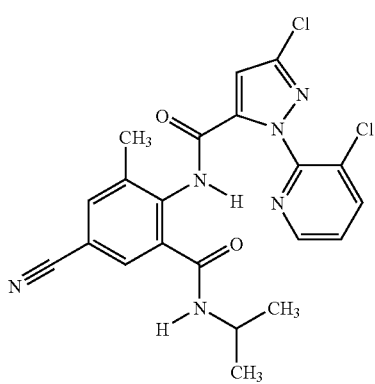

(A-26)

and TX,
and fungicides selected from the group consisting of Azaconazole (60207-31-0] and TX, Bitertanol [70585-36-3] and TX, Bromuconazole [116255-48-2] and TX, Cyproconazole [94361-06-5] and TX, Difenoconazole [119446-68-3] and TX, Diniconazole [83657-24-3] and TX, Epoxiconazole [106325-08-0] and TX, Fenbuconazole [114369-43-6] and TX, Fluquinconazole [136426-54-5] and TX, Flusilazole [85509-19-9] and TX, Flutriafol [76674-21-0] and TX, Hexaconazole [79983-71-4] and TX, Imazalil [35554-44-0] and TX, Imibenconazole [86598-92-7] and TX, Ipconazole [125225-28-7] and TX, Metconazole [125116-23-6] and TX, Myclobutanil [88671-89-0] and TX, Pefurazoate [101903-30-4] and TX, Penconazole [66246-88-6] and TX, Prothioconazole [178928-70-6] and TX, Pyrifenox [88283-41-4] and TX, Prochloraz [67747-09-5] and TX, Propiconazole [60207-90-1] and TX, Simeconazole [149508-90-7] and TX, Tebucon-azole [107534-96-3] and TX, Tetraconazole [112281-77-3] and TX, Triadimefon [43121-43-3] and TX, Triadimenol [55219-65-3] and TX, Triflumizole [99387-89-0] and TX, Triticonazole [131983-72-7] and TX, Ancymidol [12771-68-5] and TX, Fenarimol [60168-88-9] and TX, Nuarimol [63284-71-9] and TX, Bupirimate [41483-43-6] and TX, Dimethirimol [5221-53-4] and TX, Ethirimol [23947-60-6] and TX, Dodemorph [1593-77-7] and TX, Fenpropidine [67306-00-7] and TX, Fenpropimorph [67564-91-4] and TX, Spiroxamine [118134-30-8] and TX, Tridemorph [81412-43-3] and TX, Cyprodinil [121552-61-2] and TX, Mepanipyrim [110235-47-7] and TX, Pyrimethanil [53112-28-0] and TX, Fenpiclonil [74738-17-3] and TX, Fludioxonil [131341-86-1] and TX, Benalaxyl [71626-11-4] and TX, Furalaxyl [57646-30-7] and TX, Metalaxyl [57837-19-1] and TX, R-Metalaxyl [70630-17-0] and TX, Ofurace [58810-48-3] and TX, Oxadixyl [77732-09-3] and TX, Benomyl [17804-35-2] and TX, Carbendazim [10605-21-7] and TX, Debacarb [62732-91-6] and TX, Fuberidazole [3878-19-1] and TX, Thiabendazole [148-79-8] and TX, Chlozolinate [84332-86-5] and TX, Dichlozoline [24201-58-9] and TX, Iprodione [36734-19-7] and TX, Myclozoline [54864-61-8] and TX, Procymidone [32809-16-8] and TX, Vinclozoline [50471-44-8] and TX, Boscalid [188425-85-6] and TX, Carboxin [5234-68-4] and TX, Fenfuram [24691-80-3] and TX, Flutolanil [66332-96-5] and TX, Mepronil [55814-41-0] and TX, Oxycarboxin [5259-88-1] and TX, Penthiopyrad [183675-82-3] and TX, Thifluzamide [130000-40-7] and TX, Guazatine [108173-90-6] and TX, Dodine [2439-10-3][112-65-2] (freie Base) and TX, Iminoctadine [13516-27-3] and TX, Azoxystrobin [131860-33-8] and TX, Dimoxystrobin [149961-52-4] and TX, Enestroburin {Proc. BCPC and TX, Int. Congr. and TX, Glasgow and TX, 2003 and TX, 1 and TX, 93} and TX, Fluoxastrobin [361377-29-9] and TX, Kresoxim-methyl [143390-89-0] and TX, Metominostrobin [133408-50-1] and TX, Trifloxystrobin [141517-21-7] and TX, Orysastrobin [248593-16-0] and TX, Picoxystrobin [117428-22-5] and TX, Pyraclostrobin [175013-18-O] and TX, Ferbam [14484-64-1] and TX, Mancozeb [8018-01-7] and TX, Maneb [12427-38-2] and TX, Metiram [9006-42-2] and TX, Propineb [12071-83-9] and TX, Thiram [137-26-8] and TX, Zineb [12122-67-7] and TX, Ziram [137-30-4] and TX, Captafol [2425-06-1] and TX, Captan [133-06-2] and TX, Dichlofluanid [1085-98-9] and TX, Fluoroimide [41205-21-4] and TX, Folpet [133-07-3] and TX, Tolylfluanid [731-27-1] and TX, Bordeaux Mixture [8011-63-0] and TX, Copperhydroxid [20427-59-2] and TX, Copperoxychlorid [1332-40-7] and TX, Coppersulfat [7758-98-7] and TX, Copperoxid [1317-39-1] and TX, Mancopper [53988-93-5] and TX, Oxine-copper [10380-28-6] and TX, Dinocap [131-72-6] and TX, Nitrothal-isopropyl [10552-74-6] and TX, Edifenphos [17109-49-8] and TX, Iprobenphos [26087-47-8] and TX, Isoprothiolane [50512-35-1] and TX, Phosdiphen [36519-00-3] and TX, Pyrazophos [13457-18-6] and TX, Tolclofos-methyl [57018-04-9] and TX, Acibenzolar-S-methyl [135158-54-2] and TX, Anilazine [101-05-3] and TX, Benthiavalicarb [413615-35-7] and TX, Blasticidin-S [2079-00-7] and TX, Chinomethionat [2439-01-2] and TX, Chloroneb [2675-77-6] and TX, Chlorothalonil [1897-45-6] and TX, Cyflufenamid [180409-60-3] and TX, Cymoxanil [57966-95-7] and TX, Dichlone [117-80-6] and TX, Diclocymet [139920-32-4] and TX, Diclomezine [62865-36-5]

and TX, Dicloran [99-30-9] and TX, Diethofencarb [87130-20-9] and TX, Dimethomorph [110488-70-5] and TX, SYP-LI90 (Flumorph) [211867-47-9] and TX, Dithianon [3347-22-6] and TX, Ethaboxam [162650-77-3] and TX, Etridiazole [2593-15-9] and TX, Famoxadone [131807-57-3] and TX, Fenamidone [161326-34-7] and TX, Fenoxanil [115852-48-7] and TX, Fentin [668-34-8] and TX, Ferimzone [89269-64-7] and TX, Fluazinam [79622-59-6] and TX, Fluopicolide [239110-15-7] and TX, Flusulfamide [106917-52-6] and TX, Fenhexamid [126833-17-8] and TX, Fosetyl-aluminium [39148-24-8] and TX, Hymexazol [10004-44-1] and TX, Iprovalicarb [140923-17-7] and TX, IKF-916 (Cyazofamid) [120116-88-3] and TX, Kasugamycin [6980-18-3] and TX, Methasulfocarb [66952-49-6] and TX, Metrafenone [220899-03-6] and TX, Pencycuron [66063-05-6] and TX, Phthalide [27355-22-2] and TX, Polyoxins [11113-80-7] and TX, Probenazole [27605-76-1] and TX, Propamocarb [25606-41-1] and TX, Proquinazid [189278-12-4] and TX, Pyroquilon [57369-32-1] and TX, Quinoxyfen [124495-18-7] and TX, Quintozene [82-68-8] and TX, Schwefel [7704-34-9] and TX, Tiadinil [223580-51-6] and TX, Triazoxide [72459-58-6] and TX, Tricyclazole [41814-78-2] and TX, Triforine [26644-46-2] and TX, Validamycin [37248-47-8] and TX, Zoxamide (RH7281) [156052-68-5] and TX, Mandipropamid [374726-62-2] and TX, the compound of formula F-1

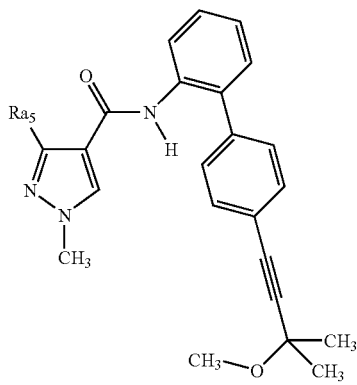

(F-1)

wherein $Ra_5$ is trifluoromethyl or difluoromethyl (WO2004/058723) and TX; the compound of formula F-2

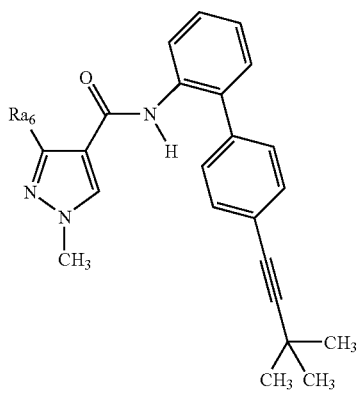

(F-2)

wherein $Ra_6$ is trifluoromethyl or difluoromethyl (WO2004/058723) and TX; the racemic compound of formula F-3 (syn)

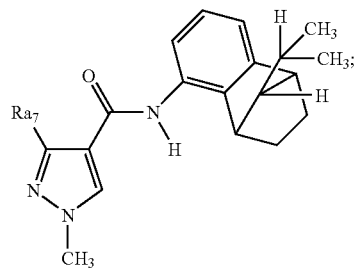

(F-3)

wherein $Ra_7$ is trifluoromethyl or difluoromethyl (WO2004/035589) and TX, the racemic mixture of formula F-4 (anti)

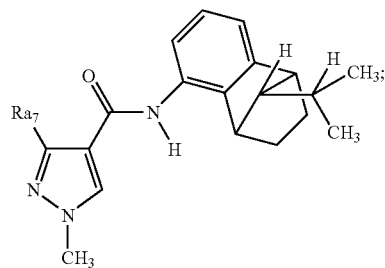

(F-4)

wherein $Ra_7$ is trifluoromethyl or difluoromethyl (WO2004/035589) and TX, the compound of formula F-5

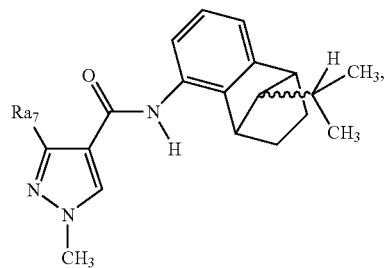

(F-5)

which is an epimeric mixture of racemic compounds of formulae F-3 (syn) and F-4 (anti), wherein the ratio from racemic compounds of formula F-3 (syn) to racemic compounds of formula F-4 (anti) is from 1000:1 to 1:1000 and wherein $Ra_7$ is trifluoromethyl or difluoromethyl (WO2004/035589) and TX, the compound of formula F-6

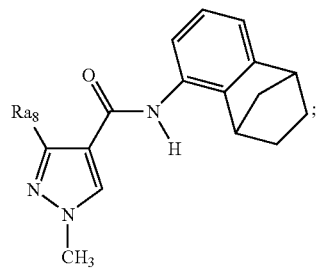

(F-6)

wherein Ra₈ is trifluoromethyl or difluoromethyl (WO2004/035589) and TX, the racemic compound of formula F-7 (trans)

(F-7)

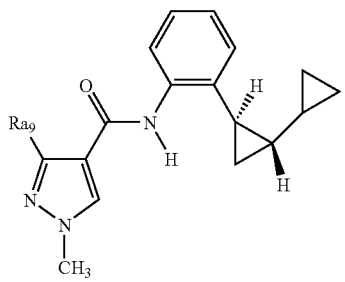

wherein Ra₉ is trifluoromethyl or difluoromethyl (WO03/074491) and TX, the racemic compound of formula F-8 (cis)

(F-8)

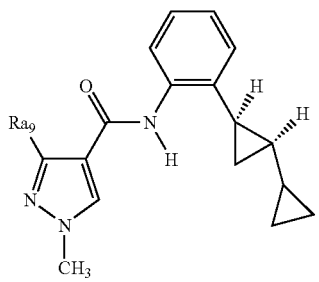

wherein Ra₉ is trifluoromethyl or difluoromethyl (WO03/074491) and TX, the compound of formula F-9

(F-9)

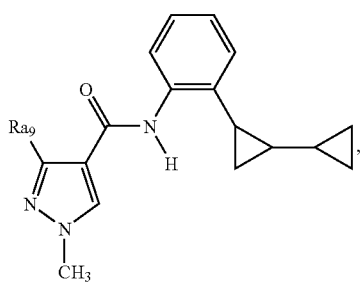

which is a mixture of the racemic compounds of formulae F-7 (trans) and F-8 (cis), wherein the ratio of the racemic compound of formula F-7 (trans) to the racemic compound of formula F-8 (cis) is 2:1 to 100:1; and wherein Ra₉ is trifluoromethyl or difluoromethyl (WO03/074491) and TX, the compound of formula F-10

(F-10)

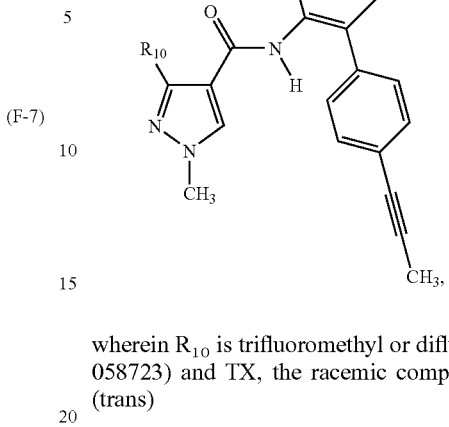

wherein R₁₀ is trifluoromethyl or difluoromethyl (WO2004/058723) and TX, the racemic compound of formula F-11 (trans)

(F-11)

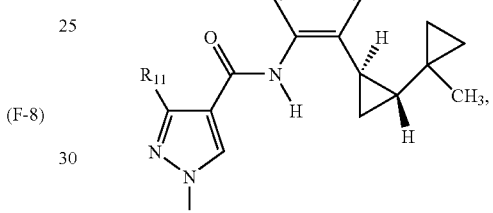

wherein R₁₁ is trifluoromethyl or difluoromethyl (WO03/074491) and TX, the racemic compound of formula F-12 (cis)

(F-12)

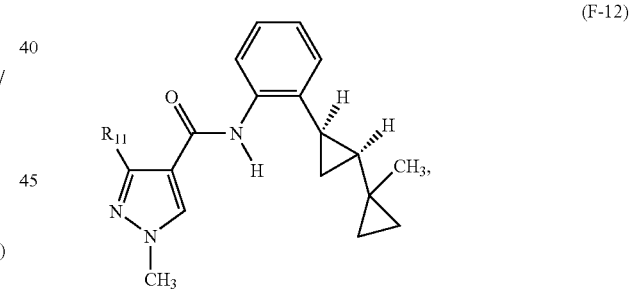

wherein R₁₁ is trifluoromethyl or difluoromethyl (WO03/074491) and TX, the compound of formula F-13

(F-13)

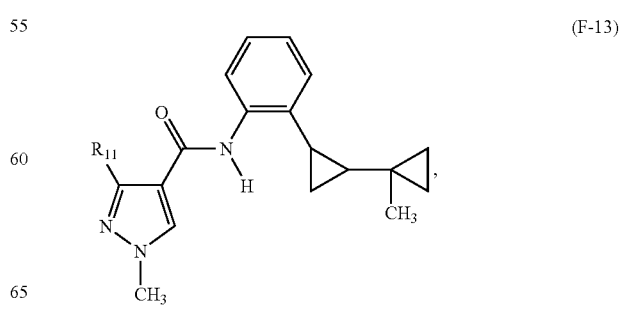

which is a racemic mixture of formulae F-11 (trans) and F-12 (cis), and wherein $R_{11}$ is trifluoromethyl or difluoromethyl (WO 03/074491) and TX, and the compound of formula F-14

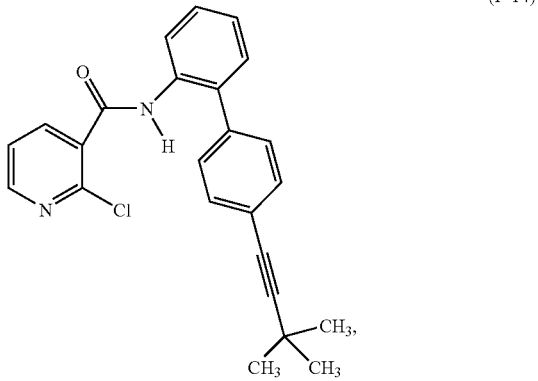

(F-14)

(WO2004/058723) and TX, and the compound of formula F-15

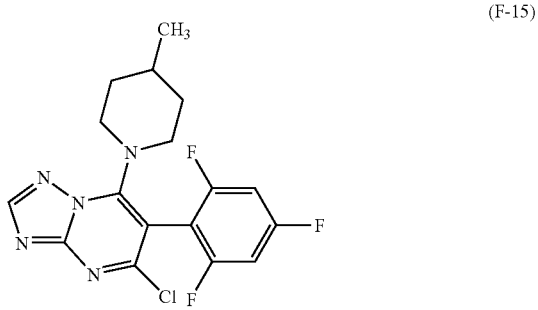 [SMILES: CC1CCN(c2c(-c3c(F)cc(F)cc3F)c(Cl)nc3ncnn23)CC1]

(F-15)

[214706-53-3],
and TX.

The references in brackets behind the active ingredients, e.g. [3878-19-1] refer to the Chemical Abstracts Registry number. The compounds of formulae A-1 to A-26 are described in WO 03/015518 or in WO 04/067528. The above described mixing partners are known. Where the active ingredients are included in "The Pesticide Manual" [The Pesticide Manual—A World Compendium; Thirteenth Edition; Editor: C. D. S. Tomlin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; Compendium of Pesticide Common Names, Copyright© 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from tables T1 to T120 with active ingredients described above comprises a compound selected from tables T1 to T120 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

The mixtures comprising a compound of formula I selected from tables T1 to T120 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from tables T1 to T120 and the active ingredients as described above is not essential for working the present invention.

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention.

BIOLOGICAL EXAMPLES

%=Percent by Weight, Unless Otherwise Specified

Example B1

Activity Against *Cydia pomonella*

Standard *Cydia* diet cubes (1.5 cm width) are pierced with a tooth-pick and are immersed in liquid paraffin (ca. 80° C.). After the paraffin coat has hardened, an aqueous emulsion containing 400 ppm of active ingredient is applied using a De Vilbis sprayer (25 ml, 1 bar). After the spray coating has dried, the cubes are put into plastic containers which are then populated with two freshly hatched *Cydia pomonella* ($1^{st}$ instar). The containers are then closed with a plastic cap. After 14 days incubation at 26° C. and 40-60% relative humidity, the survival rate of the caterpillars as well as their growth regulation is determined. In this test, compounds listed in Table P above show good activity. In particular compounds T7.1.7, T23.1.17 and T23.1.2 have an activity of over 80%.

Example B2

Activity Against *Diabrotica balteata*

Maize seedlings are sprayed with an aqueous emulsion spray mixture comprising 400 ppm of active ingredient and, after the spray coating has dried on, populated with 10 larvae (2nd instar) of *Diabrotica balteata* and introduced into a plastic container. 6 days later, the percentage reduction in the population (% activity) is determined by comparing the number of dead larvae between the treated and untreated plants.

In particular compounds T1.1.17, T3.1.7.1, T1.1.2, T1.1.8, T1.1.71, T22.1.8, T17.1.14, T23.1.88, T3.1.38, T5.1.38, T5.1.56, T3.1.53, T3.1.71, T5.1.71, T8.1.43, T8.1.1, T8.1.37, T8.1.18, T8.1.84, T8.1.82, T8.1.5, T8.1.2, T8.1.3, T8.1.9, T8.1.38, T8.1.123, T8.1.125, T8.1.22, T8.1.34, T8.1.52T8.1.14 and T8.1.7 have an activity of over 80%.

Example B3

Activity Against *Heliothis virescens* (Foliar Application)

Young soya plants are sprayed with an aqueous emulsion spray mixture comprising 400 ppm of active ingredient and, after the spray coating has dried on, populated with 10 caterpillars (1st instar) of *Heliothis virescens* and introduced into a plastic container. 6 days later, the percentage reduction in the population and in the feeding damage (% activity) are determined by comparing the number of dead caterpillars and the feeding damage between the treated and untreated plants.

In this test, compounds listed in Table P above show good activity. In particular compounds T7.1.7, T7.1.4, T7.1.1, T23.1.2 and T23.1.17 have an activity of over 80%.

Example B4

Activity Against *Heliothis virescens* (Application to Eggs)

*Heliothis virescens* eggs, which have been deposited on cotton, are sprayed with an aqueous emulsion spray mixture comprising 400 ppm of active ingredient. After 8 days, the percentage hatching rate of the eggs and the survival rate of the caterpillars (% activity) are evaluated in comparison with untreated control batches.

In this test, compounds listed in Table P above show good activity. In particular compounds T7.1.7, T1.1.17, T1.1.62, T7.1.4, T7.1.1, T3.1.38, T5.1.38, T5.1.56, T3.1.53, T3.1.71, T5.1.53, T5.1.71, T1.1.2, T1.1.8, T1.1.14, T1.1.73, T1.1.56, T1.1.68, T1.1.71, T20.1.8, T20.1.14, T20.1.2, T22.1.14, T22.1.8, T35.1.8, T21.1.8, T37.1.8, T37.1.4, T40.1.8, T51.1.8, T51.1.14, T81.1.8, T81.1.14, T23.1.8, T23.1.14, T81.1.17, T82.1.8, T23.1.2, T94.1.2, T94.1.17, T94.1.8, T115.1.8, T115.1.14, T116.1.8, T116.1.14, T116.1.17, T118.1.8, T118.1.14, T118.1.17, T23.1.17, T23.1.88, T115.1.17, T3.1.38, T5.1.38, T3.1.53, T3.1.71, T5.1.53, T5.1.71, T7.1.4, T113.1.7, T112.1.7, T14.1.7, T8.1.43, T8.1.1, T8.1.37, T8.1.18, T8.1.84, T8.1.82, T8.1.5, T8.1.2, T8.1.3, T8.1.6, T8.1.38, T8.1.122 and T8.1.123 have an activity of over 80%.

Example B5

Activity Against *Myzus persicae* (Foliar Application)

Pea seedlings are infected with *Myzus persicae*, subsequently sprayed with a spray mixture comprising 400 ppm of active ingredient and then incubated at 200.3 and 6 days later, the percentage reduction in the population (% activity) is determined by comparing the number of dead aphids between the treated and untreated plants.

In this test, compounds listed in Table P above show good activity. In particular compounds T23.1.8, T23.1.2, T116.1.17, T23.1.17, T3.1.38, T8.1.37 and T8.1.84 have an activity of over 80%.

Example B6

Systemic Insecticide Test for *Myzus persicae*

Pea seedlings are infected with *Myzus persicae*, and their roots are subsequently placed into a spray mixture comprising 400 ppm of active ingredient. The seedlings are then incubated at 20°. 3 and 6 days later, the percentage reduction in the population (% activity) is determined by comparing the number of dead aphids between the treated and untreated plants.

In this test, compounds listed in Table P above show good activity. In particular compounds T1.1.2, T35.1.8, T23.1.2 and T7.1.1 have an activity of over 80%.

Example B7

Activity Against *Plutella xylostella*

Young cabbage plants are sprayed with an aqueous emulsion spray mixture comprising 400 ppm of active ingredient and, after the spray coating has dried on, populated with 10 caterpillars (3rd instar) of *Plutella xylostella* and introduced into a plastic container. 3 days later, the percentage reduction in the population and in the feeding damage (% activity) are determined by comparing the number of dead caterpillars and the feeding damage between the treated and untreated plants.

In this test, compounds listed in Table P above show good activity. In particular compounds T7.1.7, T1.1.17, T1.1.2, T1.1.56, T1.1.62, T1.1.8, T7.1.4, T7.1.1, T3.1.38, T5.1.38, T5.1.56, T3.1.53, T3.1.71, T5.1.53, T5.1.71, T1.1.14, T1.1.73, T1.1.68, T1.1.74, T1.1.71, T20.1.8, T20.1.14, T20.1.2, T22.1.14, T22.1.8, T35.1.8, T21.1.8, T21.1.14, T37.1.8, T37.1.14, T36.1.8, T119.1.8, T119.1.14, T40.1.8, T40.1.14, T51.1.8, T51.1.14, T41.1.14, T81.1.8, T81.1.14, t23.1.8, T23.1.14, T117.1.8, T117.1.14, T41.1.17, T117.17, T81.1.17, T82.1.14, T82.1.8, T23.1.2, T94.1.2, T94.1.17, T94.1.8, T94.1.14, T115.1.8, T115.1.14, T116.1.8, T116.1.14, T116.1.17, T118.1.8, T118.1.14, T118.1.17, T23.1.17, T23.1.88, T115.1.17, T3.1.38, T5.1.38, T5.1.56, T3.1.53, T3.1.71, T5.1.53, T5.1.71, T7.1.4, T113.1.7, T112.1.7, T14.1.7, T8.1.43, T8.1.1, T8.1.37, T8.1.18, T8.1.84, T8.1.82, T8.1.88, T8.1.5, T8.1.2, T8.1.3, T8.1.6, T8.1.9, T8.1.153, T8.1.38, T8.1.122, T8.1.121 and T8.1.123 have an activity of over 80%.

Example B8

Activity Against *Spodoptera littoralis*

Young soya plants are sprayed with an aqueous emulsion spray mixture comprising 400 ppm of active ingredient and, after the spray coating has dried on, populated with 10 caterpillars (1st instar) of *Spodoptera littoralis* and introduced into a plastic container. 3 days later, the percentage reduction in the population and in the feeding damage (% activity) are determined by comparing the number of dead caterpillars and the feeding damage between the treated and untreated plants.

In this test, compounds listed in Table P above show good activity. In particular compounds T7.1.7, T1.1.17, T1.1.74, T1.1.68, T1.1.56, T1.1.62, T19.1.8, T1.1.8, T7.1.4, T7.1.1, T20.1.2, T20.1.8, T20.1.14, T22.1.8, T35.1.8, T35.1.14, T22.1.14, T1.1.2, T1.1.14, t1.1.73, T1.1.71, T20.1.8, T20.1.14, T20.1.2, T19.1.8, T22.1.14, T22.1.8, T35.1.8, T21.1.8, T37.1.8, T37.1.14, T54.1.8, T40.1.8, T81.1.8, T81.1.14, T23.1.8, T23.1.14, T53.1.8, T117.1.8, T117.1.14, T117.1.17, T81.1.17, T82.1.14, T82.1.8, T23.1.2, T94.1.2, T94.1.17, T94.1.8, T94.1.14, T115.1.8, T115.1.14, T116.1.8, T116.1.14, T116.1.17, T118.1.8, T118.1.14, T118.1.17, T23.1.17, T23.1.88, T115.1.17, T3.1.38, T5.1.38, T5.1.56, T3.1.53, T3.1.71, T5.1.53, T5.1.71, T7.1.4, T113.1.7, T112.1.7, T14.1.7, T8.1.43, T8.1.1, T8.1.37, T8.1.18, T8.1.84, T8.1.82, T8.1.5, T8.1.2, T8.1.3, T8.1.6, T8.1.9, T8.1.153, T8.1.38, T8.1.122 and T8.1.121 have an activity of over 80%.

Example B9

Systemic Insecticide Test for *Spodoptera littoralis* (Cotton Leafworm)

Four day old maize seedlings (*Zea mais*, variety *Stoneville*) are placed individual in vials containing 24 ml water into which the chemical is diluted at 12.5 ppm. Seedlings are allowed to grow for six days. Subsequently leaves are cut and placed in a Petri dish (5 cm diameter), inoculated with twelve to fifteen 1st instar *S. littoralis* larvae and incubated for four days in a growth chamber (25° C., 50% r.h., 18:6 L:D photo period). Number of alive insects are counted and percentage of dead calculated. Tests were conducted with one replicate. In this test, compounds listed in Table P above show good activity. In particular compounds T3.1.38, T3.1.56, T5.1.56, T3.1.53, T3.1.71, T5.1.53, T5.1.71, T1.1.2, T1.1.62, T1.1.71, T81.1.8, T23.1.8, T81.1.17, T82.1.14, T115.1.8, T115.1.14, T118.1.8, T118.1.17, T23.1.17, T7.1.1, T7.1.4 and T113.1.7 have an activity of over 80%.

Example B10

Activity Against *Frankliniella occidentalis*

Bean leaf discs on agar in petri dishes or bean plants in a spray chamber are treated with diluted test solutions. After drying leaf discs are cut and placed in plastic cups on the surface of an agar layer and infested with mixed population. 6 days (leaf discs) or 14 days (plants) after the infestation, samples are checked for reduction of treated population and compared to the non treated population. In this test, compounds listed in Table P above show good activity. In particular compound T7.1.7 has an activity of over 80%.

What is claimed is:

1. A compound of formula I

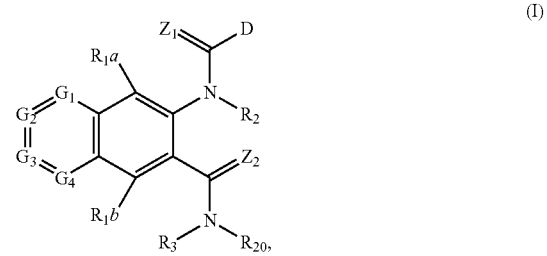

wherein $G_1$, $G_2$, $G_3$ and $G_4$ form together with the two carbon atoms to which $G_1$ and $G_4$ are attached, an aromatic ring system; wherein $G_1$ is nitrogen, sulfur, oxygen, a direct bond or $C-R_{5a}$;

$G_2$ is nitrogen, sulfur, oxygen, a direct bond or $C-R_{5b}$;

$G_3$ is nitrogen, sulfur, oxygen, a direct bond or $C-R_{5c}$;

$G_4$ is nitrogen, sulfur, oxygen, a direct bond or $C-R_{5d}$, with the provisos that a) at least one substituent G represents nitrogen, sulfur or oxygen, b) not more than 1 substituent G can at the same time form a direct bond, c) not more than 2 substituents G can be oxygen or sulfur, and d) 2 substituents G as oxygen and/or sulfur are separated by at least one carbon atom;

each of $R_{1a}$, $R_{1b}$, $R_{5a}$, $R_{5b}$, $R_{5c}$, and $R_{5d}$ which may be the same or different, represents hydrogen, halogen, nitro, cyano, hydroxy, CHO, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$alkoxy-$C_1$-$C_4$alkoxy-$C_1$-$C_4$alkyl, $C_1$-$C_4$haloalkoxy, $C_1$-$C_4$alkylthio, $C_1$-$C_4$haloalkylthio, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_1$-$C_4$alkylsulfonyl-$C_1$-$C_4$alkyl, $C_1$-$C_4$alkylsulfoximino-$C_1$-$C_4$alkyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_1$-$C_4$alkoxyimino-$C_1$-$C_4$alkyl, $C_3$-$C_6$-trialkylsilyl, phenyl, benzyl or phenoxy; or phenyl, benzyl or phenoxy mono-, di- or trisubstituted by halogen, cyano, nitro, halogen, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_3$-$C_6$trialkylsilyl or $C_1$-$C_4$-haloalkylsulfonyloxy;

each of $R_2$ and $R_3$, which may be the same or different, represents hydrogen, $C_1$-$C_6$alkyl, $C_2$-$C_6$alkenyl, $C_2$-$C_6$alkynyl or $C_3$-$C_8$cycloalkyl; or $C_1$-$C_6$alkyl, $C_2$-$C_6$alkenyl, $C_2$-$C_6$alkynyl or $C_3$-$C_8$cycloalkyl substituted by one or more substituents selected from halogen nitro, cyano, hydroxy, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino and $C_1$-$C_6$alkyl-$C_3$-$C_6$cycloalkylamino;

D is 2-pyridyl, 3-pyridyl or 4-pyridyl; or phenyl, 2-pyridyl, 3-pyridyl or 4-pyridyl mono-, di- or trisubstituted by $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl or $C_1$-$C_4$haloalkylsulfonyl;

or D is a group

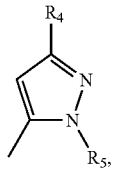
(D₁)

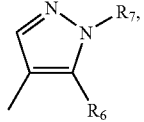
(D₂)

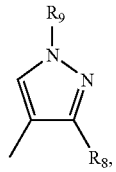
(D₃)

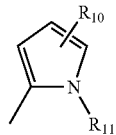
(D₄)

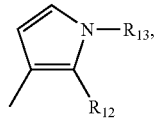
(D₅)

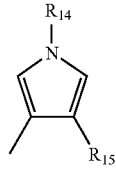
(D₆)

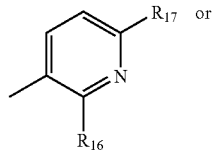
(D₇)

(D₈)

or D is additionally phenyl if $Z_1$ is sulfur;

$R_4$, $R_{10}$, $R_{17}$, and $R_{19}$ independently from each other, are hydrogen, $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_2$-$C_4$alkoxycarbonyl, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl or $C_1$-$C_4$haloalkylsulfonyl;

$R_5$, $R_6$, $R_8$, $R_{11}$, $R_{12}$, $R_{15}$, $R_{16}$ and $R_{18}$ independently from each other, are $C_1$-$C_6$alkyl, or $C_1$-$C_6$alkyl mono-, di- or trisubstituted by halogen, cyano, nitro, hydroxy, $C_1$-$C_4$alkoxy, $C_2$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylamino, $C_2$-$C_4$dialkylamino or $C_3$-$C_6$cycloalkylamino; or are phenyl, 2-pyridyl, 3-pyridyl, 4-pyridyl; or are phenyl, 2-pyridyl, 3-pyridyl or 4-pyridyl mono-, di- or trisubstituted by $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl or $C_1$-$C_4$haloalkylsulfonyl;

$R_7$, $R_9$, $R_{13}$ and $R_{14}$ independently from each other, are hydrogen, $C_1$-$C_6$alkyl, $C_1$-$C_6$haloalkyl, $C_2$-$C_6$alkenyl, $C_2$-$C_6$haloalkenyl, $C_3$-$C_6$alkenyl or $C_3$-$C_6$haloalkenyl;

$R_{20}$ is hydrogen, $C_1$-$C_6$alkyl, $C_2$-$C_6$alkenyl, $C_2$-$C_6$alkynyl, or $C_2$-$C_6$cycloalkyl; or is $C_1$-$C_6$alkyl, $C_2$-$C_6$ alkenyl, $C_2$-$C_6$ alkynyl or $C_2$-$C_6$ cycloalkyl substituted with one, two or three substituents selected from the group consisting of halogen, cyano, nitro, hydroxy, $C_1$-$C_4$alkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_2$-$C_6$ alkoxycarbonyl, $C_2$-$C_6$ alkylcarbonyl, $C_2$-$C_6$-trialkylsilyl, benzyl, phenoxy and a three- to ten-membered, monocyclic or fused bicyclic ring system which may be aromatic, partially saturated or fully saturated, it being possible for said benzyl, phenoxy and three- to ten-membered, monocyclic or fused bicyclic ring system in turn to be substituted by one to three substituents independently selected from the group consisting of $C_1$-$C_4$alkyl, $C_2$-$C_4$alkenyl, $C_2$-$C_4$alkynyl, $C_2$-$C_6$cycloalkyl, $C_1$-$C_4$haloalkyl, $C_2$-$C_4$haloalkenyl, $C_2$-$C_4$haloalkynyl, $C_2$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_2$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_2$-$C_8$ dialkylaminocarbonyl and $C_2$-$C_6$ trialkylsilyl;

or $R_{20}$ is $C_1$-$C_4$alkoxy, $C_1$-$C_4$alkylamino, $C_2$-$C_8$dialkylamino, $C_2$-$C_6$ cycloalkylamino, $C_2$-$C_6$alkoxycarbonyl or $C_2$-$C_6$alkylcarbonyl;

each of $Z_1$ and $Z_2$, which may be the same or different, represents oxygen or sulfur;

and agronomically acceptable salts/enantiomers/tautomers/N-oxides of those compounds.

2. A compound according to claim 1, wherein each of $R_{1a}$, $R_{1b}$, $R_{5a}$, $R_{5b}$, $R_{5c}$, and $R_{5d}$ which may be the same or different, represents hydrogen, halogen, nitro, cyano, hydroxy, CHO, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$alkoxy-$C_1$-$C_4$alkoxy-$C_1$-$C_4$alkyl, $C_1$-$C_4$haloalkoxy, $C_1$-$C_4$alkylthio, $C_1$-$C_4$haloalkylthio, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_1$-$C_4$alkylsulfonyl-$C_1$-$C_4$alkyl, $C_1$-$C_4$alkylsulfoximino-$C_1$-$C_4$alkyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_1$-$C_4$alkoxyimino-$C_1$-$C_4$alkyl, $C_3$-$C_6$-trialkylsilyl, phenyl, benzyl or phenoxy; or phenyl, benzyl or phenoxy mono-, di- or trisubstituted by halogen, cyano, nitro, halogen, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy or $C_3$-$C_6$-trialkylsilyl.

3. A pesticidal composition, which comprises at least one compound according to claim 1 of formula I or, where appropriate, a tautomer thereof, in each case in free form or in agrochemically utilizable salt form, as active ingredient and at least one auxiliary.

4. A composition according to claim 3 for controlling insects or representatives of the order Acarina.

5. A method for controlling pests, which comprises applying a composition according to claim 3 to the pests or their environment.

6. A method according to claim 5 for controlling insects or representatives of the order Acarina.

7. A method according to claim 5 for the protection of plant propagation material from the attack by pests, which comprises treating the propagation material or the site, where the propagation material is planted.

8. A process for the preparation of a compound of formula I according to claim 1, which process comprises a) reacting a compound of formula XVII

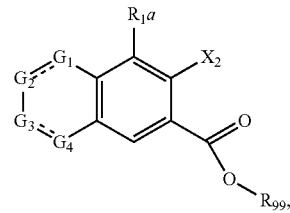

(XVII)

wherein $G_1$, $G_2$, $G_3$, $G_4$ and $R_1a$ have the meanings as given under formula I in claim 1, $R_{99}$ is $C_1$-$C_4$alkyl and $X_2$ is a leaving group, in the presence of a Pd° or Cu(I) catalyst and an inert solvent, with a compound of formula XVIII

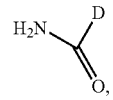

(XVIII)

wherein D has the meaning as given under formula I in claim 1, to a compound of formula XI

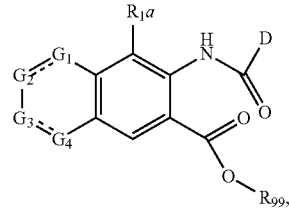

(XI)

wherein $G_1$, $G_2$, $G_3$, $G_4$, $R_1a$ and D have the meanings as given under formula I in claim 1 and $R_{99}$ is $C_1$-$C_4$alkyl, and then reacting the compound of formula XI in the presence of a base and an inert solvent to a compound of formula XII

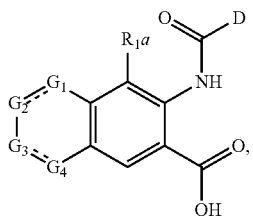

(XII)

wherein $G_1$, $G_2$, $G_3$, $G_4$, $R_1a$ and D have the meanings as given under formula I in claim 1, and then converting the compound of formula XII in the presence of $R_{20}$—$NH_2$, wherein $R_{20}$ has the meaning as given under formula I in claim 1, and a coupling agent to the compound of formula I; or b) reacting a compound of formula XVII

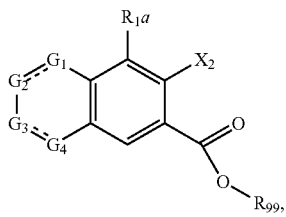

(XVII)

wherein $G_1$, $G_2$, $G_3$, $G_4$ and $R_1a$ have the meanings as given under formula I in claim 1, $R_{99}$ is $C_1$-$C_4$alkyl and $X_2$ is a leaving group, in the presence of a Pd° or Cu(I) catalyst and in an inert solvent with a compound of formula XIX

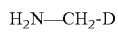 $H_2N$—$CH_2$-D (XIX), wherein D has the meaning as given under formula I in claim 1, to the compound of formula XVI

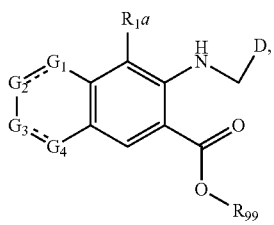

(XVI)

wherein $G_1$, $G_2$, $G_3$, $G_4$, D and $R_1a$ have the meanings as given under formula I in claim 1 and $R_{99}$ is $C_1$-$C_4$alkyl, and then reacting the compound of formula XVI with an oxidising agent to the compound of formula XI

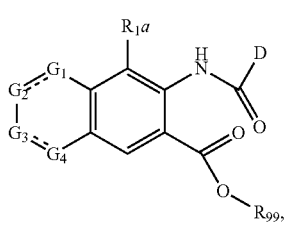

(XI)

wherein $G_1$, $G_2$, $G_3$, $G_4$, $R_1a$ and D have the meanings as given under formula I in claim 1 and $R_{99}$ is $C_1$-$C_4$alkyl, and then reacting the compound of formula XI in the presence of a base and an inert solvent to a compound of formula XII

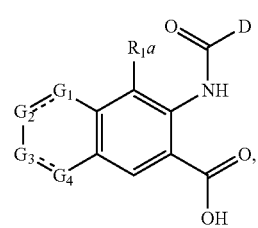

(XII)

wherein $G_1$, $G_2$, $G_3$, $G_4$, $R_1a$ and D have the meanings as given under formula I in claim 1, and then converting the compound of formula XII in the presence of $R_{20}$—$NH_2$, wherein $R_{20}$ has the meaning as given under formula I in claim 1, and a coupling agent, to the compound of formula I; or c) reacting a compound of formula X

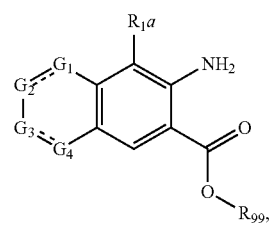

(X)

wherein $G_1$, $G_2$, $G_3$, $G_4$ and $R_1a$ have the meanings as given under formula I in claim 1 and $R_{99}$ is $C_1$-$C_4$alkyl, with a compound of formula XV

 $X_1$—$CH_2$-D (XV), wherein $X_1$ is a leaving group and D has the meaning as given under formula I in claim 1, in the presence of a base and an inert solvent to a compound of formula XVI

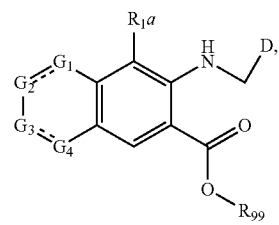

(XVI)

wherein $G_1$, $G_2$, $G_3$, $G_4$, D and $R_1a$ have the meanings as given under formula I in claim 1 and $R_{99}$ is $C_1$-$C_4$alkyl, and then reacting the compound of formula XVI with an oxidising agent to the compound of formula XI

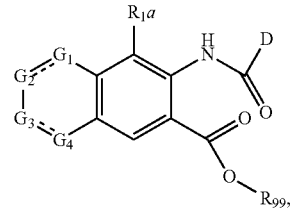

(XI)

wherein $G_1$, $G_2$, $G_3$, $G_4$, D and $R_1a$ have the meanings as given under formula I in claim 1 and $R_{99}$ is $C_1$-$C_4$alkyl, and then saponifying the compound of formula XI in the presence of a base and an inert solvent to a compound of formula XII

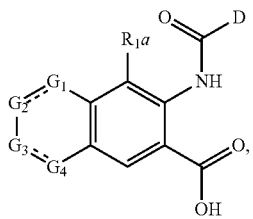

(XII)

wherein G₁, G₂, G₃, G₄, D and R₁a have the meanings as given under formula I in claim 1,
and converting the compound of formula XII in the presence of $R_{20}$—$NH_2$, wherein $R_{20}$ has the meaning as given under formula I in claim 1, and a coupling agent, to the compound of formula I; or d) reacting a compound of formula XXV

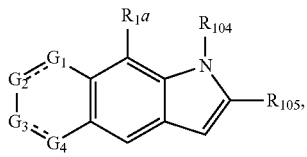

(XXV)

wherein G₁, G₂, G₃, G₄, and R₁a have the meanings as given under formula I in claim 1, $R_{104}$ is C(O)C₁-C₄alkyl and $R_{105}$ is B(OH)₂, ZnCl or SN(n-Bu)₃,
in the presence of a Pd° catalyst with a compound of formula XXVI

X₅-D     (XXV), wherein X₅ is a leaving group, and D is as defined under formula I in claim 1, to a compound of formula XXI

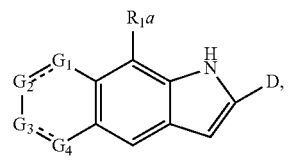

(XXI)

wherein G₁, G₂, G₃, G₄, D and R₁a have the meanings as given under formula I in claim 1,
and then reacting the compound of formula XXI in the presence of an oxidising agent to a compound of formula XII

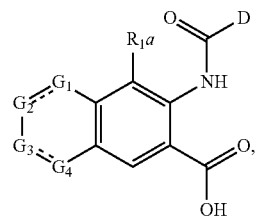

(XII)

wherein G₁, G₂, G₃, G₄, D and R₁a have the meanings as given under formula I in claim 1,
and converting the compound of formula XII in the presence of a compound of formula $R_{20}$—$NH_2$, wherein $R_{20}$ is as defined under formula I in claim 1, and a coupling agent to the compound of formula I.

* * * * *